(12) United States Patent
Dimarchi et al.

(10) Patent No.: US 10,385,107 B2
(45) Date of Patent: Aug. 20, 2019

(54) LIPIDATED AMIDE-BASED INSULIN PRODRUGS

(71) Applicant: INDIANA UNIVERSITY RESEARCH AND TECHNOLOGY CORPORATION, Indianapolis, IN (US)

(72) Inventors: Richard D. Dimarchi, Carmel, IN (US); Binbin Kou, Bloomington, IN (US); Fa Zhang, Bloomington, IN (US); John P. Mayer, Indianapolis, IN (US)

(73) Assignee: Indiana Univeresity Researc and Technology Corporation, Bloomington, IN (US)

( * ) Notice: Subject to any disclaimer, the term of this patent is extended or adjusted under 35 U.S.C. 154(b) by 0 days.

(21) Appl. No.: 15/513,762

(22) PCT Filed: Sep. 23, 2015

(86) PCT No.: PCT/US2015/051705
§ 371 (c)(1),
(2) Date: Mar. 23, 2017

(87) PCT Pub. No.: WO2016/049174
PCT Pub. Date: Mar. 31, 2016

(65) Prior Publication Data
US 2017/0283479 A1 Oct. 5, 2017

Related U.S. Application Data
(60) Provisional application No. 62/054,670, filed on Sep. 24, 2014.

(51) Int. Cl.
C07K 14/62 (2006.01)
A61K 38/28 (2006.01)
A61K 47/54 (2017.01)
A61K 47/69 (2017.01)
A61K 38/00 (2006.01)
A61K 47/00 (2006.01)

(52) U.S. Cl.
CPC .............. *C07K 14/62* (2013.01); *A61K 38/28* (2013.01); *A61K 47/54* (2017.08); *A61K 47/543* (2017.08); *A61K 47/6911* (2017.08); *A61K 38/00* (2013.01); *A61K 47/00* (2013.01)

(58) Field of Classification Search
CPC .................................. C07K 14/62; A61K 38/28
See application file for complete search history.

(56) References Cited

U.S. PATENT DOCUMENTS

| 3,740,385 A | 6/1973 | Ondetti |
|---|---|---|
| 4,275,152 A | 6/1981 | Esders et al. |
| 4,741,897 A | 5/1988 | Andrews et al. |
| 4,876,242 A | 10/1989 | Applebaum et al. |
| 4,985,407 A | 1/1991 | Foxton et al. |
| 5,028,586 A | 7/1991 | Balschmidt et al. |
| 5,359,030 A | 10/1994 | Ekwuribe |
| 5,514,646 A | 5/1996 | Chance et al. |
| 5,759,818 A | 6/1998 | Boime |
| 5,843,634 A | 12/1998 | Brate et al. |
| 6,180,767 B1 | 1/2001 | Wickstrom et al. |
| 6,197,926 B1 | 3/2001 | Gaur et al. |
| 6,476,290 B1 | 11/2002 | Wright et al. |
| 6,630,348 B1 | 10/2003 | Lee et al. |
| 6,746,853 B1 | 6/2004 | Dahiyat et al. |
| 7,045,337 B2 | 5/2006 | Schultz et al. |
| 7,326,688 B2 | 2/2008 | O'Harte |
| 7,521,422 B2 | 4/2009 | Bernard |
| 2002/0038026 A1 | 3/2002 | Rao et al. |
| 2002/0160938 A1 | 10/2002 | Brandenburg et al. |
| 2003/0195147 A1 | 10/2003 | Pillutla et al. |
| 2003/0204063 A1 | 10/2003 | Gravel et al. |
| 2004/0054130 A1 | 3/2004 | Ng et al. |
| 2004/0121940 A1 | 6/2004 | DeGroot et al. |
| 2005/0014679 A1 | 1/2005 | Beals et al. |
| 2005/0187147 A1 | 8/2005 | Newman et al. |
| 2006/0171920 A1 | 8/2006 | Schechter et al. |
| 2006/0210534 A1 | 9/2006 | Lee et al. |
| 2006/0223753 A1 | 10/2006 | Glass |
| 2007/0129284 A1 | 6/2007 | Kjeldsen et al. |
| 2007/0173452 A1 | 7/2007 | DiMarchi et al. |
| 2007/0203058 A1 | 8/2007 | Lau et al. |
| 2007/0224119 A1 | 9/2007 | McTavish |
| 2008/0113411 A1 | 5/2008 | Sheffer |

(Continued)

FOREIGN PATENT DOCUMENTS

| EP | 0220958 | 5/1987 |
|---|---|---|
| EP | 741188 | 11/1996 |

(Continued)

OTHER PUBLICATIONS

"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.

(Continued)

*Primary Examiner* — Gyan Chandra
(74) *Attorney, Agent, or Firm* — Barnes & Thornburg LLP

(57) ABSTRACT

Prodrug formulations of insulin and insulin analogs are provided wherein the insulin peptide has been modified by an amide bond linkage of a dipeptide prodrug element. The prodrugs disclosed herein have extended half-lives and are converted to the active form at physiological conditions through a non-enzymatic reaction driven by chemical instability.

13 Claims, 30 Drawing Sheets

Specification includes a Sequence Listing.

(56) References Cited

U.S. PATENT DOCUMENTS

| | | |
|---|---|---|
| 2008/0113905 A1 | 5/2008 | DiMarchi et al. |
| 2008/0214648 A1 | 9/2008 | DeKock et al. |
| 2009/0054305 A1 | 2/2009 | Schlein et al. |
| 2009/0125574 A1 | 5/2009 | Sheffer et al. |
| 2009/0176964 A1 | 7/2009 | Walensky et al. |
| 2009/0192072 A1 | 7/2009 | Pillutla et al. |
| 2009/0209453 A1 | 8/2009 | Moyle |
| 2009/0221037 A1 | 9/2009 | Lee et al. |
| 2010/0081614 A1 | 4/2010 | Fares et al. |
| 2011/0065633 A1 | 3/2011 | DiMarchi et al. |
| 2011/0257091 A1 | 10/2011 | DiMarchi |
| 2011/0288003 A1 | 11/2011 | DiMarchi et al. |
| 2012/0010134 A1 | 1/2012 | Zion et al. |
| 2013/0123171 A1 | 5/2013 | DiMarchi et al. |
| 2013/0184489 A2 | 7/2013 | Rau et al. |

FOREIGN PATENT DOCUMENTS

| | | |
|---|---|---|
| EP | 1161452 | 2/2000 |
| EP | 2036539 A1 | 3/2009 |
| EP | 2036923 A1 | 3/2009 |
| WO | 1990/12814 | 11/1990 |
| WO | 1993/03174 | 2/1993 |
| WO | 1996/34882 | 11/1996 |
| WO | 1998/11126 | 3/1998 |
| WO | 1999/46283 | 9/1999 |
| WO | WO/2000/050456 | 8/2000 |
| WO | 2002/010195 | 2/2002 |
| WO | 2004/067548 | 8/2004 |
| WO | 2004/078777 | 9/2004 |
| WO | 2005/054291 | 6/2005 |
| WO | 2006/047214 | 5/2006 |
| WO | 2006/097521 | 9/2006 |
| WO | 2007/096332 | 8/2007 |
| WO | 2008/019368 | 2/2008 |
| WO | 2008/021560 | 2/2008 |
| WO | 2008/025528 | 3/2008 |
| WO | 2008/081418 | 7/2008 |
| WO | WO09034118 A1 | 3/2009 |
| WO | WO09034119 A1 | 3/2009 |
| WO | 2009/067636 | 5/2009 |
| WO | 2009/095479 | 8/2009 |
| WO | 2009/099763 | 8/2009 |
| WO | 2010/011313 | 1/2010 |
| WO | 2010/071807 | 6/2010 |
| WO | 2010/080605 | 7/2010 |
| WO | 2010/080609 | 7/2010 |
| WO | 2011/159895 | 12/2011 |
| WO | 2011/163012 | 12/2011 |
| WO | 2011/163460 | 12/2011 |
| WO | 2011/163462 | 12/2011 |

OTHER PUBLICATIONS

Battersby et al., "Diketopiperazine Formation and N-Terminal Degradation in Recombinant Human Growth Hormone", *International Journal of Peptide & Protein Research* 44: 215-222, (1994).

Breiner, M., et al., Heterogeneity of Insulin-Receptors in Rat-Tissues as Detected with the Partial Agonist B29,B29'-Suberoyl-Insulin. Molecular Pharmacology, 1993. 44(2): p. 271-276.

Cheng et al., "The Development of an Insulin-based Prodrug," APS poster presentation, 2011.

Cloutier, et al, "Low-energy (3-24eV) electron damage to the peptide backbone" J Phys Chem B. 2007, 111(7), p. 1620-1624.

Coffman et al., "Insulin-metal ion interactions: the binding of divalent cations to insulin hexamers and tetramers and the assembly of insulin-hexamers," Biochemistry, Aug. 9, 1988, vol. 27, No. 16, pp. 6179-6187.

Coy et al, J of Medicinal Chemistry, 1973, vol. 16, No. 7, 827-829.

De et al., Synthesis and characterization of ester-based prodrugs of glucagon-like peptide 1, *Biopolymers*, 94(4): 448-56 (2010).

De, A. and DiMarchi, R. Synthesis & Analysis of Peptide Hormone-based prodrugs, (2009) Proceedings of the 21st American Peptide Society 160-161.

De, Design of peptide-based prodrug chemistry and its application to glucagon-like peptide 1. Masters Thesis Aug. 2007. [Retrieved from the Internet on Jun. 16, 2009: <https://scholarworks.iu.edu/dspace/browse?value=De%2C+ArnabBtype=author>]; p. 8, para 2; p. 16, para 3; p. 40, para. 1; p. 66, para 2; p. 77, para 1-2; p. 79, para 1.

De, et al., "Investigation of the feasibily of an amide-based prodrug under physiological conditions," Int. J. Pept. Res. Ther., 14, pp. 255-262 (2008).

Deppe, C., et al., Structure-Activity Relationship of Covalently Dimerized Insulin Derivatives—Correlation of Partial Agonist Efficacy with Cross-Linkage at Lysine B29. Naunyn-Schmiedebergs Archives of Pharmacology, 1994. 350(2): p. 213-217.

DiMarchi, "Peptides—Development of Prodrug Chemistry," RBF Symposium Feb. 1-4, 2011 India.

Du et al., "Biochemistry and Molecular Biology International," vol. 45, No. 2, Jun. 1, 1998, pp. 255-260 XP008147747.

Du X et al, Hydroxyl group of insulin A19Tyris essential for receptor binding: studies on (A9Phe) insulin, BioChem and Mol Biology International, Academic Press, Lindon, GB vol. 45, No. 2, Jun. 1, 1998, pp. 255-260. found in extended EP search report 09837982.9 (08055; 216442).

Eriksson et al., "hPEPT1 Affinity and Translocation of Selected Gln-Sar and Glu-Sar Dipeptide Derivatives", *Molecular Pharmaceutics* vol. 2, No. 3: 242-249 (May 10, 2005).

European supplemental search report for EP 09837983.7 completed by the EPO on Mar. 15, 2012.

Evans et al., "Effect of Î-Endorphin C-Terminal Peptides on Glucose Uptake in Isolated Skeletal Muscles of the Mouse", Peptides, vol. 18, No. 1, pp. 165-167, (1997).

G. Rajpal et al, "Single Chain Insulins as Receptor Agonists", Molecular Endocrinology, vol. 23, No. 5, Feb. 19, 2009 p. 679-688.

Garcia-Aparicio et al., "Design and Discovery of a Novel Dipeptidyl-peptidase IV (CD26)-Based Prodrug Approach", *J. Med. Chem.* 49: 5339-5351 (2006).

GenBank entry AAH05278, Jul. 15, 2006 [http:www/ncbi.nim.nih.gov/protein/13528972>].

Gershonov et al, A Novel Approach for a Watter-Soluble long Acting Insulin Prodrug . . . , J. Med. Chem (2000) vol. 43, pp. 2530-2537.

Goolcharran et al., "Comparison of the Rates of Deamidation, Diketopiperazine Formation, and Oxidation in Recombinant Human Vascular Endothelial Growth Factor and Model Peptides", *AAPS Pharmsci 2000* 2(1) article 5: 1-6 (Mar. 17, 2000).

Hamel et al "Cyclosporin a prodrugs: Design, systhesis and biophysical properties", J. Peptide Research, vol. 63 No. 2 pp. 147-154 (Feb. 2004).

Han et al., "IGF-based Insulin Analogs with an A-Chain Lactam," APS poster presentation, May 12, 2011.

Han et al., "Insulin Chemical Synthesis Using a Two-Step Orthogonal Formation of the Disulfides," APS poster presentation, Jun. 7, 2009.

Han et al., "Structure-Activity Relationship of Insulin at Position $A^{19}$," APS poster presentation, Jun. 7, 2009.

Harris, J. Milton, Final Word: PEGylation—A "Sunset" Technology? <http://licence.icopyright.net/user/viewFreeUse.act?fuid=OTU1NjY3OA%3D%3D>, BioPharm International, Jun. 1, 2004.

Hinds et al, Advancec Drug Delivery Reviews 2002, (54) 505-530.

Hiroshi Ogawa et al "N-Methylation of sleeted peptide bonds on the biological activity of insulin", International J of Peptide and Protein Research, vol. 30, No. 4, p. 460-473 (1987).

Hua et al, J of Bilogical Chemistry, Mar. 2008, vol. 283, No. 21, 14703-14716.

Joost, H.G., et al., Quantitative Dissociation of Glucose-Transport Stimulation and Insulin-Receptor Tyrosine Kinase Activation in Isolated Adipocytes with a Covalent Insulin Dimer (B29,B29'-Sunberoyl-Insulin). Biochemical Pharmacology, 1989. 38(14): p. 2269-2277.

Kaur et al., "Chemical Synthesis of Insulin and Related Analogs," APS poster presentation, Jun. 7, 2009.

(56) References Cited

OTHER PUBLICATIONS

Kaur et al., "Novel Single Chain Insulin Analogs Consisting of a Non-Peptide Based Connection," APS poster presentation, May 12, 2011.
Kristensen et al., "Alanine Scanning Mutagenesis of Insulin," The Journal of Biological Chemistry, 1997, 272(20):12978-12983.
Kurapkat et al "Inactive conformation of an insulin despite its wild-type sequence", Protein Science, vol. 6, No. 3, pp. 580-587 (Mar. 1997).
Madsen et al., "Structure—Activity and Protraction Relationship of Long-Acting Glucagon-like Peptide-1 Derivatives: Importance of Fatty acid Length, Polarity, and Bulkiness," J. Med. Chem. 2007, 50, pp. 6126-6132.
Mayer et al., Insulin Structure and Function, Peptide Science 2007, 88(5):687-713.
Mroz, Piotr et al., "Bioactivity of Insulin Analogs with Altered B-Chain Secondary Structure," APS poster presentation, Jun. 7, 2009.
O'Brien, Assay for DPPIV Activity using a Homogenous, Luminescent Method, Cell Notes, 2005, 11:8-11 (http://www.promega.com/resources/articles/pubhub/cellnotes/assay-for-dppiv-activity-using-a-homogeneous-luminescent-method/).
PCT International Search Report for PCT/US2009/031593 completed by the US Searching Authority on Jul. 16, 2009.
PCT International Search Report for PCT/US2009/068711 completed by the US Searching Authority on Feb. 4, 2010.
PCT International Search Report for PCT/US2009/068712 completed by the US Searching Authority on Mar. 24, 2010.
PCT International Search Report for PCT/US2009/068713.
PCT International Search Report for PCT/US2009/068716 completed by the US Searching Authority on May 3, 2010.
PCT International Search Report for PCT/US2009/068745 completed by the US Searching Authority on Feb. 1, 2010.
PCT International Search Report for PCT/US2011/041601 completed by the US Searching Authority on Nov. 10, 2011.
Phillips et al., "Supramolecular protein engineering: design of zinc-stapled insulin hexamers as a long acting depot," J. Biol. Chem., Apr. 16, 2010, vol. 285, No. 16, pp. 11755-11759.
Quan et al., "Coordinated Interaction of the Insulin B-chain Helical Domain with the aromatic Active Site," APS poster presentation, Jun. 7, 2009.
Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.
Roth, R.A., et al., Effects of Covalently Linked Insulin Dimers on Receptor Kinase-Activity and Receptor down Regulation. Febs Letters, 1984. 170(2): p. 360-364.
Santos et al., Cyclization-Activated Prodrugs. Synthesis, Reactivity and Toxicity of Dipeptide Esters of Paracetamol, *Bioorganic & Medicinal Chemistry Letters* 15: 1595-1598 (2005).
Sato, H., "Enzymatic procedure for site-specific pegylation of proteins," Advanced Drug Delivery Reviews 54, pp. 487-504 (2002).
Schilling et al., "Degradation of Insulin by Trypsin and Alphachymotrypsin," Pharmaceutical Research 1991, 8(6):721-727 (abstract).
Schuttler, A. and D. Brandenburg, Preparation and Properties of Covalently Linked Insulin Dimers. Hoppe-Seylers Zeitschrift Fur Physiologische Chemie, 1982. 363(3): p. 317-330.
Shechter et al , "Albumin-insulin conjugate releasing insulin slowly under physiologiacal conditions: a new concept for long-acting insulin", Bioconjugate Chemistry vol. 16, No. 4, p. 913-920 (2005).
Shechter et al , "Reversible pegylation of insulin facilitates its prolonged action in vitro", Eur. J. Pharm. and Biopharm. 70 (2008) p. 19-28.
Shojaee-Moradie, F., et al., Demonstration of a Relatively Hepatoselective Effect of Covalent Insulin Dimers on Glucose-Metabolism in Dogs. Diabetologia, 1995. 38(9): p. 1007-1013.
Suaifan et al, "Effects of steric bulk and stereochemistry on the rates of diketopiperazine formation from N-aminoacyl-2,2-dimethylthiazolidine-4-carboxamides (Dmt dipeptide amides)—a model for a new prodrug linker system," Tetrahedron 62, pp. 11245-11266, (2006).
Tatnell, M.A., et al., Evidence Concerning the Mechanism of Insulin-Receptor Interaction and the Structure of the Insulin-Receptor from Biological Properties of Covalently Linked Insulin Dimers. Biochemical Journal, 1983. 216(3): p. 687-694.
Tatnell, M.A., R.H. Jones, and P.H. Sonksen, Covalently-Linked Insulin Dimers—Their Metabolism and Biological Effects Invivo as Partial Competitive Antagonists of Insulin-Clearance. Diabetologia, 1984. 27(1): p. 27-31.
Wang et al., "Identification of Site(s) of Insulin Nitration by Peroxynitrite and Characterization of its Structural Change," Protein & Peptide Letters 2008, 15:1063-1067.
Ward, "Fatty Acid Acylation of Peptides: Developing strategies to enhance medicines for treating metabolic disorders," Jan. 14, 2009.
Weiland et al, "Antagonistic effects of a covalenly dimerized insulin derivatized insulin derivative on insulin receptors in 3T3-L1 adipocytes", PNAS, vol. 87, pp. 1154-1158, Feb. 1990.
Worrall et al "Synthesis of an organoinsulin molecule tha tcan be activated by antibody catalysis", PNAS vol. 98, No. 24, p. 13514-13518 (Nov. 20, 2001).
Yang et al, World J. of Gastroentero, 2000: 6(3): 371-373.
Yang et al., "A Novel Approach to Resin-Based Cysteine Alkylation," American Peptide Society, 2005.
Zhao et al., "Improved Pharmacokinetics through Site-Specific PEGylation of Insulin Analogs," APS poster presentation, May 12, 2011.
PCT International Search Report and Written Opinion completed by the ISA/US on Nov. 20, 2015 and issued in connection with PCT/US2015/051705.

COMPARATIVE INSULIN TOLERANCE TEST FOR MIU 30A,C

MIU-30a: $B^1(Y16,L17,Y25)29a : A^1(dLys(Ac),Sar-aF19)$

Fig. 4 "Irreversible" Lipidated Insulin Prodrug Concept

Fig. 5 $A^1$, $B^{29}$ di-Boc or di-Fmoc Insulin As Synthetic Intermediate to Amide Prodrugs

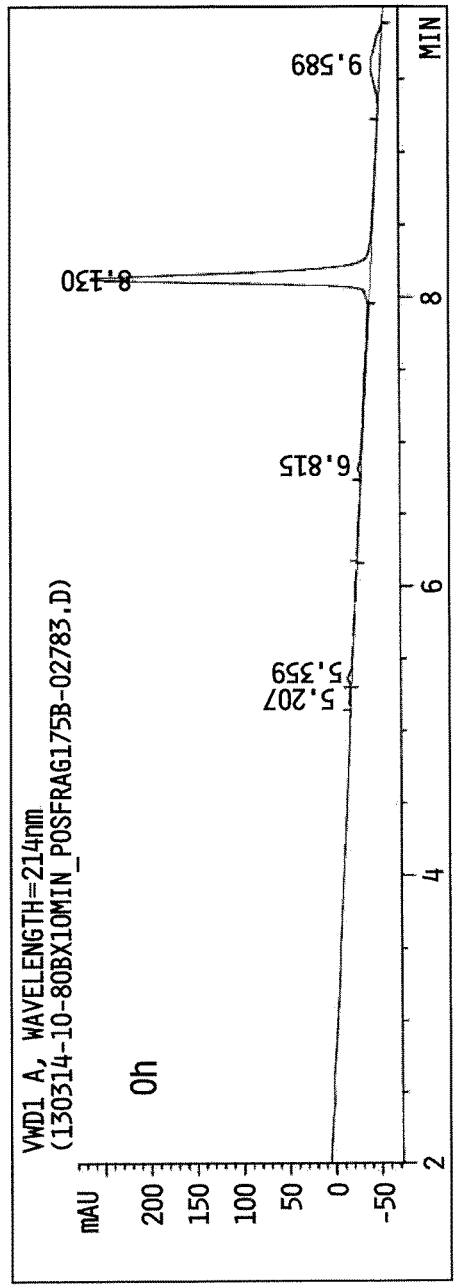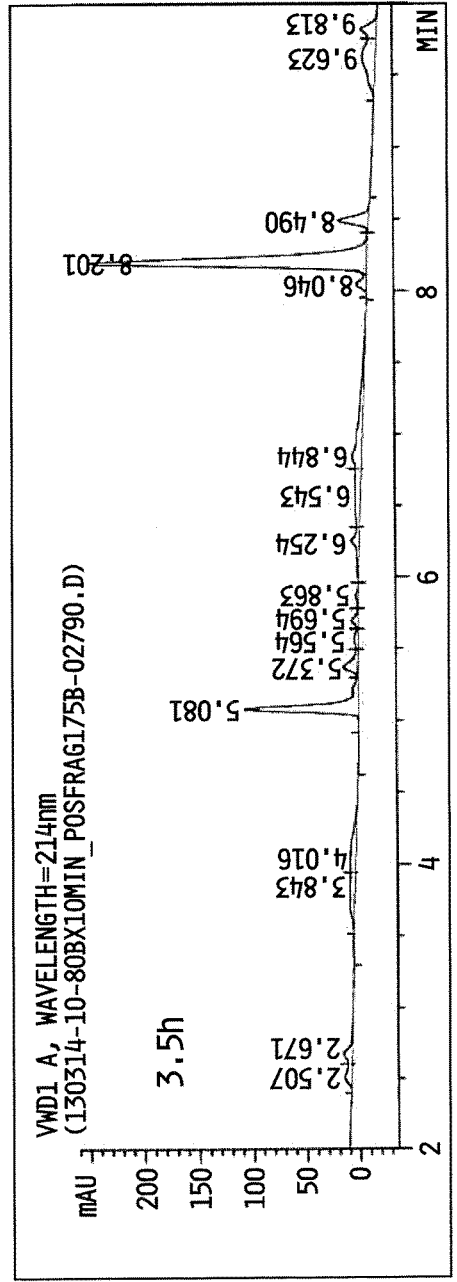
FIG. 7 CONT.

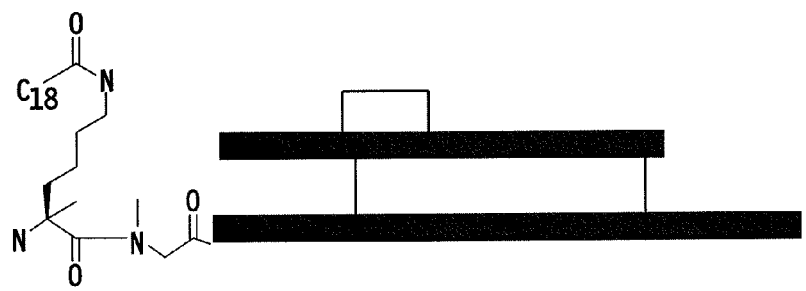
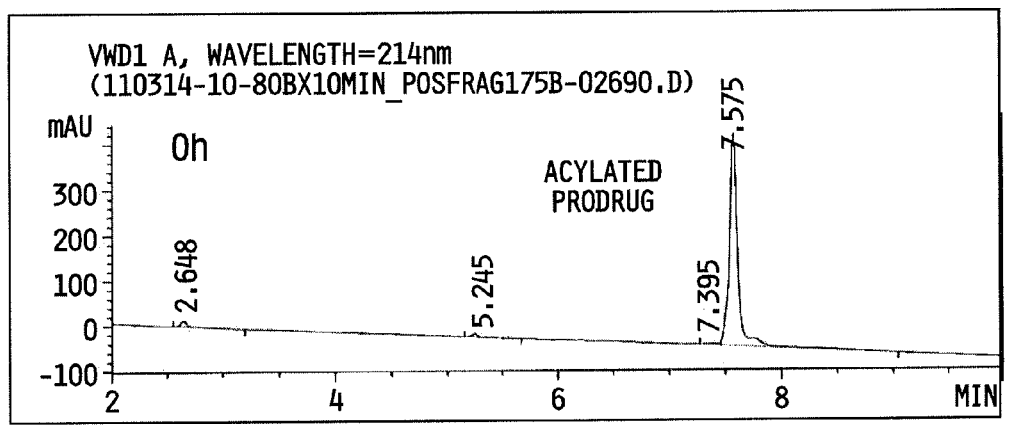
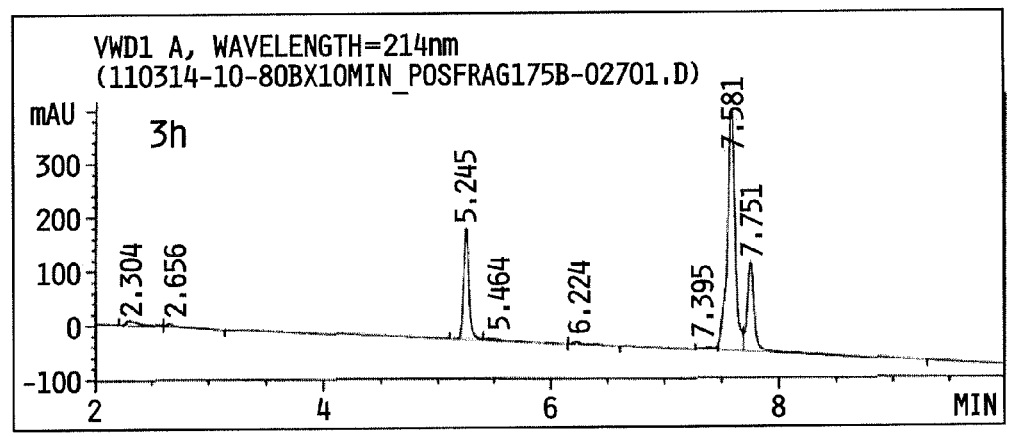
FIG. 8

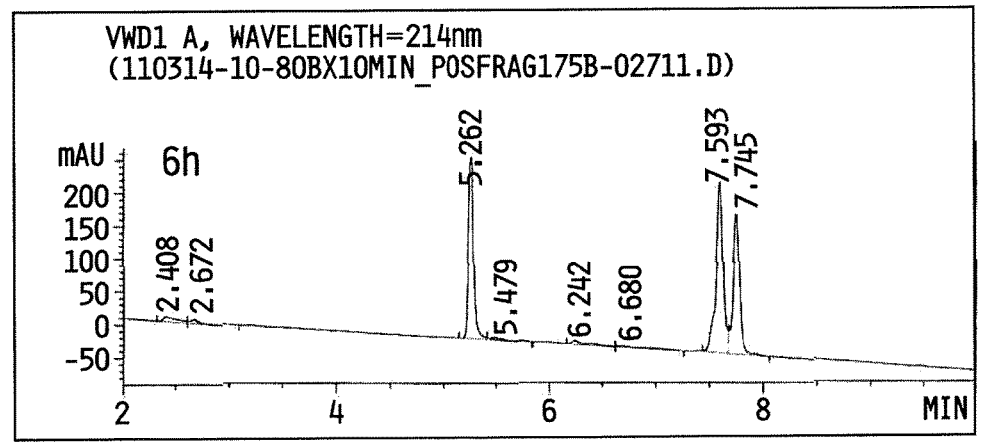
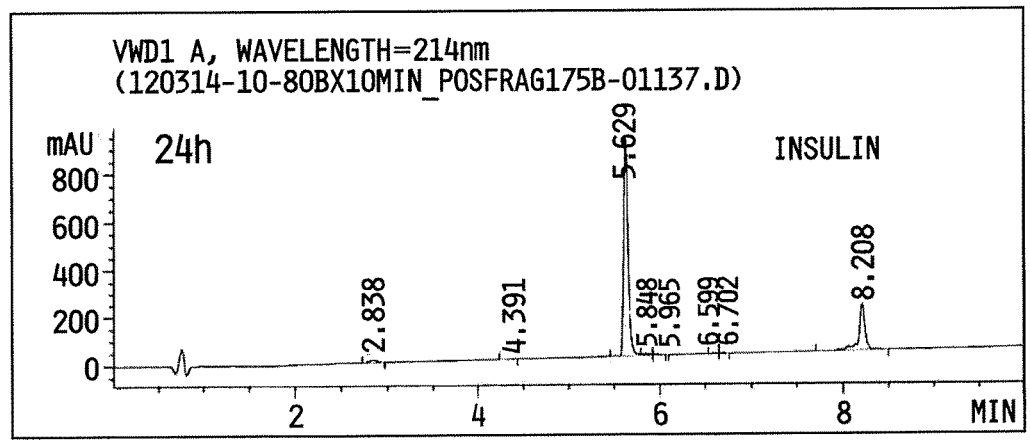
FIG. 8 CONT.

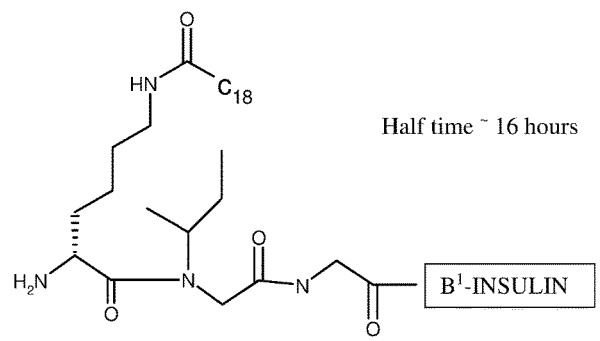
Half time ~ 16 hours
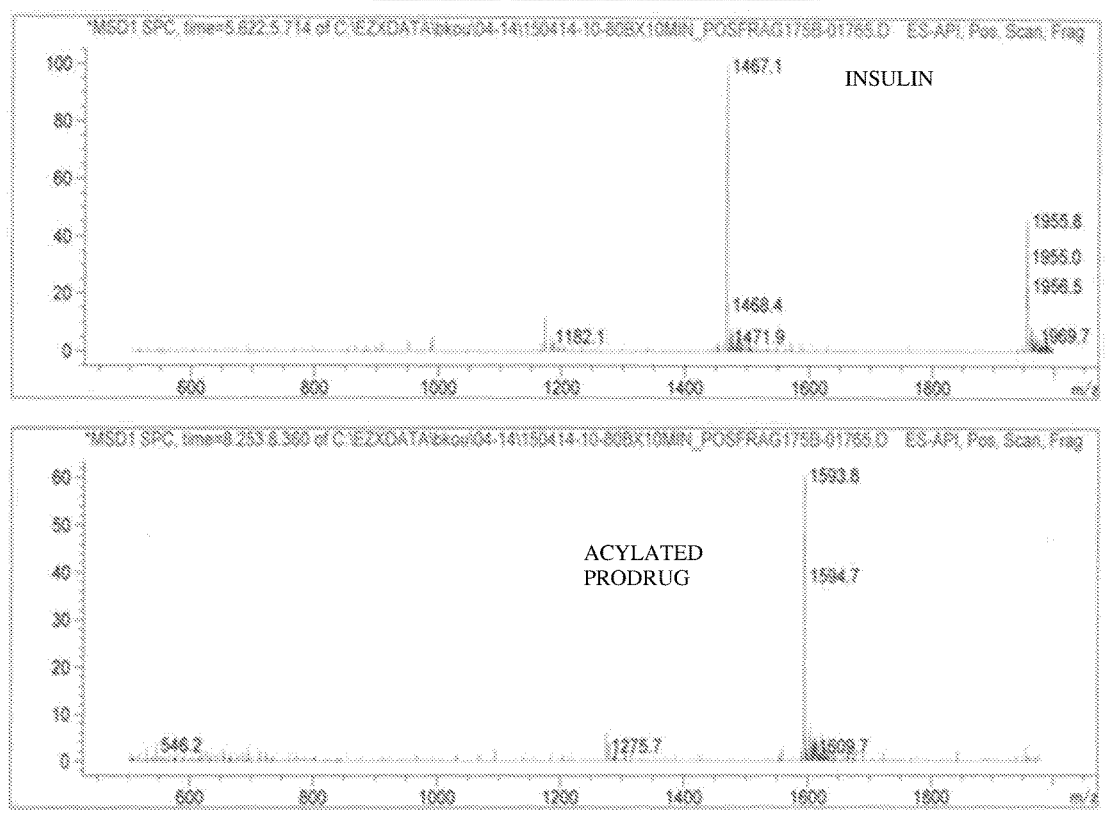
Fig. 9

CONTROL OF TIME ACTION THROUGH STERIC FIT TO DKP
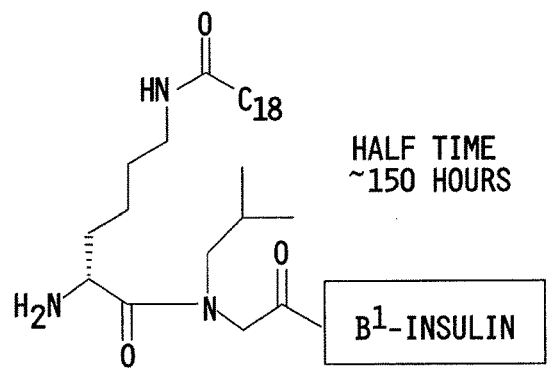
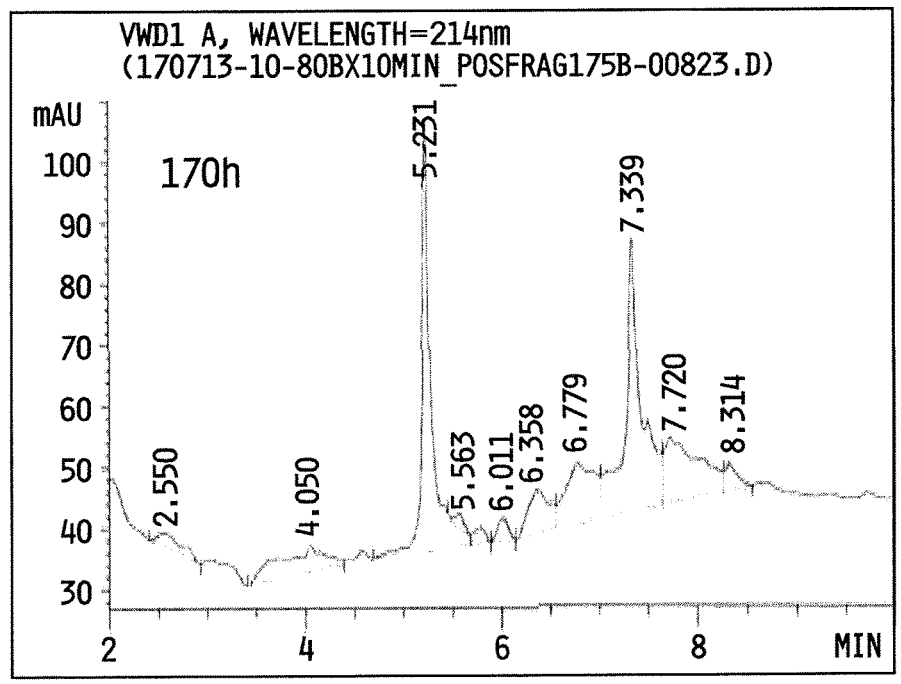
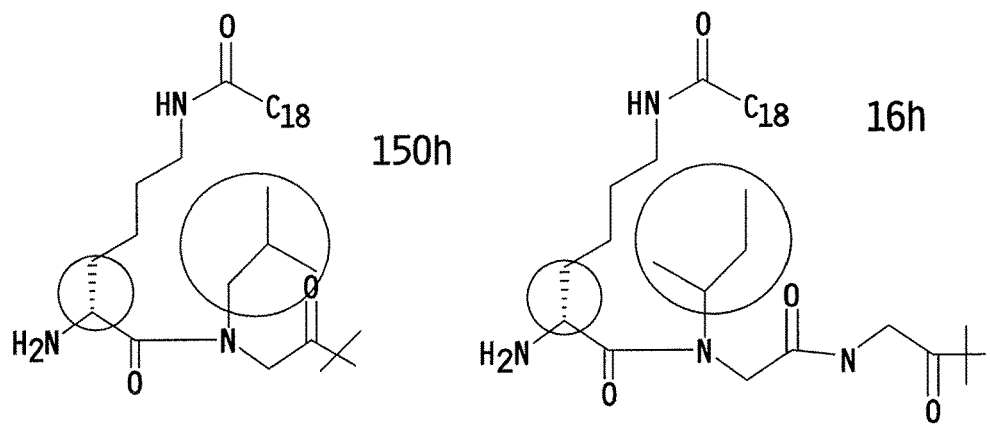
FIG. 10

Fig. 11 Continued SAR to Control Time Action

Synthetic Methodology Developed

*1: Introducing N-alkyl group by 2-bromo carboxylic acid.*

Synthetic Methodology Developed

2: Introducing N-alkyl Group & α-Substitution by Mitsunobu Reaction.

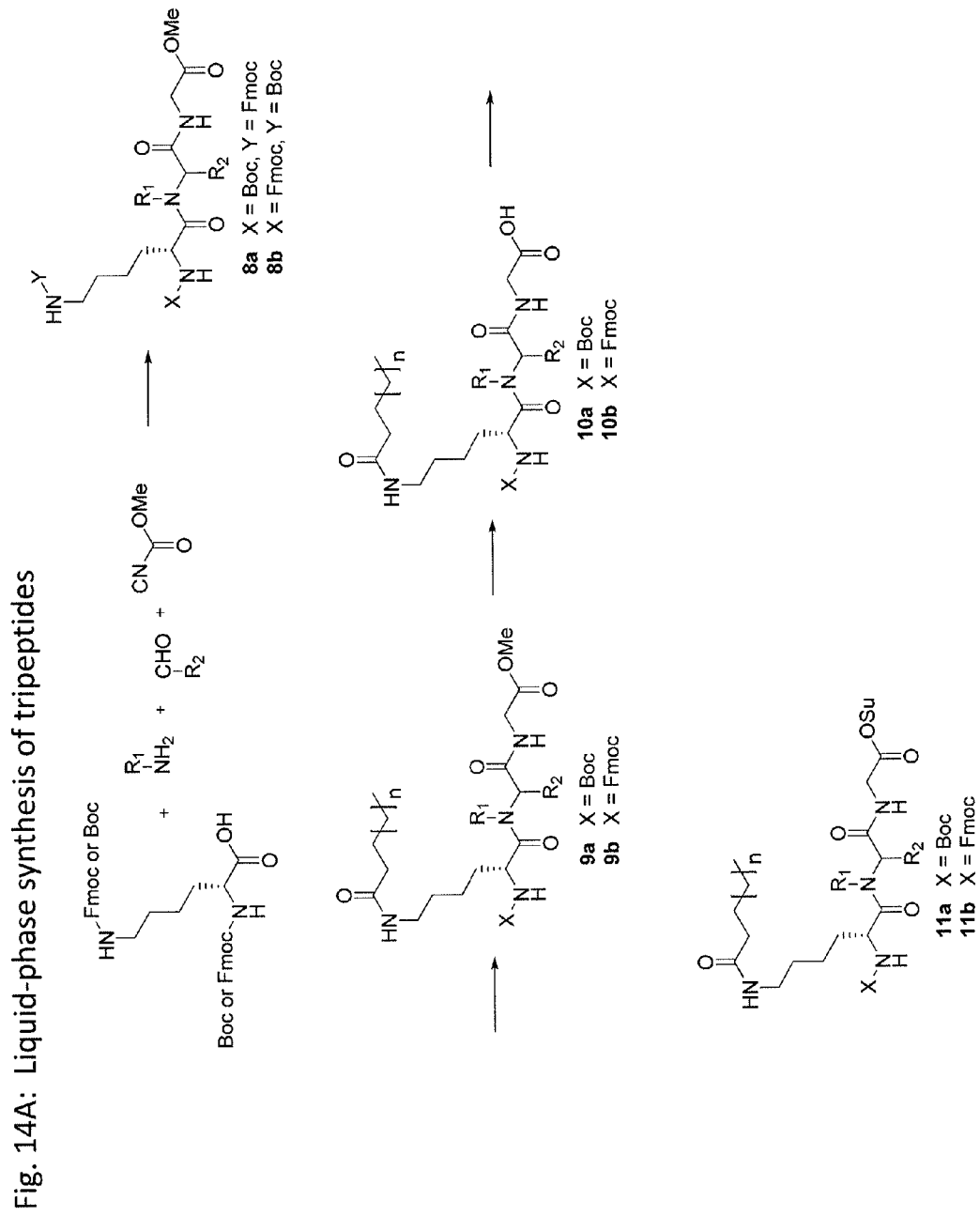
Fig. 14A: Liquid-phase synthesis of tripeptides

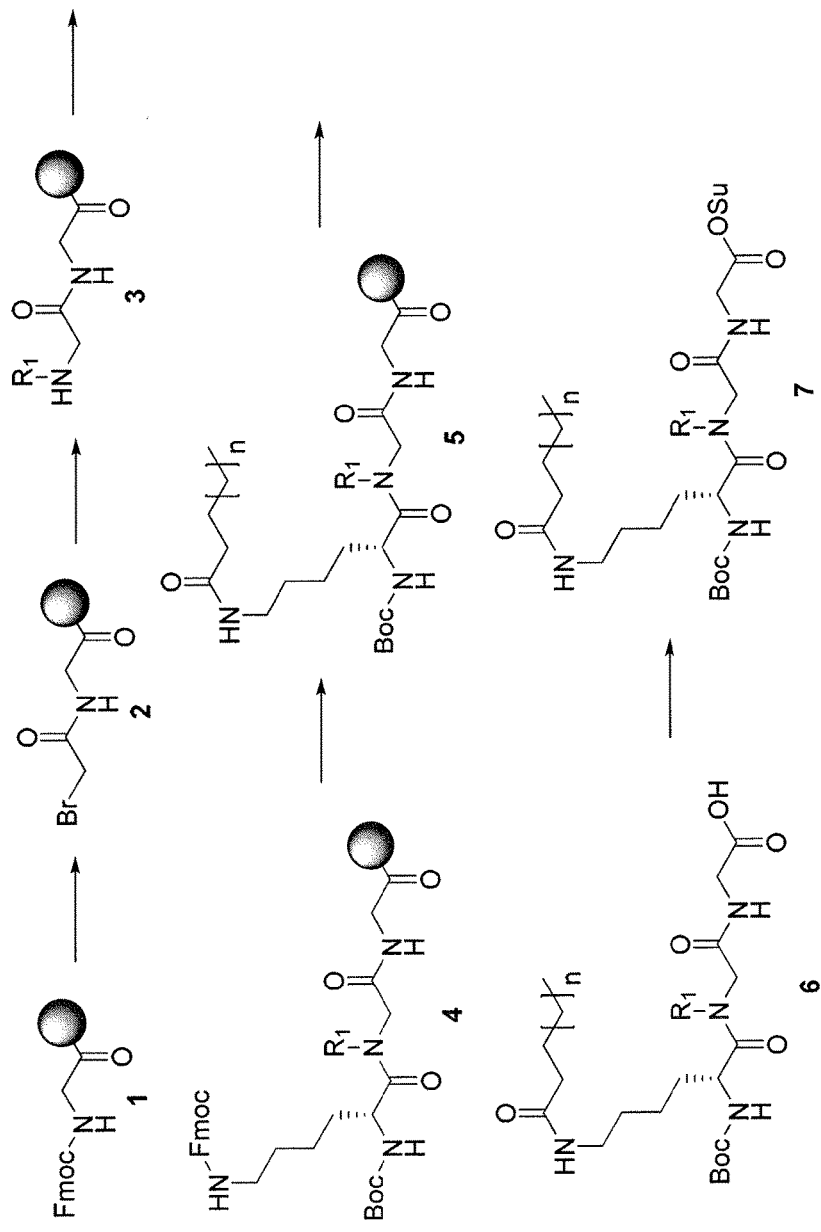
Fig. 14B: Solid-phase synthesis of tripeptides

Lipidated Prodrug: 8hr $T_{1/2}$

CIU-044 dLys(C22)-Gly-Gly, B1-INSULIN
CIU-046 dLys(C22)-(N-tert-Bu)Gly-Gly, B1-INSULIN Lipidated Prodrug: 8, 16, 24 hr T$_{1/2}$

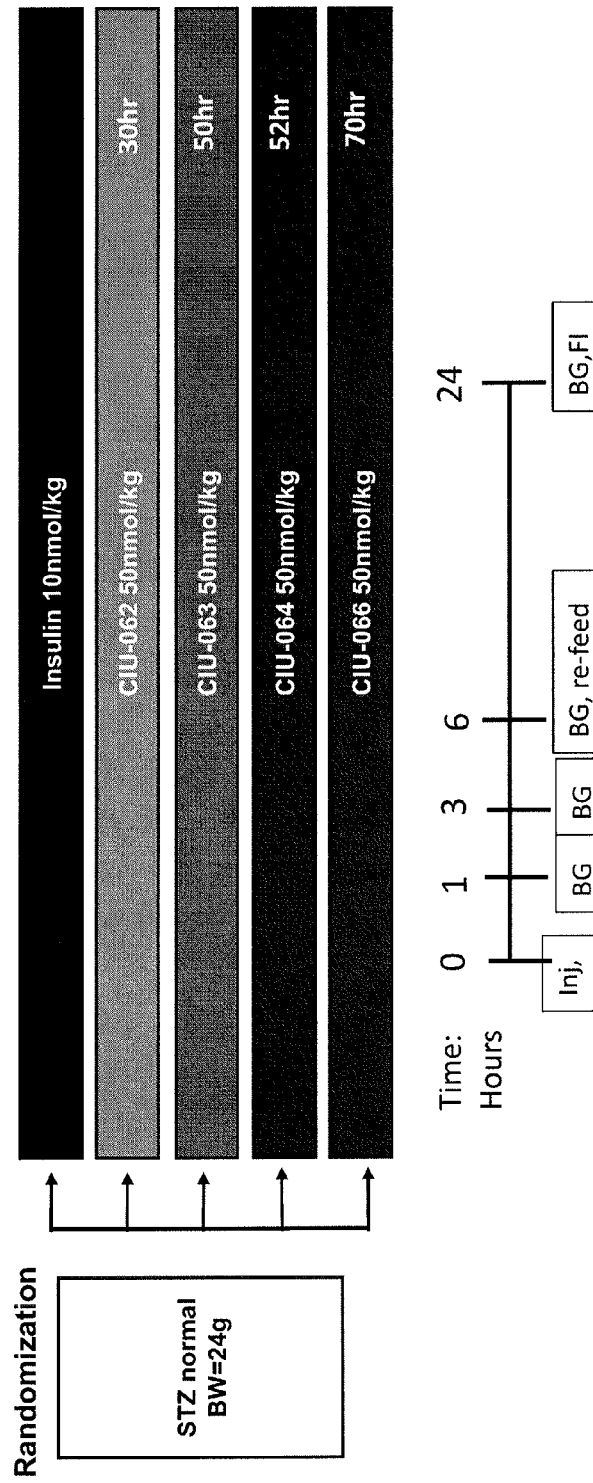

LIPIDATED AMIDE-BASED INSULIN PRODRUGS

CROSS-REFERENCE TO RELATED APPLICATIONS

This application is a U.S. national counterpart application of international application serial No. PCT/US2015/051705 filed Sep. 23, 2015, which claims priority to U.S. Provisional Application Ser. No. 62/054,670 filed on Sep. 24, 2014, the disclosures of which are expressly incorporated herein by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 22 KB ACII (Text) file named "Sub242706SequenceListing.txt" created on Aug. 15, 2018.

BACKGROUND

Insulin is a peptide hormone comprised of a two chain heterodimer that is biosynthetically derived from a low potency single chain proinsulin precursor through enzymatic processing. Human insulin is comprised of two peptide chains (an "A chain" (SEQ ID NO: 1) and "B chain" (SEQ ID NO: 2)) bound together by disulfide bonds and having a total of 51 amino acids. The C-terminal region of the B-chain and the two terminal regions of the A-chain associate in a three-dimensional structure to assemble a site for high affinity binding to the insulin receptor.

Insulin demonstrates unparalleled ability to lower glucose in virtually all forms of diabetes. Unfortunately, its pharmacology is not glucose sensitive and as such it is capable of excessive action that can lead to life-threatening hypoglycemia. Inconsistent pharmacology is a hallmark of insulin therapy such that it is extremely difficult to normalize blood glucose without occurrence of hypoglycemia. Furthermore, native insulin is of short duration of action and requires modification to render it suitable for use in control of basal glucose. Established approaches to delay the onset of insulin action include reduction in solubility, and albumin binding.

As shown in FIG. 3, current strategies for delaying the onset of insulin action in commercial insulin analogs such as Lantus & Degludec rely on creating a reserve of "insoluble" insulin in the subcutaneous tissues that is slowly released into the plasma over time ($k_1$). The soluble form present in the plasma then enters the insulin target tissue at a relatively rapid rate ($k_2$). However due to the variability associated with movement from the subcutaneous tissue to the plasma, when $k_1$ is slower than $k_2$, insulin uptake by the target tissue will reflect this variability. Commercial insulin analogs Lantus & Degludec function with $k_1$ being much slower than $k_2$. Accordingly, an insulin analog having $k_1$ much faster than $k_2$ is desirable as the variability associated with $k_1$ would have a minimal impact on insulin uptake by the target tissue.

One commercially available insulin derivative is [LysB29-tetradecanoyl, des(B30)]insulin, wherein LysB29 has been acylated with a $C_{14}$ fatty acid (Mayer et al., *Peptide Science*, 88, 5, 687-713). The presence of the fatty acid chain enhances binding of the peptide to serum albumin, resulting in increased plasma half-life. However, this derivative suffers the disadvantage of having reduced potency in vivo. In addition, this insulin derivative also exhibits variability in biological action from one patient to the next. This variability is due in part to differences in solubilization and movement from the subcutaneous tissue reserves to plasma circulation and the fact that $k_1$ is slower than $k_2$.

Prodrug chemistry offers the opportunity to precisely control the onset and duration of insulin action after clearance from the site of administration and equilibration in the plasma at a highly defined concentration. The central virtue of such an approach, relative to current long-acting insulin analogs and formulations, is that the insulin reservoir is not the subcutaneous fatty tissue where injection occurs, but rather the blood compartment (i.e., $k_1$ much faster than $k_2$). This removes the variability in absorption and solubilization encountered with prior art delayed onset insulin derivatives. It also enables administration of the peptide hormone by routes other than a subcutaneous injection.

Binding of insulin to its receptor will result in biological stimulation, but will also initiate the subsequent deactivation of insulin induced pharmacology through the enzymatic degradation of the insulin peptide. An added advantage of using a prodrug derivative of insulin is that such an approach also extends insulin's biological half-life based on a strategy of inhibiting recognition of the prodrug by the corresponding receptor. In spite of these advantages associated with prodrug derivatives, the complex nature of preparing such prodrugs has, until now, prevented the preparation of an efficacious prodrug derivative of insulin. To build a successful prodrug-hormone, an active site structural address is needed that can form the basis for the reversible attachment of a prodrug structural element. The structural address needs to offer two key features; (1) the potential for selective chemical modification and (2) the ability to provide a high degree of activity in the native form upon removal of the prodrug structural element. The insulin prodrugs disclosed herein are chemically converted to structures that can be recognized by the receptor, wherein the speed of this chemical conversion will determine the time of onset and duration of in vivo biological action. The prodrug chemistry disclosed in this application relies upon an intramolecular chemical reaction that is not dependent upon additional chemical additives, or enzymes or enzyme inhibitors.

The ideal prodrug should be soluble in water at physiological conditions (for example, a pH of 7.2 and 37° C.), and it should be stable in the powder form for long term storage. It should also be immunologically silent and exhibit a low activity relative to the parent drug. Typically the prodrug will exhibit no more than 10% of the activity of the parent drug, in one embodiment the prodrug exhibits less than 10%, less than 5%, about 1%, or less than 1% activity relative to the parent drug. Furthermore, the prodrug, when injected in the body, should be quantitatively converted to the active drug within a defined period of time. Applicants are the first to disclose insulin prodrug analogs that meet each of these objectives.

SUMMARY

Peptide-based drugs are highly effective medicines with relatively short duration of action and variable therapeutic index. The present disclosure is directed to insulin prodrugs wherein the prodrug derivative is designed to delay onset of action and extend the half-life of the drug. The delayed onset of action is advantageous in that it allows systemic distribution of the prodrug prior to its activation. Accordingly, the administration of prodrugs eliminates complications caused by peak activities upon administration and increases the therapeutic index of the parent drug.

In accordance with one embodiment, a prodrug derivative of insulin is prepared by covalently linking a dipeptide to an insulin peptide via an amide linkage wherein the dipeptide comprises a covalently linked moiety (e.g., a non-native alkyl or acyl group) that is of sufficient size to irreversibly bind a mammalian plasma protein such as mammalian serum albumin. Subsequent removal of the dipeptide via an intramolecular reaction, resulting in diketopiperazine or diketomorpholine formation, under physiological conditions and in the absence of enzymatic activity, restores full activity to the insulin polypeptide. In one embodiment the substituents of the dipeptide are selected to produce a cleavage half-life of about 2 to about 168 hours or about 12 to about 168 hours in serum and under physiological conditions. In one embodiment the substituents of the dipeptide are selected to produce a cleavage half-life of about 0.5 days to about 10 days or about 2 to about 10 days in serum and under physiological conditions.

In accordance with one embodiment a method of treating diabetes, or treating/preventing hypertension, comprises administering an insulin prodrug as disclosed herein. In one embodiment the insulin prodrug is administered daily in a fractional dosage based on the half-life of the prodrug in serum under physiological conditions. For example, if the prodrug has a half-life of n, wherein n is equal to or greater than one day, the daily dosage is 1/n of the optimal dosage of the corresponding non-prodrug form of the insulin peptide. Thus an insulin prodrug having a half-life of 10 days would be administered daily at one tenth of the optimal dosage of the corresponding non-prodrug form of the insulin peptide.

In accordance with one embodiment an insulin prodrug is provided comprising the structure: A-B-C-Q;

wherein Q is an insulin peptide;

A is an amino acid or hydroxyl acid comprising a ($C_1$-$C_8$ alkyl)$NH_2$ side chain, wherein the side chain of A is covalently linked to a moiety that irreversibly binds a mammalian plasma protein, including for example, mammalian serum albumin. In one embodiment the side chain of A is covalently linked to an acyl or alkyl group, including a fatty acid, cholic acid, bile salts or steroid moiety of a bile acid, that is preferably at least 16, 18, or 20 carbons in length. In one embodiment the side chain of A is covalently linked to a $C_{16}$-$C_{30}$ acyl group or a $C_{16}$-$C_{30}$ alkyl group;

B is an N-alkylated amino acid; and

C is an amide bond, $X_{70}$ or $X_{70}X_{71}$, wherein $X_{70}$ and $X_{71}$ are amino acids independently selected from the group consisting of glycine, aspartic acid, glutamic acid, cysteic acid, homocysteic acid, homoglutamic acid, arginine, lysine and histidine, wherein A-B-C is linked to Q through an amide bond via an aliphatic amino group of Q. Optionally, the linkage between the side chain of A and the acyl or alkyl group is via a spacer, wherein the spacer comprises one or two charged amino acids. In accordance with one embodiment the structure A-B-C is linked to Q through an amide bond linkage at an aliphatic amino group selected from the alpha amino group on the N-terminal amino acid of the A chain or the B chain, or an aliphatic amino group on a side chain of an B3, B28 or B29 amino acid of Q. In accordance with one embodiment B is an amino acid N-alkylated with $C_1$-$C_{18}$ alkyl, $C_3$-$C_{18}$ alkenyl, ($C_0$-$C_4$ alkyl)($C_4$-$C_6$ cycloalkyl), ($C_0$-$C_4$ alkyl)($C_3$-$C_5$ heterocyclic), or ($C_0$-$C_4$ alkyl)($C_6$-$C_{10}$ aryl).

In another embodiment an insulin prodrug is provided comprising the structure:

A-B-C-Q;

wherein Q is an insulin peptide and A-B-C comprises a structure of:

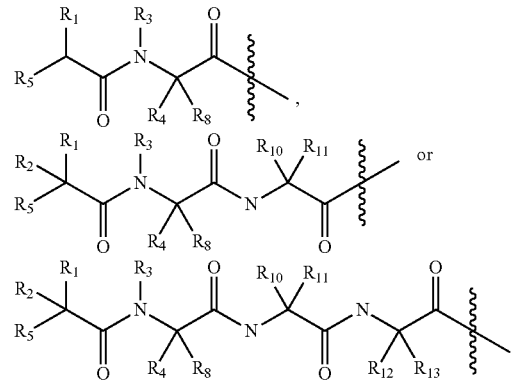

wherein $R_1$ is ($C_1$-$C_6$ alkyl)NH—$R_9$ or ($C_1$-$C_6$ alkyl)NH—$S_1$—$R_9$;

$R_2$ is H or $C_1$-$C_6$ alkyl;

$R_3$ is selected from the group consisting of $C_2$-$C_4$ alkyl, $C_3$-$C_8$ alkenyl, ($C_0$-$C_4$ alkyl)($C_4$-$C_6$ cycloalkyl), ($C_0$-$C_4$ alkyl)($C_3$-$C_5$ heterocyclic), ($C_0$-$C_4$ alkyl)($C_6$-$C_{10}$ aryl) and ($C_1$-$C_4$ alkyl)($C_6$-$C_{10}$ heteroaryl), or $R_4$ and $R_3$ together with the atoms to which they are attached form a 4, 5 or 6 member heterocyclic ring;

$R_4$, and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_4$ and $R_8$ together with the atoms to which they are attached form a $C_3$-$C_6$ cycloalkyl;

$R_5$ is $NHR_6$ or OH;

$R_6$ is H, or $C_1$-$C_8$ alkyl;

$R_7$ is selected from the group consisting of H, OH, $C_1$-$C_{18}$ alkyl, $C_2$-$C_{18}$ alkenyl, ($C_0$-$C_4$ alkyl)$NH_2$, and ($C_0$-$C_4$ alkyl)OH;

$R_9$ is selected from the group consisting of $C_{18}$-$C_{30}$ acyl;

$R_{10}$, $R_{11}$, $R_{12}$, and $R_{13}$ are independently selected from the group consisting of H, $CH_2$, CHOH, $CH_2SH$, ($C_1$-$C_4$ alkyl)COOH, ($C_1$-$C_4$ alkyl)$NH_2$, ($C_1$-$C_4$ alkyl)NHC($NH_2^+$)$NH_2$ and $CH_2$($C_3$—$N_2$ heterocyclic); and $S_1$ is a spacer consisting of one or two charged amino acids selected from the group consisting of aspartic acid, glutamic acid, cysteic acid, homocysteic acid, homoglutamic acid, arginine, lysine and histidine, wherein A-B-C is linked to Q through an amide bond via an aliphatic amino group of Q. In one embodiment $R_1$ is ($C_1$-$C_6$ alkyl)NH—$S_1$—$R_9$; $R_3$ is selected from the group consisting of $C_2$-$C_4$ alkyl; $R_2$, $R_4$, $R_{11}$, and $R_{13}$ are each H; $R_5$ is $NH_2$; $R_8$ is H or $C_1$-$C_8$ alkyl; $R_9$ is $C_{18}$-$C_{30}$ acyl; $R_{10}$ and $R_{12}$ are independently selected from the group consisting of ($C_1$-$C_4$ alkyl)COOH, ($C_1$-$C_4$ alkyl)$NH_2$ and ($C_1$-$C_4$ alkyl)$NHC(NH_2^+)NH_2$; and $S_1$ is a spacer comprising one or two charged amino acids selected from the group consisting of aspartic acid, glutamic acid, cysteic acid, homocysteic acid, homoglutamic acid, arginine, lysine and histidine, and A-B-C is linked to Q through an amide bond via the N-terminal amine of the B chain of insulin.

In one embodiment an insulin prodrug is provided comprising the structure: A-B-C-Q;

wherein Q is an insulin peptide and A-B-C comprises a structure of:

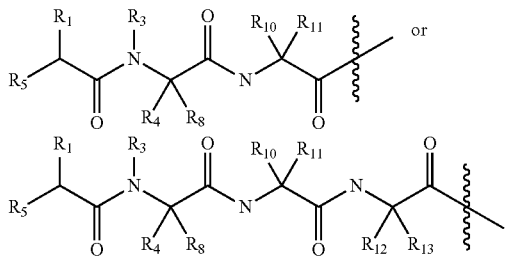

wherein $R_1$ is $C_{18}$-$C_{30}$ alkyl, ($C_1$-$C_6$ alkyl)NH—$R_9$ or ($C_1$-$C_6$ alkyl)NH—$S_1$—$R_9$;

$R_3$ is selected from the group consisting of $C_2$-$C_4$ alkyl, $R_4$, $R_{11}$ and $R_{13}$ are each H $R_5$ is $NH_2$;

$R_8$ is H or $C_1$-$C_8$ alkyl;

$R_9$ is $C_{18}$-$C_{30}$ acyl; and $R_{10}$ and $R_{12}$ are independently selected from the group consisting of ($C_1$-$C_4$ alkyl)COOH, ($C_1$-$C_4$ alkyl)$NH_2$, ($C_1$-$C_4$ alkyl)$NHC(NH_2^+)NH_2$, and $CH_2(C_3$—$N_2$ heterocyclic); and $S_1$ is a spacer consisting of one or two charged amino acids selected from the group consisting of aspartic acid, glutamic acid, cysteic acid, homocysteic acid, homoglutamic acid, arginine, lysine and histidine, wherein A-B-C is linked to Q through an amide bond via an aliphatic amino group of Q. In one embodiment $R_1$ is $(CH_2)_4$—$S_1$—$NHR_9$ or $(CH_2)_4NHR_9$; $R_3$ is $C_3$-$C_4$ alkyl; $R_5$ is $NH_2$; and $R_9$ is $C_{18}$-$C_{28}$ acyl, and A-B-C is linked to Q through an amide bond via the N-terminal amine of the B chain of insulin.

The insulin peptide of the prodrugs disclosed herein can comprise any of the insulins known to those skilled in the art that have agonist activity at the insulin receptors. In accordance with one embodiment the insulin peptide comprises an A chain sequence of GIVEQCC$X_8$SICSLYQLENYC$X_{21}$$R_{44}$ (SEQ ID NO: 3) and a B chain sequence of $R_{22}$-$X_{25}$LCG$X_{29}$$X_{30}$LV$X_{33}$$X_{34}$LYLVCG$X_{41}$$X_{42}$GF$X_{45}$ (SEQ ID NO: 20), wherein the B chain is linked to the A chain through disulfide linkages;

$X_8$ is selected from the group consisting of threonine and histidine;

$X_{21}$ is selected from the group consisting of asparagine, ornithine, glycine, alanine, threonine, and serine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, ornithine, lysine and arginine;

$X_{45}$ is tyrosine or phenylalanine;

$R_{22}$ is selected from the group consisting of AYRPSE (SEQ ID NO: 14), FVNQ (SEQ ID NO: 12), FVKQ (SEQ ID NO: 8), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and $R_{44}$ is COOH or $CONH_2$.

In one embodiment the insulin peptide of the prodrugs disclosed herein comprises an A chain sequence of GIVEQCC$X_8$SICSLYQLENYC$X_{21}$ (SEQ ID NO: 3) and a B chain sequence of $R_{22}$-HLCGSHLVEALYLVCGERGF$X_{45}$ (SEQ ID NO: 15), wherein the B chain is linked to said A chain through disulfide linkages;

$R_{22}$ is a bond, or a 1 to 4 amino acid sequence selected from the group consisting of a FVNQ (SEQ ID NO: 12), FVKQ (SEQ ID NO: 8), VNQ, NQ and Q;

$X_8$ is selected from the group consisting of threonine and histidine;

$X_{21}$ is selected from the group consisting of asparagine, lysine, glycine, alanine; and $X_{45}$ is histidine, tyrosine or phenylalanine.

In one embodiment the A chain comprises a sequence GIVEQCCTSICSLYQLENYCN-$R_{44}$ (SEQ ID NO: 1) and said B chain comprises a sequence selected from the group consisting of FVNQHLCGSHLVEALYLVCGERGFFYTPKT (SEQ ID NO: 2) FVNQHLCGSHLVEALYLVCGERGFFYTKPT (SEQ ID NO: 9) FVNQHLCGSHLVEALYLVCGERGFFYTDKT (SEQ ID NO: 5) FVKQHLCGSHLVEALYLVCGERGFFYTEKT (SEQ ID NO: 6), wherein $R_{44}$ is COOH or $CONH_2$.

In one embodiment the amino acid A and/or B of the prodrug element is an amino acid in the D stereoisomer configuration. In some exemplary embodiments, A is an amino acid in the D stereoisomer configuration and B is an amino acid in the L stereoisomer configuration. In some exemplary embodiments, A is an amino acid in the L stereoisomer configuration and B is an amino acid in the D stereoisomer configuration. In some exemplary embodiments, A is an amino acid in the D stereoisomer configuration and B is an amino acid in the D stereoisomer configuration. In one embodiment B is an N-alkylated amino acid but is not a substituted proline or proline analog.

In accordance with one embodiment an insulin analog is provided wherein the A chain of the insulin peptide comprises the sequence GIVEQCCTSICSLYQLENYCN (SEQ ID NO: 1) and the B chain comprising a sequence selected from the group consisting of Z-FVNQHLCGSHLVEALYLVCGERGFFYTPKT (SEQ ID NO: 2), Z-FVNQHLCGSHLVEALYLVCGERGFFYTDKT (SEQ ID NO: 5), Z-FVKQHLCGSHLVEALYLVCGERGFFYTEKT (SEQ ID NO: 6) and Z-FVNQHLCGSHLVEALYLVCGERGFFYTKPT (SEQ ID NO: 9) wherein Z is a peptide comprising the general structure:

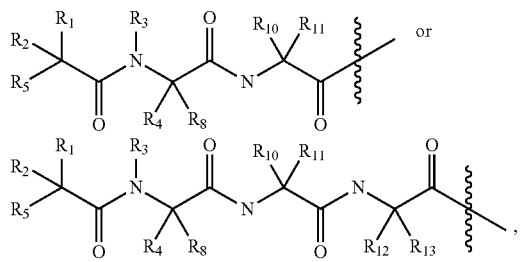

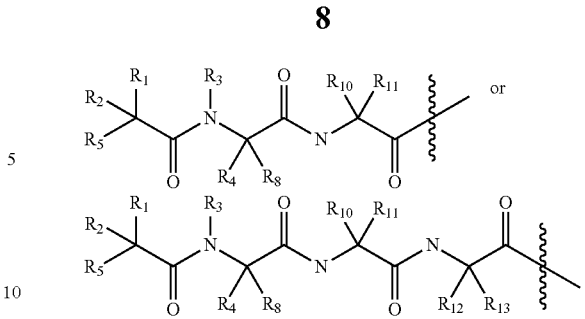

wherein

Z is linked to Q through an amide bond via the N-terminal amino acid of the B chain, or an aliphatic amino group on the side chain of B28 or B29 of the B chain;

$R_1$ is selected from the group consisting of H, $C_{18}$-$C_{30}$ alkyl, ($C_1$-$C_4$ alkyl)$NHR_9$, ($C_1$-$C_4$ alkyl)O—$S_1$—$R_9$, ($C_1$-$C_4$ alkyl)S—$S_1$—$R_9$, ($C_1$-$C_4$ alkyl)CONH—$S_1$—$R_9$, ($C_1$-$C_4$ alkyl)COO—$S_1$—$R_9$, ($C_1$-$C_6$ alkyl)NH—$S_1$—$R_9$, and ($C_0$-$C_4$ alkyl)($C_6$-$C_{10}$ aryl)-$S_1$—$R_9$;

$R_2$ and $R_8$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)$SCH_3$, ($C_1$-$C_4$ alkyl)CONHH, ($C_1$-$C_4$ alkyl)COOH, ($C_1$-$C_4$ alkyl)NHH, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl ($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl or aryl;

$R_3$ is $C_1$-$C_{18}$ alkyl, $C_3$-$C_8$ alkenyl, ($C_0$-$C_4$ alkyl)($C_4$-$C_6$ cycloalkyl), ($C_0$-$C_4$ alkyl)($C_3$-$C_5$ heterocyclic), ($C_0$-$C_4$ alkyl)($C_6$-$C_{10}$ aryl) or $R_4$ and $R_3$ together with the atoms to which they are attached form a 4, 5 or 6 member heterocyclic ring;

$R_4$ is H, $C_1$-$C_{18}$ alkyl, $C_1$-$C_6$ alkyl)NH—$R_9$ or $C_1$-$C_6$ alkyl)NH—$S_1$—$R_9$, $R_5$ is OH, $NHR_6$ or $NHR_9$;

$R_6$ is H, $C_1$-$C_8$ alkyl;

$R_7$ is selected from the group consisting of H, OH and $OR_9$;

$R_9$ is selected from the group consisting of $C_{16}$-$C_{30}$ acyl, and $C_{16}$-$C_{30}$ alkyl;

$R_{11}$, and $R_{13}$ are each H;

$R_{10}$ and $R_{12}$ are independently selected from the group consisting of H, $CH_2$, ($C_1$-$C_4$ alkyl)COOH, ($C_1$-$C_4$ alkyl)$NH_2$, ($C_1$-$C_4$ alkyl)NHC($NH_2^+$)$NH_2$, and $CH_2$($C_3$—$N_2$ heterocyclic); and $S_1$ is a bond or a spacer consisting of one or two charged amino acids selected from the group consisting of aspartic acid, glutamic acid, cysteic acid, homocysteic acid, homoglutamic acid, arginine, lysine and histidine, with the proviso that $R_1$ is other than H when $R_4$ is H or $C_1$-$C_{18}$ alkyl. In one embodiment $R_1$ is $(CH_2)_4$—$S_1$—$NHR_9$ or $(CH_2)_4NHR_9$; $R_3$ is $C_3$-$C_4$ alkyl; $R_5$ is $NH_2$; and $R_9$ is $C_{18}$-$C_{28}$ acyl, and Z is linked to the N-terminal amine of the B chain of insulin via an amide bond.

In accordance with one embodiment single-chain insulin prodrug analogs are provided. In this embodiment the carboxy terminus of the human insulin B chain, or a functional analog thereof, is covalently linked to the N-terminus of the human insulin A chain, or functional analog thereof, wherein a peptide prodrug element having the general structure:

is covalently bound at the N-terminus of the A or B chain of the insulin peptide or at the side chain of an amino acid corresponding to positions B3, B28 or B29 of the B chain via an amide bond. In one embodiment the B chain is linked to the A chain via peptide linker of 4-12 or 4-8 amino acids.

In a further embodiment the insulin prodrugs of the present invention are further modified to prevent cleavage of the peptide prodrug element during storage and prior to administration to a patient. In one embodiment the N-terminal amine of the peptide prodrug element is linked to a moiety that remains bound to the N-terminus until administration to the patient. In one embodiment, the insulin prodrug of the formula A-B-C-Q further comprises a serum enzyme cleavable moiety linked to A via the N-terminal amine of A. In one embodiment the enzyme cleavable moiety is a peptide that is cleaved by dipeptidyl peptidase IV (DPP-IV), including for example a dipeptidyl of Arg-Pro, Lys-Pro or Glu-Pro.

In another embodiment the solubility of the insulin prodrug analogs is enhanced by the covalent linkage of a hydrophilic moiety to the peptide. In one embodiment the hydrophilic moiety is linked to either the N-terminal alpha amine of the B chain, to the side chain of an amino acid of the prodrug peptide, or to the side chain of an amino acid at position A9, A14 and A15 of the A chain, or at position B1, B2, B3, B10, B22, B28 or B29 of the B chain, including for example at position 28 of SEQ ID NO: 9 or the amino acid at position 29 of SEQ ID NO: 2. In one embodiment the hydrophilic moiety is a polyethylene glycol (PEG) chain, having a molecular weight selected from the range of about 500 to about 40,000 Daltons. In one embodiment the polyethylene glycol chain has a molecular weight selected from the range of about 500 to about 5,000 Daltons. In another embodiment the polyethylene glycol chain has a molecular weight of about 10,000 to about 20,000 Daltons.

Acylation or alkylation can increase the half-life of the insulin peptides in circulation. Acylation or alkylation can advantageously delay the onset of action and/or extend the duration of action at the insulin receptors upon activation of the prodrug. The insulin analogs may be acylated or alkylated at the same amino acid position where a hydrophilic moiety is linked, or at a different amino acid position.

In accordance with one embodiment a pharmaceutical composition is provided comprising any of the novel insulin prodrug analogs disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an A19 insulin analog as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In accordance with one embodiment an improved method of regulating blood glucose levels in insulin dependent patients is provided. The method comprises the steps of administering an insulin prodrug analog of the present disclosure in an amount therapeutically effective for the control of diabetes. In one embodiment the insulin prodrug analog is acylated with an acyl group of sufficient size to bind albumin with high affinity, and/or pegylated with a PEG chain having a molecular weight selected from the range of about 5,000 to about 40,000 Daltons

BRIEF DESCRIPTION OF THE DRAWINGS

FIG. 1B represents blood glucose AUC after 8 hours in C57/Blk mice indicating that the potency of the compounds increases with time incubated in vitro prior to administration.

FIG. 8 provides HLPC traces showing the degradation of an insulin prodrug analog ((alpha-Me)Lys(C18)-Sar, B1-Insulin). The prodrug element of the insulin prodrug exhibited a half-life of about 6 hours.

FIG. 10 demonstrates the effect of N-alkylation at the second amino acid of the dipeptide prodrug element on the cleavage rate of the dipeptide.

FIGS. 14A-14D provide additional synthetic schemes. FIG. 14A provides a liquid phase synthesis for introducing an N-alkyl group into a peptide and alpha carbon substitution, by Ugi reaction. FIG. 14B provides an alternative solid phase synthesis for a lipidated tripeptide having an N-alkylated amino acid. FIG. 14C provides a synthetic scheme for the synthesis of lipidated insulin prodrugs using A1, B29-di-tBoc-insulin. FIG. 14D provides a synthetic scheme for the synthesis of lipidated insulin prodrugs using A1, B29-di-(Fmoc)-insulin.

FIG. 15A provides an outline of the experimental procedure and FIG. 15B provides the results, showing an extended time of action for the acylated prodrug insulin analog in reducing blood glucose levels. FIG. 15C demonstrates that blood insulin levels correlate with the blood glucose levels.

FIG. 16A provides an outline of the experimental procedure and FIG. 16B provides the results, showing an extended time of action for the acylated prodrug insulin analog in reducing blood glucose levels. FIG. 16C provides data for diabetic fasted mice administered either native insulin or insulin prodrugs, showing the change in blood glucose after administration.

FIGS. 17A and 17B provide data for insulin tolerance experiment wherein normal mice are administered either native insulin or native insulin based prodrugs. FIG. 17A provides an outline of the experimental procedure and FIG. 17B provides the results, showing an extended time of action for the acylated prodrug insulin analog in reducing blood glucose levels.

DETAILED DESCRIPTION

Definitions

Figure 1A:
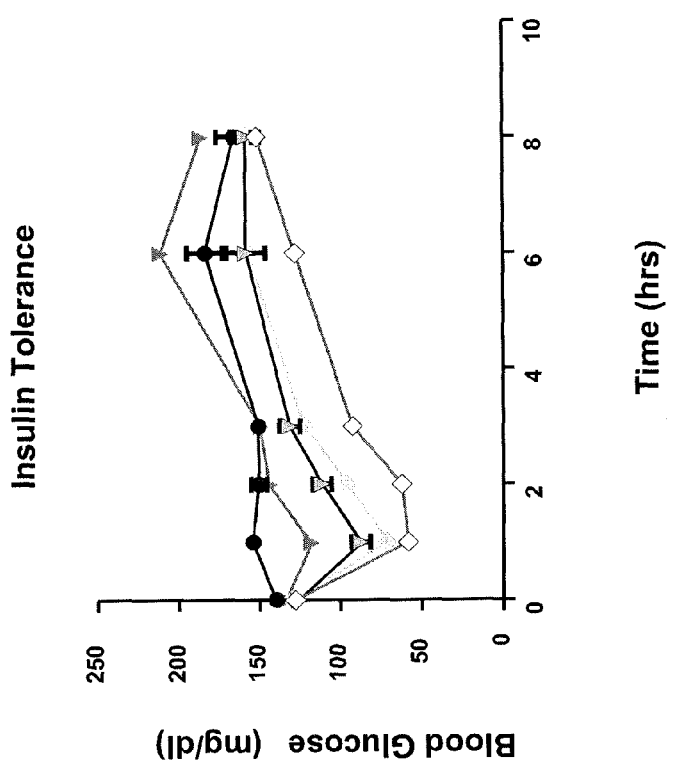
FIG. 1A & FIG. 1B represent the results obtained from a comparative insulin tolerance test for insulin prodrug analog MIU-30a: $B^1(Y16,L17,Y25)29a$: $A^1(dLys(Ac),Sar-aF19)$ (wherein the acylated dipeptide dLys(Ac), Sar is linked via an amide bond to the insulin analog through the A19 4-aminoPhe). The half-life of the prodrug is estimated to be approximately 20 hours. The data shown in FIG. 1A reveals that the parent compound has low potency, but after incubation in 20% plasma for 48 hours (generating "MIU-30c") potency is increased. •=vehicle control, ▼=MIU 30a, 90 nm/kg; ▽=MIU 30c, 90 nm/kg; ◆=MIU 30a, 270 nm/kg; ◇=MIU 30c, 270 nm/kg. Similarly.

In describing and claiming the invention, the following terminology will be used in accordance with the definitions set forth below.

As used herein, the term "prodrug" is defined as any compound that undergoes chemical modification before exhibiting its pharmacological effects.

A "bioactive polypeptide" refers to polypeptides which are capable of exerting a biological effect in vitro and/or in vivo.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. Designation of an amino acid without specifying its stereochemistry is intended to encompass either the L or D form of the amino acid or a racemic mixture. However, in the instance where an amino acid is designated by its three letter code and includes a superscript number, the D form of the amino acid is specified by inclusion of a lower case d before the three letter code and superscript number (e.g., $dLys^{-1}$), wherein the designation lacking the lower case d (e.g., $Lys^{-1}$) is intended to specify the native L form of the amino acid. In this nomenclature, the inclusion of the superscript number designates the position of the amino acid in the IGF peptide sequence, wherein amino acids that are located within the IGF sequence are designated by positive superscript numbers numbered consecutively from the N-terminus. Additional amino acids linked to the IGF peptide either at the N-terminus or through a side chain are numbered starting with 0 and increasing in negative integer value as they are further removed from the IGF sequence. For example, the position of an amino acid within a dipeptide prodrug linked to the N-terminus of IGF is designated $aa^{-1}$-$aa^0$-IGF wherein $aa^0$ represents the carboxy terminal amino acid of the dipeptide and $aa^{-1}$ designates the amino terminal amino acid of the dipeptide.

As used herein the term "hydroxyl acid" refers to amino acids that have been modified to replace the alpha carbon amino group with a hydroxyl group.

As used herein the term "non-coded amino acid" encompasses any amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr.

A "dipeptide" is a compound formed by linkage of an alpha amino acid or an alpha hydroxyl acid to another amino acid, through a peptide bond.

A peptide prodrug element as defined herein is a peptide comprising an N-terminal self-cleaving dipeptide, wherein the dipeptide spontaneously undergoes a chemical cleavage of an amide bond, under physiological conditions, to form a diketopiperazine or diketomorpholine. The peptide prodrug element may consist of the dipeptide or may include additional amino acids linked via amide bonds to the carboxy terminus of the self-cleaving dipeptide.

As used herein the term "chemical cleavage" absent any further designation encompasses a non-enzymatic reaction that results in the breakage of a covalent chemical bond.

A serum enzyme cleavable moiety is a compound that can be covalently linked to a peptide to form a stable structure in the absence of enzymatic activity. Upon exposure to enzymes found in mammalian sera the entire moiety is cleaved from the peptide. For example the serum enzyme cleavable moiety can be a serum enzyme cleavable peptide that is linked to a polypeptide via an amide bond, wherein the enzyme cleavable peptide is susceptible to cleavage by dipeptidyl peptidase IV (DPP-IV).

A "bioactive polypeptide" refers to polypeptides which are capable of exerting a biological effect in vitro and/or in vivo.

As used herein a general reference to a peptide is intended to encompass peptides that have modified amino and carboxy termini. For example, an amino acid sequence designating the standard amino acids is intended to encompass standard amino acids at the N- and C-terminus as well as a corresponding hydroxyl acid at the N-terminus and/or a corresponding C-terminal amino acid modified to comprise an amide group in place of the terminal carboxylic acid.

As used herein an "acylated" amino acid is an amino acid comprising an acyl group which is non-native to a naturally-occurring amino acid, regardless by the means by which it is produced. Exemplary methods of producing acylated amino acids and acylated peptides are known in the art and include acylating an amino acid before inclusion in the peptide or peptide synthesis followed by chemical acylation of the peptide. In one embodiment, the acyl group causes the peptide to have one or more of (i) a prolonged half-life in circulation, (ii) a delayed onset of action, (iii) an extended duration of action, (iv) an improved resistance to proteases, such as DPP-IV, and (v) increased potency at the insulin peptide receptor.

As used herein, an "alkylated" amino acid is an amino acid comprising an alkyl group which is non-native to a naturally-occurring amino acid, regardless of the means by which it is produced. Exemplary methods of producing alkylated amino acids and alkylated peptides are known in the art and including alkylating an amino acid before inclusion in the peptide or peptide synthesis followed by chemical alkylation of the peptide. Without being held to any particular theory, it is believed that alkylation of peptides will achieve similar, if not the same, effects as acylation of the peptides, e.g., a prolonged half-life in circulation, a delayed onset of action, an extended duration of action, an improved resistance to proteases, such as DPP-IV, and increased potency at the insulin peptide receptor.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to maintaining glucose blood levels near normal levels and may include increasing or decreasing blood glucose levels depending on a given situation.

As used herein an "effective" amount or a "therapeutically effective amount" of a prodrug refers to a nontoxic but sufficient amount of the prodrug to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as intranasal, inhalation, subcutaneous, intramuscular, intraspinal, or intravenous.

As used herein the term "native insulin peptide" is intended to designate the 51 amino acid heterodimer comprising the A chain of SEQ ID NO: 1 and the B chain of SEQ ID NO: 2, as well as single-chain insulin analogs that comprise SEQ ID NOS: 1 and 2. The term "insulin peptide" as used herein, absent further descriptive language is intended to encompass the 51 amino acid heterodimer comprising the A chain of SEQ ID NO: 1 and the B chain of SEQ ID NO: 2, as well as single-chain insulin analogs thereof (including for example those disclosed in published international application WO96/34882 and U.S. Pat. No. 6,630,348, the disclosures of which are incorporated herein by reference), and includes heterodimers and single-chain analogs that comprise modified derivatives of the native A chain and/or B chain, including modification of the amino acid at position A19, B16 or B25 to a 4-amino phenylalanine or one or more amino acid substitutions at positions selected from A5, A8, A9, A10, A12, A14, A15, A17, A18, A21, B1, B2, B3, B4, B5, B9, B10, B13, B14, B17, B20, B21, B22, B23, B26, B27, B28, B29 and B30 or deletions of any or all of positions B1-4 and B26-30. An "insulin prodrug analog" as used herein refers to an insulin peptide (or an IGF1-based insulin analog as disclosed in Example 9) that has been modified by the covalent attachment of a dipeptide, via an amide linkage, at a location that interferes with insulin's or IGF1-based insulin analog's activity (e.g., the ability to interact with the insulin and IGF-1 receptors).

As used herein, the term "single-chain insulin analog" encompasses a group of structurally-related proteins wherein the insulin A and B chains are covalently linked as a linear chain.

As used herein an amino acid "modification" refers to a substitution, addition or deletion of an amino acid, or the derivation of an amino acid by the addition and/or removal of chemical groups to/from the amino acid, and includes substitution with or addition of any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue. Throughout the application, all references to a particular amino acid position by letter and number (e.g. position A5) refer to the amino acid at that position of either the A chain (e.g. position A5) or the B chain (e.g. position B5) in the respective native human insulin A chain (SEQ ID NO: 1) or B chain (SEQ ID NO: 2), or the corresponding amino acid position in any analogs thereof. For example, a reference herein to "position B28" absent any further elaboration would mean the corresponding position B27 of the B chain of an insulin analog in which the first amino acid of SEQ ID NO: 2 has been deleted.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine As used herein the general term "polyethylene glycol chain" or "PEG chain", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 500 to 80,000 Daltons. "Polyethylene glycol chain" or "PEG chain" is used in combination with a numeric suffix to indicate the approximate average molecular weight thereof. For example, PEG-5,000 refers to polyethylene glycol chain having a total molecular weight average of about 5,000 Daltons.

As used herein the term "pegylated" and like terms refers to a compound that has been modified from its native state by linking a polyethylene glycol chain to the compound. A "pegylated polypeptide" is a polypeptide that has a PEG chain covalently bound to the polypeptide.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein an "insulin dimer" is a complex comprising two insulin peptides covalently bound to one another via a linker. The term insulin dimer, when used absent any qualifying language, encompasses both insulin homodimers and insulin heterodimers. An insulin homodimer comprises two identical subunits (each comprising an A and B chain), whereas an insulin heterodimer comprises two subunits (each comprising an A and B chain) that differ, although the two subunits are substantially similar to one another.

The term "$C_1$-$C_n$ alkyl" wherein n can be from 1 through n, as used herein, represents a branched or linear alkyl group having from one to the specified number of carbon atoms. Typical $C_1$-$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$-$C_n$ alkenyl" as used herein, represents an olefinically unsaturated branched or linear group having from 2 to the specified number of carbon atoms and at least one double bond. Examples of such groups include, but are not limited to, 1-propenyl, 2-propenyl (—$CH_2$—$CH$=$CH_2$), 1,3-butadienyl, (—$CH$=$CHCH$=$CH_2$), 1-butenyl (—$CH$=$CHCH_2CH_3$), hexenyl, pentenyl, and the like.

The term "$C_2$-$C_n$ alkynyl" represents an unsaturated branched or linear group having from 2 to n carbon atoms and at least one triple bond. Examples of such groups include, but are not limited to, 1-propynyl, 2-propynyl, 1-butynyl, 2-butynyl, 1-pentynyl, and the like.

As used herein the term "aryl" is defined as a mono- or bicyclic carbocyclic ring system having one or two aromatic rings including, but not limited to, phenyl, naphthyl, tetrahydronaphthyl, indanyl, indenyl, and the like. The size of the aryl ring and the presence of substituents or linking groups are indicated by designating the number of carbons present. For example, the term "($C_1$-$C_3$ alkyl)($C_6$-$C_{10}$ aryl)" refers to a 6 to 10 membered aryl that is attached to a parent moiety via a one to three membered alkyl chain.

The term "heteroaryl" as used herein is defined as a mono- or bi-cyclic ring system containing one or two aromatic rings and containing at least one nitrogen, oxygen, or sulfur atom in an aromatic ring. The size of the heteroaryl ring and the presence of substituents or linking groups are indicated by designating the number of carbons present. For example, the term "($C_1$-$C_n$ alkyl)($C_5$-$C_6$ heteroaryl)" refers to a 5 or 6 membered heteroaryl that is attached to a parent moiety via a one to "n" membered alkyl chain.

The term "$C_3$-$C_n$ cycloalkyl" is defined as a non-aromatic, monocyclic or polycyclic ring comprising carbon and hydrogen atoms with the subscript number indicating the number of carbon atoms present. For example the term $C_3$-$C_8$ cycloalkyl represents the compounds cyclopropyl, cyclobutyl, cyclopentyl, cyclohexyl, cycloheptyl, and cyclooctyl.

The term "$C_3$-$C_n$ heterocyclic" is defined as a cycloalkyl ring system containing from one to "n−1" heteroatoms wherein the heteroatoms are selected from the group consisting of oxygen, sulfur, and nitrogen. For example the phrase "5-membered heterocycle" or "$C_5$ heterocycle" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles).

The term "$C_3$-$C_n$ membered ring" as used herein is defined as a saturated or unsaturated hydrocarbon ring structure comprising a total of three to "n" number of elements linked to one another to form a ring, wherein the ring elements are selected from the group consisting of C, O, S and N. The term is intended to encompass cycloalkyls, heterocycles, aryls and heteroaryls.

As used herein, the term "halo" is defined as one or more members of the group consisting of fluorine, chlorine, bromine, and iodine.

As used herein the term "charged amino acid" is defined as an amino acid that comprises a side chain that is negatively charged (i.e., deprotonated) or positively charged (i.e., protonated) in aqueous solution at physiological pH. For example negatively charged amino acids include aspartic acid, glutamic acid, cysteic acid, homocysteic acid, and homoglutamic acid, whereas positively charged amino acids include arginine, lysine and histidine. Charged amino acids include the charged amino acids among the 20 amino acids commonly found in human proteins, as well as atypical or non-naturally occurring amino acids.

As used herein the term "acidic amino acid" is defined as an amino acid that comprises a second acidic moiety (i.e. other than the α-carboyxl group that all amino acids possess), including for example, a carboxylic acid or sulfonic acid group. As used herein the term "patient" without further designation is intended to encompass any warm blooded vertebrate domesticated animal (including for example, but not limited to livestock, horses, cats, dogs and other pets), mammals, and humans.

As used herein the phrase "irreversible binding to plasma protein" or "irreversible binding to serum albumin" is defined as a high affinity binding wherein the bound plasma protein/serum albumin is not substantially released under physiological conditions. In the context of an acylated insulin, an acyl or alkyl group that is large enough to "irreversibly bind" albumin is defined as an acyl or alkyl group that suppresses the underlying insulin peptide's ability to lower blood glucose upon administration to a patient to less than 10% of that achieved with the same insulin peptide devoid of the acyl or alkyl group, over the course of 6 hours after administration.

EMBODIMENTS

The present disclosure provides insulin prodrug derivatives that are formulated to delay onset of action and enhance the half-life of the insulin peptide, thus improving the therapeutic index of the underlying insulin peptide. The insulin prodrug chemistry disclosed herein allows for activation of the prodrug via a non-enzymatic degradation mechanism. The disclosed prodrug chemistry can be chemically linked to organic moieties that irreversibly bind mammalian plasma protein, and thus inactivate the insulin peptide upon administration. In one embodiment the organic moieties are alkyl or acyl groups of sufficient size to bind serum albumin. In another embodiment the organic moiety is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

In a specific embodiment, the insulin analog comprises a cholesterol acid, which is linked to a Lys residue of the insulin analog through an alkylated des-amino Cys spacer, i.e., an alkylated 3-mercaptopropionic acid spacer. The alkylated des-amino Cys spacer can be, for example, a des-amino-Cys spacer comprising a dodecaethylene glycol moiety.

This novel biologically friendly prodrug chemistry spontaneously degrades under physiological conditions (e.g. pH of about 7, at 37° C. in an aqueous environment), wherein cleavage of the prodrug element separates the bound plasma protein (e.g., albumin) from the insulin peptide, restoring activity to the insulin peptide. In one embodiment an acyl or alkyl group is linked to the peptide prodrug element disclosed herein, wherein the alkyl or acyl group is either linear or branched, and in one embodiment is a C18 to C30 hydrocarbon backbone chain. For example, the acyl or alkyl group can be any of a C18, C20, C22, C24, C26, C28, or a C30 hydrocarbon backbone chain. In one embodiment, the disclosed prodrug chemistry is chemically linked to a C16 to C20 fatty acid, e.g., a C18 fatty acid or a C20 fatty acid. The duration of the prodrug derivative is determined by the selection of the peptide prodrug element sequence, and thus allows for flexibility in prodrug formulation.

In one embodiment a prodrug is provided having a non-enzymatic activation half time ($t_{1/2}$) of between about 2 to about 240 hours, about 2 to about 168 hours, about 6 to about 168 hours, or about 12 to about 168 hours, or about 12 to about 120 hours under physiological conditions. In one embodiment the cleavage half-life of the prodrug element in serum and under physiological conditions is about 0.5 days to about 10 days. Physiological conditions as disclosed herein are intended to include a temperature of about 35 to 40° C. and a pH of about 7.0 to about 7.4 and more typically include a pH of 7.2 to 7.4 and a temperature of 36 to 38° C. in an aqueous environment. In one embodiment a peptide, capable of undergoing diketopiperazine formation under physiological conditions, is covalently linked through an amide linkage to an aliphatic amino group of the insulin peptide.

Advantageously, the rate of cleavage, and thus activation of the prodrug, depends on the structure and stereochemistry of the dipeptide pro-moiety and also on the strength of the nucleophile. The prodrugs disclosed herein will ultimately be chemically converted to structures that can be recognized by the native receptor of the drug, wherein the speed of this chemical conversion will determine the time of onset and duration of in vivo biological action. The prodrug chemistry disclosed in this application relies upon an intramolecular chemical reaction that is not dependent upon additional chemical additives, or enzymes. The speed of conversion is controlled by the chemical nature of the dipeptide substituent and its cleavage under physiological conditions. Since physiological pH and temperature are tightly regulated within a highly defined range, the speed of conversion from prodrug to drug will exhibit high intra and interpatient reproducibility.

As disclosed herein prodrugs are provided wherein the bioactive polypeptides have extended half-lives of at least 1 hour, and more typically greater than 24 hours but not more than 10 days, and are converted to the active form at physiological conditions through a non-enzymatic reaction driven by inherent chemical instability. In one embodiment the a non-enzymatic activation $t_{1/2}$ time of the prodrug is between about 12 to about 168 hours, and more typically between 12 to about 120 hours or 12 and 72 hours, and in one embodiment the $t_{1/2}$ is between 24-48 hrs as measured by incubating the prodrug in a phosphate buffer solution (e.g., PBS) at 37° C. and pH of 7.2. The half-lives of the various prodrugs are calculated by using the formula $t_{1/2}=0.693/k$, where 'k' is the first order rate constant for the degradation of the prodrug. In one embodiment, activation of the prodrug occurs after cleavage of an amide bond linked dipeptide, and formation of a diketopiperazine or diketomorpholine, and the active insulin peptide, wherein the dipeptide is covalently linked to an alkyl or acyl group of sufficient size (e.g., C18 to C30) to bind serum albumin.

Specific dipeptides composed of natural or synthetic amino acids have been identified that facilitate intramolecular decomposition under physiological conditions to release active insulin peptides. The dipeptide can be linked (via an amide bond) to an amino group present on native insulin, or an amino group introduced into the insulin peptide by modification of the native insulin peptide. Additional amino acids can be added to the dipeptide carboxy terminus to create tripeptides or tetrapeptides that can be linked via an amide bond to an insulin peptide. In those embodiments where an additional one or two amino acids have been added to the original dipeptide element, upon cleavage of the dipeptide to form a diketopiperazine or diketomorpholine, the additional one or two amino acids will remain attached to the insulin peptide. In one embodiment the one or two additional amino acids are charged amino acids In one embodiment the dipeptide structure is selected to resist cleavage by peptidases present in mammalian sera, including for example dipeptidyl peptidase IV (DPP-IV). Accordingly, in one embodiment the rate of cleavage of the dipeptide prodrug element from the bioactive peptide (e.g., insulin peptide (Q)) is not substantially enhanced (e.g., greater than 2×) when the reaction is conducted using physiological conditions in the presence of serum proteases, relative to conducting the reaction in the absence of the proteases. Thus the cleavage half-life of the dipeptide prodrug element from the insulin peptide (in PBS under physiological conditions) is not more than two, three, four or five fold the cleavage half-life of the dipeptide prodrug element from the insulin peptide in a solution comprising a DPP-IV protease. In one embodiment the solution comprising a DPP-IV protease is serum, more particularly mammalian serum, including human serum.

In one embodiment an insulin prodrug is provided comprising the structure:

A-B-C-Q;

wherein Q is an insulin peptide, A-B-C— is a peptide linked to Q via an amide bond wherein A is an amino acid, B is an N-alkylated amino acid and C is an amide bond, $X_{70}$ or $X_{70}X_{71}$, wherein $X_{70}$ and $X_{71}$ are amino acids independently selected from the group consisting of glycine, aspartic acid, glutamic acid, cysteic acid, homocysteic acid, homoglutamic acid, arginine, lysine and histidine, wherein one of A or B comprises a side chain that is covalently linked to a $C_{16}$-$C_{30}$ acyl group or a $C_{16}$-$C_{30}$ alkyl group. In one embodiment the amino acid linked to the $C_{16}$-$C_{30}$ acyl group or a $C_{16}$-$C_{30}$ alkyl group has a ($C_1$-$C_8$ alkyl)$NH_2$ side chain. In one embodiment, A is an amino acid or hydroxyl acid comprising a ($C_1$-$C_8$ alkyl)$NH_2$ side chain, wherein the side chain is covalently linked to a $C_{16}$-$C_{30}$ acyl group or a $C_{16}$-$C_{30}$ alkyl group. In one embodiment the linkage between the side chain of A and the acyl or alkyl group is via a spacer, said spacer comprising one or two charged amino acids. In one embodiment B is an N-alkylated amino acid; and C is an amide bond, $X_{70}$ or $X_{70}X_{71}$, wherein $X_{70}$ and $X_{71}$ are amino acids independently selected from the group consisting of glycine, aspartic acid, glutamic acid, cysteic acid, homocysteic acid, homoglutamic acid, arginine, lysine and histidine. Furthermore, A, B and C are linked to one another via amide bonds, and the A-B-C peptide is linked to Q through an amide bond via an aliphatic amino group of Q. In one embodiment the aliphatic amino group is selected from the alpha amino group on the N-terminal amino acid of the A chain or the B chain, or an aliphatic amino group on a side chain of a B3, B28 or B29 amino acid of Q. In one embodiment the A-B-C peptide is linked to Q through an amide bond via the amino group of a lysine side chain at position B3, B28 or B29 of the insulin peptide. In one embodiment the A-B-C peptide is linked to Q through an amide bond via the N-terminal amine of the insulin B chain.

In a further embodiment the A-B-C peptide is linked to Q through an amide bond via the N-terminal amine of the insulin B chain, wherein the side chain of amino acid A or amino acid B is covalently linked to a moiety that irreversibly binds to a plasma protein. In one embodiment the moiety that irreversibly binds to a plasma protein is a $C_{16}$-$C_{30}$ acyl group or a $C_{16}$-$C_{30}$ alkyl group, and in a further embodiment the A amino acid or B amino acid comprises a $(C_1-C_8$ alkyl)$NH_2$ side chain wherein the $C_{16}-C_{30}$ acyl group or a $C_{16}-C_{30}$ alkyl group is covalently bound through the aliphatic amine of the $(C_1-C_8$ alkyl)$NH_2$ side chain. In one embodiment the A amino acid is covalently linked to a moiety that irreversibly binds to a plasma protein.

As disclosed herein, in one embodiment the A or B amino acid of the prodrug element of the insulin prodrug is modified to comprise an acyl group by acylation of an amine, hydroxyl, or thiol of a side chain of A or B, either directly or through a spacer moiety. In accordance with one embodiment a C16-C30 acyl group or a C16-C30 alkyl group is linked to A via a spacer, wherein the spacer is positioned between the amino acid of the insulin peptide and the acyl or alkyl group. In exemplary embodiments, the spacer is an amino acid, a dipeptide, or a tripeptide, or a hydrophilic bifunctional spacer. In one embodiment, the spacer comprises one or two charged amino acids. In one embodiment the spacer is a single charge amino acid. In another embodiment the spacer is a dipeptide, wherein the dipeptide comprises one or two charged amino acids. In one embodiment the spacer is selected from the group consisting of: Asp, Glu, His, Arg, Lys and a spacer comprising $NH_2(CH_2CH_2O)_n(CH_2)_mCOOH$, wherein m is any integer from 1 to 6 and n is any integer from 2 to 12. In one embodiment A comprises a $(C_1-C_8$ alkyl)$NH_2$ side chain acylated with a C16-C22 fatty acid through a gamma glutamic acid spacer. In one embodiment A comprises a $(C_1-C_8$ alkyl)$NH_2$ side chain acylated with a C18-C22 fatty acid through a dipeptide gamma glutamic acid-gamma glutamic acid spacer.

The B amino acid of the structure A-B-C is an N-alkylated amino acid wherein the N-alkyl group comprises a C1-C18 branched, cyclic or straight hydrocarbon chain. In accordance with one embodiment B is an amino acid N-alkylated with $C_1-C_{18}$ alkyl, $C_3-C_{18}$ alkenyl, $(C_0-C_4$ alkyl)$(C_4-C_6$ cycloalkyl), $(C_0-C_4$ alkyl)$(C_3-C_5$ heterocyclic), or $(C_0-C_4$ alkyl)$(C_6-C_{10}$ aryl). In one embodiment the B amino acid of the structure A-B-C is N-alkylated with $C_1-C_6$ alkyl, $(C_1-C_4$ alkyl)$(C_5-C_6$ aryl) or $(C_1-C_4$ alkyl)$(C_4-C_6$ cycloalkyl). In one embodiment B is N-alkylated with n-propyl, iso-propyl, butyl, iso-butyl, sec-butyl or tert-butyl. In a further embodiment B is N-alkylated with iso-propyl, sec-butyl, or tert-butyl. In one embodiment B is selected from the group consisting of glycine(N—$C_1-C_{10}$ alkyl), isoleucine(N—$C_1-C_{10}$ alkyl), valine(N—$C_1-C_{10}$ alkyl), and threonine(N—$C_1-C_{10}$ alkyl). In one embodiment B is selected from the group consisting of glycine(N—$C_1-C_6$alkyl), isoleucine(N—$C_1-C_6$alkyl), valine(N—$C_1-C_6$alkyl), and threonine(N—$C_1-C_6$alkyl). In one embodiment B is selected from the group consisting of glycine(N-methyl), glycine(N-ethyl), glycine (N-propyl), glycine(N-butyl), glycine(sec-butyl), glycine (tert-butyl), glycine(N-pentyl), glycine(N-hexyl), glycine (N-heptyl), and glycine(N-octyl). In one embodiment B is selected from the group consisting of glycine(N-iso-propyl), glycine(N-sec-butyl) or glycine(N-tert-butyl).

In accordance with one embodiment C of the formula A-B-C is an amino acid or a dipeptide. In one embodiment the amino acids comprising C include at least one amino acid with a side chain independently selected from the group consisting of H, $(C_1-C_4$ alkyl)COOH, $(C_1-C_4$ alkyl)$SO_3H$, $(C_1-C_4$ alkyl)$NH_2$, $(C_1-C_4$ alkyl)NHC(NH$_2$+)NH$_2$. In one embodiment C is a dipeptide wherein one or both of the amino acids of the dipeptide comprise a side chain selected from the group consisting of H, $(C_1-C_4$ alkyl)COOH, $(C_1-C_4$ alkyl)$SO_3H$, $(C_1-C_4$ alkyl)$NH_2$, $(C_1-C_4$ alkyl)NHC(NH$_2$+) $NH_2$. In one embodiment the amino acids of C are independently selected from the group consisting of glycine, aspartic acid, glutamic acid, cysteic acid, homocysteic acid, homoglutamic acid, arginine, lysine and histidine. In one embodiment the amino acids of C are independently selected from the group consisting of glycine, aspartic acid, glutamic acid, cysteic acid, arginine and lysine.

In one embodiment an insulin prodrug is provided comprising the structure: A-B-C-Q;
wherein Q is an insulin peptide and A-B-C comprises a structure of:

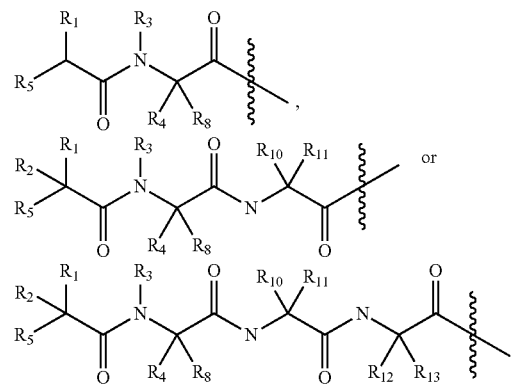

wherein
R$_1$ is $C_{18}-C_{30}$ alkyl, $(C_1-C_6$ alkyl)NH—R$_9$ or $(C_1-C_6$ alkyl)NH—S$_1$—R$_9$;
R$_2$ is H or $C_1-C_6$ alkyl;
R$_3$ is selected from the group consisting of $C_2-C_4$ alkyl, $C_3-C_8$ alkenyl, $(C_0-C_4$ alkyl)$(C_4-C_6$ cycloalkyl), $(C_0-C_4$ alkyl)$(C_3-C_5$ heterocyclic), $(C_0-C_4$ alkyl)$(C_6-C_{10}$ aryl) or R$_4$ and R$_3$ together with the atoms to which they are attached form a 4, 5 or 6 member heterocyclic ring;
R$_4$, and R$_8$ are independently selected from the group consisting of H, $C_1-C_{18}$ alkyl, $C_2-C_{18}$ alkenyl, $(C_1-C_{18}$ alkyl)OH, $(C_1-C_{18}$ alkyl)SH, $(C_2-C_3$ alkyl)$SCH_3$, $(C_1-C_4$ alkyl)$CONH_2$, $(C_1-C_4$ alkyl)COOH, $(C_1-C_4$ alkyl) $NH_2$, $(C_1-C_4$ alkyl)NHC(NH$_2$+)$NH_2$, $(C_0-C_4$ alkyl)$(C_3-C_6$ cycloalkyl), $(C_0-C_4$ alkyl)$(C_2-C_5$ heterocyclic), $(C_0-C_4$ alkyl)$(C_6-C_{10}$ aryl)R$_7$, $(C_1-C_4$ alkyl)$(C_3-C_9$ heteroaryl), and $C_1-C_{12}$ alkyl$(W_1)C_1-C_{12}$ alkyl, wherein $W_1$ is a heteroatom selected from the group consisting of N, S and O, or R$_4$ and R$_8$ together with the atoms to which they are attached form a $C_3-C_6$ cycloalkyl;
R$_5$ is NHR$_6$ or OH;
R$_6$ is H, or $C_1-C_8$ alkyl;
R$_7$ is selected from the group consisting of H, OH, $C_1-C_{18}$ alkyl, $C_2-C_{18}$ alkenyl, $(C_0-C_4$ alkyl)$NH_2$, and $(C_0-C_4$ alkyl)OH;
R$_9$ is selected from the group consisting of $C_{18}-C_{30}$ acyl;
R$_{10}$, R$_{11}$, R$_{12}$, and R$_{13}$ are independently selected from the group consisting of H, CH$_2$, CH$_2$OH, CH$_2$SH, $(C_1-C_4$ alkyl)$CONH_2$, $(C_1-C_4$ alkyl)COOH, $(C_1-C_4$ alkyl)$NH_2$, $(C_1-C_4$ alkyl)NHC(NH$_2$+)$NH_2$ and CH$_2$ $(C_3-N_2$ heterocyclic); and
S$_1$ is a spacer consisting of one or two charged amino acids selected from the group consisting of aspartic acid, glutamic acid, cysteic acid, homocysteic acid, homoglutamic acid, arginine, lysine and histidine, wherein A-B-C is linked to Q through an amide bond via an aliphatic amino group of Q. In one embodiment R$_1$ is $(C_1-C_6$ alkyl)NH—S$_1$—R$_9$; R$_3$ is selected from the group consisting of $C_2-C_4$ alkyl; R$_2$, R$_4$, R$_{11}$, and $R_{13}$ are each H; $R_5$ is $NH_2$; $R_8$ is H or $C_1$-$C_8$ alkyl; $R_9$ is $C_{18}$-$C_{30}$ acyl; $R_{10}$ and $R_{12}$ are independently selected from the group consisting of ($C_1$-$C_4$ alkyl)COOH, ($C_1$-$C_4$ alkyl)$NH_2$, ($C_1$-$C_4$ alkyl)NHC($NH_2^+$)$NH_2$, and $CH_2$($C_3$—$N_2$ heterocyclic); and $S_1$ is a spacer comprising one or two charged amino acids selected from the group consisting of aspartic acid, glutamic acid, cysteic acid, homocysteic acid, homoglutamic acid, arginine, lysine and histidine, and A-B-C is linked to Q through an amide bond via the N-terminal amine of the B chain of insulin.

In one embodiment an insulin prodrug is provided comprising the structure: A-B-C-Q;

wherein Q is an insulin peptide and A-B-C comprises a structure of:

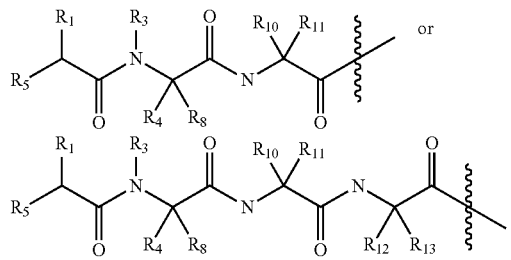

wherein $R_1$ is $C_{18}$-$C_{30}$ alkyl, ($C_1$-$C_6$ alkyl)NH—$S_1$—$R_9$ or ($C_1$-$C_6$ alkyl)NH—$S_1$—$R_9$;

$R_3$ is selected from the group consisting of $C_2$-$C_4$ alkyl, $R_4$, $R_{11}$, and $R_{13}$ are each H $R_5$ is $NH_2$;

$R_8$ is H or $C_1$-$C_8$ alkyl;

$R_9$ is $C_{18}$-$C_{30}$ acyl; and $R_{10}$ and $R_{12}$ are independently selected from the group consisting of ($C_1$-$C_4$ alkyl)COOH, ($C_1$-$C_4$ alkyl)$NH_2$, ($C_1$-$C_4$ alkyl)NHC($NH_2^+$)$NH_2$, and $CH_2$($C_3$—$N_2$ heterocyclic); and $S_1$ is a spacer consisting of one or two charged amino acids selected from the group consisting of aspartic acid, glutamic acid, cysteic acid, homocysteic acid, homoglutamic acid, arginine, lysine and histidine, wherein A-B-C is linked to Q through an amide bond via an aliphatic amino group of Q. In one embodiment $R_1$ is $(CH_2)_4$—$S_1$—$NHR_9$ or $(CH_2)_4NHR_9$; $R_3$ is $C_3$-$C_4$ alkyl; $R_5$ is $NH_2$; and $R_9$ is $C_{18}$-$C_{28}$ acyl, and A-B-C is linked to Q through an amide bond via the N-terminal amine of the B chain of insulin.

The insulin peptide of the prodrugs disclosed herein can comprise any of the known insulins known to those skilled in the art that have agonist activity at the insulin receptors. In accordance with one embodiment the insulin peptide comprises an A chain sequence of GIVEQCC$X_8$SICSLYQLENYC$X_{21}R_{44}$ (SEQ ID NO: 3) and a B chain sequence of $R_{22}$-$X_{25}$LCG$X_{29}X_{30}$LV$X_{33}X_{34}$LYLVCG$X_{41}X_{42}$GF$X_{45}$ (SEQ ID NO: 20), wherein the B chain is linked to the A chain through disulfide linkages;

$X_8$ is selected from the group consisting of threonine and histidine;

$X_{21}$ is selected from the group consisting of asparagine, ornithine, glycine, alanine, threonine, and serine;

$X_{25}$ is selected from the group consisting of histidine and threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, ornithine, lysine and arginine;

$X_{45}$ is tyrosine or phenylalanine;

$R_{22}$ is selected from the group consisting of AYRPSE (SEQ ID NO: 14), FVNQ (SEQ ID NO: 12), FVKQ (SEQ ID NO: 8), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and $R_{44}$ is COOH or $CONH_2$.

In one embodiment the insulin peptide comprises an A chain sequence of GIVEQCC$X_8$SICSLYQLENYC$X_{21}$ (SEQ ID NO: 3) and a B chain sequence of $R_{22}$-HLCGSHLVEALYLVCGERGF$X_{45}$ (SEQ ID NO: 15), wherein said B chain is linked to said A chain through disulfide linkages;

$R_{22}$ is a bond, or a 1 to 4 amino acid sequence selected from the group consisting of a FVNQ (SEQ ID NO: 12), FVKQ (SEQ ID NO: 8), VNQ, NQ and Q;

$X_8$ is selected from the group consisting of threonine and histidine;

$X_{21}$ is selected from the group consisting of asparagine, lysine, glycine, and alanine; and $X_{45}$ is histidine, tyrosine or phenylalanine.

In one embodiment the A chain comprises a sequence GIVEQCCTSICSLYQLENYCN-$R_{44}$ (SEQ ID NO: 1) and said B chain comprises a sequence selected from the group consisting of FVNQHLCGSHLVEALYLVCGERGFFYTPKT (SEQ ID NO: 2) FVNQHLCGSHLVEALYLVCGERGFFYTKPT (SEQ ID NO: 9) FVNQHLCGSHLVEALYLVCGERGFFYTDKT (SEQ ID NO: 5) FVKQHLCGSHLVEALYLVCGERGFFYTEKT (SEQ ID NO: 6), wherein $R_{44}$ is COOH or $CONH_2$.

The insulin prodrugs disclosed herein can be further modified to improve their stability during storage. In one embodiment the N-terminal amine of the dipeptide element is linked to a moiety that remains bound to the N-terminus until administration to the patient. In one embodiment, the insulin prodrug of the formula A-B-C-Q further comprises a serum enzyme cleavable moiety linked to A via the N-terminal amine of A. Linkage of the serum enzyme cleavable moiety to the N-terminus of A prevents the formation of the diketopiperazine or diketomorpholine and the cleavage of A-B from the insulin in the absence of enzymatic activity. Upon exposure to serum enzymes, the serum enzyme cleavable moiety will be removed, and subsequent activation of the prodrug will be dependent on a non-enzymatic degradation mechanism that cleaves A-B based on the structure of A-B. In one embodiment the enzyme cleavable moiety is a peptide that is cleaved by dipeptidyl peptidase IV (DPP-IV). In one embodiment the serum enzyme cleavable peptide is linked to A via the N-terminal amine of A and is selected from dipeptides have the sequence Z-proline, or Z-alanine wherein Z is selected from the group consisting of Glycine, Alanine, Valine, Leucine, Isoleucine, Proline, Phenylalanine, Tyrosine, Tryptophan, Serine, Threonine, Methionine, Asparagine, Glutamine, Lysine, Arginine, Histidine, Aspartic acid, and Glutamic acid. In one embodiment the enzyme cleavable moiety is a peptide that is cleaved by dipeptidyl peptidase IV (DPP-IV), including for example a dipeptide of Arg-Pro, Lys-Pro or Glu-Pro.

In one embodiment the cleavage half-life of A-B-C from Q in serum under physiological conditions is about 2 to about 168 hours. In another embodiment the cleavage half-life of A-B-C from Q in serum under physiological conditions is about 0.5 days to about 10 days.

In one embodiment an insulin prodrug is provided comprising the structure:

A-B-C-Q;

wherein Q is an insulin peptide;

A is an amino acid comprising a $(C_1-C_8$ alkyl$)NH_2$ side chain, wherein the side chain is covalently linked to a moiety that irreversibly binds to a plasma protein, wherein said moiety is linked to the side chain of A via a spacer, wherein the spacer comprising one or two charged amino acids;

B is an N-alkylated amino acid; and

C is an amide bond, $X_{70}$ or $X_{70}X_{71}$, wherein $X_{70}$ and $X_{71}$ are amino acids with a side chain independently selected from the group consisting of H, $(C_1-C_4$ alkyl$)$COOH, $(C_1-C_4$ alkyl$)SO_3H$, $(C_1-C_4$ alkyl$)NH_2$, $(C_1-C_4$ alkyl$)NHC(NH_2^+)NH_2$, wherein A-B-C is linked to Q through an amide bond via an aliphatic amino group of Q, said aliphatic amino group selected from the alpha amino group on the N-terminal amino acid of the A chain or the B chain, or an aliphatic amino group on a side chain of an B3, B28 or B29 amino acid of Q. In one embodiment the moiety that irreversibly binds to a plasma protein is a $C_{16}-C_{30}$ acyl group or a $C_{16}-C_{30}$ alkyl group, wherein the linkage between the side chain of A and the acyl or alkyl group is via said spacer. In one embodiment C is an amino acid or dipeptide wherein the amino acids of C are selected from the group consisting of glycine, aspartic acid, glutamic acid, cysteic acid, arginine, and lysine. In one embodiment C is a dipeptide wherein the amino acids of the dipeptide are selected from the group consisting of aspartic acid, glutamic acid, cysteic acid, arginine, and lysine. In one embodiment C is a dipeptide wherein one of the two amino acids is glycine or alanine and the other amino acid of the dipeptide is selected from the group consisting of aspartic acid, glutamic acid, cysteic acid, arginine, and lysine. In a further embodiment B is an amino acid N-alkylated with $C_1-C_{18}$ alkyl, $C_3-C_{18}$ alkenyl, $(C_0-C_4$ alkyl$)(C_4-C_6$ cycloalkyl$)$, $(C_0-C_4$ alkyl$)(C_3-C_5$ heterocyclic$)$, or $(C_0-C_4$ alkyl$)(C_6-C_{10}$ aryl$)$.

In one embodiment the insulin prodrug comprise a peptide of the general structure

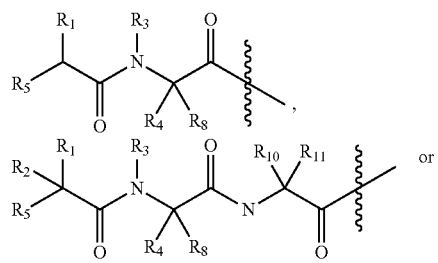

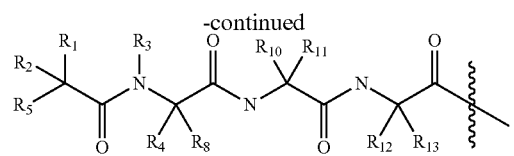

linked to the N-terminal amino group of the A or B chain of insulin or to the side chain of a lysine at position B3, B28 or B29, wherein $R_1$ is $(C_1-C_6$ alkyl$)NH-S_1-R_9$;

$R_2$ is H or $C_1-C_6$ alkyl:

$R_3$ is selected from the group consisting of $C_2-C_4$ alkyl, $C_3-C_8$ alkenyl, $(C_0-C_4$ alkyl$)(C_4-C_6$ cycloalkyl$)$, $(C_0-C_4$ alkyl$)(C_3-C_5$ heterocyclic$)$, $(C_0-C_4$ alkyl$)(C_6-C_{10}$ aryl$)$ or $R_4$ and $R_3$ together with the atoms to which they are attached form a 4, 5 or 6 member heterocyclic ring;

$R_4$, and $R_8$ are independently selected from the group consisting of H, $C_1-C_{18}$ alkyl, $C_2-C_{18}$ alkenyl, $(C_1-C_{18}$ alkyl$)OH$, $(C_1-C_{18}$ alkyl$)SH$, $(C_2-C_3$ alkyl$)SCH_3$, $(C_1-C_4$ alkyl$)CONH_2$, $(C_1-C_4$ alkyl$)COOH$, $(C_1-C_4$ alkyl$)NH_2$, $(C_1-C_4$ alkyl$)NHC(NH_2^+)NH_2$, $(C_0-C_4$ alkyl$)(C_3-C_6$ cycloalkyl$)$, $(C_0-C_4$ alkyl$)(C_2-C_5$ heterocyclic$)$, $(C_0-C_4$ alkyl$)(C_6-C_{10}$ aryl$)R_7$, $(C_1-C_4$ alkyl$)(C_3-C_9$ heteroaryl$)$, and $C_1-C_{12}$ alkyl$(W_1)C_1-C_{12}$ alkyl, wherein $W_1$ is a heteroatom selected from the group consisting of N, S and O, or $R_4$ and $R_8$ together with the atoms to which they are attached form a $C_3-C_6$ cycloalkyl;

$R_{10}$, $R_{11}$, $R_{12}$, and $R_{13}$ are independently selected from the group consisting of H, $CH_3$, $(C_1-C_4$ alkyl$)COOH$, $(C_1-C_4$ alkyl$)NH_2$, $(C_1-C_4$ alkyl$)NHC(NH_2^+)NH_2$ and $CH_2(C_3-N_2$ heterocyclic$)$;

$R_5$ is $NHR_6$ or OH;

$R_6$ is H, or $C_1-C_8$ alkyl;

$R_7$ is selected from the group consisting of H, OH, $C_1-C_{18}$ alkyl, $C_2-C_{18}$ alkenyl, $(C_0-C_4$ alkyl$)NH_2$, and $(C_0-C_4$ alkyl$)OH$;

$R_9$ is selected from the group consisting of $C_{18}-C_{30}$ acyl; and $S_1$ is a bond or a spacer consisting of one to six amino acids, wherein said spacer comprises one or more charged amino acids selected from the group consisting of aspartic acid, glutamic acid, cysteic acid, arginine and lysine. In one embodiment $S_1$ is a spacer consisting of one or two charged amino acids selected from the group consisting of aspartic acid, glutamic acid, cysteic acid, homocysteic acid, homoglutamic acid, arginine, lysine and histidine.

In one embodiment the insulin prodrug comprise a peptide of the general structure

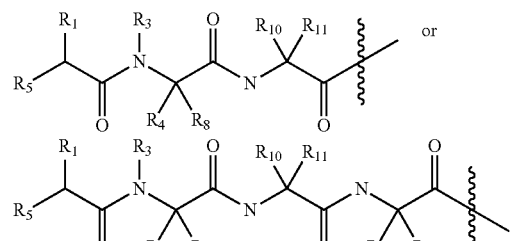

$R_1$ is $C_{18}-C_{30}$ alkyl, $(C_1-C_6$ alkyl$)NH-R_9$ or $(C_1-C_6$ alkyl$)NH-S_1-R_9$;

$R_3$ is selected from the group consisting of $C_2$-$C_4$ alkyl, $R_4$, $R_{11}$ and $R_{13}$ are each H $R_5$ is $NH_2$;

$R_8$ is H or $C_1$-$C_8$ alkyl;

$R_9$ is $C_{18}$-$C_{30}$ acyl;

$R_{10}$ and $R_{12}$ are independently selected from the group consisting of ($C_1$-$C_4$ alkyl)COOH, ($C_1$-$C_4$ alkyl)$NH_2$ and ($C_1$-$C_4$ alkyl)NHC($NH_2^+$)$NH_2$; and $S_1$ is a spacer consisting of one or two charged amino acids selected from the group consisting of aspartic acid, glutamic acid, cysteic acid, arginine and lysine linked to the N-terminal amino group of the A or B chain of insulin or to the side chain of a lysine at position B3, B28 or B29. In one embodiment $S_1$ is a spacer consisting of one or two charged amino acids selected from the group consisting of aspartic acid, glutamic acid, cysteic acid, homocysteic acid, homoglutamic acid, arginine, lysine and histidine. In one embodiment the peptide represented by the formula A-B-C is linked to the N-terminal amino group of the B chain of insulin. In a further embodiment $R_1$ is $(CH_2)_4$—$R_9$ or $(CH_2)_4$—$S_1$—$NHR_9$, $R_3$ is $C_3$-$C_4$ alkyl; $R_5$ is $NH_2$; and $R_9$ is $C_{18}$-$C_{28}$ acyl. In a further embodiment $R_1$ is selected from the group consisting of $(CH_2)_4NHCO(CH_2)_{17}CH_3$, $(CH_2)_4NHCO(CH_2)_{19}CH_3$ and $(CH_2)_4NHCO(CH_2)_{21}CH_3$.

In accordance with one embodiment an insulin prodrug is provided wherein the insulin protein comprises an A chain sequence of GIVEQCCTSICSLYQLENYCN-$R_{44}$ (SEQ ID NO: 1) and a B chain sequence selected from the group consisting of FVNQHLCGSHLVEALYLVCGERGFFYT-PKT (SEQ ID NO: 2) FVNQHLCGSHLVEALYL-VCGERGFFYTKPT (SEQ ID NO: 9) FVNQHLCG-SHLVEALYLVCGERGFFYTDKT (SEQ ID NO: 5) FVKQHLCGSHLVEALYLVCGERGFFYTEKT (SEQ ID NO: 6), wherein $R_{44}$ is COOH or $CONH_2$ and a prodrug element covalently linked to said insulin peptide at the N-terminal amino group of the A chain or B chain or at the side chain amine of a lysine a position B3, B28 or B29 wherein the prodrug element comprises the structure:

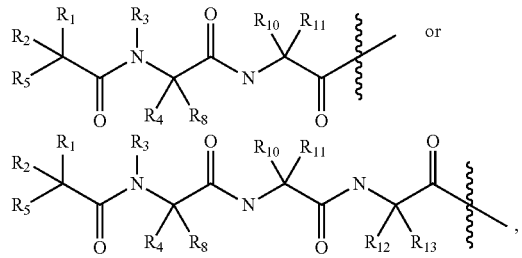

wherein $R_1$ is selected from the group consisting of H, ($C_1$-$C_4$ alkyl)O—$S_1$—$R_9$, ($C_1$-$C_4$ alkyl)S—$S_1$—$R_9$, ($C_1$-$C_4$ alkyl) CONH—$S_1$—$R_9$, ($C_1$-$C_4$ alkyl)COO—$S_1$—$R_9$, ($C_1$-$C_6$ alkyl)NH—$S_1$—$R_9$, ($C_1$-$C_6$ alkyl)$NHR_9$ and ($C_0$-$C_4$ alkyl) ($C_6$-$C_{10}$ aryl)-$S_1$—$R_9$;

$R_2$ and $R_8$ are independently selected from the group consisting of H, $C_1$-$C_8$ alkyl, $C_2$-$C_8$ alkenyl, ($C_1$-$C_4$ alkyl) OH, ($C_1$-$C_4$ alkyl)SH, ($C_2$-$C_3$ alkyl)$SCH_3$, ($C_1$-$C_4$ alkyl) CONHH, ($C_1$-$C_4$ alkyl)COOH, ($C_1$-$C_4$ alkyl)NHH, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl ($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl or aryl;

$R_3$ is $C_1$-$C_{18}$ alkyl, $C_3$-$C_8$ alkenyl, ($C_0$-$C_4$ alkyl)($C_4$-$C_6$ cycloalkyl), ($C_0$-$C_4$ alkyl)($C_3$-$C_5$ heterocyclic), ($C_0$-$C_4$ alkyl)($C_6$-$C_{10}$ aryl) or $R_4$ and $R_3$ together with the atoms to which they are attached form a 4, 5 or 6 member heterocyclic ring;

$R_4$ is H, $C_1$-$C_{18}$ alkyl, ($C_1$-$C_6$ alkyl)$NHR_9$ or $C_1$-$C_6$ alkyl) NH—$S_1$—$R_9$, $R_5$ is OH, or $NHR_6$;

$R_6$ is H, $C_1$-$C_8$ alkyl;

$R_7$ is selected from the group consisting of H, OH and $OR_9$;

$R_9$ is selected from the group consisting of $C_{16}$-$C_{30}$ acyl, and $C_{16}$-$C_{30}$ alkyl;

$R_{11}$, and $R_{13}$ are each H or $C_1$-$C_6$ alkyl;

$R_{10}$ and $R_{12}$ are independently selected from the group consisting of H, $CH_3$, ($C_1$-$C_4$ alkyl)COOH, ($C_1$-$C_4$ alkyl) $NH_2$, ($C_1$-$C_4$ alkyl)NHC($NH_2^+$)$NH_2$, and $CH_2$($C_3$—$N_2$ heterocyclic); and $S_1$ is a bond or a spacer consisting of one to six amino acids, wherein said spacer comprises one or more charged amino acids selected from the group consisting of aspartic acid, glutamic acid, cysteic acid, arginine and lysine, with the proviso that $R_1$ is other than H when $R_4$ is H or $C_1$-$C_{18}$ alkyl. In a further embodiment $R_1$ is ($C_1$-$C_6$ alkyl)$NHR_9$ or ($C_1$-$C_6$ alkyl)NH—$S_1$—$R_9$; $R_2$, $R_4$, $R_{11}$, and $R_{13}$ are each H; $R_5$ is $NH_2$; $R_8$ is H or $C_1$-$C_8$ alkyl; $R_9$ is $C_{18}$-$C_{30}$ acyl; and $S_1$ is a spacer consisting of one or two charged amino acids selected from the group consisting of aspartic acid, glutamic acid, cysteic acid, arginine and lysine. In another embodiment $R_1$ is ($C_3$-$C_5$ alkyl)NH—$S_1R_9$, or ($C_3$-$C_5$ alkyl)$NHR_9$; $R_2$, $R_4$, $R_{11}$, and $R_{13}$ are each H; $R_5$ is $NH_2$; $R_8$ is H or $C_1$-$C_8$ alkyl; and $R_9$ is $C_{18}$-$C_{30}$ acyl.

In another embodiment the insulin prodrug comprises the structure:

A-B-C-Q;

wherein Q is an insulin peptide; and

A-B-C comprises the structure:

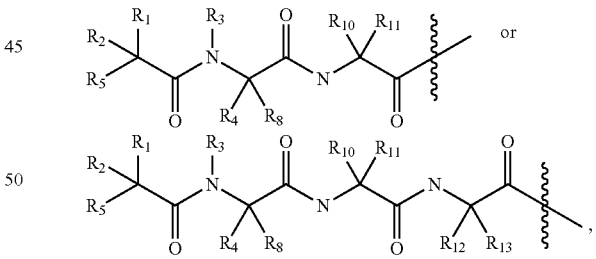

wherein

A-B-C is linked to Q through an amide bond via the N-terminal amino acid of the A chain or the B chain, or an aliphatic amino group on a side chain of an B3, B28 or B29 amino acid of Q, $R_2$, $R_4$, $R_8$, $R_{11}$, and $R_{13}$ are each H; $R_1$ is ($C_1$-$C_6$ alkyl)$NHR_9$ or ($C_1$-$C_6$ alkyl)NH—$S_1$—$R_9$; $R_3$ is $C_2$-$C_8$ alkyl, $R_5$ is $NH_2$, $R_{10}$ and $R_{12}$ are independently selected from the group consisting of H, $CH_3$, ($C_1$-$C_4$ alkyl)COOH, ($C_1$-$C_4$ alkyl)$NH_2$, ($C_1$-$C_4$ alkyl)NHC($NH_2^+$) $NH_2$, and $CH_2$($C_3$—$N_2$ heterocyclic), $R_9$ is selected from the group consisting of $C_{18}$-$C_{30}$ acyl and $C_{18}$-$C_{30}$ alkyl; and $S_1$ is a spacer consisting of one or two charged amino acids selected from the group consisting of aspartic acid, glutamic acid, cysteic acid, arginine and lysine. In a further embodiment $R_1$ is $(CH_2)_4NHR_9$ or $(CH_2)_4NH-S_1-R_9$; $R_3$ is $C_3-C_4$ alkyl; and $R_9$ is $C_{18}-C_{28}$ acyl.

In accordance with one embodiment the insulin component of the prodrugs disclosed herein comprises an A chain sequence of GIVEQCCX$_8$SICSLYQLENYCX$_{21}$ (SEQ ID NO: 3) and a B chain sequence of R$_{22}$-HLCGSHLVEALYL-VCGERGFX$_{45}$ (SEQ ID NO: 15), wherein the B chain is linked to said A chain through disulfide linkages; $R_{22}$ is a bond, or a 1 to 4 amino acid sequence selected from the group consisting of a FVNQ (SEQ ID NO: 12), FVKQ (SEQ ID NO: 8), VNQ, NQ and Q;

$X_8$ is selected from the group consisting of threonine and histidine; $X_{21}$ is selected from the group consisting of asparagine, lysine, ornithine, glycine, and alanine; and $X_{45}$ is histidine, tyrosine or phenylalanine. In one embodiment the insulin peptide comprises an A and B chain wherein the A chain comprises a sequence GIVEQCCTSICSLY-QLENYCN (SEQ ID NO: 1) and the B chain comprises a sequence selected from the group consisting of FVNQHL-CGSHLVEALYLVCGERGFFYTPKT (SEQ ID NO: 2) FVNQHLCGSHLVEALYLVCGERGFFYTKPT (SEQ ID NO: 9) FVNQHLCGSHLVEALYLVCGERGFFYTDKT (SEQ ID NO: 5) FVKQHLCGSHLVEALYL-VCGERGFFYTEKT (SEQ ID NO: 6).

In accordance with one embodiment the insulin component of the prodrugs disclosed herein comprises an A chain sequence of GIVX$_4$X$_5$CCX$_8$X$_9$X$_{10}$CX$_{12}$LX$_{14}$X$_{15}$LX$_{17}$X$_{18}$YCX$_{21}$—R$_{44}$ (SEQ ID NO: 19), and a B chain sequence of R$_{22}$-X$_{25}$LCGX$_{29}$X$_{30}$LVX$_{33}$X$_{34}$LYLVCGX$_{41}$X$_{42}$GFX$_{45}$ (SEQ ID NO: 20), wherein said B chain is linked to said A chain through disulfide linkages;

$X_4$ is glutamic acid or aspartic acid;

$X_5$ is glutamine or glutamic acid $X_8$ is histidine, threonine or phenylalanine;

$X_9$ is serine, arginine, lysine, ornithine or alanine;

$X_{10}$ is isoleucine or serine;

$X_{12}$ is serine or aspartic acid;

$X_{14}$ is tyrosine, arginine, lysine, ornithine or alanine;

$X_{15}$ is glutamine, glutamic acid, arginine, alanine, lysine, ornithine or leucine;

$X_{17}$ is glutamic acid, aspartic acid, asparagine, lysine, ornithine or glutamine;

$X_{18}$ is methionine, asparagine, glutamine, aspartic acid, glutamic acid or threonine;

$X_{21}$ is selected from the group consisting of alanine, glycine, serine, valine, threonine, isoleucine, leucine, glutamine, glutamic acid, asparagine, aspartic acid, histidine, tryptophan, tyrosine, and methionine;

$X_{25}$ is histidine or threonine;

$X_{29}$ is selected from the group consisting of alanine, glycine and serine;

$X_{30}$ is selected from the group consisting of histidine, aspartic acid, glutamic acid, homocysteic acid and cysteic acid;

$X_{33}$ is selected from the group consisting of aspartic acid and glutamic acid;

$X_{34}$ is selected from the group consisting of alanine and threonine;

$X_{41}$ is selected from the group consisting of glutamic acid, aspartic acid or asparagine;

$X_{42}$ is selected from the group consisting of alanine, ornithine, lysine and arginine;

$X_{45}$ is tyrosine or phenylalanine;

$R_{22}$ is selected from the group consisting of AYRPSE (SEQ ID NO: 14), FVNQ (SEQ ID NO: 12), FVKQ (SEQ ID NO: 8), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and $R_{44}$ is COOH or CONH$_2$.

In accordance with one embodiment the insulin prodrug comprises the structure:

A-B-C-Q;

wherein Q is an insulin peptide; and
A-B-C comprises the structure:

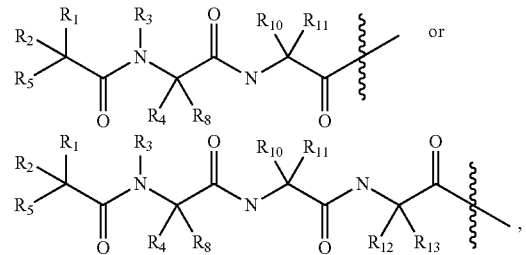

wherein

A-B-C is linked to Q through an amide bond via the N-terminal amino acid of the A chain or the B chain, or an aliphatic amino group on a side chain of an B3, B28 or B29 amino acid of Q, $R_1$ is selected from the group consisting of H, $(C_1-C_6$ alkyl)NH—$S_1$—$R_9$, $(C_1-C_4$ alkyl)O—$S_1$—$R_9$, $(C_1-C_4$ alkyl)S—$S_1$—$R_9$, $(C_1-C_4$ alkyl)CONH—$S_1$—$R_9$, $(C_1-C_4$ alkyl)COO—$S_1$—$R_9$, $(C_1-C_6$ alkyl)NH—$S_1$—$R_9$, $(C_1-C_6$ alkyl)NHR$_9$ and $(C_0-C_4$ alkyl)$(C_6-C_{10}$ aryl)-$S_1$—$R_9$;

$R_2$ and $R_8$ are independently selected from the group consisting of H, $C_1-C_8$ alkyl, $C_2-C_8$ alkenyl, $(C_1-C_4$ alkyl)OH, $(C_1-C_4$ alkyl)SH, $(C_2-C_3$ alkyl)SCH$_3$, $(C_1-C_4$ alkyl)CONHH, $(C_1-C_4$ alkyl)COOH, $(C_1-C_4$ alkyl)NHH, $(C_1-C_4$ alkyl)NHC(NH$_2^+$)NH$_2$, $(C_0-C_4$ alkyl)$(C_3-C_6$ cycloalkyl), $(C_0-C_4$ alkyl)$(C_2-C_5$ heterocyclic), $(C_0-C_4$ alkyl)$(C_6-C_{10}$ aryl)R$_7$, $(C_1-C_4$ alkyl)$(C_3-C_9$ heteroaryl), and $C_1-C_{12}$ alkyl $(W_1)C_1-C_{12}$ alkyl, wherein $W_1$ is a heteroatom selected from the group consisting of N, S and O, or $R_1$ and $R_2$ together with the atoms to which they are attached form a $C_3-C_{12}$ cycloalkyl or aryl;

$R_3$ is $C_1-C_{18}$ alkyl, $C_3-C_8$ alkenyl, $(C_0-C_4$ alkyl)$(C_4-C_6$ cycloalkyl), $(C_0-C_4$ alkyl)$(C_3-C_5$ heterocyclic), $(C_0-C_4$ alkyl)$(C_6-C_{10}$ aryl) or $R_4$ and $R_3$ together with the atoms to which they are attached form a 4, 5 or 6 member heterocyclic ring;

$R_4$ is H, $C_1-C_{18}$ alkyl or $(C_1-C_6$ alkyl)NH—$S_1$—$R_9$, $R_5$ is OH, or NHR$_6$;

$R_6$ is H, $C_1-C_8$ alkyl;

$R_7$ is selected from the group consisting of H, OH and OR$_9$;

$R_9$ is selected from the group consisting of $C_{16}-C_{30}$ acyl, and $C_{16}-C_{30}$ alkyl;

$R_{11}$, and $R_{13}$ are each H;

$R_{10}$ and $R_{12}$ are independently selected from the group consisting of $(C_1-C_4$ alkyl)COOH, $(C_1-C_4$ alkyl)NH$_2$, $(C_1-C_4$ alkyl)NHC(NH$_2^+$)NH$_2$, and CH$_2(C_3$—N$_2$ heterocyclic); and $S_1$ is a bond or a spacer consisting of one or two charged amino acids selected from the group consisting of aspartic acid, glutamic acid, cysteic acid, homocysteic acid, homoglutamic acid, arginine, lysine and histidine, with the proviso that $R_1$ is other than H when $R_4$ is H or, $C_1$-$C_{18}$ alkyl.
In one embodiment
$R_1$ is ($C_3$-$C_5$ alkyl)NH—$S_1$—$R_9$ or ($C_3$-$C_5$ alkyl)NHR$_9$; $R_2$, $R_4$, $R_{11}$, and $R_{13}$ are each H; $R_5$ is NH$_2$; $R_8$ is H or $C_1$-$C_8$ alkyl; $R_9$ is $C_{18}$-$C_{30}$ acyl; $R_{10}$ and $R_{12}$ are independently selected from the group consisting of ($C_1$-$C_4$ alkyl)COOH, ($C_1$-$C_4$ alkyl)NH$_2$, and ($C_1$-$C_4$ alkyl)NHC(NH$_2^+$)NH$_2$; and $S_1$ is a spacer consisting of one or two charged amino acids selected from the group consisting of aspartic acid, glutamic acid, cysteic acid, arginine, and lysine.

In one embodiment $R_3$ is $C_1$-$C_8$ alkyl or $R_4$ and $R_3$ together with the atoms to which they are attached form a 4, 5 or 6 member heterocyclic ring. In one embodiment $R_1$ is (CH$_2$)$_4$NHR$_9$ or (CH$_2$)$_4$NH—$S_1$—$R_9$; $R_3$ is $C_3$-$C_4$ alkyl; and $R_9$ is $C_{18}$-$C_{28}$ acyl.

In accordance with one embodiment the first amino acid of the prodrug dipeptide element has D-stereochemistry.

In accordance with one embodiment a method of treating hyperglycemia or diabetes is provided wherein the method comprises administering an effective amount of a pharmaceutical composition comprising an insulin prodrug as disclosed herein. In one embodiment the insulin prodrug is designed to have a half-life in mammalian serum of greater than on day. In such embodiments the insulin prodrug can be administered in a daily dosage that is a fraction of the dosage that would be administered if the corresponding active non-prodrug form of the insulin protein was administered. In one embodiment the prodrug is administered daily at a fraction, 1/n, of the optimal dosage of the corresponding non-prodrug insulin peptide, wherein n represents the half-life, in days, of the cleavage of A-B-C from Q in serum under physiological conditions.

The dipeptide prodrug element is designed to spontaneously cleave its amide linkage to the insulin analog under physiological conditions and in the absence of enzymatic activity. In one embodiment the N-terminal amino acid of the dipeptide extension comprises a C-alkylated amino acid (e.g. amino isobutyric acid). In one embodiment the C-terminal amino acid of the dipeptide comprises an N-alkylated amino acid (e.g., proline or N-methyl glycine). In one embodiment the dipeptide comprises the sequence of an N-terminal C-alkylated amino acid followed by an N-alkylated amino acid.

The A chain and B chain comprising the insulin prodrug analog may comprise the native sequence of the respective peptides (i.e., SEQ ID NO: 1 and SEQ ID NO: 2) or may comprise a derivative of SEQ ID NO: 1 and/or SEQ ID NO: 2 wherein the derivative includes modification of the amino acid at position A19 to a 4-amino phenylalanine and/or one or more amino acid substitutions at positions selected from A5, A8, A9, A10, A14, A15, A17, A18, A19 and A21, B1, B2, B3, B4, B5, B9, B10, B13, B14, B17, B20, B22, B23, B26, B27, B28, B29 and B30 or deletions of any or all of positions B1-4 and B26-30. In one embodiment the peptide prodrug element, A-B-C is linked to an N-terminal amino group of the insulin A or B chain, wherein the B amino acid of the peptide prodrug element comprises an N-alkylated amino acid and the A amino acid of the peptide prodrug element is any amino acid, with the proviso that when the B amino acid of the peptide prodrug element is proline, the A amino acid of the peptide prodrug element comprises a C-alkylated amino acid.

In one embodiment the peptide prodrug element comprises the general structure of:

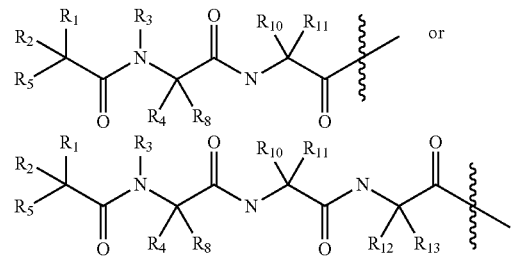

wherein $R_1$ and $R_8$ are independently selected from the group consisting of H, ($C_1$-$C_6$ alkyl)NH—$R_9$, ($C_1$-$C_6$ alkyl)NH—$S_1$—$R_9$, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_8$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, ($C_1$-$C_4$ alkyl)($C_3$-$C_9$ heteroaryl), and $C_1$-$C_{12}$ alkyl (W)$C_1$-$C_{12}$ alkyl, wherein W is a heteroatom selected from the group consisting of N, S and O, or $R_1$ and $R_2$ together with the atoms to which they are attached form a $C_3$-$C_{12}$ cycloalkyl or aryl;

$R_2$ and $R_4$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_8$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, ($C_1$-$C_4$ alkyl)($C_3$-$C_9$ heteroaryl), and $C_1$-$C_{12}$ alkyl (W)$C_1$-$C_{12}$ alkyl, wherein W is a heteroatom selected from the group consisting of N, S and O, or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)R$_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_2$ together with the atoms to which they are attached form a 4, 5 or 6 member heterocyclic ring;

$R_7$ is selected from the group consisting of H and OH, with the proviso that when $R_4$ and $R_3$ together with the atoms to which they are attached form a 4, 5 or 6 member heterocyclic ring, both $R_1$ and $R_2$ are other than H $R_9$ is selected from the group consisting of $C_{16}$-$C_{30}$ acyl, and $C_{16}$-$C_{30}$ alkyl;

$R_{11}$, and $R_{13}$ are each H;

$R_{10}$ and $R_{12}$ are independently selected from the group consisting of ($C_1$-$C_4$ alkyl)COOH, ($C_1$-$C_4$ alkyl)NH$_2$, ($C_1$-$C_4$ alkyl)NHC(NH$_2^+$)NH$_2$, and CH$_2$(C$_3$—N$_2$ heterocyclic); and $S_1$ is a bond or a spacer comprising a 1-6 peptide wherein the 1-6 peptide comprises 1, 2, or 3 charged amino acids selected from the group consisting of aspartic acid, glutamic acid, cysteic acid, homocysteic acid, homoglutamic acid, arginine, lysine and histidine, with the proviso that one of $R_1$ or $R_8$ is ($C_1$-$C_6$ alkyl)NH—$R_9$, or ($C_1$-$C_6$ alkyl)NH—$S_1$—$R_9$. In one embodiment $R_1$ is ($C_1$-$C_6$ alkyl)NH—$R_9$, or ($C_1$-$C_6$ alkyl)NH—$S_1$—$R_9$ and $R_2$ and $R_4$ are H.

In another embodiment the peptide prodrug element comprises the general structure:

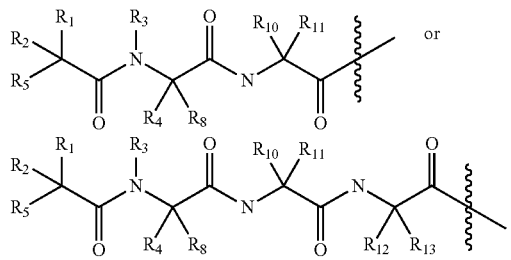

wherein $R_1$ is ($C_1$-$C_6$ alkyl)NH—$R_9$, or ($C_1$-$C_6$ alkyl)NH—$S_1$—$R_9$;

$R_2$ and $R_8$ is H or $C_1$-$C_8$ alkyl;

$R_4$ is selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$+) NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, and CH$_2$($C_3$-$C_9$ heteroaryl);

$R_3$ is selected from the group consisting of $C_1$-$C_8$ alkyl, ($C_3$-$C_6$)($C_5$-$C_6$ cycloalkyl) or $R_4$ and $R_3$ together with the atoms to which they are attached form a 5 or 6 member heterocyclic ring;

$R_5$ is NHR$_6$;

$R_6$ is H, $C_1$-$C_8$ alkyl; and $R_7$ is selected from the group consisting of hydrogen, $C_1$-$C_{18}$ alkyl, ($C_0$-$C_4$ alkyl)COOH, ($C_0$-$C_4$ alkyl)NH$_2$, ($C_0$-$C_4$ alkyl)OH and halo;

$R_9$ is selected from the group consisting of $C_{16}$-$C_{30}$ acyl, and $C_{16}$-$C_{30}$ alkyl;

$R_{11}$, and $R_{13}$ are each H;

$R_{10}$ and $R_{12}$ are independently selected from the group consisting of ($C_1$-$C_4$ alkyl)COOH, ($C_1$-$C_4$ alkyl)NH$_2$, ($C_1$-$C_4$ alkyl)NHC(NH$_2$+)NH$_2$, and CH$_2$($C_3$—N$_2$ heterocyclic); and $S_1$ is a bond or a spacer consisting of one or two charged amino acids selected from the group consisting of aspartic acid, glutamic acid, cysteic acid, homocysteic acid, homoglutamic acid, arginine, lysine and histidine.

In one embodiment either the first amino acid and/or the second amino acid of the dipeptide prodrug element is an amino acid in the D stereoisomer configuration.

In one embodiment the prodrug element of the general formula:

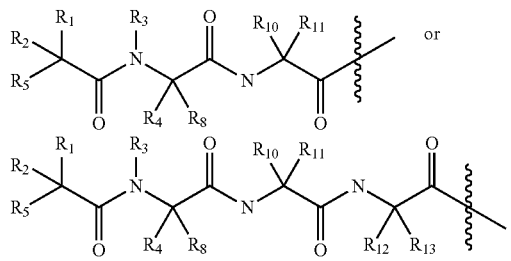

is provided wherein $R_1$ is ($C_1$-$C_6$ alkyl)NH—$R_9$, or ($C_1$-$C_6$ alkyl)NH—$S_1$—$R_9$ $R_2$ is H; and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)COOH, ($C_1$-$C_4$ alkyl)NH$_2$, ($C_1$-$C_4$ alkyl)NHC(NH$_2$+) NH$_2$, ($C_0$-$C_4$ alkyl)($C_3$-$C_6$ cycloalkyl), ($C_0$-$C_4$ alkyl)($C_6$-$C_{10}$ aryl)$R_7$, and CH$_2$($C_5$-$C_9$ heteroaryl);

$R_3$ is selected from the group consisting of $C_1$-$C_8$ alkyl, ($C_1$-$C_4$ alkyl)($C_6$-$C_{10}$ aryl)$R_7$, ($C_1$-$C_4$ alkyl)($C_5$-$C_{10}$ cycloalkyl) and CH$_2$($C_5$-$C_9$ heteroaryl) or $R_4$ and $R_3$ together with the atoms to which they are attached form a 5 or 6 member heterocyclic ring;

$R_5$ is NH$_2$;

$R_7$ is selected from the group consisting of H and OH and $R_8$ is H $R_9$ is selected from the group consisting of $C_{16}$-$C_{30}$ acyl, and $C_{16}$-$C_{30}$ alkyl;

$R_{11}$, and $R_{13}$ are each H;

$R_{10}$ and $R_{12}$ are independently selected from the group consisting of ($C_1$-$C_4$ alkyl)COOH, ($C_1$-$C_4$ alkyl)NH$_2$, ($C_1$-$C_4$ alkyl)NHC(NH$_2$)NH$_2$, and CH$_2$($C_3$—N$_2$ heterocyclic); and $S_1$ is a bond or a spacer consisting of one or two charged amino acids selected from the group consisting of aspartic acid, glutamic acid, cysteic acid, homocysteic acid, homoglutamic acid, arginine, lysine and histidine, with the proviso that $R_1$ is other than H when $R_4$ is H or, $C_1$-$C_{18}$ alkyl. In one embodiment $R_3$ is $C_1$-$C_8$ alkyl and $R_4$ is selected from the group consisting of H, $C_1$-$C_6$ alkyl, ($C_0$-$C_4$ alkyl)($C_6$-$C_{10}$ aryl)$R_7$, and CH$_2$ ($C_5$-$C_9$ heteroaryl) or $R_4$ and $R_3$ together with the atoms to which they are attached form a 5 or 6 member heterocyclic ring.

In one embodiment either the first amino acid and/or the second amino acid of the dipeptide prodrug element is a non-coded amino acid and in one embodiment is an amino acid in the D stereoisomer configuration.

In one embodiment an insulin prodrug is provided having the general structure of: A-B-C-Q, wherein Q is an insulin peptide comprises an A and B chain wherein the A chain comprises a sequence GIVEQCCTSICSLYQLENYCN (SEQ ID NO: 1) and the B chain comprises a sequence selected from the group consisting of FVNQHLCG-SHLVEALYLVCGERGFFYTPKT (SEQ ID NO: 2) FVN-QHLCGSHLVEALYLVCGERGFFYTKPT (SEQ ID NO: 9) FVNQHLCGSHLVEALYLVCGERGFFYTDKT (SEQ ID NO: 5) FVKQHLCGSHLVEALYLVCGERGFFYTEKT (SEQ ID NO: 6); and A-B-C is a peptide prodrug element having the structure of

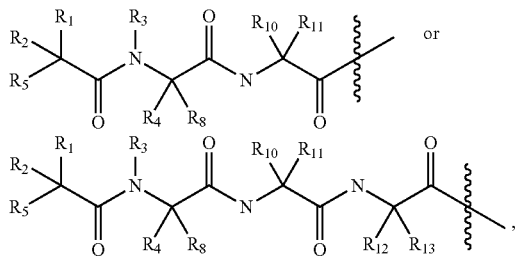

wherein $R_1$ is ($C_1$-$C_6$ alkyl)NH—$R_9$, or ($C_1$-$C_6$ alkyl)NH—$S_1$—$R_9$;

$R_2$ is selected from the group consisting of hydrogen, and $C_1$-$C_8$ alkyl;

$R_3$ is $C_1$-$C_8$ alkyl;

$R_4$ is H, $C_1$-$C_8$ alkyl or ($C_1$-$C_4$ alkyl)($C_6$-$C_{10}$ aryl)$R_7$;
$R_5$ is $NH_2$;
$R_7$ is selected from the group consisting of hydrogen, $C_1$-$C_8$ alkyl and ($C_0$-$C_4$ alkyl)OH;
$R_8$ is hydrogen;
$R_9$ is selected from the group consisting of $C_{16}$-$C_{30}$ acyl, and $C_{16}$-$C_{30}$ alkyl;
$R_{11}$, and $R_{13}$ are each H;
$R_{10}$ and $R_{12}$ are independently selected from the group consisting of ($C_1$-$C_4$ alkyl)COOH, ($C_1$-$C_4$ alkyl)$NH_2$, ($C_1$-$C_4$ alkyl)NHC($NH_2^+$)$NH_2$, and $CH_2$($C_3$—$N_2$ heterocyclic); and
$S_1$ is a spacer consisting of one or two charged amino acids selected from the group consisting of aspartic acid, glutamic acid, cysteic acid, homocysteic acid, homoglutamic acid, arginine, lysine and histidine. In a further embodiment $R_2$ is hydrogen;
$R_3$ is $C_1$-$C_{18}$ alkyl;
$R_4$ and $R_8$ are each hydrogen;
$R_5$ is $NH_2$;
$R_9$ is selected from the group consisting of $C_{16}$-$C_{30}$ acyl, and $C_{16}$-$C_{30}$ alkyl;
$R_{11}$, and $R_{13}$ are each H;
$R_{10}$ and $R_{12}$ are independently selected from the group consisting of ($C_1$-$C_4$ alkyl)COOH, ($C_1$-$C_4$ alkyl)$NH_2$, and ($C_1$-$C_4$ alkyl)NHC($NH_2^+$)$NH_2$; and
$S_1$ is a spacer consisting of one or two charged amino acids selected from the group consisting of aspartic acid, glutamic acid, cysteic acid, homocysteic acid, homoglutamic acid, arginine, lysine and histidine.

In accordance with one embodiment an insulin prodrug analog is provided comprising an insulin peptide and an amide linked prodrug element. More particularly, the insulin prodrug analog comprises an A chain sequence and a B chain sequence wherein the A chain comprises the sequence Z-GIVEQCCX$_8$SICSLYQLENYCX$_{21}$R$_{44}$ (SEQ ID NO: 3) (SEQ ID NO: 3), or an analog thereof comprising a sequence that differs from SEQ ID NO: 3 by 1 to 9, 1 to 5 or 1 to 3 amino acid modifications, selected from positions A5, A8, A9, A10, A14, A15, A17, A18 (relative to the native insulin A chain), and the B chain sequence comprises the sequence of J-R$_{22}$-X$_{25}$LCGX$_{29}$X$_{30}$LVEALYLVCGERGFX$_{45}$ (SEQ ID NO:), or an analog thereof comprising a sequence that differs from SEQ ID NO: 14 sequence by 1 to 10, 1 to 5 or 1 to 3 amino acid modifications, selected from positions B1, B2, B3, B4, B5, B13, B14, B17, B20, B22, B23, B26, B27, B28, B29 and B30 (relative to the native insulin B chain; i.e., amino acid X$_{25}$ of SEQ ID NO: corresponds to position B5 in native insulin), wherein
$X_8$ is selected from the group consisting of threonine and histidine;
$X_{21}$ is selected from the group consisting of asparagine, ornithine, glycine, alanine, threonine, and serine;
$X_{25}$ is selected from the group consisting of histidine and threonine;
$X_{29}$ is selected from the group consisting of alanine, glycine and serine;
$X_{30}$ is selected from the group consisting of histidine, aspartic acid, glutamic acid, homocysteic acid and cysteic acid;
$X_{45}$ is tyrosine or phenylalanine;
$R_{22}$ is selected from the group consisting of FVNQ (SEQ ID NO: 12), FVKQ (SEQ ID NO: 8), a tripeptide valine-asparagine-glutamine, a dipeptide asparagine-glutamine, glutamine, glutamic acid and an N-terminal amine; and $R_{44}$ is COOH or $CONH_2$. Z and J are independently H or a peptide prodrug element comprising the general structure of

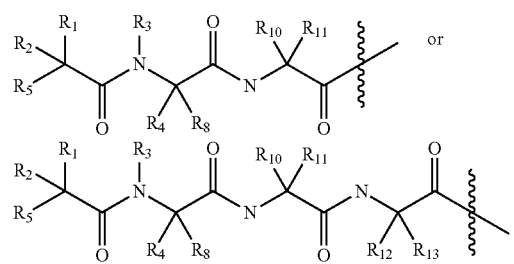

linked to the N-terminal amine of the insulin A or B chain, wherein
$R_1$ is selected from the group consisting of ($C_1$-$C_6$ alkyl)NH—$R_9$, and ($C_1$-$C_6$ alkyl)NH—$S_1$—$R_9$;
$R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_6$ alkyl)NH—$R_9$, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl(W)$C_1$-$C_{12}$ alkyl, wherein W is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;
$R_3$ is selected from the group consisting of $C_1$-$C_{18}$ alkyl, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;
$R_5$ is NHR$_6$;
$R_6$ is H, $C_1$-$C_8$ alkyl; and
$R_7$ is selected from the group consisting of H and OH;
$R_{13}$ is COOH or CONH$_2$;
$R_9$ is selected from the group consisting of $C_{16}$-$C_{30}$ acyl, and $C_{16}$-$C_{30}$ alkyl;
$R_{11}$, and $R_{13}$ are each H;
$R_{10}$ and $R_{12}$ are independently selected from the group consisting of ($C_1$-$C_4$ alkyl)COOH, ($C_1$-$C_4$ alkyl)NH$_2$, ($C_1$-$C_4$ alkyl)NHC($NH_2^+$)$NH_2$, and CH$_2$($C_3$—$N_2$ heterocyclic); and
$S_1$ is a bond or a spacer consisting of one or two charged amino acids selected from the group consisting of aspartic acid, glutamic acid, cysteic acid, homocysteic acid, homoglutamic acid, arginine, lysine and histidine.

In a further embodiment, the A chain comprises the sequence GIVEQCCX$_8$SICSLYQLENYCX$_{21}$R$_{13}$ (SEQ ID NO: 3), the B chain sequence comprises a sequence selected from the group consisting of FVNQHLCGSHLVEALYL-VCGERGFFYTPKT (SEQ ID NO: 2) FVNQHLCG-SHLVEALYLVCGERGFFYTKPT (SEQ ID NO: 9) FVN-QHLCGSHLVEALYLVCGERGFFYTDKT (SEQ ID NO: 5); and FVKQHLCGSHLVEALYLVCGERGFFYTEKT (SEQ ID NO: 6),
wherein $R_{13}$ is COOH and the carboxy terminal amino acid of the B chain optionally has an amide (CONH$_2$) in place of the natural alpha carbon carboxy group, with the remaining designations defined as immediately above. In one embodiment the A chain comprises a sequence GIVEQCCTSIC-SLYQLENYCN-$R_{44}$ (SEQ ID NO: 1) and the B chain comprises a sequence selected from the group consisting of FVNQHLCGSHLVEALYLVCGERGFFYTPKT (SEQ ID NO: 2) FVNQHLCGSHLVEALYLVCGERGFFYTKPT (SEQ ID NO: 9) FVNQHLCGSHLVEALYL-VCGERGFFYTDKT (SEQ ID NO: 5) or FVKQHLCG-SHLVEALYLVCGERGFFYTEKT (SEQ ID NO: 6).

In one embodiment insulin analogs disclosed herein comprise a C-terminal amide or ester in place of a C-terminal carboxylate on the A chain and/or B chain.

In accordance with one embodiment the peptide prodrug element as disclosed herein having the general structure of

[chemical structures]

is further modified to comprise a large polymer that interferes with the insulin analog's ability to interact with the insulin or IGF-1 receptor. Subsequent cleavage of the dipeptide releases the insulin analog from the dipeptide complex wherein the released insulin analog is fully active. In accordance with one embodiment the prodrug element is linked via an amide bond to an aliphatic amine selected form the N-terminal amine of the A chain or B chain or the side chain amine of a lysine at position B3, B27 or B28, wherein the substituents of $R_1$, $R_2$, $R_4$, $R_8$, $R_{10}$, $R_{11}$, $R_{12}$ and $R_{13}$ are defined throughout the present disclosure. In one embodiment, the prodrug element is covalently bound to the insulin peptide via an amide linkage at the N-terminal amine of the A chain or the B chain, or attached to an amine bearing side chain of an internal amino acid, wherein the prodrug element further comprises a depot polymer linked to prodrug element. In accordance with one embodiment the peptide prodrug element as disclosed herein has the general structure of

[chemical structures]

wherein $D_1$ is a serum enzyme cleavable moiety covalently linked via an amide bond to the peptide prodrug element. In one embodiment $D_1$ is a peptide that is cleaved by dipeptidyl peptidase IV (DPP-IV), including for example a dipeptide of Arg-Pro, Lys-Pro or Glu-Pro. The substituents of $R_1$, $R_2$, $R_4$, $R_8$, $R_{10}$, $R_{11}$, $R_{12}$ and $R_{13}$ are defined throughout the present disclosure.

In one embodiment a native amino acid of the insulin peptide is substituted with an amino acid suitable for forming an amide bond with the prodrug element disclosed herein. In one embodiment a depot bearing prodrug element is linked at a position selected from A14, A19, B3 B16, B28 and B29. In one embodiment two or more depot polymer bearing prodrug elements are linked to an insulin peptide, wherein the first depot polymer bearing prodrug element is linked to the N-terminal amine of the B chain and the second depot polymer bearing prodrug element is linked to the N-terminal amine of the A chain or to the side chain amine of a lysine at position B3, B28 or B29 of insulin. In one embodiment the depot polymer is a moiety that irreversibly binds to a mammalian plasma protein, and in one embodiment the depot polymer is an acyl or alkyl group that is of sufficient size to irreversible bind mammalian serum albumin. In one embodiment the depot polymer is selected to be biocompatible and of sufficient size (or is capable of irreversibly binding to a plasma protein of sufficient size) that the insulin peptide modified by covalent attachment of the prodrug element remains sequestered at an injection site and/or incapable of interacting with its corresponding receptor upon administration to a patient. Subsequent cleavage of the prodrug element releases the insulin peptide to interact with its intended target.

In accordance with one embodiment the depot polymer is selected from biocompatible polymers known to those skilled in the art. The depot polymers typically have a size selected from a range of about 20,000 to 120,000 Daltons. In one embodiment the depot polymer has a size selected from a range of about 40,000 to 100,000 or about 40,000 to 80,000 Daltons. In one embodiment the depot polymer has a size of about 40,000, 50,000, 60,000, 70,000 or 80,000 Daltons. Suitable depot polymers include but are not limited to dextrans, polylactides, polyglycolides, caprolactone-based polymers, poly(caprolactone), polyanhydrides, polyamines, polyesteramides, polyorthoesters, polydioxanones, polyacetals, polyketals, polycarbonates, polyphosphoesters, polyesters, polybutylene terephthalate, polyorthocarbonates, polyphosphazenes, succinates, poly(malic acid), poly(amino acids), polyvinylpyrrolidone, polyethylene glycol, polyhydroxycellulose, polysaccharides, chitin, chitosan, hyaluronic acid, and copolymers, terpolymers and mixtures thereof, and biodegradable polymers and their copolymers including caprolactone-based polymers, polycaprolactones and copolymers which include polybutylene terephthalate. In one embodiment the depot polymer is selected from the group consisting of polyethylene glycol, dextran, polylactic acid, polyglycolic acid and a copolymer of lactic acid and glycolic acid, and in one specific embodiment the depot polymer is polyethylene glycol. In one embodiment the depot polymer is polyethylene glycol and the combined molecular weight of depot polymer(s) linked to the dipeptide element is about 40,000 to 80,000 Daltons. In one embodiment the depot polymer is a moiety that irreversibly binds to a mammalian plasma protein, and in one embodiment the depot polymer is an acyl or alkyl group that is of sufficient size to irreversible bind mammalian serum albumin.

In accordance with one embodiment the prodrug element further comprises a polyethylene oxide, alkyl or acyl group. In one embodiment one or more polyethylene oxide chains are linked to the peptide prodrug element wherein the combined molecular weight of the polyethylene oxide chains ranges from about 20,000 to about 80,000 Daltons, or 40,000 to 80,000 Daltons or 40,000 to 60,000 Daltons. In one embodiment the polyethylene oxide is polyethylene glycol. In one embodiment at least one polyethylene glycol chain having a molecular weight of about 40,000 Daltons or about 20,000 Daltons is linked to the prodrug element either directly or through a linker/spacer. In another embodiment the self-cleaving dipeptide of the peptide prodrug element is acylated with an acyl group of sufficient size to bind serum albumin, and thus inactivate the insulin analog upon administration. The acyl group can be linear or branched, and in one embodiment is a C16 to C30 fatty acid. For example, the acyl group can be any of a C16 fatty acid, C18 fatty acid, C20 fatty acid, C22 fatty acid, C24 fatty acid, C26 fatty acid, C28 fatty acid, or a C30 fatty acid. In one embodiment, the acyl group is a C16 to C20 fatty acid, e.g., a C18 fatty acid or a C20 fatty acid or is a C18 or C30 fatty acid.

Selection of the substituents on the dipeptide element and the attachment site of the dipeptide prodrug element can impact the rate of chemical cleavage of the dipeptide prodrug element from the insulin peptide. In one embodiment an insulin prodrug is provided comprising an A chain sequence and a B chain sequence, wherein the A chain comprises the sequence GIVEQCCX$_8$SICSLYQLENYCX$_{21}$R$_{13}$ (SEQ ID NO: 3) and the B chain sequence comprises the sequence of X$_{14}$-X$_4$LCGX$_5$X$_6$LVEALYLVCGERGFF (SEQ ID NO: 4) wherein X$_8$ is selected from the group consisting of threonine and histidine;

X$_{21}$ is selected from the group consisting of asparagine, glycine, alanine, threonine and serine;

X$_4$ is selected from the group consisting of histidine and threonine;

X$_5$ is selected from the group consisting of alanine, glycine and serine;

X$_6$ is selected from the group consisting of histidine, aspartic acid, glutamic acid, homocysteic acid and cysteic acid; and X$_{14}$ is selected from the group consisting of a bond, X$_9$VNQ (SEQ ID NO: 21), VNQ, NQ and Q, and X$_9$ is selected from the group consisting of phenylalanine and desamino-phenylalanine, further wherein a peptide prodrug element comprising the structure:

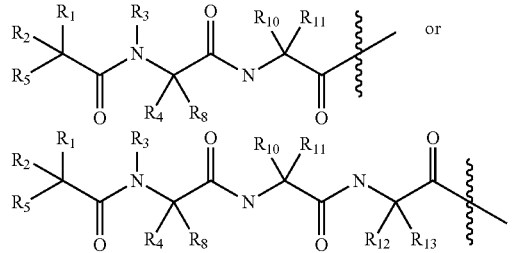

is linked to the N-terminal amine of the peptide of SEQ ID NO: 3 or SEQ ID NO: 4, wherein R$_1$ is selected from the group consisting of (C$_1$-C$_6$ alkyl)NH—R$_9$, (C$_1$-C$_6$ alkyl)NH—S$_1$—R$_9$;

R$_2$, R$_4$ and R$_8$ are H;

R$_3$ is C$_1$-C$_6$ alkyl;

R$_5$ is NH$_2$;

R$_9$ is selected from the group consisting of C$_{16}$-C$_{30}$ acyl, and C$_{16}$-C$_{30}$ alkyl;

R$_{11}$, and R$_{13}$ are each H;

R$_{10}$ and R$_{12}$ are independently selected from the group consisting of (C$_1$-C$_4$ alkyl)COOH, (C$_1$-C$_4$ alkyl)NH$_2$, (C$_1$-C$_4$ alkyl)NHC(NH$_2{}^+$)NH$_2$, and CH$_2$(C$_3$—N$_2$ heterocyclic); and S$_1$ is a bond or a spacer consisting of one or two charged amino acids selected from the group consisting of aspartic acid, glutamic acid, cysteic acid, homocysteic acid, homoglutamic acid, arginine, lysine and histidine. In one embodiment the A chain comprises a sequence GIVEQCCX$_8$SICSLYQLENYCX$_{21}$R$_{13}$ (SEQ ID NO: 3) and the B chain comprises a sequence R$_{22}$-X$_{25}$LCGAX$_{30}$LVDALYLVCGDX$_{42}$GFY (SEQ ID NO: 65), wherein X$_8$ is phenylalanine or histidine;

X$_{21}$ is alanine or asparagine;

X$_{25}$ is histidine or threonine;

X$_{30}$ is selected from the group consisting of histidine, aspartic acid, glutamic acid, homocysteic acid and cysteic acid;

X$_{42}$ is selected from the group consisting of alanine ornithine and arginine;

R$_{22}$ is selected from the group consisting of AYRPSE (SEQ ID NO: 14), FVNQ (SEQ ID NO: 12), FVKQ (SEQ ID NO: 8), PGPE (SEQ ID NO: 11), a tripeptide glycine-proline-glutamic acid, a tripeptide valine-asparagine-glutamine, a dipeptide proline-glutamic acid, a dipeptide asparagine-glutamine, glutamine, glutamic acid and an N-terminal amine; and R$_{44}$ is COOH or CONH$_2$. In a further embodiment, the A chain comprises a sequence GIVEQCCTSICSLY-QLENYCN-R$_{44}$ (SEQ ID NO: 1) and the B chain comprises a sequence selected from the group consisting of FVNQHL-CGSHLVEALYLVCGERGFFYTPKT (SEQ ID NO: 2) FVNQHLCGSHLVEALYLVCGERGFFYTKPT (SEQ ID NO: 9) FVNQHLCGSHLVEALYLVCGERGFFYTDKT (SEQ ID NO: 5) FVKQHLCGSHLVEALYL-VCGERGFFYTEKT (SEQ ID NO: 6).

In one embodiment, prodrugs having the dipeptide prodrug element linked to the N-terminal amino acid of the insulin A or B chain peptide and having a t$_{1/2}$, e.g., between about 12 to about 72 hours, or in one embodiment between about 12 to about 48 hours, comprise a dipeptide prodrug element with the structure:

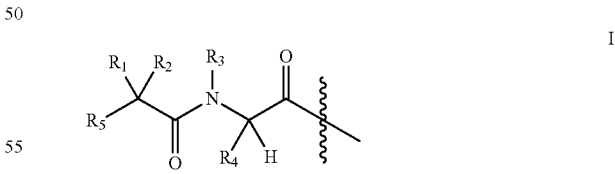

wherein R$_1$ and R$_2$ are independently selected from the group consisting of hydrogen, C$_1$-C$_8$ alkyl and (C$_1$-C$_4$ alkyl)NH$_2$, or R$_1$ and R$_2$ are linked through (CH$_2$)$_p$, wherein p is 2-9;

R$_3$ is C$_1$-C$_8$ alkyl or R$_3$ and R$_4$ together with the atoms to which they are attached form a 4-6 heterocyclic ring;

R$_4$ is selected from the group consisting of hydrogen and C$_1$-C$_8$ alkyl; and R$_5$ is NH$_2$. with the proviso that both R$_1$ and R$_2$ are not hydrogen.

In other embodiments, prodrugs having the dipeptide prodrug element linked to the N-terminal amino acid of the insulin A or B chain peptide and having a $t_{1/2}$, e.g., between about 12 to about 72 hours, or in one embodiment between about 12 to about 48 hours, comprise a dipeptide prodrug element with the structure:

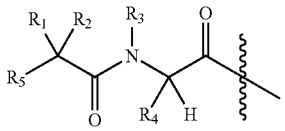

I wherein
$R_1$ and $R_2$ are independently selected from the group consisting of hydrogen, $C_1$-$C_8$ alkyl and ($C_1$-$C_4$ alkyl)$NH_2$;
$R_3$ is $C_1$-$C_6$ alkyl;
$R_4$ is hydrogen; and
$R_5$ is $NH_2$. with the proviso that both $R_1$ and $R_2$ are not hydrogen.

In one embodiment, prodrugs having the dipeptide prodrug element linked to the N-terminal amino acid of the insulin A or B chain peptide and having a $t_{1/2}$, e.g., between about 12 to about 72 hours, or in one embodiment between about 12 to about 48 hours, comprise a dipeptide prodrug element with the structure:

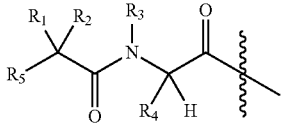

I wherein
$R_1$ and $R_2$ are independently selected from the group consisting of hydrogen and $C_1$-$C_8$ alkyl, ($C_1$-$C_4$ alkyl)$NH_2$, or $R_1$ and $R_2$ are linked through $(CH_2)_p$, wherein p is 2-9;
$R_3$ is $C_1$-$C_8$ alkyl;
$R_4$ is ($C_0$-$C_4$ alkyl)($C_6$-$C_{10}$ aryl)$R_7$;
$R_5$ is $NH_2$; and
$R_7$ is selected from the group consisting of hydrogen, $C_1$-$C_8$ alkyl and ($C_0$-$C_4$ alkyl)OH. with the proviso that both $R_1$ and $R_2$ are not hydrogen.

In addition a prodrug having the dipeptide prodrug element linked to the N-terminal alpha amino acid of the insulin A or B chain peptide and having a $t_{1/2}$, e.g., of about 72 to about 168 hours is provided wherein the dipeptide prodrug element has the structure:

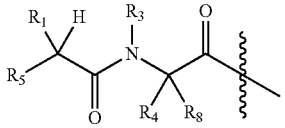

wherein $R_1$ is selected from the group consisting of hydrogen, $C_1$-$C_8$ alkyl and ($C_0$-$C_4$ alkyl)($C_6$-$C_{10}$ aryl)$R_7$;
$R_3$ is $C_1$-$C_{18}$ alkyl;
$R_4$ and $R_8$ are each hydrogen;
$R_5$ is $NHR_6$ or OH;

$R_6$ is H, $C_1$-$C_8$ alkyl, or $R_6$ and $R_1$ together with the atoms to which they are attached form a 4, 5 or 6 member heterocyclic ring; and
$R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo. with the proviso that, if $R_1$ is alkyl or ($C_0$-$C_4$ alkyl)($C_6$-$C_{10}$ aryl)$R_7$, then $R_1$ and $R_5$ together with the atoms to which they are attached form a 4-11 heterocyclic ring.

In one embodiment the dipeptide prodrug element is linked to a side chain amine of an internal amino acid of the insulin peptide wherein the internal amino acid comprises the structure of Formula IV:

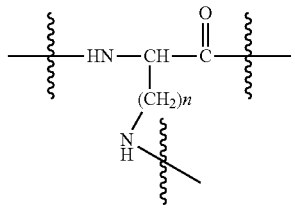

wherein
n is an integer selected from 1 to 4. In one embodiment n is 3 or 4 and in one embodiment the internal amino acid is lysine. In one embodiment the dipeptide prodrug element is linked to a primary amine on a side chain of an amino acid located at position 3, 28, or 29 of the B-chain of the insulin peptide.

In one embodiment an insulin prodrug is provided comprising an
A chain sequence and a B chain sequence, wherein the A chain comprises the sequence GIVEQCCX$_1$SICSLYQLENYCX$_3$ (SEQ ID NO: 3) and the B chain sequence comprises the sequence of X$_{14}$-X$_4$LCGX$_5$X$_6$LVEALX$_7$LVCGERGFX$_8$ (SEQ ID NO: 14) wherein
$X_1$ is selected from the group consisting of threonine and histidine;
In another embodiment an insulin prodrug analog is provided comprising an A chain sequence of GIVEQCCX$_1$SICSLYQLENYCX$_3$ (SEQ ID NO: 3) and a B chain sequence comprising a sequence of Z-X$_4$LCGX$_8$X$_6$LVEALYLVCGERGFF (SEQ ID NO: 4) wherein
Z is a peptide comprising the general structure:

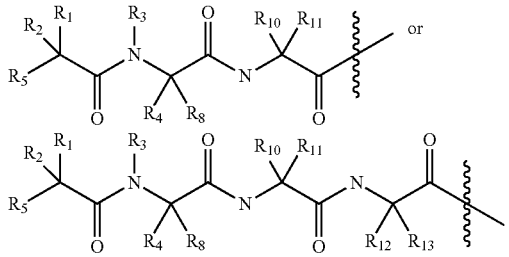

wherein
$X_1$ is selected from the group consisting of threonine and histidine;
$X_3$ is selected from the group consisting of asparagine, glycine, alanine, threonine, or serine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

wherein $R_1$ is selected from the group consisting of H, ($C_1$-$C_6$ alkyl)NH—$R_9$, ($C_1$-$C_6$ alkyl)NH—$S_1$—$R_9$ and $C_1$-$C_8$ alkyl;

$R_2$ and $R_8$ are independently selected from H or $C_1$-$C_4$ alkyl;

$R_4$ is selected from the group consisting of H, ($C_1$-$C_6$ alkyl)NH—$R_9$, ($C_1$-$C_6$ alkyl)NH—$S_1$—$R_9$, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$) $NH_2$, ($C_1$-$C_4$ alkyl)($C_3$-$C_6$ cycloalkyl), ($C_1$-$C_4$ alkyl)($C_6$-$C_{10}$ aryl)$R_7$, $CH_2$($C_5$-$C_9$ heteroaryl), or $R_1$ and $R_2$ together with the atoms to which they are attached form a $C_3$-$C_6$ cycloalkyl;

$R_3$ is selected from the group consisting of $C_1$-$C_8$ alkyl, ($C_1$-$C_4$ alkyl)($C_3$-$C_6$ cycloalkyl), ($C_1$-$C_4$ alkyl)($C_6$-$C_{10}$ aryl) $R_7$ and ($C_1$-$C_4$ alkyl)OH;

$R_5$ is $NH_2$;

$R_7$ is selected from the group consisting of H and OH;

$R_9$ is selected from the group consisting of $C_{16}$-$C_{30}$ acyl, and $C_{16}$-$C_{30}$ alkyl;

$R_{11}$, and $R_{13}$ are each H;

$R_{10}$ and $R_{12}$ are independently selected from the group consisting of ($C_1$-$C_4$ alkyl)COOH, ($C_1$-$C_4$ alkyl)$NH_2$, ($C_1$-$C_4$ alkyl)NHC($NH_2^+$)$NH_2$, and $CH_2$($C_3$—$N_2$ heterocyclic); and $S_1$ is a bond or a spacer consisting of one or two charged amino acids selected from the group consisting of aspartic acid, glutamic acid, cysteic acid, homocysteic acid, homoglutamic acid, arginine, lysine and histidine.

In one embodiment the A chain comprises a sequence of GIVEQCCXiSICSLYQLENYCX$_3$ (SEQ ID NO: 3) and the B chain sequence comprises the sequence Z-$X_9$VNQ$X_4$LCG$X_8$$X_6$LVEALYLVCGERGFFYTPKT (SEQ ID NO: 10) or Z—$X_9$VNQ$X_4$LCG$X_5$$X_6$LVEALYLVCGERGFFYTKPT (SEQ ID NO: 13), wherein $X_1$ is selected from the group consisting of threonine and histidine;

$X_3$ is asparagine, glycine, alanine, threonine, or serine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

$X_9$ is selected from the group consisting of phenylalanine and desamino-phenylalanine.

In accordance with one embodiment a single-chain insulin prodrug analog is provided wherein the carboxy terminus of the human insulin B chain, or a functional analog of the human insulin B chain, is covalently linked to the N-terminus of the human insulin A chain, or functional analog of the human insulin B chain, and further wherein a peptide prodrug moiety having the general structure:

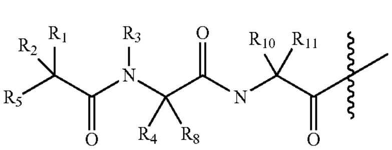

or

-continued 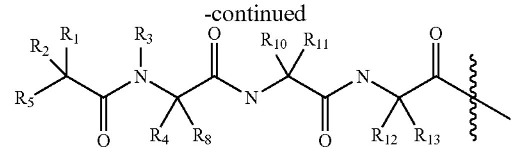 is linked via an amide bond to the N-terminal amine of the single chain insulin analog wherein $R_1$ is ($C_1$-$C_6$ alkyl)NH—$S_1$—$R_9$ or ($C_1$-$C_6$ alkyl)NH—$R_9$;

$R_2$ is H or $C_1$-$C_6$ alkyl:

$R_3$ is selected from the group consisting of $C_1$-$C_6$ alkyl, $C_3$-$C_8$ alkenyl, ($C_0$-$C_4$ alkyl)($C_4$-$C_6$ cycloalkyl), ($C_0$-$C_4$ alkyl)($C_3$-$C_5$ heterocyclic), ($C_0$-$C_4$ alkyl)($C_6$-$C_{10}$ aryl) or $R_4$ and $R_3$ together with the atoms to which they are attached form a 4, 5 or 6 member heterocyclic ring;

$R_4$, and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl ($W_1$)$C_1$-$C_{12}$ alkyl, wherein $W_1$ is a heteroatom selected from the group consisting of N, S and O, or $R_4$ and $R_8$ together with the atoms to which they are attached form a $C_3$-$C_6$ cycloalkyl;

$R_{10}$, $R_{11}$, $R_{12}$, and $R_{13}$ are independently selected from the group consisting of H, $CH_3$, ($C_1$-$C_4$ alkyl)COOH, ($C_1$-$C_4$ alkyl)$NH_2$, ($C_1$-$C_4$ alkyl)NHC($NH_2^+$)$NH_2$ and $CH_2$($C_3$—$N_2$ heterocyclic);

$R_5$ is $NH_2$;

$R_7$ is selected from the group consisting of H, OH, $C_1$-$C_{18}$ alkyl, $C_2$-$C_{18}$ alkenyl, ($C_0$-$C_4$ alkyl)$NH_2$, and ($C_0$-$C_4$ alkyl) OH;

$R_9$ is selected from the group consisting of $C_{18}$-$C_{30}$ acyl, and $C_{16}$-$C_{30}$ alkyl; and $S_1$ is a bond or a spacer consisting of one to six amino acids, wherein said spacer comprises one or more charged amino acids selected from the group consisting of aspartic acid, glutamic acid, cysteic acid, arginine and lysine. In one embodiment $R_1$ is ($C_1$-$C_6$ alkyl)NH—$S_1$—$R_9$ or ($C_1$-$C_6$ alkyl)NH—$R_9$; $R_2$ and $R_8$ are both H; and $R_3$ is $C_1$-$C_6$ alkyl. In a further embodiment $R_9$ is $C_{18}$-$C_{30}$ acyl; $R_{11}$, and $R_{13}$ are each H; $R_{10}$ and $R_{12}$ are independently selected from the group consisting of ($C_1$-$C_4$ alkyl)COOH, ($C_1$-$C_4$ alkyl)$NH_2$, ($C_1$-$C_4$ alkyl)NHC($NH_2^+$)$NH_2$, and $CH_2$($C_3$—$N_2$ heterocyclic); and $S_1$ is a spacer consisting of one or two charged amino acids selected from the group consisting of aspartic acid, glutamic acid, cysteic acid, homocysteic acid, homoglutamic acid, arginine, lysine and histidine. In one embodiment the insulin peptide comprises an A chain sequence of GIVEQCC$X_8$SICSLYQLENYC$X_{21}$ (SEQ ID NO: 3) and a B chain sequence of $R_{22}$-HLCGSHLVEALYLVCGERGF$X_{45}$ (SEQ ID NO: 15), wherein said B chain is linked to said A chain through disulfide linkages;

$R_{22}$ is an amino group, or a 1 to 4 amino acid sequence selected from the group consisting of a FVNQ (SEQ ID NO: 12), FVKQ (SEQ ID NO: 8), VNQ, NQ and Q;

$X_8$ is selected from the group consisting of threonine and histidine;

$X_{21}$ is selected from the group consisting of asparagine, lysine, glycine, alanine; and $X_{45}$ is histidine, tyrosine or phenylalanine. In a further embodiment the A chain comprises a sequence GIVEQC- CTSICSLYQLENYCN-R$_{44}$ (SEQ ID NO: 1) and said B chain comprises a sequence selected from the group consisting of FVNQHLCGSHLVEALYLVCGERGFFYTPKT (SEQ ID NO: 2) FVNQHLCGSHLVEALYL-VCGERGFFYTKPT (SEQ ID NO:9) FVNQHLCG-SHLVEALYLVCGERGFFYTDKT (SEQ ID NO: 5) and FVKQHLCGSHLVEALYLVCGERGFFYTEKT (SEQ ID NO: 6).

In accordance with one embodiment the single-chain insulin analog comprises a compound of the formula: B-P-A, wherein: B represents the B-chain of human insulin or one of the functional or prodrug analogs of a B chain as disclosed herein, A represents the A chain of human insulin or one of the functional analogs of an A chain as disclosed herein, and P represents a linker, including a peptide linker, that covalently joins the A chain to the B chain. In one embodiment the linker is a peptide linker of about 5 to about 18, or about 10 to about 14, or about 4 to about 8, or about 6 amino acids. In one embodiment the B chain is linked to the A chain via peptide linker of 4-12 or 4-8 amino acids. In one embodiment the peptide linker of the single chain analog is selected from the group consisting of GYGSSS-RRAPQT; SEQ ID NO: 23, GYGSSSRR (SEQ ID NO: 61), GYGSSSOR (SEQ ID NO: 63), GAGSSSRR (SEQ ID NO: 66), or GAGSSSRRAPQT (SEQ ID NO: 64) or a sequence that differs from SEQ ID NOs: 23 or 66 by 1 to 3 amino acid substitutions, or 1 to 2 amino acid substitutions. Optionally, the linking moiety of the single chain analogs can also serve as a site for the attachment of the peptide prodrug element, and in one embodiment the linking moiety is a peptide linker that comprises an amino acid having a side chain group suitable for attaching the peptide prodrug element of the present invention via an amide linkage.

In accordance with one embodiment the peptide linker is 5 to 18 amino acids in length and comprises a sequence selected from the group consisting of: Gly-Gly-Gly-Pro-Gly-Lys-Arg (SEQ ID NO: 22), Gly-Tyr-Gly-Ser-Ser-Ser-Arg-Arg-Ala-Pro-Gln-Thr (SEQ ID NO: 23), Arg-Arg-Gly-Pro-Gly-Gly-Gly (SEQ ID NO: 32), Gly-Gly-Gly-Gly-Gly-Lys-Arg (SEQ ID NO: 24), Arg-Arg-Gly-Gly-Gly-Gly-Gly (SEQ ID NO: 25), Gly-Gly-Ala-Pro-Gly-Asp-Val-Lys-Arg (SEQ ID NO: 26), Arg-Arg-Ala-Pro-Gly-Asp-Val-Gly-Gly (SEQ ID NO: 27), Gly-Gly-Tyr-Pro-Gly-Asp-Val-Lys-Arg (SEQ ID NO: 28), Arg-Arg-Tyr-Pro-Gly-Asp-Val-Gly-Gly (SEQ ID NO: 29), Gly-Gly-His-Pro-Gly-Asp-Val-Lys-Arg (SEQ ID NO: 30) and Arg-Arg-His-Pro-Gly-Asp-Val-Gly-Gly (SEQ ID NO: 31). In one embodiment the peptide linker is 7 to 12 amino acids in length and comprises the sequence Gly-Gly-Gly-Pro-Gly-Lys-Arg (SEQ ID NO: 22) or Gly-Tyr-Gly-Ser-Ser-Ser-Arg-Arg-Ala-Pro-Gln-Thr (SEQ ID NO: 23).

In a further embodiment the peptide linker comprises a sequence selected from the group consisting of AGRGSGK (SEQ ID NO: 35), AGLGSGK (SEQ ID NO: 36), AGMGSGK (SEQ ID NO: 37), ASWGSGK (SEQ ID NO: 38), TGLGSGQ (SEQ ID NO: 39), TGLGRGK (SEQ ID NO: 40). TGLGSGK (SEQ ID NO: 41). HGLYSGK (SEQ ID NO: 42), KGLGSGQ (SEQ ID NO: 43), VGLMSGK (SEQ ID NO: 44), VGLSSGQ (SEQ ID NO: 45), VGLYSGK (SEQ ID) NO: 46), VOLSSGK (SEQ ID NO: 47), VGMSSGK (SEQ ID) NO: 48), VWSSSGK (SEQ II) NO: 49). VGSSSGK (SEQ ID NO: 50), VGMSSGK (SEQ ID NO: 51), TGLGSGR (SEQ ID NO: 52), TGLGKGQ (SEQ ID NO: 53), KGLSSGQ (SEQ ID NO: 54), VKLSSGQ (SEQ ID NO: 55), VGLKSGQ (SEQ ID NO: 56), TGLGKGQ (SEQ ID NO: 57) SRVSRRSR (SEQ ID NO: 60), GYGSSSRRAPQT (SEQ ID NO: 23) and VGL-SKGQ (SEQ ID NO: 58). In one embodiment the linker comprises GSSSRRAP (SEQ ID NO: 62) or SRVSRRSR (SEQ ID NO: 60).

In one embodiment the single-chain insulin analog has the amino acid sequence: Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-Thr-Gly-Ile-Val-Glu-Gln-Cys-Cys-Thr-Ser-Ile-Cys-Ser-Leu-Tyr-Gln-Leu-Glu-Asn-Tyr-Cys-Asn (SEQ ID NO: 33) or Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-Thr-Gln-Pro-Leu-Ala-Leu-Glu-Gly-Ser-Leu-Gln-Lys-Arg-Gly-Ile-Val-Glu-Gln-Cys-Cys-Thr-Ser-Ile-Cys-Ser-Leu-Tyr-Gln-Leu-Glu-Asn-Tyr-Cys-Asn (SEQ ID NO: 34).

The insulin prodrugs disclosed herein may be part of a dimer, trimer or higher order multimer comprising at least two, three, or more peptides bound via a linker, wherein at least one or both peptides comprises a peptide prodrug element linked to the insulin peptide. The dimer may be a homodimer or heterodimer, comprising peptides selected from the group consisting of native insulin, native IGF-1, native IGF-II and insulin analog peptides as disclosed herein. In one embodiment, the linker is selected from the group consisting of a bifunctional thiol crosslinker and a bi-functional amine crosslinker. In certain embodiments, the linker is PEG, e.g., a 5 kDa PEG, 20 kDa PEG. In some embodiments, the linker is a disulfide bond.

For example, each monomer of the dimer may comprise a Cys residue (e.g., a terminal or internally positioned Cys) and the sulfur atom of each Cys participates in the formation of the disulfide bond between the insulin monomers. Each monomer of the dimer represents a heterodimer of an A and B chain. The A and B chain are either linked via disulfide bonds or are prepared as single chain peptides. In some aspects of the invention, the insulin peptide monomers (each comprising an insulin A and B chain) are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together. A conjugate moiety may be covalently linked to any of the insulin peptides described herein, including a dimer, trimer or higher order multimer.

The prodrugs disclosed herein can be further modified to improve the peptide's solubility in aqueous solutions at physiological pH, while enhancing the effective duration of the peptide by preventing renal clearance of the peptide. Peptides are easily cleared because of their relatively small molecular size when compared to plasma proteins. Increasing the molecular weight of a peptide above 40 kDa exceeds the renal threshold and significantly extends duration in the plasma. Accordingly, in one embodiment the peptide prodrugs are further modified to comprise a covalently linked hydrophilic moiety. In one embodiment the hydrophilic moiety is a plasma protein, polyethylene oxide chain or the Fc portion of an immunoglobin. Therefore, in one embodiment the presently disclosed prodrugs are further modified to comprise one or more hydrophilic groups covalently linked to the side chains of amino acids of the insulin peptide.

In accordance with one embodiment the insulin prodrugs disclosed herein are further modified by linking a hydrophilic moiety to either the N-terminal amino acid of the B chain or to the side chain of a lysine amino acid located at the carboxy terminus of the B chain, including for example, at position 28 of SEQ ID NO: 9 or at position 29 of SEQ ID NO: 2. In one embodiment a single-chain insulin prodrug analog is provided wherein one of the amino acids of the peptide linker is modified by linking a hydrophilic moiety to the side chain of the peptide linker. In one embodiment the modified amino acid is cysteine, lysine or acetyl phenylalanine.

In another embodiment the insulin prodrug analogs disclosed herein are further modified by the addition of a modified amino acid to the carboxy terminus of the B chain of the insulin prodrug, wherein the C-terminally added amino acid is modified to comprise a hydrophilic moiety linked to the amino acid. In one embodiment the amino acid added to the C-terminus is a modified cysteine, lysine or acetyl phenylalanine In one embodiment a peptide prodrug element as disclosed herein is linked to the side chain amine of a lysine residue that has been added to the C-terminus of the B chain. In one embodiment the hydrophilic moiety is selected from the group consisting of a plasma protein, polyethylene oxide chain and an Fc portion of an immunoglobin.

In one embodiment the hydrophilic group is a polyethylene oxide chain, and in one embodiment two or more polyethylene oxide chains are covalently attached to two or more amino acid side chains of the insulin prodrug analog. In accordance with one embodiment the hydrophilic moiety is covalently attached to an amino acid side chain of an insulin prodrug analog disclosed herein at a position selected from the group consisting of A9, A14, A15, B3, B22, B28, B29 and the C-terminus or N-terminus of the B chain. For insulin prodrug analogs having multiple polyethylene oxide chains, the polyethylene oxide chains can be attached at the N-terminal amino acid of the B chain or to the side chain of a lysine amino acid located at the carboxy terminus of the B chain, or by the addition of a single amino acid at the C-terminus of the peptide wherein the added amino acid has a polyethylene oxide chain linked to its side chain. In accordance with one embodiment the polyethylene oxide chain or other hydrophilic moiety is linked to the side chain of one of the two amino acids comprising the dipeptide prodrug element. In one embodiment the peptide prodrug element comprises a lysine (in the D or L configuration) with a polyethylene oxide chain attached to the side chain amine of the lysine.

Linkage of Hydrophilic Moieties

In one embodiment the solubility of the insulin analogs disclosed herein are enhanced by the covalent linkage of a hydrophilic moiety to the peptide. Hydrophilic moieties can be attached to the insulin analogs under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane and 5-pyridyl. If attached to the peptide by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1, 3-dioxolane, poly-1,3,6-trioxane, ethylene/maleic anhydride copolymer, poly (.beta.-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof.

The hydrophilic moiety, e.g., polyethylene glycol chain in accordance with one embodiment has a molecular weight selected from the range of about 500 to about 40,000 Daltons. In one embodiment the hydrophilic moiety, e.g. PEG, has a molecular weight selected from the range of about 500 to about 5,000 Daltons, or about 1,000 to about 5,000 Daltons. In another embodiment the hydrophilic moiety, e.g., PEG, has a molecular weight of about 10,000 to about 20,000 Daltons. In yet other exemplary embodiments the hydrophilic moiety, e.g., PEG, has a molecular weight of about 20,000 to about 40,000 Daltons.

In one embodiment dextrans are used as the hydrophilic moiety. Dextrans are polysaccharide polymers of glucose subunits, predominantly linked by al-6 linkages. Dextran is available in many molecular weight ranges, e.g., about 1 kDa to about 100 kDa, or from about 5, 10, 15 or 20 kDa to about 20, 30, 40, 50, 60, 70, 80 or 90 kDa.

Linear or branched polymers are contemplated. Resulting preparations of conjugates may be essentially monodisperse or polydisperse, and may have about 0.5, 0.7, 1, 1.2, 1.5 or 2 polymer moieties per peptide. In one embodiment the hydrophilic moiety is linked to an amino acid of the peptide prodrug element.

In accordance with one embodiment, the insulin prodrug analogs disclosed herein are further modified by amino acid substitutions, wherein the substituting amino acid comprises a side chain suitable for crosslinking with hydrophilic moieties, including for example, polyethylene glycol. In one embodiment the amino acid at the position of the insulin prodrug analog where the hydrophilic moiety is to be linked is substituted (or added at the C-terminus) with a natural or synthetic amino acid to introduce, or allow for ease in attaching, the hydrophilic moiety. For example, in one embodiment a native amino acid at position selected from A5, A8, A9, A10, A12, A14, A15, A17, A18, B1, B2, B3, B4, B5, B13, B14, B17, B21, B22, B26, B27, B28, B29 and B30 is substituted with a lysine, cysteine or acetyl phenylalanine residue (or a lysine, cysteine or acetyl phenylalanine residue is added to the C-terminus) to allow for the covalent attachment of a polyethylene glycol chain.

In one embodiment the insulin prodrug analog has a single cysteine residue added to the carboxy terminus of the B chain, or the insulin prodrug analog is substituted with at least one cysteine residue, wherein the side chain of the cysteine residue is further modified with a thiol reactive reagent, including for example, maleimido, vinyl sulfone, 2-pyridylthio, haloalkyl, and haloacyl. These thiol reactive reagents may contain carboxy, keto, hydroxyl, and ether groups as well as other hydrophilic moieties such as polyethylene glycol units. In an alternative embodiment, the insulin prodrug analog has a single lysine residue added to the carboxy terminus of the B chain, or the insulin prodrug analog is substituted with lysine, and the side chain of the substituting lysine residue is further modified using amine reactive reagents such as active esters (succinimido, anhydride, etc) of carboxylic acids or aldehydes of hydrophilic moieties such as polyethylene glycol.

In those embodiments wherein the insulin prodrug analog comprises a polyethylene glycol chain, the polyethylene glycol chain may be in the form of a straight chain or it may be branched. In accordance with one embodiment the polyethylene glycol chain has an average molecular weight selected from the range of about 20,000 to about 60,000 Daltons. Multiple polyethylene glycol chains can be linked to the insulin prodrug analog to provide an insulin prodrug analog with optimal solubility and blood clearance properties. In one embodiment the insulin prodrug analog is linked to a single polyethylene glycol chain that has an average molecular weight selected from the range of about 20,000 to about 60,000 Daltons. In another embodiment the insulin prodrug analog is linked to two polyethylene glycol chains wherein the combined average molecular weight of the two chains is selected from the range of about 40,000 to about 80,000 Daltons. In one embodiment a single polyethylene glycol chain having an average molecular weight of 20,000 or 60,000 Daltons is linked to the insulin prodrug analog. In another embodiment a single polyethylene glycol chain is linked to the insulin prodrug analog and has an average molecular weight selected from the range of about 40,000 to about 50,000 Daltons. In one embodiment two polyethylene glycol chains are linked to the insulin prodrug analog wherein the first and second polyethylene glycol chains each have an average molecular weight of 20,000 Daltons. In another embodiment two polyethylene glycol chains are linked to the insulin prodrug analog wherein the first and second polyethylene glycol chains each have an average molecular weight of 40,000 Daltons.

In a further embodiment an insulin prodrug analog comprising two or more polyethylene glycol chains covalently bound to the peptide is provided, wherein the total molecular weight of the polyethylene glycol chains is about 40,000 to about 60,000 Daltons. In one embodiment the pegylated insulin prodrug analog comprises a polyethylene glycol chain linked to one or more amino acids selected from the N-terminus of the B chain and/or position 28 of SEQ ID NO: 9 or at position 29 of SEQ ID NO: 2, wherein the combined molecular weight of the PEG chain(s) is about 40,000 to about 80,000 Daltons.

In accordance with one embodiment, an insulin prodrug analog is provided wherein a linear amino acid sequence representing the Fc portion of an immunoglobin molecule has been covalently linked to an amino acid side chain of an insulin prodrug analog disclosed herein to improve the solubility, stability and/or pharmacokinetics of the insulin prodrug analog. For example, the amino acid sequence representing the Fc portion of an immunoglobin molecule can be covalently bound to the N-terminus of the B chain or the C-terminus of the A or B chain, or the C-terminus of an A or B chain that has been terminally extended. For example, the amino acid sequence representing the Fc portion of an immunoglobin molecule can be covalently bound to the C-terminus of the B chain, including for example linkage to an amino acid corresponding to position 28 of SEQ ID NO: 9 or at position 29 of SEQ ID NO: 2. The Fc portion is typically one isolated from IgG, but the Fc peptide fragment from any immunoglobin should function equivalently.

In a specific aspect of the invention, the insulin prodrug analog is modified to comprise an alkyl or acyl group by direct alkylation or acylation of an amine, hydroxyl, or thiol of a side chain of an amino acid of the insulin prodrug analog, including for example the A or B amino acid of the peptide prodrug element. In one embodiment, the insulin prodrug analog is directly acylated through the side chain amine, hydroxyl, or thiol of an amino acid. In one embodiment, acylation is at one or more positions selected from A9, A14, A15, B3, B22, B28 or B29 or an amino acid of the peptide prodrug element. In this regard, the acylated insulin prodrug analog can comprise an A chain amino acid sequence of SEQ ID NO: 3 and a B chain of SEQ ID NO: 5, or a modified amino acid sequence of SEQ ID NO: 3 and/or SEQ ID NO: 5 with at least one of the amino acids at positions A9, A14, A15, B22, B28 or B29 modified to any amino acid comprising a side chain amine, hydroxyl, or thiol. In some specific embodiments, the direct acylation of the insulin prodrug analog occurs through the side chain amine, hydroxyl, or thiol of the amino acid at position B28 or B29 or the A or B amino acid of the peptide prodrug element. In one further embodiment the insulin prodrug analog comprises an acyl group of a carboxylic acid with 18-24 carbon atoms bound to the epsilon-amino group of a Lys present at position B28 or B29 or the A or B amino acid of the peptide prodrug element. In one embodiment a single-chain insulin prodrug analog is provided wherein one of the amino acids of the peptide linker is modified to comprise an acyl group by direct acylation of an amine, hydroxyl, or thiol of a side chain of an amino acid of the peptide linker. In accordance with one embodiment the peptide linker of the single-chain insulin analog is selected from the group consisting of AGRGSGK (SEQ ID NO: 35), AGLGSGK (SEQ ID NO: 36), AGMGSGK (SEQ ID NO: 37), ASWGSGK (SEQ ID NO: 38), TGLGSGQ (SEQ ID NO: 39), TGLGRGK (SEQ ID NO: 40), TGLGSGK (SEQ ID NO: 41), HGLYSGK (SEQ ID NO: 42), KGLGSGQ (SEQ ID NO: 43), VGLMSGK (SEQ ID NO: 44), VGLSSGQ (SEQ ID NO: 45), VGLYSGK (SEQ ID NO: 46), VGLSSGK (SEQ ID NO: 47), VGMSSGK (SEQ ID NO: 48), VWSSSGK (SEQ ID NO: 49), VGSSSGK (SEQ ID NO: 50), VGMSSGK (SEQ ID NO: 51), TGLGSGR (SEQ ID NO: 52), TGLGKGQ (SEQ ID NO: 53), KGLSSGQ (SEQ ID NO: 54), VKLSSGQ (SEQ ID NO: 55), VGLKSGQ (SEQ ID NO: 56), TGLGKGQ (SEQ ID NO: 57) and VGLSKGQ (SEQ ID NO: 58) wherein at least one lysine residue in the A-chain, in the B-chain or in the connecting peptide has been chemically modified by acylation. In one embodiment the acylating group comprises a 1-5, 10-12 or 18-24 carbon chain. In one embodiment at least one lysine residue in the linking peptide of a single chain insulin analog is linked to a peptide prodrug element disclosed herein via an amide linkage between A-B-C and the side chain amine of the linking peptide.

In accordance with one embodiment the insulin prodrug analogs as disclosed herein are further modified to link an additional compound to the peptide prodrug element of the analog. In one embodiment the side chain of an amino acid comprising the dipeptide prodrug element (A-B of A-B-C) is pegylated, acylated or alkylated. In one embodiment the dipeptide (A-B) is acylated with a group comprising a 18-24 carbon chain. In one embodiment the dipeptide (A-B) is pegylated with a 40-80 KDa polyethylene glycol chain. In one embodiment the dipeptide (A-B) of the peptide prodrug element is pegylated and the insulin peptide linked to the peptide prodrug element is acylated, including, for example, acylation at the C-terminal lysine (B28 or B29) of the B chain. In accordance with one embodiment a hydrophilic moiety or a sequestering macromolecule is covalently linked to the $R_1$ side chain of the peptide prodrug element comprising the general structure:

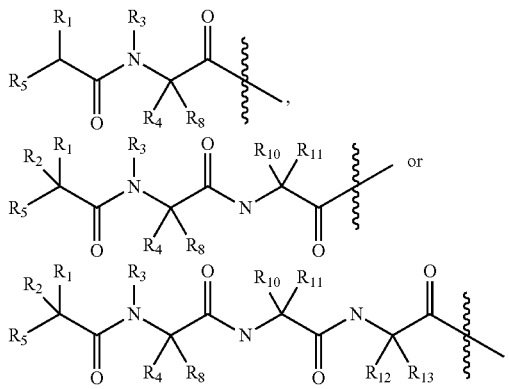

wherein $R_1$ is selected from the group consisting of $(C_1\text{-}C_4$ alkyl$)$OH, $(C_1\text{-}C_4$ alkyl$)$SH, and $(C_1\text{-}C_4$ alkyl$)$NH$_2$. In one embodiment $R_1$ is $(C_3\text{-}C_4$ alkyl$)$NH$_2$. Sequestering macromolecules are known to those skilled in the art and include dextrans and large molecular weight polyethylene glycol (i.e., greater than or equal to 80 KDa) By linking the sequestering macromolecule to the dipeptide moiety, the prodrug will remain sequestered, while the active insulin peptide is slowly released based on the kinetics of the cleavage of the dipeptide amide bond. In one embodiment the peptide prodrug element further comprises a second peptide covalently linked to the N-terminal amine of the peptide prodrug element, wherein the second peptide is cleaved from the peptide prodrug element only upon exposure to an enzyme present in mammalian sera. Furthermore, the second peptide is selected and linked to the peptide prodrug element in a manner that cleavage of the second peptide leaves the peptide prodrug element linked to the insulin peptide and retaining the ability to spontaneously chemically cleave from the insulin peptide to form a diketopiperazine. In one embodiment the second peptide is a peptide that is cleaved by dipeptidyl peptidase IV (DPP-IV), including for example a dipeptide of Arg-Pro, Lys-Pro or Glu-Pro. In one embodiment the peptide prodrug element comprises the structure:

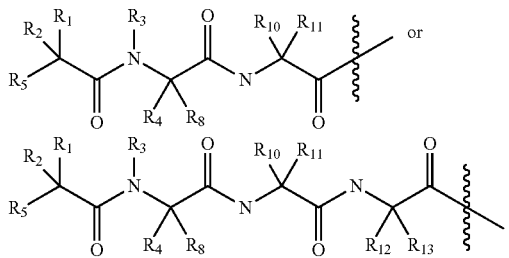

The present disclosure also encompasses other conjugates in which insulin prodrug analogs of the invention are linked, optionally via covalent bonding, and optionally via a linker, to a conjugate. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

Exemplary conjugates include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising an insulin prodrug analog of the present disclosure and a plasma protein, wherein the plasma protein is selected from the group consisting of albumin, transferin and fibrinogen. In one embodiment the plasma protein moiety of the conjugate is albumin or transferin. In one embodiment, the linker comprises a chain of atoms from 1 to about 60, or 1 to 30 atoms or longer, 2 to 5 atoms, 2 to 10 atoms, 5 to 10 atoms, or 10 to 20 atoms long. In one embodiment, the chain atoms are all carbon atoms. In one embodiment, the chain atoms in the backbone of the linker are selected from the group consisting of C, O, N, and S. Chain atoms and linkers may be selected according to their expected solubility (hydrophilicity) so as to provide a more soluble conjugate. In one embodiment, the linker provides a functional group that is subject to cleavage by an enzyme or other catalyst or hydrolytic conditions found in the target tissue or organ or cell. In one embodiment, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

Acylation and Alkylation

In accordance with one embodiment, the insulin analogs disclosed herein are modified to comprise an acyl group or alkyl group. Acylation or alkylation can increase the half-life of the insulin analogs in circulation. Acylation or alkylation can advantageously delay the onset of action and/or extend the duration of action at the insulin and/or IGF-1 receptors and/or improve resistance to proteases such as DPP-IV and/or improve solubility. Insulin analogs may be acylated or alkylated at the same amino acid position where a hydrophilic moiety is linked, or at a different amino acid position.

In one embodiment, the invention provides an insulin analog modified to comprise an acyl group or alkyl group covalently linked to the amino acid at a position corresponding to A10, B28, B29 of native insulin, or at the C-terminus or N-terminus of the A or B chain. The Insulin analog may further comprise a spacer between the Insulin analog amino acid and the acyl group or alkyl group. In one embodiment, the acyl group is a fatty acid or bile acid, or salt thereof, e.g. a C4 to C30 fatty acid, a C8 to C24 fatty acid, cholic acid, a C4 to C30 alkyl, a C8 to C24 alkyl, or an alkyl comprising a steroid moiety of a bile acid. The spacer is any moiety with suitable reactive groups for attaching acyl or alkyl groups. In exemplary embodiments, the spacer comprises an amino acid, a dipeptide, or a tripeptide, or a hydrophilic bifunctional spacer. In one embodiment, the spacer is selected from the group consisting of: Trp, Glu, Asp, Cys and a spacer comprising NH$_2$(CH$_2$CH$_2$O)n(CH$_2$)mCOOH, wherein m is any integer from 1 to 6 and n is any integer from 2 to 12. Such acylated or alkylated insulin peptides may also further comprise a hydrophilic moiety, optionally a polyethylene glycol. Any of the foregoing insulin analogs may comprise two acyl groups or two alkyl groups, or a combination thereof.

Acylation can be carried out at any positions within the insulin analog, provided that insulin analog insulin agonist activity is retained. The acyl group can be covalently linked directly to an amino acid of the insulin analog, or indirectly to an amino acid of the insulin analog via a spacer, wherein the spacer is positioned between the amino acid of the insulin peptide and the acyl group. In a specific aspect of the invention, the insulin analog is modified to comprise an acyl group by direct acylation of an amine, hydroxyl, or thiol of a side chain of an amino acid of the insulin peptide. In one embodiment, the insulin analog is directly acylated through the side chain amine, hydroxyl, or thiol of an amino acid. In one embodiment, acylation is at a position corresponding to A10, B28, B29 of native insulin, or at the C-terminus or N-terminus of the A or B chain. In this regard, the acylated insulin analog can comprise the amino acid sequence of SEQ ID NO: 9 and SEQ ID NO: 2, or a modified amino acid sequence thereof comprising one or more of the amino acid modifications described herein, with at least one of the amino acids at a position corresponding to B3, B28, B29 of native insulin, or at the C-terminus or N-terminus of the A or B chain modified to any amino acid comprising a side chain amine, hydroxyl, or thiol. In some specific embodiments, the direct acylation of the insulin peptide occurs through the side chain amine, hydroxyl, or thiol of the amino acid at a position corresponding to B3, B28, B29 of native insulin. In accordance with one embodiment one of the amino acid side chains of the peptide prodrug element is acylated.

In one embodiment, the amino acid to be acylated is an amino acid of Formula IV:

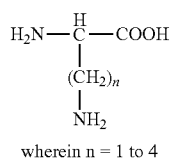

[Formula IV]

wherein n = 1 to 4

In some exemplary embodiments, the amino acid of Formula IV, is the amino acid wherein n is 4 (Lys) or n is 3 (Orn).

In other embodiments, the amino acid comprising a side chain hydroxyl is an amino acid of Formula V:

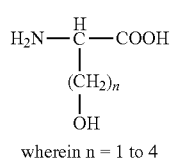

[Formula V]

wherein n = 1 to 4

In some exemplary embodiments, the amino acid of Formula V is the amino acid wherein n is 1 (Ser).

In yet other embodiments, the amino acid comprising a side chain thiol is an amino acid of Formula VI:

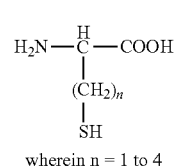

[Formula VI]

wherein n = 1 to 4

In some exemplary embodiments, the amino acid of Formula VI is the amino acid wherein n is 1 (Cys).

In some exemplary embodiments, the insulin analog is modified to comprise an acyl group by acylation of an amine, hydroxyl, or thiol of a spacer, which spacer is attached to a side chain of an amino acid at position B3, B28 or B29 (according to the amino acid numbering of wild type insulin) or attached to the A or B amino acid of the peptide prodrug element. The amino acid to which the spacer is attached can be any amino acid comprising a moiety which permits linkage to the spacer. For example, an amino acid comprising a side chain NH2, —OH, or —COOH (e.g., Lys, Orn, Ser, Asp, or Glu) is suitable. In one embodiment, the spacer is an amino acid comprising a side chain amine, hydroxyl, or thiol, or a dipeptide or tripeptide comprising an amino acid comprising a side chain amine, hydroxyl, or thiol.

When acylation occurs through an amine group of a spacer the acylation can occur through the alpha amine of the amino acid or a side chain amine. In the instance in which the alpha amine is acylated, the spacer amino acid can be any amino acid. For example, the spacer amino acid can be a hydrophobic amino acid, e.g., Gly, Ala, Val, Leu, Ile, Trp, Met, Phe, Tyr. Alternatively, the spacer amino acid can be an acidic residue, e.g., Asp and Glu. In the instance in which the side chain amine of the spacer amino acid is acylated, the spacer amino acid is an amino acid comprising a side chain amine, e.g., an amino acid of Formula I (e.g., Lys or Orn). In this instance, it is possible for both the alpha amine and the side chain amine of the spacer amino acid to be acylated, such that the insulin peptide is diacylated. The present disclosure further contemplates diacylated insulin analogs.

When acylation occurs through a hydroxyl group of a spacer, the amino acid or one of the amino acids of the dipeptide or tripeptide can be an amino acid of Formula II. In a specific exemplary embodiment, the amino acid is Ser.

When acylation occurs through a thiol group of a spacer, the amino acid or one of the amino acids of the dipeptide or tripeptide can be an amino acid of Formula III. In a specific exemplary embodiment, the amino acid is Cys.

In one embodiment, the spacer comprises a hydrophilic bifunctional spacer. In a specific embodiment, the spacer comprises an amino poly(alkyloxy)carboxylate. In this regard, the spacer can comprise, for example, NH$_2$(CH$_2$CH$_2$O)$_n$(CH$_2$)$_m$COOH, wherein m is any integer from 1 to 6 and n is any integer from 2 to 12, such as, e.g., 8-amino-3,6-dioxaoctanoic acid, which is commercially available from Peptides International, Inc. (Louisville, Ky.).

Suitable methods of peptide acylation via amines, hydroxyls, and thiols are known in the art. See, for example, Miller, *Biochem Biophys Res Commun* 218: 377-382 (1996); Shimohigashi and Stammer, *Int J Pept Protein Res* 19: 54-62

(1982); and Previero et al., *Biochim Biophys Acta* 263: 7-13 (1972) (for methods of acylating through a hydroxyl); and San and Silvius, *J Pept Res* 66: 169-180 (2005) (for methods of acylating through a thiol); *Bioconjugate Chem.* "Chemical Modifications of Proteins: History and Applications" pages 1, 2-12 (1990); Hashimoto et al., *Pharmacuetical Res.* "Synthesis of Palmitoyl Derivatives of Insulin and their Biological Activity" Vol. 6, No: 2 pp. 171-176 (1989).

The acyl group of the acylated insulin peptide can be of any size, e.g., any length carbon chain, and can be linear or branched. In some specific embodiments of the invention, the acyl group is a C4 to C30 fatty acid. For example, the acyl group can be any of a C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In one embodiment, the acyl group is a C18 to C20 fatty acid, e.g., a C18 fatty acid, C19 fatty acid or a C20 fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

In a specific embodiment, the insulin analog comprises a cholesterol acid, which is linked to a Lys residue of the insulin analog through an alkylated des-amino Cys spacer, i.e., an alkylated 3-mercaptopropionic acid spacer. The alkylated des-amino Cys spacer can be, for example, a des-amino-Cys spacer comprising a dodecaethylene glycol moiety. In one embodiment, the insulin analog comprises the structure:

specific embodiments the hydrophilic moiety can comprise a polyethylene glycol (PEG) chain. The incorporation of a hydrophilic moiety can be accomplished through any suitable means, such as any of the methods described herein.

Alternatively, the acylated insulin peptide can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In accordance with one embodiment, the insulin analog is modified to comprise an alkyl group which is attached to the insulin analog via an ester, ether, thioether, amide, or alkyl amine linkage for purposes of prolonging half-life in circulation and/or delaying the onset of and/or extending the duration of action and/or improving resistance to proteases such as DPP-IV.

The alkyl group of the alkylated insulin peptide can be of any size, e.g., any length carbon chain, and can be linear or branched. In one embodiment of the invention, the alkyl group is a C1 to C30 alkyl. For example, the alkyl group can be any of a C1 alkyl, C2 alkyl, C3 alkyl, C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In one embodiment, the alkyl group is a C18 to C20 alkyl, e.g., a C18 alkyl, C19 alkyl or a C20 alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

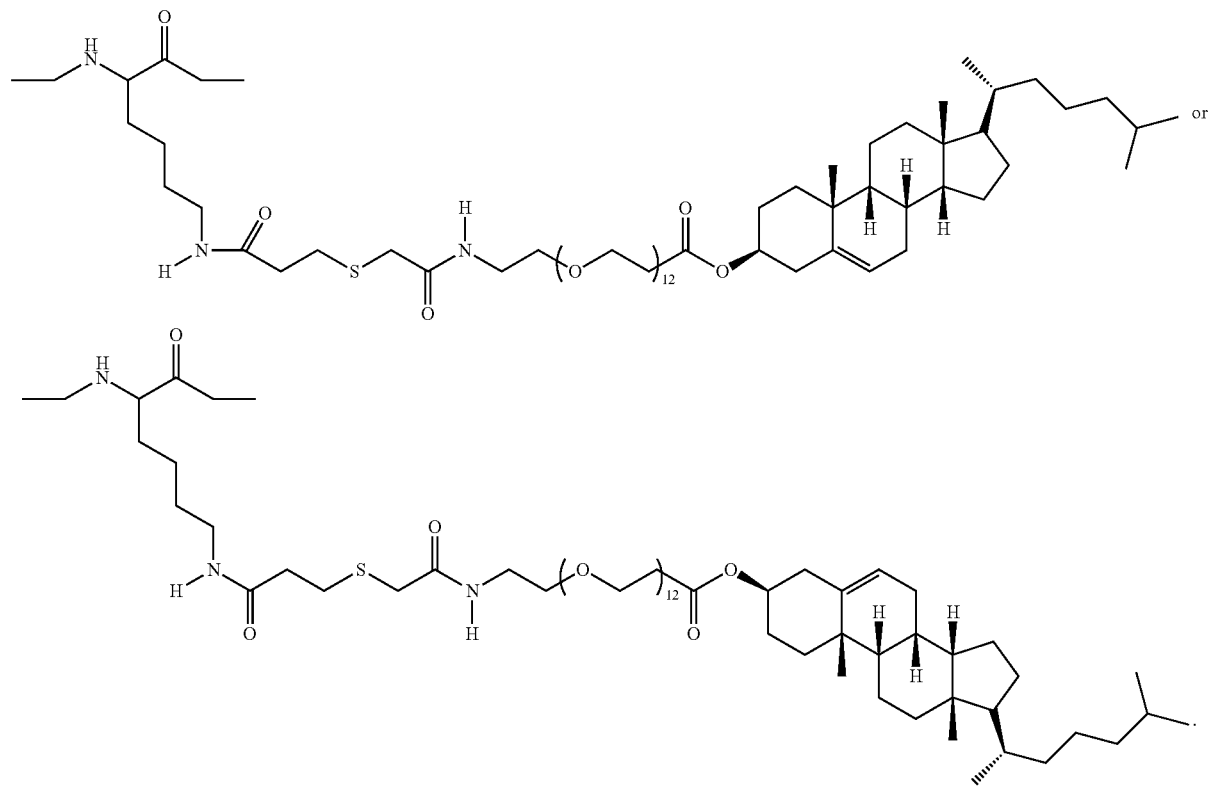

The acylated insulin analogs described herein can be further modified to comprise a hydrophilic moiety. In some In accordance with some embodiments the peptide prodrug element can be further modified to comprise a hydrophilic moiety. In some embodiments the hydrophilic moiety is a polyethylene glycol chain. In accordance with some embodiments a polyethylene glycol chain of 40 k or higher is covalently bound to the side chain of the A or B amino acid of the peptide prodrug element. In another embodiment the dipeptide (A-B) of the peptide prodrug element is additionally or alternatively acylated or alkylated with a fatty acid or bile acid, or salt thereof, e.g. a C4 to C30 fatty acid, a C18 to C24 fatty acid, cholic acid, a C18 to C30 alkyl, a C18 to C24 alkyl, or an alkyl comprising a steroid moiety of a bile acid. The 'A' amino acid of the dipeptide prodrug element can include, for example, d-lysine covalently bound to an acyl or alkyl group through its side chain amino group, or d-cysteine covalently bound to a PEG molecule through its side chain sulfhydryl group. The dipeptide prodrug element can be directly bound to the hydrophilic moiety, acyl group, or alkyl group, or bound to the hydrophilic moiety, acyl group, or alkyl group through a spacer, as described herein. Alternatively, the dipeptide prodrug element can be linked to a depot protein such as dextran or a large PEG molecule (greater or equal to 80,000 daltons) that serves to sequester the prodrug at an injection site until cleavage of the dipeptide releases the active insulin peptide (Q).

Effect of Dipeptide Prodrug Element Structure on Cleavage Rate

As previously described herein, the rate of cleavage of the dipeptide prodrug element A-B from the bioactive peptide (e.g., insulin peptide (Q)), and thus activation of the prodrug, depends on the structure (including N-alkylation, number of substituents, length or bulkiness), and stereochemistry of the amino acids of the dipeptide prodrug element. The rate of cleavage of the dipeptide prodrug element A-B from the (e.g., insulin peptide (Q)) also depends on the steric hindrance, nucleophilicity, and stability of the leaving group of Q during diketopiperazine formation. Some of these structural features are described in Category I, Category II, and Category III below, which form part of the invention. Explicitly excluded from any of these categories are peptide sequences disclosed in Int'l Application No. PCT/US2009/68745, filed Dec. 18, 2009 or its sequence listing, and sub-categories of (1) dipeptide prodrug elements, (2) A amino acids, and/or (3) B amino acids disclosed in Int'l Application No. PCT/US2009/68745, filed Dec. 18, 2009, to the extent they fall completely within and/or overlap with a portion of any of the sub-categories described herein, and only to the extent necessary to confer novelty on claimed subject matter.

In accordance with one embodiment an auto-cleaving dipeptide element (A-B) is covalently linked to the insulin peptide (Q) through an amide bond between A-B-C and an aliphatic amino group of Q. For example, the aliphatic amino group can be the alpha amino group on the N-terminal amino acid of the A chain or the B chain. Alternatively, the aliphatic amino group can be an aliphatic amino group on a side chain of Q. In one embodiment A-B-C is linked to the side chain amine of a lysine, including for example at position B29 of the B chain sequence FVNQHLCGSHLVEALYLVCGERGFFYTPKT (SEQ ID NO: 2) or at position B28 of the B chain sequence FVNQHLCGSHLVEALYLVCGERGFFYTKPT (SEQ ID NO: 9).

In one embodiment Q is an insulin peptide comprising an A chain and a B chain wherein the A chain comprises the sequence GIVEQCCX$_1$SICSLYQLENYCX$_3$ (SEQ ID NO: 3) and the B chain comprises a sequence selected from the group consisting of FVNQHLCGSHLVEALYL-VCGERGFFYTPKT (SEQ ID NO: 2) FVNQHLCG-SHLVEALYLVCGERGFFYTKPT (SEQ ID NO: 9) FVN-QHLCGSHLVEALYLVCGERGFFYTDKT (SEQ ID NO: 5) and FVKQHLCGSHLVEALYLVCGERGFFYTEKT (SEQ ID NO: 6).

Category I: Composition of Amino Acid B of the Dipeptide Prodrug Element

In some embodiments, the half-life of the prodrug, e.g., the chemical cleavage half-life ($t_{1/2}$) of A-B-C from Q of at least about 1 hour to about 1 week in PBS, under physiological conditions, is dependent on the presence and length of the N-alkyl substituent on the B amino acid. For example, a prodrug that has a shorter N-alkyl substituent on the B amino acid (e.g. Gly(N-methyl)), will undergo a slower rate of cleavage of A-B-C, and have a longer half-life, than a prodrug that has a longer N-alkyl substituent on the B amino acid (e.g., Gly(N-hexyl)).

In some embodiments, the half-life of the prodrug is dependent on the presence or absence of an alkyl side chain, and the degree of substitution at the beta position of the alkyl side chain, of the B amino acid of the dipeptide prodrug element. For example, a prodrug that has an N-alkylated B amino acid that is disubstituted at the beta position (e.g., N-alkylated isoleucine) will undergo slower cleavage of A-B-C, and have a longer half-life, than a prodrug that has an N-alkylated B amino acid that is monosubstituted at the beta position (e.g., N-alkylated leucine). Further, a prodrug that has an N-alkylated B amino acid that is monosubstituted at the beta position (e.g., N-alkylated leucine) will undergo slower cleavage of A-B-C, and have a longer half-life, than a prodrug that has an N-alkylated B amino acid that is unsubstituted at the beta position (e.g., N-alkylated alanine). Further still, a prodrug with an N-alkylated B amino acid that has an unsubstituted beta position (e.g., N-alkylated alanine) will undergo slower cleavage of A-B-C, and have a longer half-life, than a prodrug that has glycine or N-alkylated glycine as the B amino acid.

In some embodiments, the half-life of the prodrug is dependent on the bulkiness of the side chain of the B amino acid. For example, a prodrug that has a bulkier side chain on the B amino acid (e.g., N-alkylated phenylalanine), will undergo slower cleavage of A-B-C, and have a longer half-life, than a prodrug that has a less bulky side chain on the B amino acid (e.g., N-alkylated alanine). Cleavage rates of dipeptides can be further differentiated by the amine of the drug (e.g., insulin) to which they are attached. More particularly the same dipeptide will cleave at a faster rate when linked to an aromatic amine relative to an N-terminal amine, where the dipeptide linked to an N-terminal amine will cleave at a faster rate relative to when the dipeptide is linked to the side chain amine of a lysine residue.

The composition of the B amino acid of the dipeptide prodrug element can be classified into the below sub-categories IA, IB, and IC. Generally, the dipeptide prodrug elements in sub-category IA undergo cleavage the fastest and the dipeptide prodrug elements in sub-category IC undergo cleavage the slowest.

Sub-Category IA: Amino Acid B of the Dipeptide Prodrug Element is N-Alkylated Glycine In some embodiments, the insulin prodrug comprises the structure:

A-B-C-Q;

wherein Q is an insulin peptide;
wherein A-B-C comprises the structure:

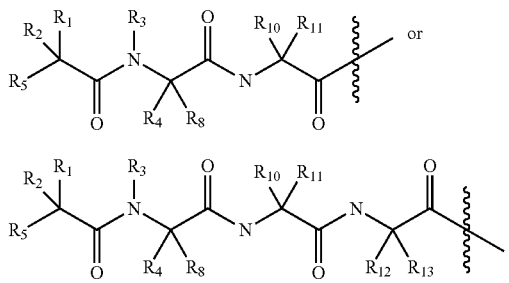

I wherein $R_1$ is $(C_1$-$C_6$ alkyl)NH—$R_9$, or $(C_1$-$C_6$ alkyl)NH—$S_1$—$R_9$;

$R_2$ is selected from the group consisting of H, $C_1$-$C_{18}$ alkyl, $C_2$-$C_{18}$ alkenyl, $(C_1$-$C_{18}$ alkyl)OH, $(C_1$-$C_{18}$ alkyl)SH, $(C_2$-$C_3$ alkyl)SCH$_3$, $(C_1$-$C_4$ alkyl)CONH$_2$, $(C_1$-$C_4$ alkyl)COOH, $(C_1$-$C_4$ alkyl)NH$_2$, $(C_1$-$C_4$ alkyl)NHC(NH$_2^+$)NH$_2$, $(C_0$-$C_4$ alkyl)($C_3$-$C_6$ cycloalkyl), $(C_0$-$C_4$ alkyl)($C_2$-$C_5$ heterocyclic), $(C_0$-$C_4$ alkyl)($C_6$-$C_{10}$ aryl)$R_7$, $(C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl;

$R_3$ is $C_1$-$C_{18}$ alkyl;

$R_4$ and $R_8$ are each H;

$R_5$ is NHR$_6$;

$R_6$ is H or $C_1$-$C_4$ alkyl, or $R_5$ and $R_2$ together with the atoms to which they are attached form a 4, 5 or 6 member heterocyclic ring;

$R_7$ is selected from the group consisting of H and OH;

$R_9$ is selected from the group consisting of $C_{16}$-$C_{30}$ acyl, and $C_{16}$-$C_{30}$ alkyl;

$R_{11}$, and $R_{13}$ are each H;

$R_{10}$ and $R_{12}$ are independently selected from the group consisting of $(C_1$-$C_4$ alkyl)COOH, $(C_1$-$C_4$ alkyl)NH$_2$, $(C_1$-$C_4$ alkyl)NHC(NH$_2^+$)NH$_2$, and CH$_2$($C_3$—N$_2$ heterocyclic); and $S_1$ is a bond or a spacer consisting of one or two charged amino acids selected from the group consisting of aspartic acid, glutamic acid, cysteic acid, homocysteic acid, homoglutamic acid, arginine, lysine and histidine.

In some embodiments, the B amino acid is selected from the group consisting of glycine(N-methyl), glycine(N-ethyl), glycine(N-propyl), glycine(N-butyl), glycine(N-pentyl), glycine(N-hexyl), glycine(N-heptyl), and glycine(N-octyl). For example, the B amino acid can be glycine(N-methyl) or glycine(N-hexyl).

In some embodiments $R_2$ is hydrogen, and $R_3$ is $C_1$-$C_4$ alkyl.

Sub-Category IB: Amino Acid B of the Dipeptide Prodrug Element is Unsubstituted or Monosubstituted at the Beta Position In some embodiments, the insulin prodrug comprises the structure:

A-B-C-Q;

wherein Q is an insulin peptide;
wherein A-B-C comprises the structure:

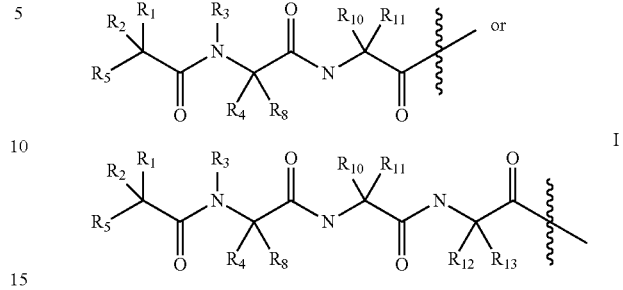

I wherein $R_1$ is selected from the group consisting of H, $(C_1$-$C_6$ alkyl)NH—$R_9$, $(C_1$-$C_6$ alkyl)NH—$S_1$—$R_9$, $R_2$ is selected from the group consisting of H, $C_1$-$C_{18}$ alkyl, $C_2$-$C_{18}$ alkenyl, $(C_1$-$C_{18}$ alkyl)OH, $(C_1$-$C_{18}$ alkyl)SH, $(C_2$-$C_3$ alkyl)SCH$_3$, $(C_1$-$C_4$ alkyl)CONH$_2$, $(C_1$-$C_4$ alkyl)COOH, $(C_1$-$C_4$ alkyl)NH$_2$, $(C_1$-$C_4$ alkyl)NHC(NH$_2^+$)NH$_2$, $(C_0$-$C_4$ alkyl)($C_3$-$C_6$ cycloalkyl), $(C_0$-$C_4$ alkyl)($C_2$-$C_5$ heterocyclic), $(C_0$-$C_4$ alkyl)($C_6$-$C_{10}$ aryl)$R_7$, $(C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl;

$R_3$ is $C_1$-$C_{18}$ alkyl;

$R_4$ is selected from the group consisting of CH$_3$, CH$_2$($C_1$-$C_{10}$ alkyl), CH$_2$($C_2$-$C_{10}$ alkenyl), CH$_2$($C_0$-$C_{10}$ alkyl)OH, CH$_2$($C_0$-$C_{10}$ alkyl)SH, CH$_2$($C_0$-$C_3$ alkyl)SCH$_3$, CH$_2$($C_0$-$C_3$ alkyl)CONH$_2$, CH$_2$($C_0$-$C_3$ alkyl)COOH, CH$_2$($C_0$-$C_3$ alkyl)NH$_2$, $(C_1$-$C_6$ alkyl)NH—$R_9$, $(C_1$-$C_6$ alkyl)NH—$S_1$—$R_9$, CH$_2$($C_0$-$C_3$ alkyl)NHC(NH$_2^+$)NH$_2$, CH$_2$($C_0$-$C_3$ alkyl)($C_3$-$C_6$ cycloalkyl), CH$_2$($C_0$-$C_3$ alkyl)($C_2$-$C_5$ heterocyclic), CH$_2$($C_0$-$C_3$ alkyl)($C_6$-$C_{10}$ aryl)$R_7$, CH$_2$($C_1$-$C_3$ alkyl)($C_3$-$C_9$ heteroaryl), and CH$_2$($C_0$-$C_{12}$ alkyl)($W_1$)$C_1$-$C_{12}$ alkyl, wherein $W_1$ is a heteroatom selected from the group consisting of N, S and O; or $R_4$ and $R_3$ together with the atoms to which they are attached form a 4, 5 or 6 member heterocyclic ring;

$R_8$ is H, $R_5$ is NHR$_6$, or $R_5$ and $R_2$ together with the atoms to which they are attached form a 4, 5 or 6 member heterocyclic ring;

$R_6$ is H or $C_1$-$C_4$ alkyl;

$R_7$ is selected from the group consisting of H and OH $R_9$ is selected from the group consisting of $C_{16}$-$C_{30}$ acyl, and $C_{16}$-$C_{30}$ alkyl;

$R_1$, and $R_{13}$ are each H;

$R_{10}$ and $R_{12}$ are independently selected from the group consisting of $(C_1$-$C_4$ alkyl)COOH, $(C_1$-$C_4$ alkyl)NH$_2$, $(C_1$-$C_4$ alkyl)NHC(NH$_2^+$)NH$_2$, and CH$_2$($C_3$—N$_2$ heterocyclic); and $S_1$ is a bond or a spacer consisting of one or two charged amino acids selected from the group consisting of aspartic acid, glutamic acid, cysteic acid, homocysteic acid, homoglutamic acid, arginine, lysine and histidine, with the proviso that $R_1$ is H when $R_4$ is $(C_1$-$C_6$ alkyl)NH—$R_9$, or $(C_1$-$C_6$ alkyl)NH—$S_1$—$R_9$.

In some embodiments, $R_1$ is $(C_1$-$C_6$ alkyl)NH—$R_9$, or $(C_1$-$C_6$ alkyl)NH—$S_1$—$R_9$ and $R_4$ is selected from the group consisting of CH$_3$, CH$_2$($C_1$-$C_4$ alkyl), CH$_2$($C_1$-$C_4$) alkenyl, CH$_2$($C_0$-$C_4$ alkyl)OH, CH$_2$($C_0$-$C_4$ alkyl)SH, CH$_2$($C_0$-$C_3$ alkyl)SCH$_3$, CH$_2$(C$_0$-C$_3$ alkyl)CONH$_2$, CH$_2$(C$_0$-C$_3$ alkyl)COOH, CH$_2$(C$_0$-C$_4$ alkyl)NH$_2$, and CH$_2$(C$_0$-C$_3$ alkyl)NHC(NH$_2^+$)NH$_2$.

Nonlimiting examples of the B amino acid in these embodiments include alanine(N—C$_1$-C$_{10}$ alkyl), leucine (N—C$_1$-C$_{10}$ alkyl), methionine(N—C$_1$-C$_{10}$ alkyl), asparagine(N—C$_1$-C$_{10}$ alkyl), glutamic acid(N—C$_1$-C$_{10}$ alkyl), aspartic acid(N—C$_1$-C$_{10}$ alkyl), glutamine(N—C$_1$-C$_{10}$ alkyl), histidine(N—C$_1$-C$_{10}$ alkyl), lysine(N—C$_1$-C$_{10}$ alkyl), arginine(N—C$_1$-C$_{10}$ alkyl), serine(N—C$_1$-C$_{10}$ alkyl), and cysteine(N—C$_1$-C$_{10}$ alkyl).

In some embodiments, R$_1$ is (C$_1$-C$_6$ alkyl)NH—R$_9$, or (C$_1$-C$_6$ alkyl)NH—S$_1$—R$_9$ and the B amino acid is selected from the group consisting of alanine(N—C$_1$-C$_6$alkyl), leucine(N—C$_1$-C$_6$alkyl), methionine(N—C$_1$-C$_6$alkyl), asparagine(N—C$_1$-C$_6$alkyl), glutamic acid(N—C$_1$-C$_6$alkyl), aspartic acid(N—C$_1$-C$_6$alkyl), glutamine(N—C$_1$-C$_6$alkyl), histidine(N—C$_1$-C$_6$alkyl), lysine(N—C$_1$-C$_6$alkyl), arginine(N—C$_1$-C$_6$alkyl), serine(N—C$_1$-C$_6$alkyl), and cysteine(N—C$_1$-C$_6$alkyl).

For example, the B amino acid can include alanine(N-methyl), leucine(N-methyl), methionine(N-methyl), asparagine(N-methyl), glutamic acid(N-methyl), aspartic acid(N-methyl), glutamine(N-methyl), histidine(N-methyl), lysine(N-methyl), arginine(N-methyl), serine(N-methyl), and cysteine(N-methyl).

In some embodiments, R$_1$ is (C$_1$-C$_6$ alkyl)NH—R$_9$, or (C$_1$-C$_6$ alkyl)NH—S$_1$—R$_9$ and R$_4$ is selected from the group consisting of CH$_2$(C$_0$-C$_3$ alkyl)(C$_3$-C$_6$ cycloalkyl), CH$_2$(C$_0$-C$_3$ alkyl)(C$_2$-C$_5$ heterocyclic), CH$_2$(C$_0$-C$_3$ alkyl)(C$_6$-C$_{10}$ aryl)R$_7$, CH$_2$(C$_1$-C$_3$ alkyl)(C$_3$-C$_9$ heteroaryl), and CH$_2$(C$_0$-C$_{12}$ alkyl)(W$_1$)C$_1$-C$_{12}$ alkyl, wherein W$_1$ is a heteroatom selected from the group consisting of N, S and O, and wherein R$_7$ is selected from the group consisting of H and OH.

Nonlimiting examples of the B amino acid in these embodiments include phenylalanine(N—C$_1$-C$_{10}$alkyl), tyrosine(N—C$_1$-C$_{10}$alkyl), and tryptophan(N—C$_1$-C$_{10}$alkyl). In some embodiments, the B amino acid is selected from the group consisting of phenylalanine(N—C$_1$-C$_6$alkyl), tyrosine(N—C$_1$-C$_6$alkyl), and tryptophan(N—C$_1$-C$_6$alkyl). For example, the B amino acid can include phenylalanine(N-methyl), tyrosine(N-methyl), and tryptophan(N-methyl).

In some embodiments, the B amino acid is proline. In some embodiments, proline is excluded from Sub-Category IB.

Sub-Category IC: Amino Acid B of the Dipeptide Prodrug Element Disubstituted at the Beta Position In some embodiments, the insulin prodrug comprises the structure:

A-B-C-Q;

wherein Q is an insulin peptide;
wherein A-B-C comprises the structure:

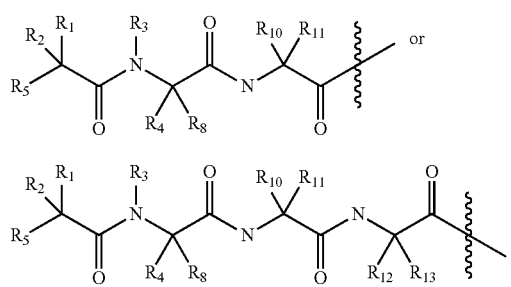

I wherein
R$_1$ is (C$_1$-C$_6$ alkyl)NH—R$_9$, or (C$_1$-C$_6$ alkyl)NH—S$_1$—R$_9$;
R$_2$ is selected from the group consisting of H, C$_1$-C$_{18}$ alkyl, C$_2$-C$_{18}$ alkenyl, (C$_1$-C$_{18}$ alkyl)OH, (C$_1$-C$_{18}$ alkyl)SH, (C$_2$-C$_3$ alkyl)SCH$_3$, (C$_1$-C$_4$ alkyl)CONH$_2$, (C$_1$-C$_4$ alkyl)COOH, (C$_1$-C$_4$ alkyl)NH$_2$, (C$_1$-C$_4$ alkyl)NHC(NH$_2^+$)NH$_2$, (C$_0$-C$_4$ alkyl)(C$_3$-C$_6$ cycloalkyl), (C$_0$-C$_4$ alkyl)(C$_2$-C$_5$ heterocyclic), (C$_0$-C$_4$ alkyl)(C$_6$-C$_{10}$ aryl)R$_7$, (C$_1$-C$_4$ alkyl)(C$_3$-C$_9$ heteroaryl), and C$_1$-C$_{12}$ alkyl(W$_1$)C$_1$-C$_{12}$ alkyl, wherein W$_1$ is a heteroatom selected from the group consisting of N, S and O, or R$_1$ and R$_2$ together with the atoms to which they are attached form a C$_3$-C$_{12}$ cycloalkyl; or R$_1$ and R$_2$ together with the atoms to which they are attached form a C$_3$-C$_{12}$ cycloalkyl;

R$_3$ is C$_1$-C$_{18}$ alkyl;
R$_4$ is independently selected from the group consisting of CH(C$_1$-C$_8$ alkyl)$_2$, CH (C$_2$-C$_8$ alkenyl)$_2$, CH(C$_1$-C$_8$ alkyl)(OH), CH(C$_1$-C$_8$ alkyl)((C$_1$-C$_8$ alkyl)SH), CH(C$_1$-C$_3$ alkyl)((C$_1$-C$_8$ alkyl)(NH$_2$));
R$_3$ is H or C$_1$-C$_{18}$ alkyl;
R$_5$ is NHR$_6$, or R$_5$ and R$_2$ together with the atoms to which they are attached form a 4, 5 or 6 member heterocyclic ring;
R$_6$ is H or C$_1$-C$_4$ alkyl; and,
R$_7$ is selected from the group consisting of H and OH
R$_9$ is selected from the group consisting of C$_{16}$-C$_{30}$ acyl, and C$_{16}$-C$_{30}$ alkyl;
R$_{11}$, and R$_{13}$ are each H;
R$_{10}$ and R$_{12}$ are independently selected from the group consisting of (C$_1$-C$_4$ alkyl)COOH, (C$_1$-C$_4$ alkyl)NH$_2$, (C$_1$-C$_4$ alkyl)NHC(NH$_2^+$)NH$_2$, and CH$_2$(C$_3$—N$_2$ heterocyclic); and
S$_1$ is a bond or a spacer consisting of one or two charged amino acids selected from the group consisting of aspartic acid, glutamic acid, cysteic acid, homocysteic acid, homoglutamic acid, arginine, lysine and histidine.

In some embodiments, R$_4$ is CH(C$_1$-C$_8$ alkyl)$_2$ or CH(C$_1$-C$_8$ alkyl)OH. Nonlimiting examples of the B amino acid include isoleucine(N—C$_1$-C$_{10}$alkyl), valine(N—C$_1$-C$_{10}$alkyl), and threonine(N—C$_1$-C$_{10}$alkyl). In some embodiments, the B amino acid is selected from the group consisting of isoleucine(N—C$_1$-C$_6$alkyl), valine(N—C$_1$-C$_6$alkyl), and threonine(N—C$_1$-C$_6$alkyl). For example, the B amino acid can include isoleucine(N-methyl), valine(N-methyl), and threonine(N-methyl).

Category II: Composition of Amino Acid a of the Dipeptide Prodrug Element

In some embodiments, the half-life of the prodrug is dependent on the number of substituents at the alpha position of the A amino acid. For example, a prodrug comprising an A amino acid that is an α-monosubstituted amino acid (e.g., Ala) will undergo cleavage more slowly, and have a longer half-life than, a prodrug comprising an A amino acid that is an α,α-disubstituted amino acid (e.g., Aib).

In some embodiments, the half-life of the prodrug is dependent on the degree of alkylation on the alpha amino group of the A amino acid. Generally, the greater the degree of alkylation, the slower the rate of cleavage and the longer the half-life of the prodrug. For example, a dipeptide prodrug element having N-alkylated Ala will cleave at a slower rate, and have a longer half-life, than Ala.

The composition of the A amino acid of the dipeptide prodrug element can be classified into the below sub-categories IIA and IIB. Generally, the dipeptide prodrug elements in sub-category IIA cleave faster than dipeptide prodrug elements in sub-category IIB.

Sub-Category IIA: Amino Acid A of the Dipeptide Prodrug Element is Disubstituted at the Alpha Position In some embodiments, the A amino acid of the dipeptide prodrug element is disubstituted at the alpha position. In these embodiments, $R_1$ and $R_2$ of the structures described in sub-categories IA, IB, and IC are independently selected from the group consisting of $C_1$-$C_{10}$ alkyl, $C_2$-$C_{10}$ alkenyl, ($C_1$-$C_{10}$ alkyl)OH, ($C_1$-$C_{10}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl, and wherein $R_7$ is selected from the group consisting of H and OH.

For example, the A amino acid can include aminoisobutyric acid (Aib).

Sub-Category IIB: Amino Acid A of the Dipeptide Prodrug Element is Unsubstituted or Monosubstituted at the Alpha Position In some embodiments, the A amino acid of the dipeptide prodrug element is unsubstituted or monosubstituted at the alpha position. In these embodiments, $R_1$ of the structures described in sub-categories IA, IB, and IC is H, and $R_2$ of the structures described in sub-categories IA, IB, and IC is selected from the group consisting of H, $C_1$-$C_{10}$ alkyl, $C_2$-$C_{10}$ alkenyl, ($C_1$-$C_{10}$ alkyl)OH, ($C_1$-$C_{10}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $R_7$ is selected from the group consisting of H and OH, wherein $W_1$ is a heteroatom selected from the group consisting of N, S and O, or $R_1$ and $R_2$ together with the atoms to which they are attached form a $C_3$-$C_{12}$ cycloalkyl, or $R_2$ and $R_5$ together with the atoms to which they are attached form a 4, 5 or 6 member heterocyclic ring.

In some embodiments, the A amino acid of the dipeptide prodrug element has 'D' stereochemistry. Nonlimiting examples of the A amino acid in these embodiments include lysine, cysteine, and alanine. For example, d-lysine, d-cysteine, and d-alanine. In some embodiments, d-stereochemistry may enhance half-life through reducing proteolytic degradation of the prodrug peptide.

In some embodiments, the A amino acid is N-alkylated with a group that has 1 to 4 carbon atoms such as Ala(N—$C_1$-$C_4$alkyl), Lys(N—$C_1$-$C_4$alkyl), and Cys(N—$C_1$-$C_4$alkyl). For example, the A amino acid can be Ala(N-methyl), Lys(N-methyl), and Cys(N-methyl). N-alkylation of the A amino acid decreases the rate of cleavage of the dipeptide prodrug element from Q and provides a longer half-life.

Category III: Conjugation Site of the Dipeptide Prodrug Element (A-B) to the Peptide Drug (Q)

In some embodiments, the half-life of the prodrug depends on the steric hindrance, nucleophilicity, and stability of the leaving group on Q during diketopiperazine formation. The less sterically hindered the leaving group, the less nucleophilic the leaving group, or the more stable the leaving group after cleavage, the shorter the half-life of the prodrug. The type of leaving group on Q can be determined by the type of the linkage between A-B-C and an amino group of Q, as described in sub-categories IIIA and IIIB below. Generally, dipeptide prodrug elements in sub-category IIIB cleave faster from Q and have a shorter half-life than dipeptide prodrug elements in subcategory IIIA.

Sub-Category IIIA: A-B Linked to an Aliphatic Amino Group of Q

In some embodiments, A-B-C is linked to Q through an amide bond between A-B-C and an aliphatic amino group of Q to result in a prodrug with a chemical cleavage half-life ($t_{1/2}$) of A-B from Q of at least about 1 hour to about 1 week in PBS, under physiological conditions, as previously described herein.

In some embodiments, A-B-C is linked to Q through an amide bond between A-B-C and the alpha amino group of the N-terminal amino acid of Q. For example, a dipeptide prodrug element having a B amino acid from any of sub-categories IA, IB, and IC and an A amino acid from any of sub-categories IIA and IIB can be linked to the N-terminal amino acid of Q, more particularly, to the N-terminal amine of the insulin A or B chain, to result in a prodrug with a chemical cleavage half-life ($t_{1/2}$) of A-B from Q of at least about 1 hour to about 1 week in PBS, under physiological conditions.

In some embodiments, A-B-C is linked to Q through an amide bond between A-B-C and an aliphatic amino group on a side chain of an amino acid of Q. For example, a dipeptide prodrug element having a B amino acid from any of sub-categories IA, IB, and IC and an A amino acid from any of sub-categories IIA and IIB can be linked to an aliphatic amino group of a side chain of an amino acid of Q to result in a prodrug with a chemical cleavage half-life (tin) of A-B from Q of at least about 1 hour to about 1 week in PBS, under physiological conditions.

In some embodiments, when A-B-C is linked to Q through an amide bond between A-B-C and an aliphatic amino group of Q, either A should be an α,α-disubstituted amino acid (Sub-category IIA) or B should be N-alkylated (any of Sub-categories IA, IB or IC), or both. For example, when A is an α-monosubstituted amino acid (e.g., Ala), B is not N-alkylated, and A-B-C is attached to Q through an aliphatic amino group of Q, then there will not be significant cleavage of A-B.

In other embodiments, when A-B-C is linked to Q through an amide bond between A-B-C and an aliphatic amino group of Q, and A is an amino acid that is unsubstituted at the alpha position (e.g. glycine) and B is an amino acid from Sub-category IA (N-alkylated glycine), the N-alkyl substituent of the B amino acid has a length of at least five carbon atoms (for example, N—$C_5$-$C_8$alkyl).

In yet other embodiments, when A-B-C is linked to Q through an amide bond between A-B-C and an aliphatic amino group of Q, and the A amino acid is unsubstituted or monosubstituted at the alpha position (Sub-category IIB), the B amino acid is not proline.

Sub-Category IIIB: A-B Linked to an Aromatic Amino Group of Q

In some embodiments, A-B-C is linked to Q through an amide bond between A-B-C and an aromatic amino group of a side chain of an amino acid of Q to result in a prodrug with a chemical cleavage half-life (tin) of A-B from Q of at least about 1 hour to about 1 week in PBS, under physiological conditions, as previously described herein. For example, a dipeptide prodrug element having a B amino acid from any of sub-categories IA, IB, and IC and an A amino acid from any of sub-categories IIA and IIB can be linked to an aromatic amino group of a side chain of an amino acid of Q to result in a prodrug with a chemical cleavage half-life ($t_{1/2}$) of A-B from Q of at least about 1 hour to about 1 week in PBS, under physiological conditions.

Any of the B amino acids defined by Category I can be combined with any of the A amino acids defined by Category II to form a dipeptide prodrug element. This dipeptide prodrug element can be linked to any of the positions described in Category III. The half-life of the prodrug can be tuned through the selection of:
(i) the number of substituents on the alpha position of the A amino acid;
(ii) the degree of N-alkylation of the A and the B amino acids;
(iii) the number of substituents on the beta position of the B amino acid;
(iv) the bulkiness of the side chain of the B amino acid; and,
(v) the steric hindrance, nucleophilicity, and stability of the leaving group on Q during diketopiperazine formation.

Modification of Dipeptide Prodrug Element A-B

The dipeptide prodrug elements described above can be further modified to comprise a hydrophilic moiety, an acyl group, or an alkyl group, as previously described herein. In some embodiments, the dipeptide prodrug element includes lysine that is conjugated to an acyl group or an alkyl group through its side chain amino group. In some embodiments, the dipeptide prodrug element includes cysteine that is conjugated to a hydrophilic moiety (e.g., 40 kD PEG) through the side chain sulfhydryl group. The hydrophilic moiety, acyl group, or alkyl group can be conjugated directly to the dipeptide prodrug element or through a spacer. In some exemplary embodiments, the hydrophilic group, the alkyl group and/or the acyl group are conjugated to the A amino acid of the dipeptide prodrug element.

In some embodiments, the following dipeptide prodrug elements are PEGylated: dCys-Gly(N-Hexyl) dCys-Gly(N-Methyl), and dCys-Phe(N-Methyl). In some embodiments, the following dipeptide prodrug elements include an acyl group: dLys-Gly(N-Hexyl), dLys-Gly(N-Methyl), and dLys-Phe(N-Methyl). In some embodiments, the following dipeptide prodrug elements include an alkyl group: dLys-Gly(N-Hexyl), dLys-Gly(N-Methyl), and dLys-Phe(N-Methyl).

EXEMPLARY EMBODIMENTS

The dipeptide prodrug element of the invention can include combinations of any of the B amino acids from Category I with any of the A amino acids from Category II. Nonlimiting examples of amino acids suitable for the A amino acid and for the B amino acid of the dipeptide prodrug element are listed in the below Table.

| Amino Acid # | Amino Acid 'A' | Amino Acid 'B' |
|---|---|---|
| 1 | Aib | Gly(N—$C_1$-$C_8$alkyl) |
| 2 | Gly | Ala(N—$C_1$-$C_8$alkyl) |
| 3 | Ala | Leu(N—$C_1$-$C_8$alkyl) |
| 4 | Leu | Met(N—$C_1$-$C_8$alkyl) |
| 5 | Met | Asn(N—$C_1$-$C_8$alkyl) |
| 6 | Asn | Glu(N—$C_1$-$C_8$alkyl) |
| 7 | Glu | Asp(N—$C_1$-$C_8$alkyl) |
| 8 | Asp | Gln(N—$C_1$-$C_8$alkyl) |
| 9 | Gln | His(N—$C_1$-$C_8$alkyl) |
| 10 | His | Lys(N—$C_1$-$C_8$alkyl) |
| 11 | Lys | Arg(N—$C_1$-$C_8$alkyl) |
| 12 | Arg | Ser(N—$C_1$-$C_8$alkyl) |
| 13 | Ser | Cys(N—$C_1$-$C_8$alkyl) |
| 14 | Cys | Pro |
| 15 | Pro | Phe(N—$C_1$-$C_8$alkyl) |
| 16 | Phe | Tyr(N—$C_1$-$C_8$alkyl) |
| 17 | Tyr | Trp(N—$C_1$-$C_8$alkyl) |
| 18 | Trp | Ile(N—$C_1$-$C_8$alkyl) |
| 19 | Ile | Val(N—$C_1$-$C_8$alkyl) |
| 20 | Val | Thr(N—$C_1$-$C_8$alkyl) |
| 21 | Thr | d-Ala(N—$C_1$-$C_8$alkyl) |
| 22 | d-Ala | d-Leu(N—$C_1$-$C_8$alkyl) |
| 23 | d-Leu | d-Met(N—$C_1$-$C_8$alkyl) |
| 24 | d-Met | d-Asn(N—$C_1$-$C_8$alkyl) |
| 25 | d-Asn | d-Glu(N—$C_1$-$C_8$alkyl) |
| 26 | d-Glu | d-Asp(N—$C_1$-$C_8$alkyl) |
| 27 | d-Asp | d-Gln(N—$C_1$-$C_8$alkyl) |
| 28 | d-Gln | d-His(N—$C_1$-$C_8$alkyl) |
| 29 | d-His | d-Lys(N—$C_1$-$C_8$alkyl) |
| 30 | d-Lys | d-Arg(N—$C_1$-$C_8$alkyl) |
| 31 | d-Arg | d-Ser(N—$C_1$-$C_8$alkyl) |
| 32 | d-Ser | d-Cys(N—$C_1$-$C_8$alkyl) |
| 33 | d-Cys | d-Pro |
| 34 | d-Pro | d-Phe(N—$C_1$-$C_8$alkyl) |
| 35 | d-Phe | d-Tyr(N—$C_1$-$C_8$alkyl) |
| 36 | d-Tyr | d-Trp(N—$C_1$-$C_8$alkyl) |
| 37 | d-Trp | d-Ile(N—$C_1$-$C_8$alkyl) |
| 38 | d-Ile | d-Val(N—$C_1$-$C_8$alkyl) |
| 39 | d-Val | d-Thr(N—$C_1$-$C_8$alkyl) |
| 40 | d-Thr | Gly(N-methyl) |
| 41 | Gly(N-methyl) | Ala(N-methyl) |
| 42 | Ala(N-methyl) | Leu(N-methyl) |
| 43 | Leu(N-methyl) | Met(N-methyl) |
| 44 | Met(N-methyl) | Asn(N-methyl) |
| 45 | Asn(N-methyl) | Glu(N-methyl) |
| 46 | Glu(N-methyl) | Asp(N-methyl) |
| 47 | Asp(N-methyl) | Gln(N-methyl) |
| 48 | Gln(N-methyl) | His(N-methyl) |
| 49 | His(N-methyl) | Lys(N-methyl) |
| 50 | Lys(N-methyl) | Arg(N-methyl) |
| 51 | Arg(N-methyl) | Ser(N-methyl) |
| 52 | Ser(N-methyl) | Cys(N-methyl) |
| 53 | Cys(N-methyl) | Phe(N-methyl) |
| 54 | Phe(N-methyl) | Tyr(N-methyl) |
| 55 | Tyr(N-methyl) | Trp(N-methyl) |
| 56 | Trp(N-methyl) | Ile(N-methyl) |
| 57 | Ile(N-methyl) | Val(N-methyl) |
| 58 | Val(N-methyl) | Thr(N-methyl) |
| 59 | Thr(N-methyl) | d-Ala(N-methyl) |
| 60 | d-Ala(N-methyl) | d-Leu(N-methyl) |
| 61 | d-Leu(N-methyl) | d-Met(N-methyl) |
| 62 | d-Met(N-methyl) | d-Asn(N-methyl) |
| 63 | d-Asn(N-methyl) | d-Glu(N-methyl) |
| 64 | d-Glu(N-methyl) | d-Asp(N-methyl) |
| 65 | d-Asp(N-methyl) | d-Gln(N-methyl) |
| 66 | d-Gln(N-methyl) | d-His(N-methyl) |
| 67 | d-His(N-methyl) | d-Lys(N-methyl) |
| 68 | d-Lys(N-methyl) | d-Arg(N-methyl) |
| 69 | d-Arg(N-methyl) | d-Ser(N-methyl) |
| 70 | d-Ser(N-methyl) | d-Cys(N-methyl) |
| 71 | d-Cys(N-methyl) | d-Phe(N-methyl) |
| 72 | d-Phe(N-methyl) | d-Tyr(N-methyl) |
| 73 | d-Tyr(N-methyl) | d-Trp(N-methyl) |
| 74 | d-Trp(N-methyl) | d-Ile(N-methyl) |
| 75 | d-Ile(N-methyl) | d-Val(N-methyl) |
| 76 | d-Val(N-methyl) | d-Thr(N-methyl) |
| 77 | d-Thr(N-methyl) | Gly(N-hexyl) |
| 78 | | Ala(N-hexyl) |
| 79 | | Leu(N-hexyl) |
| 80 | | Met(N-hexyl) |
| 81 | | Asn(N-hexyl) |
| 82 | | Glu(N-hexyl) |
| 83 | | Asp(N-hexyl) |
| 84 | | Gln(N-hexyl) |
| 85 | | His(N-hexyl) |
| 86 | | Lys(N-hexyl) |
| 87 | | Arg(N-hexyl) |
| 88 | | Ser(N-hexyl) |
| 89 | | Cys(N-hexyl) |
| 90 | | Phe(N-hexyl) |
| 91 | | Tyr(N-hexyl) |
| 92 | | Trp(N-hexyl) |
| 93 | | Ile(N-hexyl) |
| 94 | | Val(N-hexyl) |
| 95 | | Thr(N-hexyl) |
| 96 | | d-Ala(N-hexyl) |

| Amino Acid # | Amino Acid 'A' | Amino Acid 'B' |
| --- | --- | --- |
| 97 | | d-Leu(N-hexyl) |
| 98 | | d-Met(N-hexyl) |
| 99 | | d-Asn(N-hexyl) |
| 100 | | d-Glu(N-hexyl) |
| 101 | | d-Asp(N-hexyl) |
| 102 | | d-Gln(N-hexyl) |
| 103 | | d-His(N-hexyl) |
| 104 | | d-Lys(N-hexyl) |
| 105 | | d-Arg(N-hexyl) |
| 106 | | d-Ser(N-hexyl) |
| 107 | | d-Cys(N-hexyl) |
| 108 | | d-Phe(N-hexyl) |
| 109 | | d-Tyr(N-hexyl) |
| 110 | | d-Trp(N-hexyl) |
| 111 | | d-Ile(N-hexyl) |
| 112 | | d-Val(N-hexyl) |
| 113 | | d-Thr(N-hexyl) |

Sub-Category IA: Amino Acid B of the Dipeptide Prodrug Element is N-Alkylated Glycine In some embodiments, the B amino acid of the dipeptide prodrug element is N-alkylated glycine. Nonlimiting examples of dipeptide prodrug elements having N-alkylated glycine as the B amino acid are shown in the below Table.

| Dipeptide Prodrug Element # | Amino Acid 'A' | Amino Acid 'B' |
| --- | --- | --- |
| 1 | Aib | Gly(N—$C_1$-$C_8$alkyl) |
| 2 | d-Ala | Gly(N—$C_1$-$C_8$alkyl) |
| 3 | d-Lys | Gly(N—$C_1$-$C_8$alkyl) |
| 4 | d-Cys | Gly(N—$C_1$-$C_8$alkyl) |
| 5 | Aib | Gly(N-methyl) |
| 6 | d-Ala | Gly(N-methyl) |
| 7 | d-Lys | Gly(N-methyl) |
| 8 | d-Cys | Gly(N-methyl) |
| 9 | Aib | Gly(N-hexyl) |
| 10 | d-Ala | Gly(N-hexyl) |
| 11 | d-Lys | Gly(N-hexyl) |
| 12 | d-Cys | Gly(N-hexyl) |

Sub-Category IB: Amino Acid B of the Dipeptide Prodrug Element is Unsubstituted or Monosubstituted at the Beta Position In some embodiments, the B amino acid of the dipeptide prodrug element is unsubstituted or monosubstituted at the beta position and has a relatively non-bulky side chain. Nonlimiting examples of dipeptide prodrug elements having a B amino acid that is unsubstituted or monosubstituted at the beta position and a relatively non-bulky side chain are shown in the below Table.

| Dipeptide Prodrug Element # | Amino Acid 'A' | Amino Acid 'B' |
| --- | --- | --- |
| 13 | Aib | Ala(N—$C_1$-$C_8$alkyl) |
| 14 | d-Ala | Ala(N—$C_1$-$C_8$alkyl) |
| 15 | d-Lys | Ala(N—$C_1$-$C_8$alkyl) |
| 16 | d-Cys | Ala(N—$C_1$-$C_8$alkyl) |
| 17 | Aib | Leu(N—$C_1$-$C_8$alkyl) |
| 18 | d-Ala | Leu(N—$C_1$-$C_8$alkyl) |
| 19 | d-Lys | Leu(N—$C_1$-$C_8$alkyl) |
| 20 | d-Cys | Leu(N—$C_1$-$C_8$alkyl) |
| 21 | Aib | Met(N—$C_1$-$C_8$alkyl) |
| 22 | d-Ala | Met(N—$C_1$-$C_8$alkyl) |
| 23 | d-Lys | Met(N—$C_1$-$C_8$alkyl) |
| 24 | d-Cys | Met(N—$C_1$-$C_8$alkyl) |
| 25 | Aib | Asn(N—$C_1$-$C_8$alkyl) |
| 26 | d-Ala | Asn(N—$C_1$-$C_8$alkyl) |
| 27 | d-Lys | Asn(N—$C_1$-$C_8$alkyl) |
| 28 | d-Cys | Asn(N—$C_1$-$C_8$alkyl) |
| 29 | Aib | Glu(N—$C_1$-$C_8$alkyl) |
| 30 | d-Ala | Glu(N—$C_1$-$C_8$alkyl) |
| 31 | d-Lys | Glu(N—$C_1$-$C_8$alkyl) |
| 32 | d-Cys | Glu(N—$C_1$-$C_8$alkyl) |
| 33 | Aib | Asp(N—$C_1$-$C_8$alkyl) |
| 34 | d-Ala | Asp(N—$C_1$-$C_8$alkyl) |
| 35 | d-Lys | Asp(N—$C_1$-$C_8$alkyl) |
| 36 | d-Cys | Asp(N—$C_1$-$C_8$alkyl) |
| 37 | Aib | Gln(N—$C_1$-$C_8$alkyl) |
| 38 | d-Ala | Gln(N—$C_1$-$C_8$alkyl) |
| 39 | d-Lys | Gln(N—$C_1$-$C_8$alkyl) |
| 40 | d-Cys | Gln(N—$C_1$-$C_8$alkyl) |
| 41 | Aib | His(N—$C_1$-$C_8$alkyl) |
| 42 | d-Ala | His(N—$C_1$-$C_8$alkyl) |
| 43 | d-Lys | His(N—$C_1$-$C_8$alkyl) |
| 44 | d-Cys | His(N—$C_1$-$C_8$alkyl) |
| 45 | Aib | Lys(N—$C_1$-$C_8$alkyl) |
| 46 | d-Ala | Lys(N—$C_1$-$C_8$alkyl) |
| 47 | d-Lys | Lys(N—$C_1$-$C_8$alkyl) |
| 48 | d-Cys | Lys(N—$C_1$-$C_8$alkyl) |
| 49 | Aib | Arg(N—$C_1$-$C_8$alkyl) |
| 50 | d-Ala | Arg(N—$C_1$-$C_8$alkyl) |
| 51 | d-Lys | Arg(N—$C_1$-$C_8$alkyl) |
| 52 | d-Cys | Arg(N—$C_1$-$C_8$alkyl) |
| 53 | Aib | Ser(N—$C_1$-$C_8$alkyl) |
| 54 | d-Ala | Ser(N—$C_1$-$C_8$alkyl) |
| 55 | d-Lys | Ser(N—$C_1$-$C_8$alkyl) |
| 56 | d-Cys | Ser(N—$C_1$-$C_8$alkyl) |
| 57 | Aib | Cys(N—$C_1$-$C_8$alkyl) |
| 58 | d-Ala | Cys(N—$C_1$-$C_8$alkyl) |
| 59 | d-Lys | Cys(N—$C_1$-$C_8$alkyl) |
| 60 | d-Cys | Cys(N—$C_1$-$C_8$alkyl) |
| 61 | Aib | Pro |
| 62 | d-Ala | Pro |
| 63 | d-Lys | Pro |
| 64 | d-Cys | Pro |
| 65 | Aib | Ala(N-methyl) |
| 66 | d-Ala | Ala(N-methyl) |
| 67 | d-Lys | Ala(N-methyl) |
| 68 | d-Cys | Ala(N-methyl) |
| 69 | Aib | Leu(N-methyl) |
| 70 | d-Ala | Leu(N-methyl) |
| 71 | d-Lys | Leu(N-methyl) |
| 72 | d-Cys | Leu(N-methyl) |
| 73 | Aib | Met(N-methyl) |
| 74 | d-Ala | Met(N-methyl) |
| 75 | d-Lys | Met(N-methyl) |
| 76 | d-Cys | Met(N-methyl) |
| 77 | Aib | Asn(N-methyl) |
| 78 | d-Ala | Asn(N-methyl) |
| 79 | d-Lys | Asn(N-methyl) |
| 80 | d-Cys | Asn(N-methyl) |
| 81 | Aib | Glu(N-methyl) |
| 82 | d-Ala | Glu(N-methyl) |
| 83 | d-Lys | Glu(N-methyl) |
| 84 | d-Cys | Glu(N-methyl) |
| 85 | Aib | Asp(N-methyl) |
| 86 | d-Ala | Asp(N-methyl) |
| 87 | d-Lys | Asp(N-methyl) |
| 88 | d-Cys | Asp(N-methyl) |
| 89 | Aib | Gln(N-methyl) |
| 90 | d-Ala | Gln(N-methyl) |
| 91 | d-Lys | Gln(N-methyl) |
| 92 | d-Cys | Gln(N-methyl) |
| 93 | Aib | His(N-methyl) |
| 94 | d-Ala | His(N-methyl) |
| 95 | d-Lys | His(N-methyl) |
| 96 | d-Cys | His(N-methyl) |
| 97 | Aib | Lys(N-methyl) |
| 98 | d-Ala | Lys(N-methyl) |
| 99 | d-Lys | Lys(N-methyl) |
| 100 | d-Cys | Lys(N-methyl) |
| 101 | Aib | Arg(N-methyl) |
| 102 | d-Ala | Arg(N-methyl) |
| 103 | d-Lys | Arg(N-methyl) |
| 104 | d-Cys | Arg(N-methyl) |
| 105 | Aib | Ser(N-methyl) |

| Dipeptide Prodrug Element # | Amino Acid 'A' | Amino Acid 'B' |
|---|---|---|
| 106 | d-Ala | Ser(N-methyl) |
| 107 | d-Lys | Ser(N-methyl) |
| 108 | d-Cys | Ser(N-methyl) |
| 109 | Aib | Cys(N-methyl) |
| 110 | d-Ala | Cys(N-methyl) |
| 111 | d-Lys | Cys(N-methyl) |
| 112 | d-Cys | Cys(N-methyl) |
| 113 | Aib | Ala(N-hexyl) |
| 114 | d-Ala | Ala(N-hexyl) |
| 115 | d-Lys | Ala(N-hexyl) |
| 116 | d-Cys | Ala(N-hexyl) |
| 117 | Aib | Leu(N-hexyl) |
| 118 | d-Ala | Leu(N-hexyl) |
| 119 | d-Lys | Leu(N-hexyl) |
| 120 | d-Cys | Leu(N-hexyl) |
| 121 | Aib | Met(N-hexyl) |
| 122 | d-Ala | Met(N-hexyl) |
| 123 | d-Lys | Met(N-hexyl) |
| 124 | d-Cys | Met(N-hexyl) |
| 125 | Aib | Asn(N-hexyl) |
| 126 | d-Ala | Asn(N-hexyl) |
| 127 | d-Lys | Asn(N-hexyl) |
| 128 | d-Cys | Asn(N-hexyl) |
| 129 | Aib | Glu(N-hexyl) |
| 130 | d-Ala | Glu(N-hexyl) |
| 131 | d-Lys | Glu(N-hexyl) |
| 132 | d-Cys | Glu(N-hexyl) |
| 133 | Aib | Asp(N-hexyl) |
| 134 | d-Ala | Asp(N-hexyl) |
| 135 | d-Lys | Asp(N-hexyl) |
| 136 | d-Cys | Asp(N-hexyl) |
| 137 | Aib | Gln(N-hexyl) |
| 138 | d-Ala | Gln(N-hexyl) |
| 139 | d-Lys | Gln(N-hexyl) |
| 140 | d-Cys | Gln(N-hexyl) |
| 141 | Aib | His(N-hexyl) |
| 142 | d-Ala | His(N-hexyl) |
| 143 | d-Lys | His(N-hexyl) |
| 144 | d-Cys | His(N-hexyl) |
| 145 | Aib | Lys(N-hexyl) |
| 146 | d-Ala | Lys(N-hexyl) |
| 147 | d-Lys | Lys(N-hexyl) |
| 148 | d-Cys | Lys(N-hexyl) |
| 149 | Aib | Arg(N-hexyl) |
| 150 | d-Ala | Arg(N-hexyl) |
| 151 | d-Lys | Arg(N-hexyl) |
| 152 | d-Cys | Arg(N-hexyl) |
| 153 | Aib | Ser(N-hexyl) |
| 154 | d-Ala | Ser(N-hexyl) |
| 155 | d-Lys | Ser(N-hexyl) |
| 156 | d-Cys | Ser(N-hexyl) |
| 157 | Aib | Cys(N-hexyl) |
| 158 | d-Ala | Cys(N-hexyl) |
| 159 | d-Lys | Cys(N-hexyl) |
| 160 | d-Cys | Cys(N-hexyl) |

In some embodiments, the B amino acid of the dipeptide prodrug element is monosubstituted at the beta position and has a relatively bulky side chain, as shown in the below Table.

| Dipeptide Prodrug Element # | Amino Acid 'A' | Amino Acid 'B' |
|---|---|---|
| 161 | Aib | Phe(N—$C_1$-$C_8$alkyl) |
| 162 | d-Ala | Phe(N—$C_1$-$C_8$alkyl) |
| 163 | d-Lys | Phe(N—$C_1$-$C_8$alkyl) |
| 164 | d-Cys | Phe(N—$C_1$-$C_8$alkyl) |
| 165 | Aib | Tyr(N—$C_1$-$C_8$alkyl) |
| 166 | d-Ala | Tyr(N—$C_1$-$C_8$alkyl) |
| 167 | d-Lys | Tyr(N—$C_1$-$C_8$alkyl) |
| 168 | d-Cys | Tyr(N—$C_1$-$C_8$alkyl) |
| 169 | Aib | Trp(N—$C_1$-$C_8$alkyl) |
| 170 | d-Ala | Trp(N—$C_1$-$C_8$alkyl) |
| 171 | d-Lys | Trp(N—$C_1$-$C_8$alkyl) |
| 172 | d-Cys | Trp(N—$C_1$-$C_8$alkyl) |
| 173 | Aib | Phe(N-methyl) |
| 174 | d-Ala | Phe(N-methyl) |
| 175 | d-Lys | Phe(N-methyl) |
| 176 | d-Cys | Phe(N-methyl) |
| 177 | Aib | Tyr(N-methyl) |
| 178 | d-Ala | Tyr(N-methyl) |
| 179 | d-Lys | Tyr(N-methyl) |
| 180 | d-Cys | Tyr(N-methyl) |
| 181 | Aib | Trp(N-methyl) |
| 182 | d-Ala | Trp(N-methyl) |
| 183 | d-Lys | Trp(N-methyl) |
| 184 | d-Cys | Trp(N-methyl) |
| 185 | Aib | Phe(N-hexyl) |
| 186 | d-Ala | Phe(N-hexyl) |
| 187 | d-Lys | Phe(N-hexyl) |
| 188 | d-Cys | Phe(N-hexyl) |
| 189 | Aib | Tyr(N-hexyl) |
| 190 | d-Ala | Tyr(N-hexyl) |
| 191 | d-Lys | Tyr(N-hexyl) |
| 192 | d-Cys | Tyr(N-hexyl) |
| 193 | Aib | Trp(N-hexyl) |
| 194 | d-Ala | Trp(N-hexyl) |
| 195 | d-Lys | Trp(N-hexyl) |
| 196 | d-Cys | Trp(N-hexyl) |

Sub-Category IC: Amino Acid B of the Dipeptide Prodrug Element Disubstituted at the Beta Position In some embodiments, the B amino acid of the dipeptide prodrug element is disubstituted at the beta position. Non-limiting examples of dipeptide prodrug elements having a B amino acid that is disubstituted at the beta position are shown in the below Table.

| Dipeptide Prodrug Element # | Amino Acid 'A' | Amino Acid 'B' |
|---|---|---|
| 197 | Aib | Ile(N—$C_1$-$C_8$alkyl) |
| 198 | d-Ala | Ile(N—$C_1$-$C_8$alkyl) |
| 199 | d-Lys | Ile(N—$C_1$-$C_8$alkyl) |
| 200 | d-Cys | Ile(N—$C_1$-$C_8$alkyl)) |
| 201 | Aib | Val(N—$C_1$-$C_8$alkyl) |
| 202 | d-Ala | Val(N—$C_1$-$C_8$alkyl) |
| 203 | d-Lys | Val(N—$C_1$-$C_8$alkyl) |
| 204 | d-Cys | Val(N—$C_1$-$C_8$alkyl) |
| 205 | Aib | Thr(N—$C_1$-$C_8$alkyl) |
| 206 | d-Ala | Thr(N—$C_1$-$C_8$alkyl) |
| 207 | d-Lys | Thr(N—$C_1$-$C_8$alkyl) |
| 208 | d-Cys | Thr(N—$C_1$-$C_8$alkyl) |
| 209 | Aib | Ile(N-methyl) |
| 210 | d-Ala | Ile(N-methyl) |
| 211 | d-Lys | Ile(N-methyl) |
| 212 | d-Cys | Ile(N-methyl)) |
| 213 | Aib | Val(N-methyl) |
| 214 | d-Ala | Val(N-methyl) |
| 215 | d-Lys | Val(N-methyl) |
| 216 | d-Cys | Val(N-methyl) |
| 217 | Aib | Thr(N-methyl) |
| 218 | d-Ala | Thr(N-methyl) |
| 219 | d-Lys | Thr(N-methyl) |
| 220 | d-Cys | Thr(N-methyl) |
| 221 | Aib | Ile(N-hexyl) |
| 222 | d-Ala | Ile(N-hexyl) |
| 223 | d-Lys | Ile(N-hexyl) |
| 224 | d-Cys | Ile(N-hexyl) |
| 225 | Aib | Val(N-hexyl) |
| 226 | d-Ala | Val(N-hexyl) |
| 227 | d-Lys | Val(N-hexyl) |
| 228 | d-Cys | Val(N-hexyl) |
| 229 | Aib | Thr(N-hexyl) |
| 230 | d-Ala | Thr(N-hexyl) |
| 231 | d-Lys | Thr(N-hexyl) |
| 232 | d-Cys | Thr(N-hexyl)) |

In some exemplary embodiments, Aib-Gly(N-Hexyl), dLys-Gly(N-Hexyl), dCys-Gly(N-Hexyl), dAla-Gly(N-Hexyl), Aib-Gly(N-Methyl), dLys-Gly(N-Methyl), dCys-Gly(N-Methyl), dAla-Gly(N-Hexyl), Aib-Phe(N-Methyl), dLys-Phe(N-Methyl), dCys-Phe(N-Methyl), or dAla-Phe(N-Methyl) is conjugated to the N-terminal alpha amino group of the insulin peptide via the structure A-B-C.

In accordance with one embodiment the dipeptide element comprises one of three amino acids at the B of the A-B dipeptide: Gly(N-Hexyl), Gly(N-Methyl) or Phe(N-Methyl). Dipeptides selected from one of these three groups of dipeptides have relative cleavage rates wherein Gly(N-Hexyl)>Gly(N-Methyl)>Phe(N-Methyl) all other factors being equal. In one embodiment Cys or Lys is provided in the first position (i.e., the A amino acid) to provides a location for acylation or pegylation. Ala is used as the A amino acid in one embodiment where no acylation or pegylation is desired. In one embodiment an Aib in first position (i.e., the A amino acid) increases speed of cleavage relative to natural amino acids such as Ala, Cys, & Lys. Exemplary dipeptides include:
dAla-Phe(N-Methyl)
dCys-Phe(N-Methyl)
dLys-Phe(N-Methyl)
Aib-Phe(N-Methyl)
dAla-Gly(N-Methyl)
dCys-Gly(N-Methyl)
dLys-Gly(N-Methyl)
Aib-Gly(N-Methyl)
dAla-Gly(N-Hexyl)
dCys-Gly(N-Hexyl)
dLys-Gly(N-Hexyl)
Aib-Gly(N-Hexyl)

In accordance with one embodiment a pharmaceutical composition is provided comprising any of the novel insulin prodrug analogs disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an A19 insulin analog as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In one embodiment, a composition is provided comprising a mixture of a first and second insulin prodrug analog, wherein the first and second insulin prodrug analogs differ from one another based on the structure of the prodrug element. More particularly, the first insulin prodrug analog may comprise a dipeptide prodrug element that has a half-life substantially different from the dipeptide prodrug element of the second insulin prodrug analog. Accordingly, selection of different combinations of substituents on the dipeptide element will allow for the preparation of compositions that comprise a mixture of insulin prodrug analogs that are activated in a controlled manner over a desired time frame and at specific time intervals. For example, the compositions can be formulated to release active insulin at mealtimes followed by a subsequent activation of insulin during nighttime with suitable dosages being released based on time of activation. In another embodiment the pharmaceutical composition comprises a mixture of an insulin prodrug analog disclosed herein and native insulin, or a known bioactive derivative of insulin.

The disclosed insulin prodrug analogs are believed to be suitable for any use that has previously been described for insulin peptides. Accordingly, the insulin prodrug analogs described herein can be used to treat hyperglycemia, or treat other metabolic diseases that result from high blood glucose levels. Accordingly, the present invention encompasses pharmaceutical compositions comprising an insulin prodrug analog of the present disclosure, and a pharmaceutically acceptable carrier for use in treating a patient suffering from high blood glucose levels. In accordance with one embodiment the patient to be treated using the insulin prodrug analogs disclosed herein is a domesticated animal, and in another embodiment the patient to be treated is a human.

One method of treating hyperglycemia in accordance with the present disclosure comprises the steps of administering the presently disclosed insulin prodrug analog to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the insulin prodrug analog composition is prepackaged in a syringe.

The insulin prodrug analogs disclosed herein may be administered alone or in combination with other anti-diabetic agents. Anti-diabetic agents known in the art or under investigation include native insulin, native glucagon and functional derivatives thereof, sulfonylureas, such as tolbutamide (Orinase®), acetohexamide (Dymelor™), tolazamide (Tolinase™), chlorpropamide (Diabinese®), glipizide (Glucotrol®), glyburide (Diabeta®, Micronase®, Glynase®), glimepiride (Amaryl®), or gliclazide (Diamicron®); meglitinides, such as repaglinide (Prandin®) or nateglinide (Starlix®); biguanides such as metformin (Glucophage®) or phenformin; thiazolidinediones such as rosiglitazone (Avandia®), pioglitazone (Actos®), or troglitazone (Rezulin™), or other PPARγ inhibitors; alpha glucosidase inhibitors that inhibit carbohydrate digestion, such as miglitol (Glyset®), acarbose (Precose/Glucobay); exenatide (Byetta®) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bisphosphatase) inhibitors.

Pharmaceutical compositions comprising the insulin prodrug analogs disclosed herein can be formulated and administered to patients using standard pharmaceutically acceptable carriers and routes of administration known to those skilled in the art. Accordingly, the present disclosure also encompasses pharmaceutical compositions comprising one or more of the insulin prodrug analogs disclosed herein, or a pharmaceutically acceptable salt thereof, in combination with a pharmaceutically acceptable carrier. In one embodiment the pharmaceutical composition comprises a 1 mg/ml concentration of the insulin prodrug analog at pH of about 4.0 to about 7.0 in a phosphate buffer system. The pharmaceutical compositions may comprise the insulin prodrug analog as the sole pharmaceutically active component, or the insulin prodrug analog can be combined with one or more additional active agents. In accordance with one embodiment a pharmaceutical composition is provided comprising one of the insulin prodrug analogs disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain an insulin prodrug analog wherein the resulting active peptide is present at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various containers. The compounds of the present invention can be used in accordance with one embodiment to prepare pre-formulated solutions ready for injection. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

All therapeutic methods, pharmaceutical compositions, kits and other similar embodiments described herein contemplate that insulin prodrug analogs include all pharmaceutically acceptable salts thereof.

In one embodiment the kit is provided with a device for administering the insulin prodrug analog composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the insulin analog composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

Example 1

Synthesis of Insulin A & B Chains

Insulin A & B chains were synthesized on 4-methylbenzhyryl amine (MBHA) resin or 4-Hydroxymethyl-phenylacetamidomethyl (PAM) resin using Boc chemistry. The peptides were cleaved from the resin using HF/p-cresol 95:5 for 1 hour at 0° C. Following HF removal and ether precipitation, peptides were dissolved into 50% aqueous acetic acid and lyophilized. Alternatively, peptides were synthesized using Fmoc chemistry. The peptides were cleaved from the resin using Trifluoroacetic acid (TFA)/Triisopropylsilane (TIS)/H$_2$O (95:2.5:2.5), for 2 hour at room temperature. The peptide was precipitated through the addition of an excessive amount of diethyl ether and the pellet solubilized in aqueous acidic buffer. The quality of peptides were monitored by RP-HPLC and confirmed by Mass Spectrometry (ESI or MALDI).

Insulin A chains were synthesized with a single free cysteine at amino acid 7 and all other cysteines protected as acetamidomethyl A-(SH)[7](Acm)[6,11,20]. Insulin B chains were synthesized with a single free cysteine at position 7 and the other cysteine protected as acetamidomethyl B-(SH)[7] (Acm)[19]. The crude peptides were purified by conventional RP-HPLC.

The synthesized A and B chains were linked to one another through their native disulfide bond linkage as previously disclosed in US-2011-0257076, the disclosure of which is incorporated herein by reference. The respective B chain was activated to the Cys[7]-Npys derivative through dissolution in DMF or DMSO and reacted with 2,2'-Dithiobis (5-nitropyridine) (Npys) at a 1:1 molar ratio, at room temperature. The activation was monitored by RP-HPLC and the product was confirmed by ESI-MS.

The first B7-A7 disulfide bond was formed by dissolution of the respective A-(SH) (Acm)[6,11,20] and B-(Npys)[7](Acm)[19] at 1:1 molar ratio to a total peptide concentration of 10 mg/ml. When the chain combination reaction was complete the mixture was diluted to a concentration of 50% aqueous acetic acid. The last two disulfide bonds were formed simultaneously through the addition of iodine. A 40 fold molar excess of iodine was added to the solution and the mixture was stirred at room temperature for an additional hour. The reaction was terminated by the addition of an aqueous ascorbic acid solution. The mixture was purified by RP-HPLC and the final compound was confirmed by MALDI-MS. As shown in the data in Table 1, the synthetic insulin prepared in accordance with this procedure compares well with purified insulin for insulin receptor binding.

Insulin peptides comprising a modified amino acid (such as 4-amino phenylalanine at position A19) can also be synthesized in vivo using a system that allows for incorporation of non-coded amino acids into proteins, including for example, the system taught in U.S. Pat. Nos. 7,045,337 and 7,083,970.

TABLE 1

Activity of synthesized insulin relative to native insulin

|  | Insulin Standard | | A7-B7 Insulin | |
| --- | --- | --- | --- | --- |
|  | AVER. | STDEV | AVER. | STDEV |
| IC$_{50}$ (nM) | 0.24 | 0.07 | 0.13 | 0.08 |
| % of Insulin Activity | 100 | | 176.9 | |

Example 2

Pegylation of Amine Groups (N-Terminus and Lysine) by Reductive Alkylation a. Synthesis Insulin (or an insulin analog), mPEG20 k-Aldyhyde, and NaBH$_3$CN, in a molar ratio of 1:2:30, were dissolved in acetic acid buffer at a pH of 4.1-4.4. The reaction solution was composed of 0.1 N NaCl, 0.2 N acetic acid and 0.1 N Na$_2$CO$_3$. The insulin peptide concentration was approximately 0.5 mg/ml. The reaction occurs over six hours at room temperature. The degree of reaction was monitored by RP-HPLC and the yield of the reaction was approximately 50%.

b. Purification

The reaction mixture was diluted 2-5 fold with 0.1% TFA and applied to a preparative RP-HPLC column. HPLC condition: C4 column; flow rate 10 ml/min; A buffer 10%

ACN and 0.1% TFA in water; B buffer 0.1% TFA in ACN; A linear gradient B % from 0-40% (0-80 min); PEG-insulin or analogues was eluted at approximately 35% buffer B. The desired compounds were verified by MALDI-TOF, following chemical modification through sulftolysis or trypsin degradation.

Pegylation of Amine Groups (N-Terminus and Lysine) by N-Hydroxysuccinimide Acylation.

a. Synthesis

Insulin (or an insulin analog) along with mPEG20k-NHS were dissolved in 0.1 N Bicine buffer (pH 8.0) at a molar ratio of 1:1. The insulin peptide concentration was approximately 0.5 mg/ml. Reaction progress was monitored by HPLC. The yield of the reaction is approximately 90% after 2 hours at room temperature.

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was collected at approximately 35% B. The desired compounds were verified by MAIDI-TOF, following chemical modification through sulftolysis or trypsin degradation.

Reductive Aminated Pegylation of Acetyl Group on the Aromatic Ring of the Phenylalanine a. Synthesis Insulin (or an insulin analogue), mPEG20k-Hydrazide, and $NaBH_3CN$ in a molar ratio of 1:2:20 were dissolved in acetic acid buffer (pH of 4.1 to 4.4). The reaction solution was composed of 0.1 N NaCl, 0.2 N acetic acid and 0.1 N $Na_2CO_3$. Insulin or insulin analogue concentration was approximately 0.5 mg/ml. at room temperature for 24 h. The reaction process was monitored by HPLC. The conversion of the reaction was approximately 50%. (calculated by HPLC)

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin, or the PEG-insulin analogue was collected at approximately 35% B. The desired compounds were verified by MAIDI-TOF, following chemical modification through sulftolysis or trypsin degradation.

Example 3

Insulin Receptor Binding Assay:

The affinity of each peptide for the insulin or IGF-1 receptor was measured in a competition binding assay utilizing scintillation proximity technology. Serial 3-fold dilutions of the peptides were made in Tris-Cl buffer (0.05 M Tris-HCl, pH 7.5, 0.15 M NaCl, 0.1% w/v bovine serum albumin) and mixed in 96 well plates (Corning Inc., Acton, Mass.) with 0.05 nM (3-[125I]-iodotyrosyl) A TyrA14 insulin or (3-[125I]-iodotyrosyl) IGF-1 (Amersham Biosciences, Piscataway, N.J.). An aliquot of 1-6 micrograms of plasma membrane fragments prepared from cells over-expressing the human insulin or IGF-1 receptors were present in each well and 0.25 mg/well polyethylene imine-treated wheat germ agglutinin type A scintillation proximity assay beads (Amersham Biosciences, Piscataway, N.J.) were added. After five minutes of shaking at 800 rpm the plate was incubated for 12 h at room temperature and radioactivity was measured with MicroBeta1450 liquid scintillation counter (Perkin-Elmer, Wellesley, Mass.). Non-specifically bound (NSB) radioactivity was measured in the wells with a four-fold concentration excess of "cold" native ligand than the highest concentration in test samples. Total bound radioactivity was detected in the wells with no competitor. Percent specific binding was calculated as following: % Specific Binding=(Bound-NSB/Total bound-NSB)×100. IC50 values were determined by using Origin software (OriginLab, Northampton, Mass.).

Example 4

Insulin Receptor Phosphorylation Assay:

To measure receptor phosphorylation of insulin or insulin analog, receptor transfected HEK293 cells were plated in 96 well tissue culture plates (Costar #3596, Cambridge, Mass.) and cultured in Dulbecco's modified Eagle medium (DMEM) supplemented with 100 IU/ml penicillin, 100 μg/ml streptomycin, 10 mM HEPES and 0.25% bovine growth serum (HyClone SH30541, Logan, Utah) for 16-20 hrs at 37° C., 5% $CO_2$ and 90% humidity. Serial dilutions of insulin or insulin analogs were prepared in DMEM supplemented with 0.5% bovine serum albumin (Roche Applied Science #100350, Indianapolis, Ind.) and added to the wells with adhered cells. After 15 min incubation at 37° C. in humidified atmosphere with 5% $CO_2$ the cells were fixed with 5% paraformaldehyde for 20 min at room temperature, washed twice with phosphate buffered saline pH 7.4 and blocked with 2% bovine serum albumin in PBS for 1 hr. The plate was then washed three times and filled with horseradish peroxidase-conjugated antibody against phosphotyrosine (Upstate biotechnology #16-105, Temecula, Calif.) reconstituted in PBS with 2% bovine serum albumin per manufacturer's recommendation. After 3 hrs incubation at room temperature the plate was washed 4 times and 0.1 ml of TMB single solution substrate (Invitrogen, #00-2023, Carlbad, Calif.) was added to each well. Color development was stopped 5 min later by adding 0.05 ml 1 N HCl. Absorbance at 450 nm was measured on Titertek Multiscan MCC340 (ThermoFisher, Pittsburgh, Pa.). Absorbance vs. peptide concentration dose response curves were plotted and $EC_{50}$ values were determined by using Origin software (OriginLab, Northampton, Mass.).

Example 5

Determination of Rate of Model Dipeptide Cleavage (in PBS)

A specific hexapeptide (HSRGTF-$NH_2$; SEQ ID NO: 17) was used as a model peptide upon which the rate of cleavage of dipeptide N-terminal extensions could be studied. The dipeptide-extended model peptides were prepared Boc-protected sarcosine and lysine were successively added to the model peptide-bound resin to produce peptide A (Lys-Sar-HSRGTF-$NH_2$; SEQ ID NO: 18). Peptide A was cleaved by HF and purified by preparative HPLC.

The rate of cleavage was determined for the respective propeptides. The concentrations of the propeptides and the model parent peptide were determined by their respective peak areas. The first order dissociation rate constants of the prodrugs were determined by plotting the logarithm of the concentration of the prodrug at various time intervals. The slope of this plot provides the rate constant 'k'. The half-lives for cleavage of the various prodrugs were calculated by using the formula $t_{1/2}$=0.693/k. The half-life of the Lys-Sar extension to this model peptide HSRGTF-$NH_2$ (SEQ ID NO: 17) was determined to be 14.0 h.

Example 6

Rate of Dipeptide Cleavage Half Time in Plasma as Determined with an all d-Isoform Model Peptide An additional model hexapeptide (dHdTdRGdTdF-NH$_2$ SEQIDNO: 21) was used to determine the rate of dipeptide cleavage in plasma. The d-isomer of each amino acid was used to prevent enzymatic cleavage of the model peptide, with the exception of the prodrug extension. This model d-isomer hexapeptide was synthesized in an analogous fashion to the l-isomer. The sarcosine and lysine were successively added to the N-terminus as reported previously for peptide A to prepare peptide B (dLys-dSar-dHdTdRGdTdF-NH$_2$ SEQ ID NO: 59)

The rate of cleavage was determined for the respective propeptides. The concentrations of the propeptides and the model parent peptide were determined by their respective peak areas. The first order dissociation rate constants of the prodrugs were determined by plotting the logarithm of the concentration of the prodrug at various time intervals. The slope of this plot provides the rate constant 'k'. The half-life of the Lys-Sar extension to this model peptide dHdT-dRGdTdF-NH$_2$ (SEQ ID NO: 21) was determined to be 18.6 h.

Example 7

The rate of cleavage for additional dipeptides linked to the model hexapeptide (HSRGTF-NH$_2$; SEQ ID NO: 17) were determined using the procedures described in Example 5. The results generated in these experiments are presented in Tables 2 and 3.

TABLE 2

Cleavage of the Dipeptides O—U that are linked to the side chain of an N-terminal para-amino-Phe from the Model Hexapeptide (HSRGTF—NH$_2$; SEQ ID NO: 17) in PBS

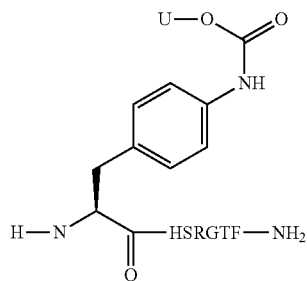

| Compounds | U (amino acid) | O (amino acid) | t$_{1/2}$ |
|---|---|---|---|
| 1 | F | P | 58 h |
| 2 | Hydroxyl-F | P | 327 h |
| 3 | d-F | P | 20 h |
| 4 | d-F | d-P | 39 h |
| 5 | G | P | 72 h |
| 6 | Hydroxyl-G | P | 603 h |
| 7 | L | P | 62 h |
| 8 | tert-L | P | 200 h |
| 9 | S | P | 34 h |
| 10 | P | P | 97 h |
| 11 | K | P | 33 h |
| 12 | dK | P | 11 h |
| 13 | E | P | 85 h |
| 14 | Sar | P | ≈1000 h |
| 15 | Aib | P | 69 min |
| 16 | Hydroxyl-Aib | P | 33 h |
| 17 | cyclohexane | P | 6 min |
| 18 | G | G | No cleavage |
| 19 | Hydroxyl-G | G | No cleavage |
| 20 | S | N-Methyl-Gly | 4.3 h |
| 21 | K | N-Methyl-Gly | 5.2 h |
| 22 | Aib | N-Methyl-Gly | 7.1 min |
| 23 | Hydroxyl-Aib | N-Methyl-Gly | 1.0 h |

TABLE 3

Cleavage of the Dipeptides U-O linked to histidine (or histidine derivative) at position 1 (X) from the Model Hexapeptide (XSRGTF-NH$_2$; SEQ ID NO: 17) in PBS
NH$_2$-U-O-XSRGTF-NH$_2$

| Cmp | U (amino acid) | O (amino acid) | X (amino acid) | t$_{1/2}$ |
|---|---|---|---|---|
| 1 | F | P | H | No cleavage |
| 2 | Hydroxyl-F | P | H | No cleavage |
| 3 | G | P | H | No cleavage |
| 4 | Hydroxyl-G | P | H | No cleavage |
| 5 | A | P | H | No cleavage |
| 6 | C | P | H | No cleavage |
| 7 | S | P | H | No cleavage |
| 8 | P | P | H | No cleavage |
| 9 | K | P | H | No cleavage |
| 10 | E | P | H | No cleavage |
| 11 | Dehydro V | P | H | No cleavage |
| 12 | P | d-P | H | No cleavage |
| 13 | d-P | P | H | No cleavage |
| 14 | Aib | P | H | 32 h |
| 15 | Aib | d-P | H | 20 h |
| 16 | Aib | P | d-H | 16 h |
| 17 | Cyclohexyl- | P | H | 5 h |
| 18 | Cyclopropyl- | P | H | 10 h |
| 19 | N-Me-Aib | P | H | >500 h |
| 20 | α,α-diethyl-Gly | P | H | 46 h |
| 21 | Hydroxyl-Aib | P | H | 61 |
| 22 | Aib | P | A | 58 |
| 23 | Aib | P | N-Methyl-His | 30 h |
| 24 | Aib | N-Methyl-Gly | H | 49 min |
| 25 | Aib | N-Hexyl-Gly | H | 10 min |
| 26 | Aib | Azetidine-2-carboxylic acid | H | >500 h |
| 27 | G | N-Methyl-Gly | H | 104 h |
| 28 | Hydroxyl-G | N-Methyl-Gly | H | 149 h |
| 29 | G | N-Hexyl-Gly | H | 70 h |
| 30 | dK | N-Methyl-Gly | H | 27 h |
| 31 | dK | N-Methyl-Ala | H | 14 h |
| 32 | dK | N-Methyl-Phe | H | 57 h |
| 33 | K | N-Methyl-Gly | H | 14 h |
| 34 | F | N-Methyl-Gly | H | 29 h |
| 35 | S | N-Methyl-Gly | H | 17 h |
| 36 | P | N-Methyl-Gly | H | 181 h |

In addition various prodrug derivatives of IGF1YL insulin analogs have been prepared wherein a dipeptide element has been linked via an amide bond through the 4-amino-phenylalanine residue present at A19 of the IGF1YL. The in vitro analysis of these compounds using the procedures of Example 5 reveals that the activity of these compounds increases with time incubated in either a PBS buffer or in 20% plasma. In addition, the in vitro activity of the IGF analog prodrug MIU30: A1(aF19-dLys(Ac),Sar) (dipeptide linked through and amide bond to the A19 4-aminoPhe) was measured for insulin receptor binding relative to native insulin over time (1 hour, 3 hours, 6 hours, 9 hours and 10.5 hours) incubated in 20% plasma. Table 3A compares the relative insulin receptor binding of over time incubated in 20% plasma/PBS at 37° C. As indicated by the data presented in an in vitro binding assay, see Table 3A and an in vitro phosphorylation assay, see Table 3B, increased activity is recovered from the A19 IGF prodrug derivative sample over time, as the prodrug form is converted to the active IGF1YL peptide.

TABLE 3A

| Time (hr) | % Activity of Insulin |
|---|---|
| 0 | 34.44% |
| 9 | 100.09% |
| 95 | 115.42% |

TABLE 3B

| Time (hr) | % Activity of Insulin |
|---|---|
| 1 | 23.0 |
| 3 | 26.8 |
| 6 | 32.5 |
| 9 | 41.1 |
| 10.5 | 43.2 |

Figure 1B:
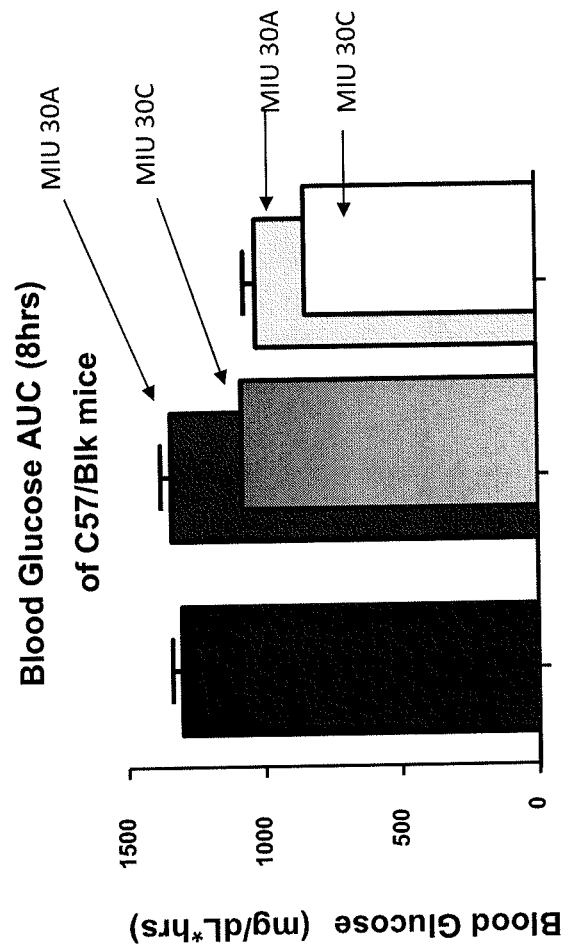

In vivo glucose tolerance tests using C57/Blk mice administered insulin analog MIU-30a: $B^1$(Y16,L17,Y25)29a: $A^1$(dLys(Ac),Sar-aF19) (dipeptide linked through and amide bond to the A19 4-aminoPhe), MIU 30 dissolved in PBS (pH 7.4) with 20% plasma and incubated for 48 hours at 37° C. (generating "MIU-30c"). Samples incubated for 0 hr (MIU 30a) and 48 hr (MIU 30c) were withdrawn and injected to C57 black mice at 90 nmol/kg and 270 nmol/kg to measure glucose lowering (insulin tolerance test). In FIG. 1A the glucose lowering profile of MIU 30a and MIU 30c at various times through 8 hr are shown. The parent compound has low potency, but after incubation in 20% plasma for 48 hours (generating "MIU-30c") potency is increased (See FIG. 1A). In FIG. 1B total blood glucose of MIU 30a and MIU 30c as compared to vehicle is reported as differential area under curve (AUC). At 90 nmol/kg, MIU 30a indicates little change in glucose, while MIU 30c causes a sizable decrease. At 270 nmol/kg, both MIU 30a and MIU 30c demonstrate glucose lowering, but the latter sample possesses significantly more hypoglycemic potency. In summary, the prodrug form of the insulin analog MIU30 shows appreciably lesser glucose lowering potency when injected prior to ex vivo conversion under physiological conditions to the parent insulin analog. These in vivo results are consistent with the in vitro analysis. The half-life of the prodrug is estimated to be approximately 20 hours.

Example 8

Comparative Insulin Tolerance for Insulin Prodrug Analogs

Normal mice were administered either an insulin heterodimer analog [$B^1$(Y16,L17,Y25)29a: $A^1$(aF19-NH2)], or a prodrug derivative thereof. The prodrug derivative MIU-29: [$B^1$(Y16,L17,Y25)29a: $A^1$(aF19-dLys(Ac),NLeu)] comprises a 4-amino-phenylalnine substitution at position A19 wherein a dipeptide dLys(Ac),NLeu have been covalently linked at the 4-amino position of the A19 residue. This dipeptide will auto-cleave under physiological conditions with a half-life of approximately 4.4 hours. After incubating the prodrug derivative [$B^1$(Y16,L17,Y25)29a: $A^1$(aF19-dLys(Ac),NLeu)] for 24 hours ex vivo, the resultant compound was administered to mice and its ability to lower blood glucose was compared to parent compound. The two compounds performed almost identically.

Figure 2:
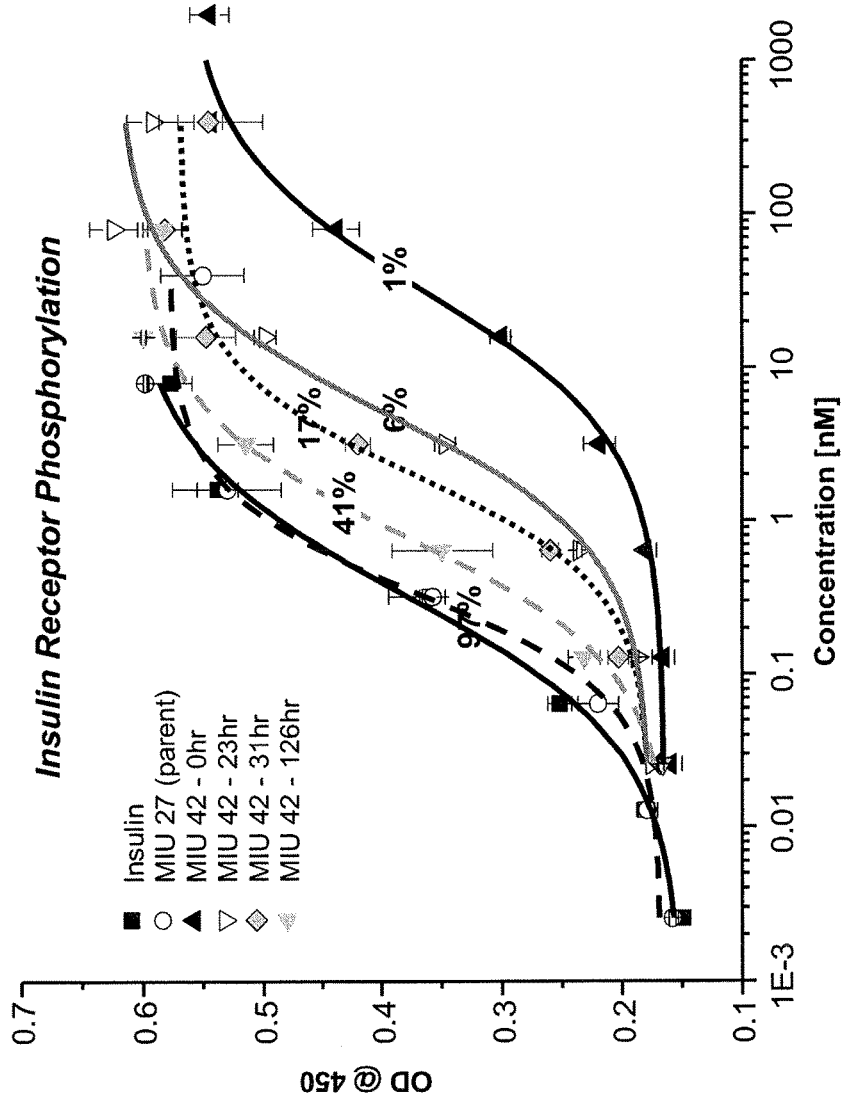
FIG. 2 is a graph depicting the in vitro activity of the acylated prodrug MIU 42: $B^1(Y16,L17,Y25)29a$: $A^1(dLys(rE-C14),Sar-aF19)$ (wherein an amino acid of the dipeptide prodrug element is acylated, linked at the gamma position "rE" of a glutamic acid linker) relative to time incubated ex vivo in 30% ACN/PBS at pH 7.4 and 37° C. As shown by the data, activity is restored to parent compound MIU 42 with increased time incubated ex vivo.
Figure 3:
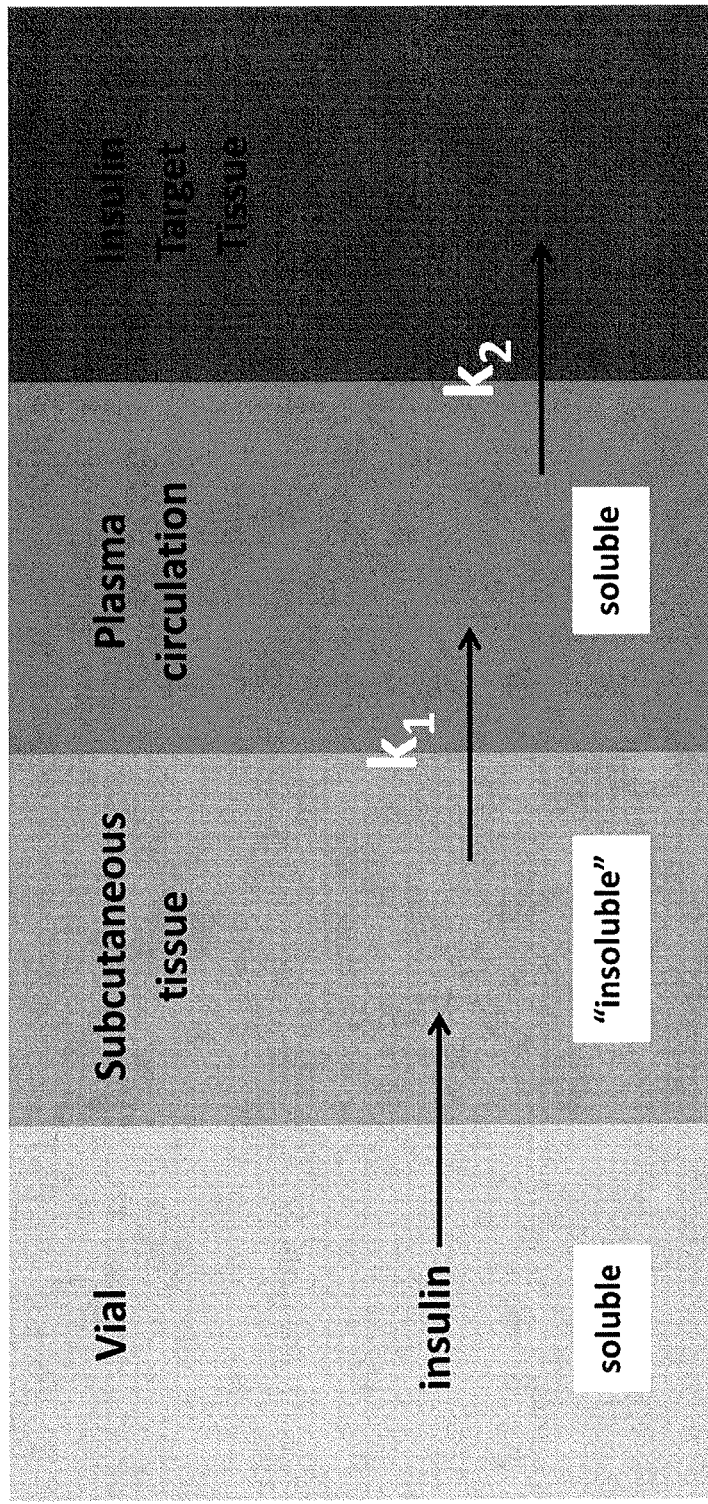
FIG. 3 demonstrates the Ultra-basal/Basal/Bolus Insulin Therapy. Current strategies for delaying the onset of insulin action in commercial insulin analogs rely on creating a reserve of "insoluble" insulin in the subcutaneous tissues that is slowly released into the plasma over time (k1). The soluble form present in the plasma then enters the insulin target tissue at a relatively rapid rate (k2). Purposeful fractional daily dosing (qd) with a soluble long-acting insulin (qw) minimizes variability inherent to single administration.
Figure 4:
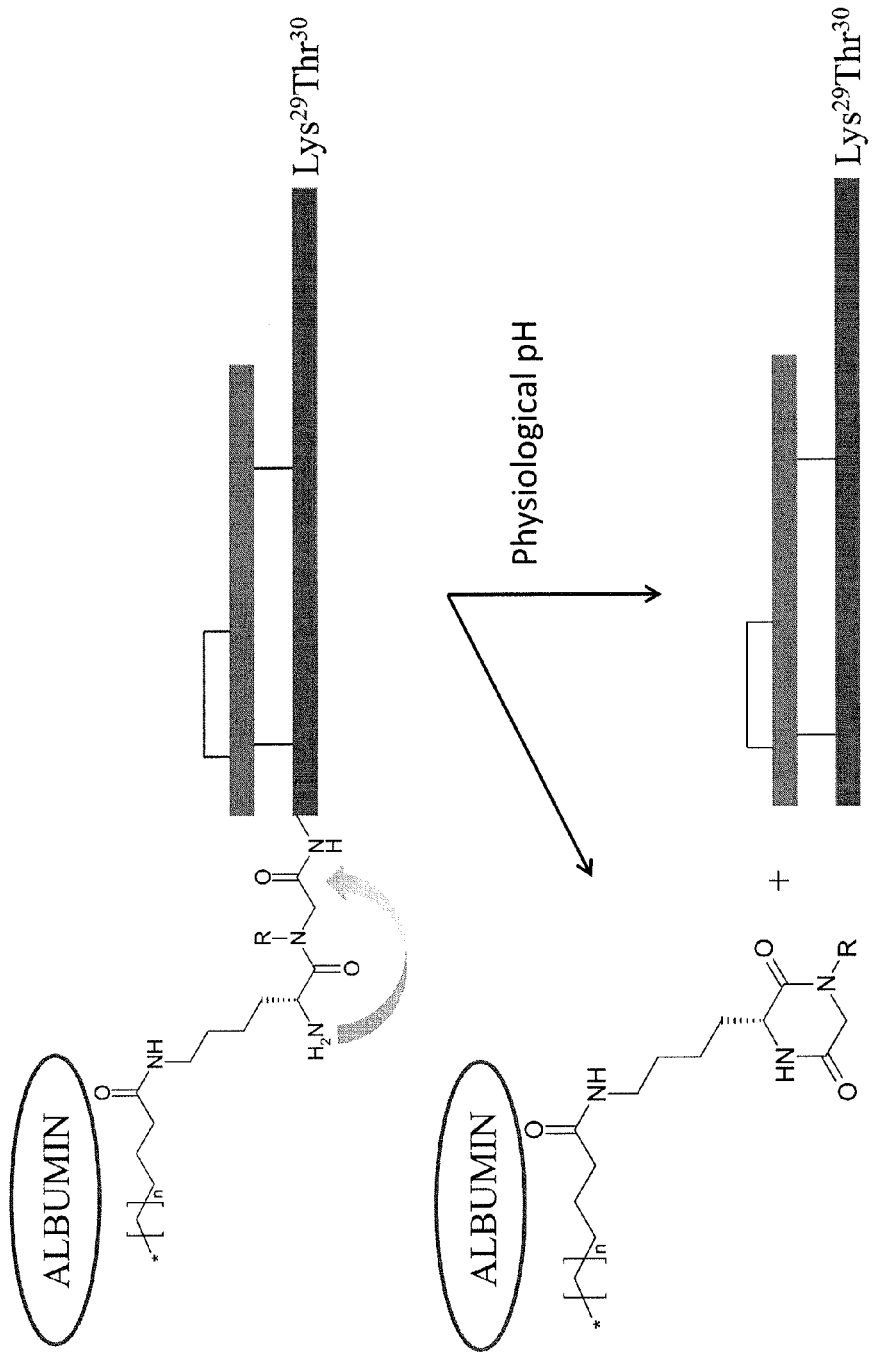
FIG. 4 shows a schematic drawing showing inactivation of an insulin analog by irreversible binding of serum albumin to a lipidated prodrug element linked to the N-terminal amine of the B chain. Subsequent cleavage of the dipeptide element under physiological conditions and in the absence of enzymatic activity, results in activation of the insulin by release of the dipeptide prodrug element.
Figure 5:
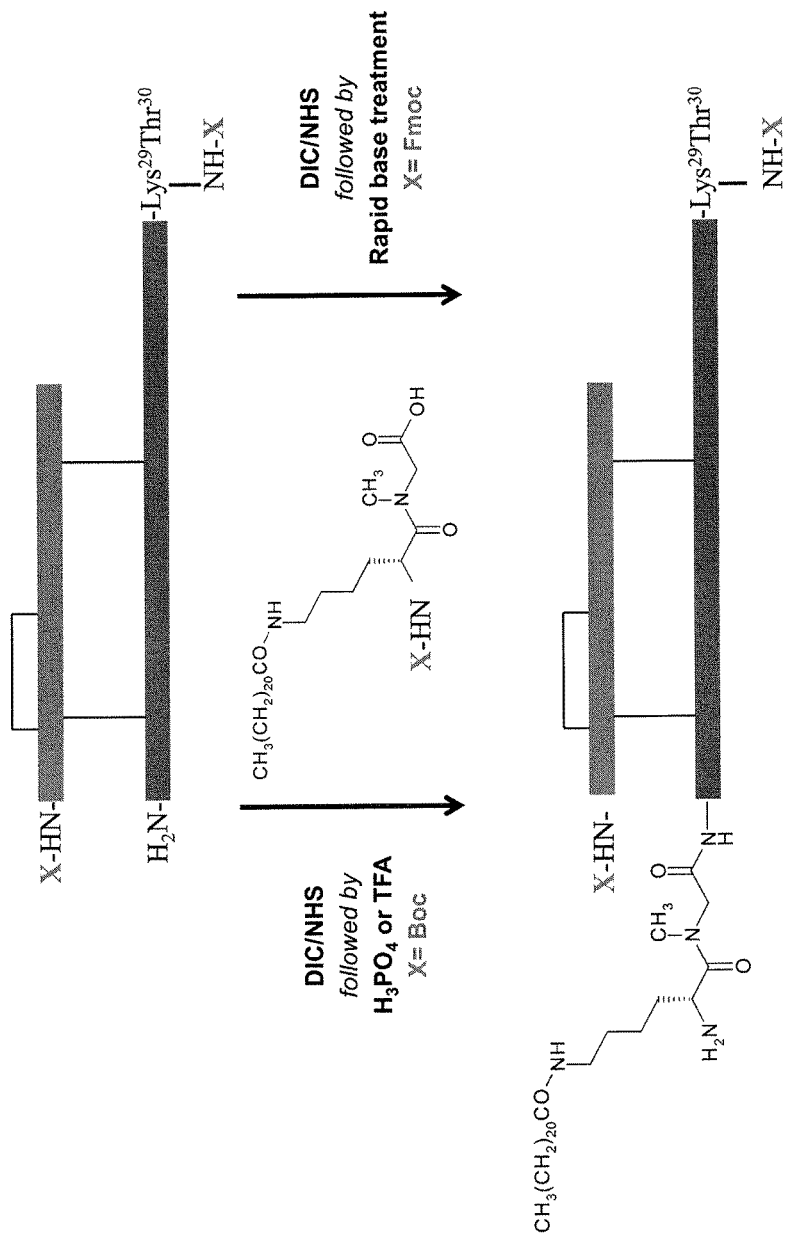
FIG. 5 provides a synthetic scheme for preparing a two chain insulin analog comprising a lipidated prodrug element linked to the N-terminal amine of the B chain.
Figure 6:
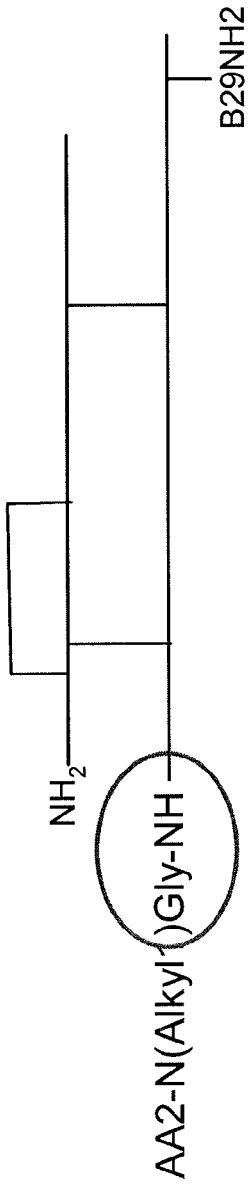
FIG. 6 provides the cleavage half-lives of a lipidated prodrug element linked to the N-terminal amine of the B chain, wherein the N-alkylation of the first amino acid is modified and the length of the alkyl chain linked to the second amino acid is varied.
Figure 7:
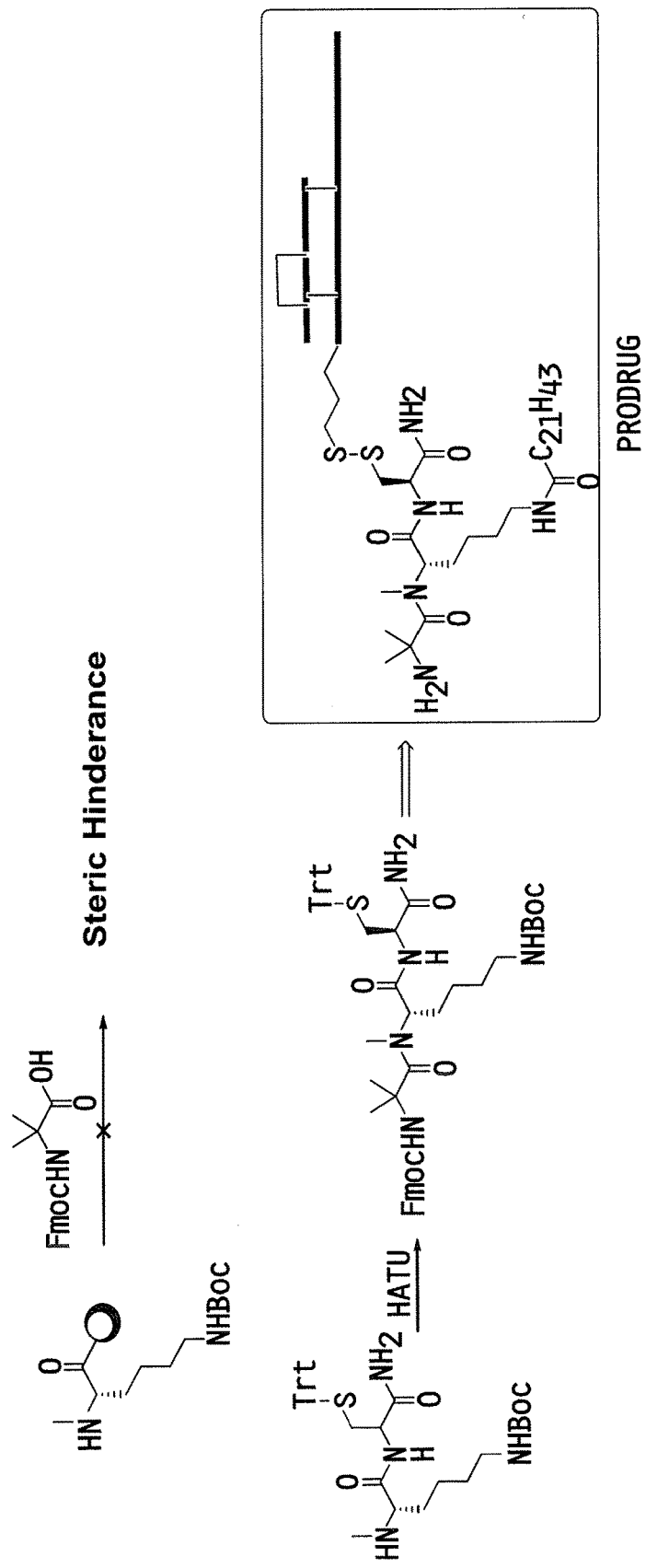
FIG. 7 provides HLPC traces showing the degradation of an insulin prodrug analog (Aib-(N-Me)Lys(C22)-Cys-(S-Propyl)B1-Insulin). The prodrug element of the insulin prodrug exhibited a half-life of about 8 hours.
Figure 7:
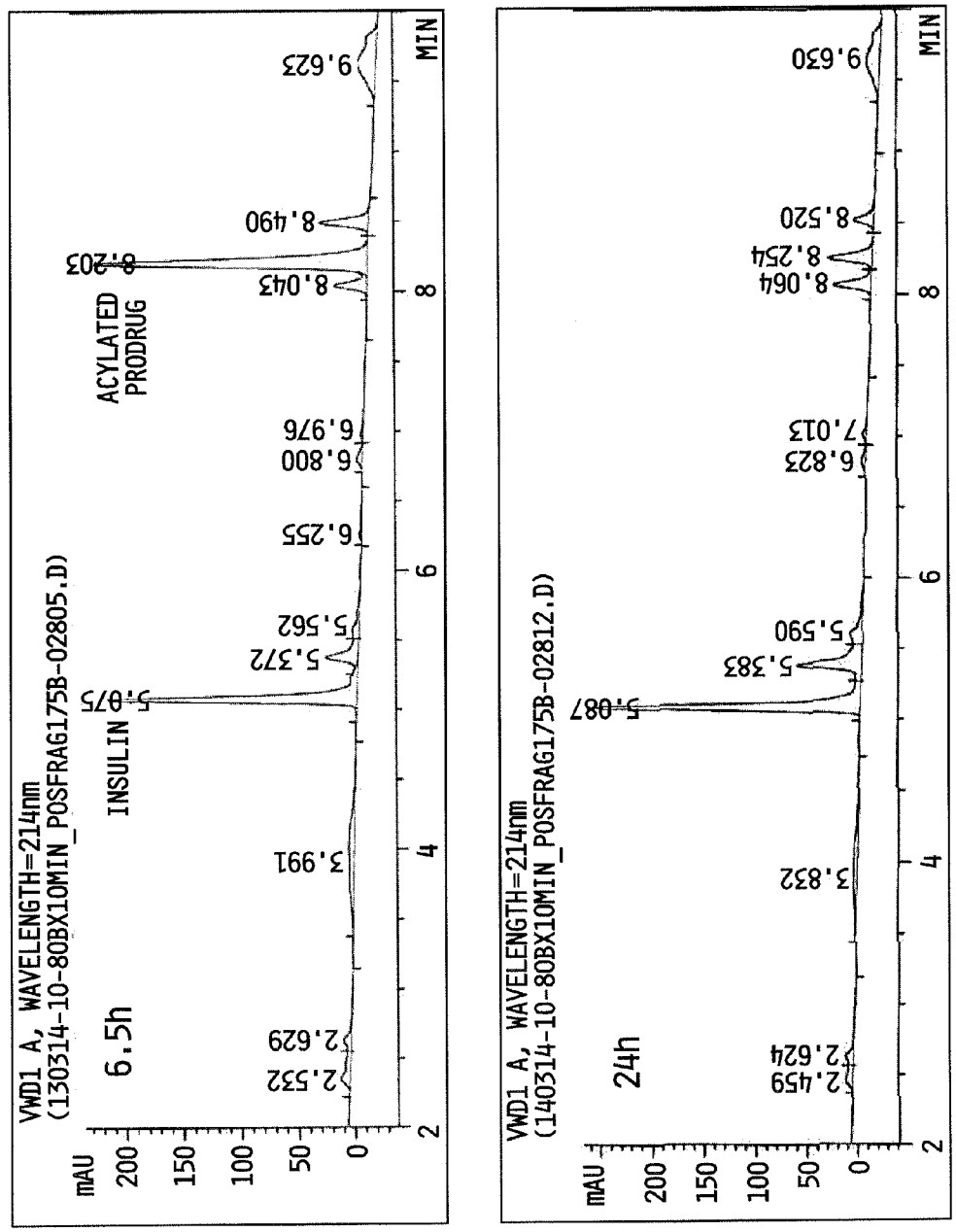
Figure 9:
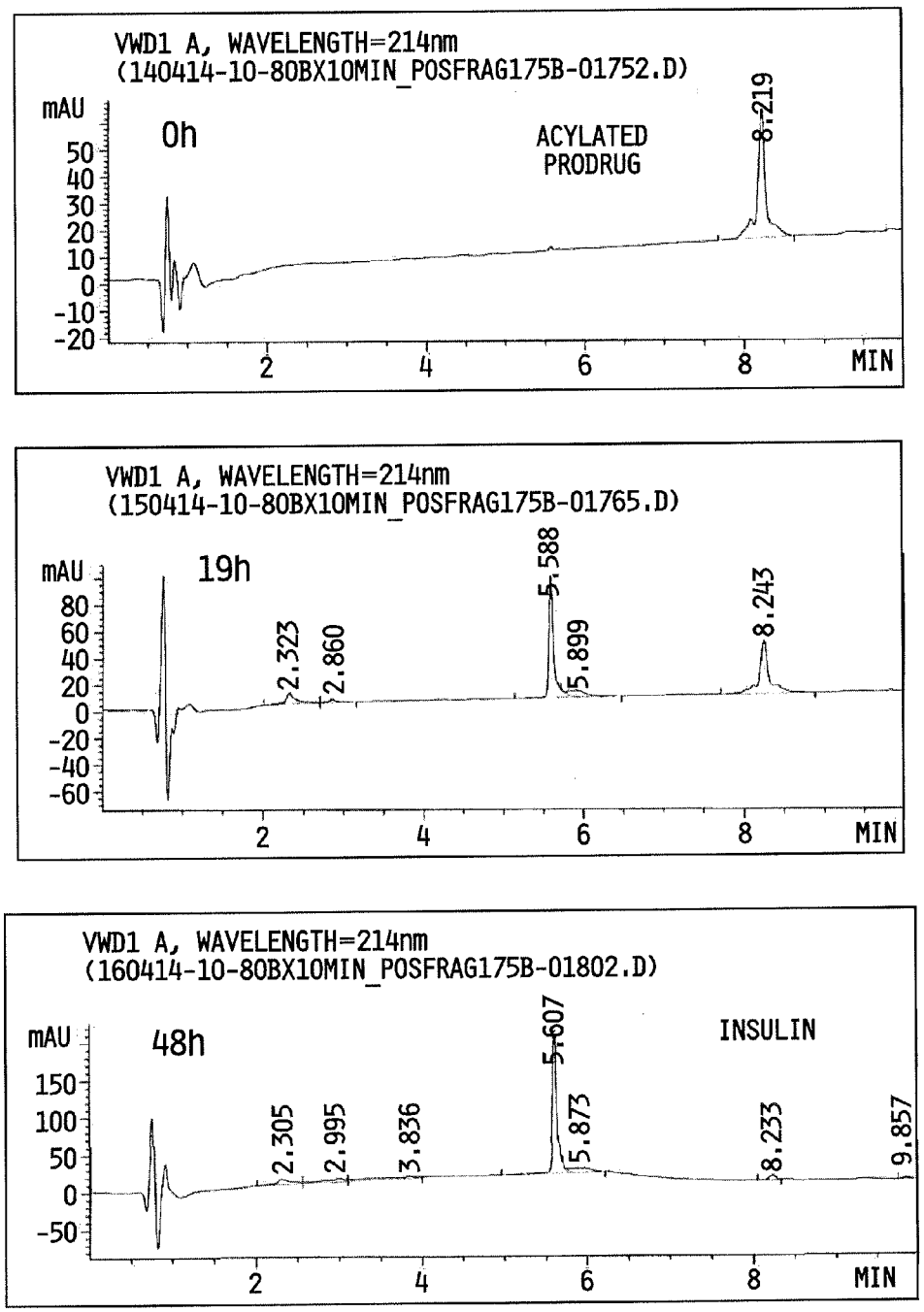
FIG. 9 provides HLPC traces showing the degradation of an insulin prodrug analog (Lys(C18)-N(sBu)Gly,Gly B1-Insulin). The prodrug element of the insulin prodrug exhibited a half-life of about 16 hours.
Figure 11:
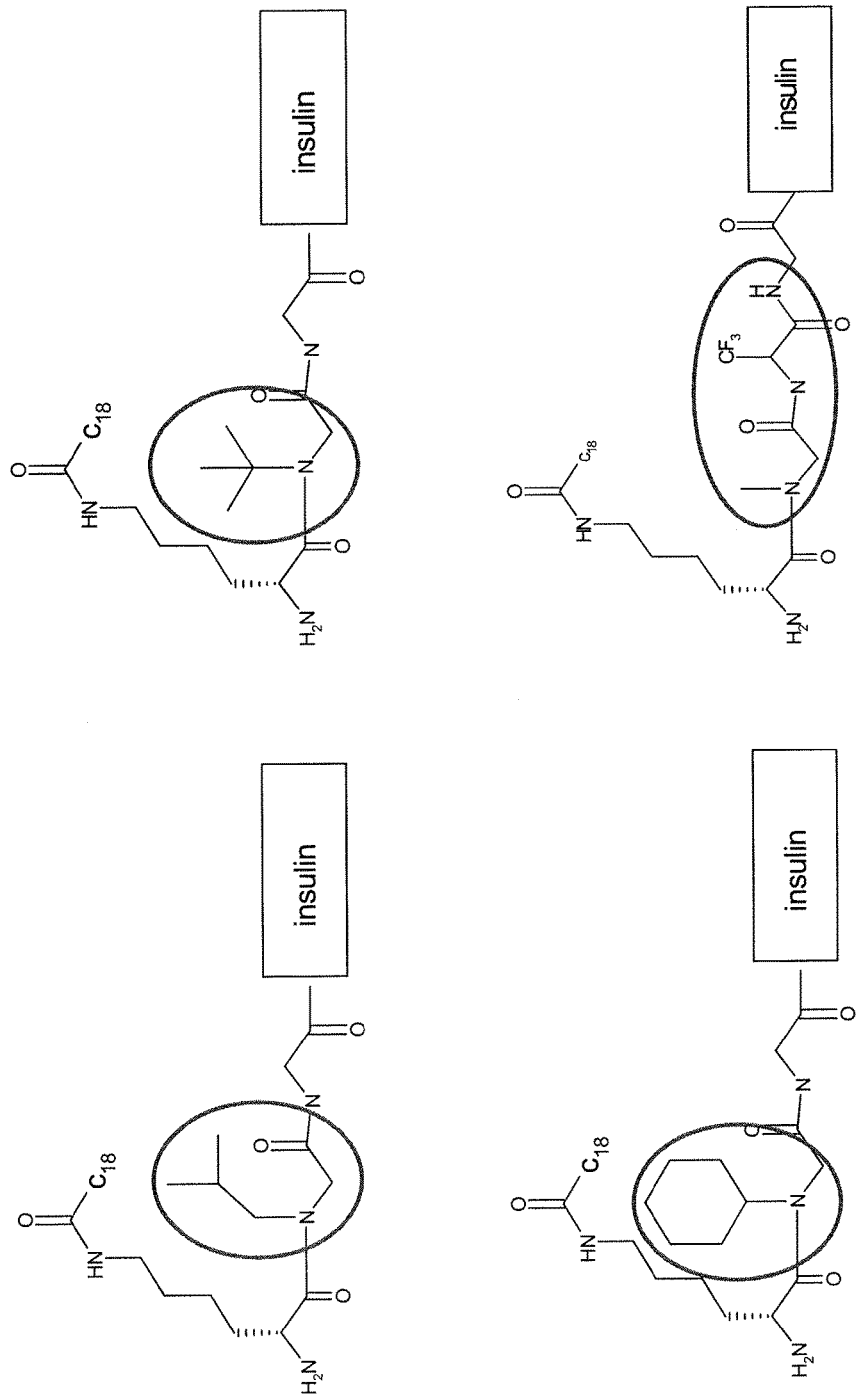
FIG. 11 provides additional embodiments for the structure of the prodrug element.
Figure 12:
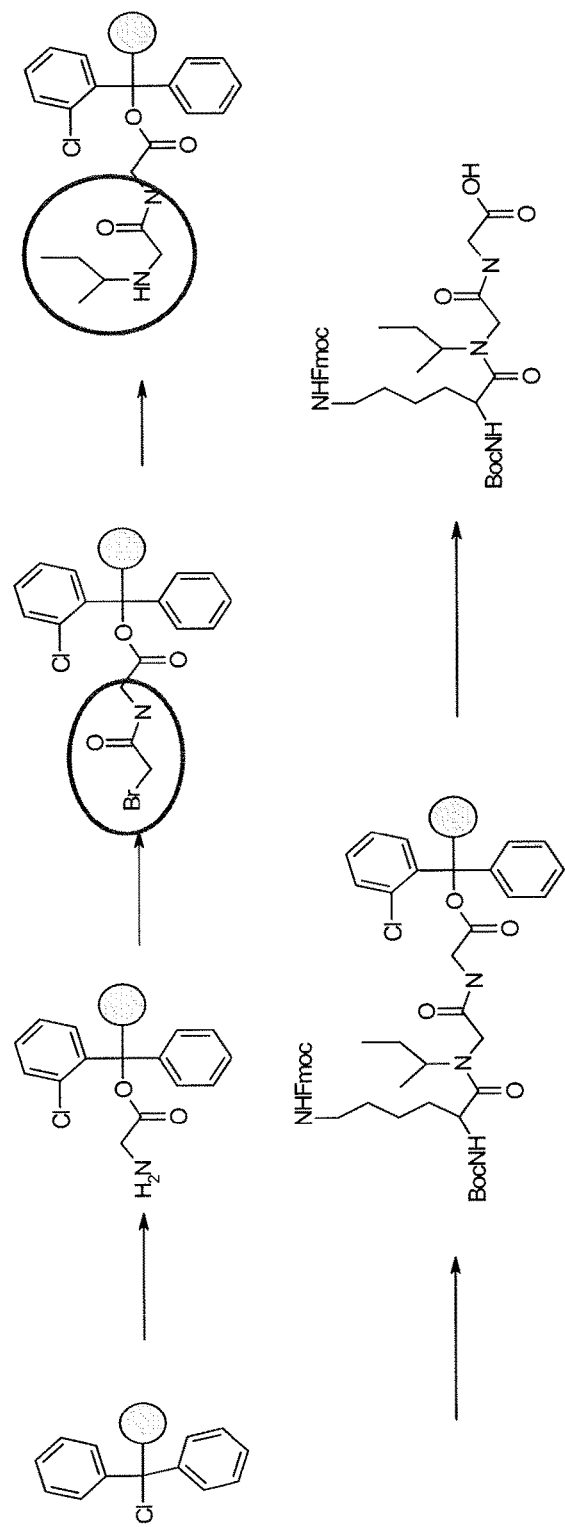
FIG. 12 provides a synthetic scheme for introducing an N-alkyl group into a peptide by 2-bromo carboxylic acid.
Figure 13:
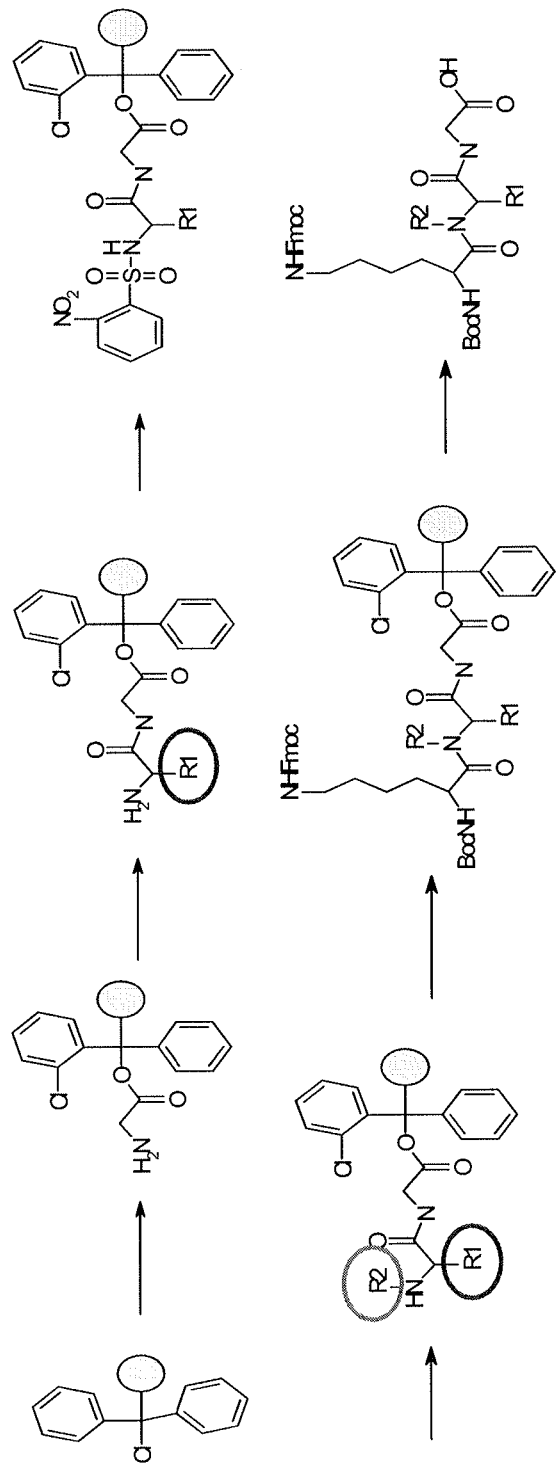
FIG. 13 provides a synthetic scheme for introducing an N-alkyl group into a peptide and alpha carbon substitution, by Mitsunobu Reaction.

Acylation of the insulin prodrug analogs was investigated to determine if retention times in vivo could be enhanced. The in vitro activity of MIU 42 [$B^1$(Y16,L17,Y25)29a: $A^1$(dLys(rE-C14),Sar-aF19)], having an acylated dipeptide prodrug element, increases with time incubated ex vivo in 30% ACN/PBS @ pH7.4 37° C. (providing time for prodrug conversion) relative to the non-acylated prodrug (see FIG. 2). Comparative insulin potency tests conducted using the MIU 42 prodrug administered without a pre-incubation step show that the prodrug is not very potent relative to the non-prodrug parent compound (MIU-27). This was also found to be true for an acylated insulin analog MIU-46 [$B^1$(H5,10 Y16,L17,Y25, K29-C14)28a: $A^1$(N18,21, aF19NH2)] having acylation at the B29 position. The compound did not exhibit a desired in vivo potency or a basal profile when tested in vivo in mice. Accordingly, at least in mice the acylation does not produce the desired profile.

Example 9

Biosynthesis and Purification of Pegylated Insulin Prodrug Analogs

IGF1 B chain (2-25) $H^{5,10}$ $Y^{16}$ $L^{17}$ $SH^7$ $Acm^{19}$ amide was synthesized on an MBHA resin using solid phase Boc-chemistry. After cleavage of the peptide from the resin with simultaneous removal of amino acid side chain protection, crude B chain was mixed with 2,2'-dithiobis(5-nitropyridine) in DMSO to yield a cysteine-NpyS derivative at $Cys^7$. Addition of Boc-aminooxyacetyl (Aoa) to the N-terminal of B chain was achieved through reaction between B chain and Boc-Aoa-OSu. Purified IGF1 B chain (2-25)(BocAoa)$^0$ $H^{5,10}$ $Y^{16}$ $L^{17}$ $SH^7$ $Acm^{19}$ amide was combined with IGF1 A chain $Acm^{6,7,11}$ $N^{18,21}$ (aa1aa2)-pNH-$F^{19}$ acid using the "1+2" method described in US-2011-0257076, the disclosure of which is incorporated herein by reference to generate the insulin analog with Boc-Aoa at the N terminal of B chain. Boc was removed by treatment of the peptide with brief treatment with 6N HCl in the presence of O-(Carboxymethyl)hydroxylamine hemihydrochloride as scavenger. After Boc removal and purification, the peptide was dissolved in 1% aniline/30% ACN/0.2M NaOAc (pH4.6) at the concentration of 3 mg/ml. Two-fold excess amount of 20 KD PEG-propionic aldehyde was added to the solution, the reaction was conducted with stirring for one hour at room temperature, followed by the final purification to yield the pegylated insulin analog.

The addition of a 20 kDa PEG to the amino terminus of a two chain insulin analog reduces the potency of the insulin analog. The addition of an auto-cleavable dipeptide prodrug element (dLys(rE-C14),Nleu) at position A19 further reduces the potency of the compound by approximately 100 fold. However preincubation of the prodrug in PBS at 37° C. for 78 hours (the dipeptide has a half-life of approximately 4.4 hours) restores the potency to a value close to the parent pegylated compound. See Table 4 which lists the EC50 of the analogs at the insulin receptor A and B subtypes as measured in an in vitro phosphorylation assay.

TABLE 4

Activity of Pegylated Insulin Prodrug

|   |   | Insulin | Unpegylated pNH$_2$F | PEG-pNH$_2$F | PEG-dKAcNleu 0 h | PEG-dKAcNleu 78 h |
|---|---|---|---|---|---|---|
| IR-A | EC50 | 0.17 | 0.21 | 0.94 | 15.49 | 2.06 |
|  | % |  | 81% | 18% | 1.1% | 8.3% |
| IR-B | EC50 | 0.24 | 0.50 | 3.72 | 20.0 | 3.8 |
|  | % |  | 48% | 6.5% | 1.2% | 6.3% |

Example 10

Biosynthesis and Purification of Single Chain Insulin Analogs

An insulin-IGF-I minigene comprising a native insulin B and A chain linked via the IGF-I C chain (B$^0$-C$^1$-A$^0$) was cloned into expression vector pGAPZα A (purchased from Invitrogen) under GAP promoter (promoter of the glyceraldehyde-3-phosphate dehydrogenase (GAPDH)) for constitutive expression and purification of recombinant protein in yeast *Pichia pastoris*. The minigene was fused to an N-terminal peptide encoding *Saccharomyces cerevisiae* α-mating factor leader signal for secretion of the recombinant protein into the medium. A Kex2 cleavage site between the minigene and the leading α-mating factor sequence was used to cleave the leader sequence for secretion of the minigene with native amino termini. Single-site alanine mutations were introduced into C peptide at positions 1 (G1A), 2 (Y2A), 3 (G3A), 4 (S4A), 5 (S5A), 6 (S6A), 7 (R7A), 8 (R8A), 10 (P10A), 11 (Q11A), and 12 (T12A) of the B$^0$-C$^1$-A$^0$ minigene.

The minigenes including B$^0$-C$^1$-A$^0$, eleven alanine mutants, and other select derivatives were transformed into yeast *Pichia pastoris* by electroporation. Positive transformants were selected on minimal methanol plates and a genomic preparation of each *Pichia* isolate was performed and integration of the constructs into the yeast genome was confirmed by PCR. An 833 base pair PCR product was visualized on an agarose DNA gel. The insulin analogs were produced by fermentation of a corresponding yeast line. The yeast cells were pelleted by centrifugation at 5 K for 20 minutes in 500 ml Beckman centrifuge tubes and the media was kept for subsequent protein purification.

Growth media supernatants were filtered through 0.2 μm Millipore filter. Acetonitrile (ACN) was added to the supernatant to a final volume of 20%. The supernatant was purified over a Amberlite XAD7HP resin from Sigma, pre-equilibrated with 20% aqueous ACN. The resin was then rinsed twice with 30 ml of 20% aqueous ACN and contaminants were removed with 30% aqueous ACN containing 0.1% TFA. Partially purified insulin analogs were eluted from the column with 54% aqueous ACN containing 0.1% TFA and lyophilizied. Lyophilized samples were re-suspended in 0.025M NH$_3$HCO$_3$ pH 8 and purified on a Luna C18 column (10 μm particle size, 300A° pore size). Protein was eluted from the column using a linear gradient of 20-60% aqueous ACN. MALDI-MS positive fractions were pooled and transferred to a disposable scintillation vial for subsequent lyophilization. Lyophilized samples were then resuspended in 20% aqueous ACN containing 0.1% TFA, and purified on a Luna C18 column (10 μm particle size, 300A° pore size). The protein was eluted from the column using a linear gradient of 18-54% aqueous ACN with 0.1% TFA. Protein elution was monitored at an absorbance 280 nm. MALDI-TOF MS positive fractions were analyzed via a C8 analytical column to insure purity.

The B$^0$-C$^1$-A$^0$ analog demonstrated potency that was equally effective at both insulin receptor isoforms and the IGF-1 receptor. Mutation of the tyrosine at position 2 to alanine or the shortening of the C-peptide to eight amino acids through deletion of C9-12 provided a selective enhancement in the specificity of insulin action by significant reduction in the IGF-1 receptor activity. See the data provided in Tables 5A and 5B:

TABLE 5A

Insulin Binding & Phosphorylation Analysis (B$^0$C$^1$A$^0$)

|  | Insulin Binding | | Insulin Phosphorylation | |
|---|---|---|---|---|
| Peptide | IC$_{50}$, nM | N | EC$_{50}$, nM | n |
| Insulin | 0.54 +/− 0.02 | 4 | 1.67 +/− 0.13 | 1 |
| IGF-1 | 18.81 +/− 1.77 | 3 | 29.20 +/− 8.41 | 1 |
| 010 (B$^0$C$^1$A$^0$) | 2.83 +/− 0.52 | 2 | 1.93 +/− 0.43 | 1 |
| G1A | 1.21 +/− 0.15 | 1 | 2.4 +/− 0.24 | 1 |
| Y2A | 1.95 +/− 0.28 | 3 | 1.86 +/− 0.42 | 1 |
| G3A | 1.41 +/− 0.05 | 2 | 2.13 +/− 0.02 | 1 |
| S4A | 0.84 +/− 0.47 | 2 | 0.76 +/− 0.35 | 1 |
| S5A | 0.93 +/− 0.44 | 1 | 2.23 +/− 1.27 | 1 |
| S6A | 1.15 +/− 0.24 | 1 | 2.33 +/− 1.65 | 2 |
| R7A | 6.04 +/− 0.82 | 1 | 5.21 +/− 4.14 | 1 |
| R8A | 0.63 +/− 0.09 | 1 | 2.03 +/− 0.06 | 2 |
| P10A | 2.86 +/− 0.93 | 1 | 2.59 +/− 1.2 | 1 |
| Q11A | 1.79 +/− 0.47 | 1 | 2.58 +/− 0.83 | 1 |
| T12A | 1.2 +/− 0.18 | 1 | 2.81 +/− 1.31 | 1 |

TABLE 5B

IGF-1 Binding & Phosphorylation Analysis (B$^0$C$^1$A$^0$)

|  | IGF-1 Binding | | IGF-1 Phosphorylation | |
|---|---|---|---|---|
| Peptide | IC$_{50}$, nM | N | EC$_{50}$, nM | n |
| Insulin | 60.63 +/− 4.43 | 1 | 48.66 +/− 1.59 | 1 |
| IGF-1 | 0.38 +/− 0.07 | 1 | 0.88 +/− 0.41 | 1 |
| 010 (B$^0$C$^1$A$^0$) | 4.49 +/− 1.04 | 1 | 1.29 +/− 2.28 | 1 |
| G1A | 42.36 +/− 16.24 | 1 | 1.4 +/− 0.62 | 1 |
| Y2A | 257.9 +/− 29.59 | 1 | 35.6 +/− 14.55 | 1 |
| G3A | 34.02 +/− 16.09 | 1 | 7.85 +/− 0.78 | 1 |
| S4A | 15.30 +/− 3.10 | 1 | 1.64 +/− 1.65 | 1 |
| S5A | 13.06 +/− 3.0 | 1 | 2.63 +/− 1.88 | 1 |
| S6A | 2.44 +/− 0.79 | 1 | 1.54 +/− 0.62 | 2 |
| R7 | 43.86 +/− 8.72 | 1 | 1.26 +/− 1.55 | 1 |
| R8 | 10.85 +/− 1.47 | 1 | 0.50 +/− 0.23 | 2 |
| P10A | 6.42 +/− 0.47 | 1 | 2.79 +/− 1.12 | 1 |
| Q11A | 4.23 +/− 0.43 | 1 | 0.41 +/− 0.69 | 1 |
| T12A | 9.15 +/− 0.83 | 1 | 1.44 +/− 1.36 | 1 |

Position 2 and 3 in the C-peptide are most sensitive to modification at the IGF-1 receptor with the insulin receptor proving to be relatively immune to modification. All of the analogs maintained single unit nanomolar activity with certain specific analogs proving to be slightly enhanced in potency (low single unit nanomolar). The most insulin selective analogs were those that we missing the last four residues of the C-peptide, had an alanine mutation at position two of the C-peptide, or a combination of the two changes.

The stability of insulin/IGF chimeras was investigated by exposing insulin analogs to insulin-specific degrading enzyme (IDE) and assaying for activity.

Insulin Degradation assays: rDNA rat IDE was obtained from EMD Chemicals Inc. Peptides were prepared as 15 mM aliquots in ammonium bicarbonate buffer. Initial concentration was estimated based on UV absorbance at 276 nm, and further confirmed by HPLC analyze with internal standard. The pH of the solution was kept between 7.8-8.4. The IDE was added and digestion was conducted at 37° C. over time (12 to 48H). Ratio 1:350-450 (enzyme:substrate) was used depending on experiment. Aliquots were withdraw over time intervals into TFA buffered solution with internal reference peptide for the HPLC analysis. Additional aliquots were withdraw into DMEM assay medium for activity evaluation. All aliquots were immediately frozen on dry ice and kept at −55° C. until analyzed.

HPLC assay: Degradation profile of investigated peptides was evaluated in an HPLC assay. The two runs on an Agilant Zorbax C8 column attached to a Beckman-Coulter system using TFA buffer were performed for each aliquot (gradient 20 to 60% B in 10 min, where B=90% AcN).

Bioactivity: The residual potency of analogs after incubation with IDE was determined as a half maximal effective concentration (EC50) in an insulin receptor phosphorylation ELISA assay. When peptides prepared during enzymatic degradation were subjected to bioactivity assay by insulin receptor phosphorylation, we observed that all insulin and IGF-2 A-chain analogs lose substantially all activity while, all IGF-1 A-chain analogs retain it. The cleavage of insulin analogs by the insulin-specific degrading enzyme (IDE) is extremely robust and easily detected in those insulin analogs where the A-chain is derived from the native insulin sequence. In contrast those analogs where the A-chain is derived from the sequence of IGF-1 appear to be extremely resistant to proteolysis.

The prospect that the increased stability might engender increased mitogenicity, however there did not appear to be a correlation of the higher insulin potency analogs with increased proliferation. Furthermore, and of specific importance to proteolytic stability, the analogs that were more resistant to IDE did not appear to be of any greater mitogenic potential.

A set of insulin analogs were subjected to in vivo testing in normal mice (Melior Research Labs). All peptides of interest demonstrated similar or enhanced glucose lowering potency when compared to standard insulin treatment. However, when analogs with insulin A vs. IGF1 A-chain with the same B-chains were compared, no significant difference in potency was observed. This supports a conclusion that IDE degradation and clearance of insulin is not a primary or physiologically relevant mechanism.

Example 11

Biosynthesis and Purification of N-Alkylated and Lipidated Insulin Prodrugs

1. Liquid-Phase Synthesis of Tripeptides as Outlined in FIG. 14A

General procedure for Ugi Reaction (8a, 8b)

A solution of primary amine and aldehyde in MeOH was stirred at room temperature for 1 hour followed by the addition of t-Boc-D-Lys(Fmoc) or Fmoc-D-Lys(t-Boc) and methyl isocyanoacetate. The reaction mixture was stirred for 10 hour at room temperature and concentrated under reduced pressure. The residue was purified with flash column chromatography to give the product.

General Procedure for Fatty Acid Acylation (9a, 9b)

The protecting group on side chain of lysine was removed with 1% piperidine/1% 1,8-diazabicycloundec-7-ene (DBU)/dichloromethane (for 8a) or 50% TFA/DCM (for 8b). The free amine was acylated with the appropriate fatty acid in the presence of N-(3-dimethylaminopropyl)-N'-ethylcarbodiimide hydrochloride/6-chloro-1-hydroxybenzotriazole dehydrate in DCM and the resulting product purified by flash chromatography.

General Procedure for Hydrolysis of Methyl Ester (10a, 10b)

The methyl ester was hydrolyzed in a solution of lithium hydroxide in THF/water under basic conditions. The reaction was then adjusted to pH 2 by addition of HCl solution, the reaction mixture was extracted with DCM and the product recovered by flash column chromatography.

General Procedure for Carboxylic Acid Activation (11a, 11b)

The carboxylic acid was activated NMP using DIC/NHS in NMP, or activated by DIC/NHS/NMP, and used in the next step.

2. Solid-Phase Synthesis of Tripeptides (FIG. 14B)

General Procedure for Loading Fmoc Protected-Amino Acids (1)

1.0 g (1.1 mmol) 2-chlorotrityl chloride resin (100-200 mesh; 1% DVB; loading 1.1 mmol/g), the Fmoc-protected amino acid (2.2 mmol, 2 eq.) and 350 µl N,N-diisopropylethylamine (2.2 mmol, 2 eq.) were suspended in DCM (10 ml) and shaken overnight at room temperature. The resin was drained, washed h 3 times with DMF (10 ml) and 3 times with DCM (10 ml), then treated with a solution of DCM (10 ml), MeOH (2 ml) and N,N-diisopropylethylamine (1 ml) to deactivate unreacted 2-chlorotrityl chloride sites. Finally, the resin was washed 3 times with DMF (10 ml) and 3 times with DCM (10 ml) and vacuum dried.

General Procedure for Resin-Bound-α-Bromoacyl-Gly-Amino Acids (2)

Resin bound 1 was treated twice for 15 minutes with 20% piperidine in DMF, the resin was washed repeatedly with DMF (10 ml), DCM (10 ml) and DMF (10 ml) again. 0.2 g (0.22 mmol) portion of resin was treated with 146 mg a-bromo acetic acid (1.1 mmol, 5 eq.), 187 mg 6-chloro-1-hydroxybenzotriazole dehydrate (1.1 mmol, 5 eq.) and 154 µl N,N-diisopropylcarbodiimide (1.1 mmol, 5 eq.) in DMF (3 ml) at room temperature. After 2 h, the resin was drained, washed 3 times with DMF (10 ml) and DCM (10 ml).

General Procedure for Resin-Bound a-N-(R1)-Gly (3)

0.2 g Resin was treated with 3.0 mmol primary amine and 525 µl (3 mmol) DIEA in 3 ml DMSO at room temperature overnight. Then resin was drained, washed with DMF and DCM.

Resin-bound-t-Boc-D-Lys (Fmoc)-N-(R1)-Gly (4)

0.2 g (0.22 mmol) resin 3 was treated with 20% piperidine in DMF (10 ml), the resin was washed with DMF (10 ml), DCM (10 ml) and DMF (10 ml) again, then was mixed with 515 mg t-Boc-D-Lys (Fmoc1)-OH (1.1 mmol, 5 eq.), 330 mg 3-(Diethoxyphosphoryloxy)-1,2,3-benzotriazin-4(3H)-one (DEPBT) (1.1 mmol, 5 eq.) and 192 µl DIEA (1.1 mmol, 5 eq.) in DMF (3 ml) at room temperature overnight. The resin was drained, washed with DMF (10 ml) and DCM (10 ml).

Resin-Bound-t-Boc-D-Lys (Fatty Acyl)-N-R1-Gly-Amino Acid (5)

Resin bound 4 was deprotected with 20% piperidine in DMF, the resin was washed with DMF (10 ml), DCM (10 ml) and DMF (10 ml) again. A 0.2 g (0.22 mmol) portion of resin was treated with a long chain fatty acid (1.1 mmol, 5 eq.), 399 mg 1-[Bis(dimethylamino)methylene]-1H-1,2,3-triazolo[4,5-b]pyridinium 3-oxid hexafluorophosphate (HATU)(1.05 mmol, 4.75 eq.) and 193 µl of DIEA (1.05 mmol, 4.75 eq.) in DCM (2 ml) and DMF (2 ml) at room temperature overnight. The resin was drained, washed with DMF (10 ml) and DCM (10 ml) and dried under vacuum.

t-Boc-D-Lys (Fatty Acyl)-N-R1-Gly-Amino Acid (6)

Resin bound 5 was cleaved in 10 ml 0.1% TFA, 20% trifluoroethanol (TFE) in DCM. After 1 h, the filtrate was collected and the resin was rinsed with 5 ml DCM. The combined filtrate and DCM washes were combined and evaporated under reduced pressure to yield a yellow oil. This crude material was purified by flash column chromatography (4%-12% MeOH in DCM as eluent) to yield the products as a white solid or light yellow oil.

t-Boc-D-Lys (Fatty Acyl)-N-R1-Gly-Amino Acid-NHS Ester (7)

12.8 mg of the free acid 6 (0.02 mmol) was activated using 4.6 mg NHS (0.04 mmol, 2 eq.) and 5.6 µl DIC (0.04 mmol, 2 eq.) in 1 ml NMP overnight and used without further purification.

3. Linkage of Lipidated Tripeptide to Insulin (See FIGS. 14C & 14D)

Figure 14C:
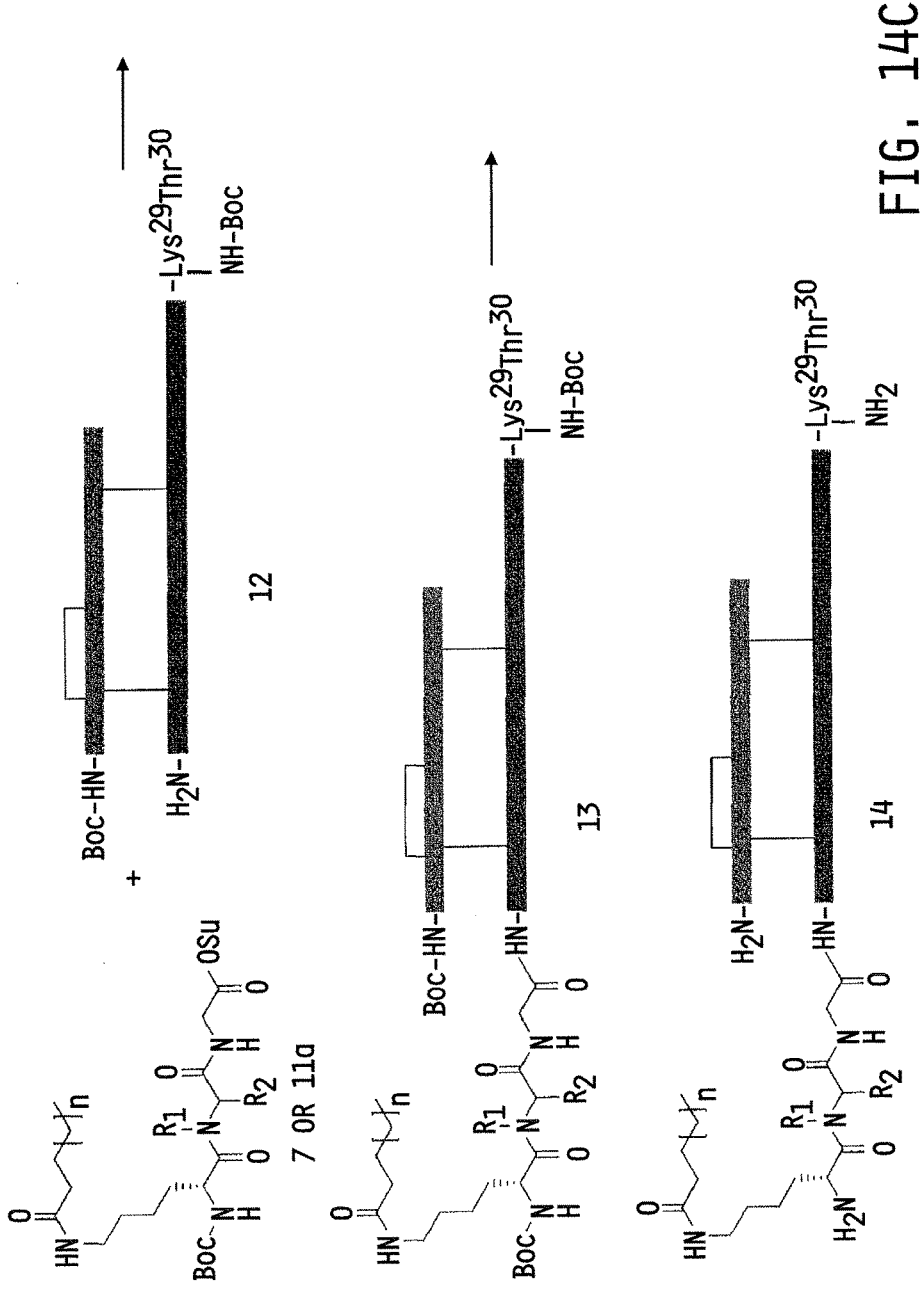

Synthesis of Lipidated Insulin Prodrugs using A1, B29-di-tBoc-insulin (FIG. 14C)

Preparation of A1, B29-di-tBoc-insulin (12)

Insulin (150 mg, 0.026 mmol) was suspended in 2% DIEA/DMF (15 mL) and 12.7 mg 2-(tert-butyloxycarbonyloxyimino)-2-phenylacetonitrile (0.052 mmol, 2 eq.) was added to the cloudy solution and stirred for 4 hours at room temperature. After 4 h the solution turned clear and the reaction was then quenched with 135 ml 1% AcOH and 20% ACN buffer. Preparative HPLC afforded desired product as a white powder (60.2 mg, 38.5% yield).

General Procedure for Coupling Tripeptide to A1, B29-Di-tBoc-Insulin (14)

To a solution of A1, B29-di-tBoc-insulin in a mixture of NMP/bicine buffer (pH 8.2) (3:1) was added 2 eq. of tripeptide succinate ester (2 eq.) in NMP. The reaction progress was monitored with LC-MS. After 4 hours at room temperature the reaction mixture was treated with an excess of 85% phosphoric acid, quenched by dilution with water and purified by preparative HPLC to give the product.

Figure 14D:
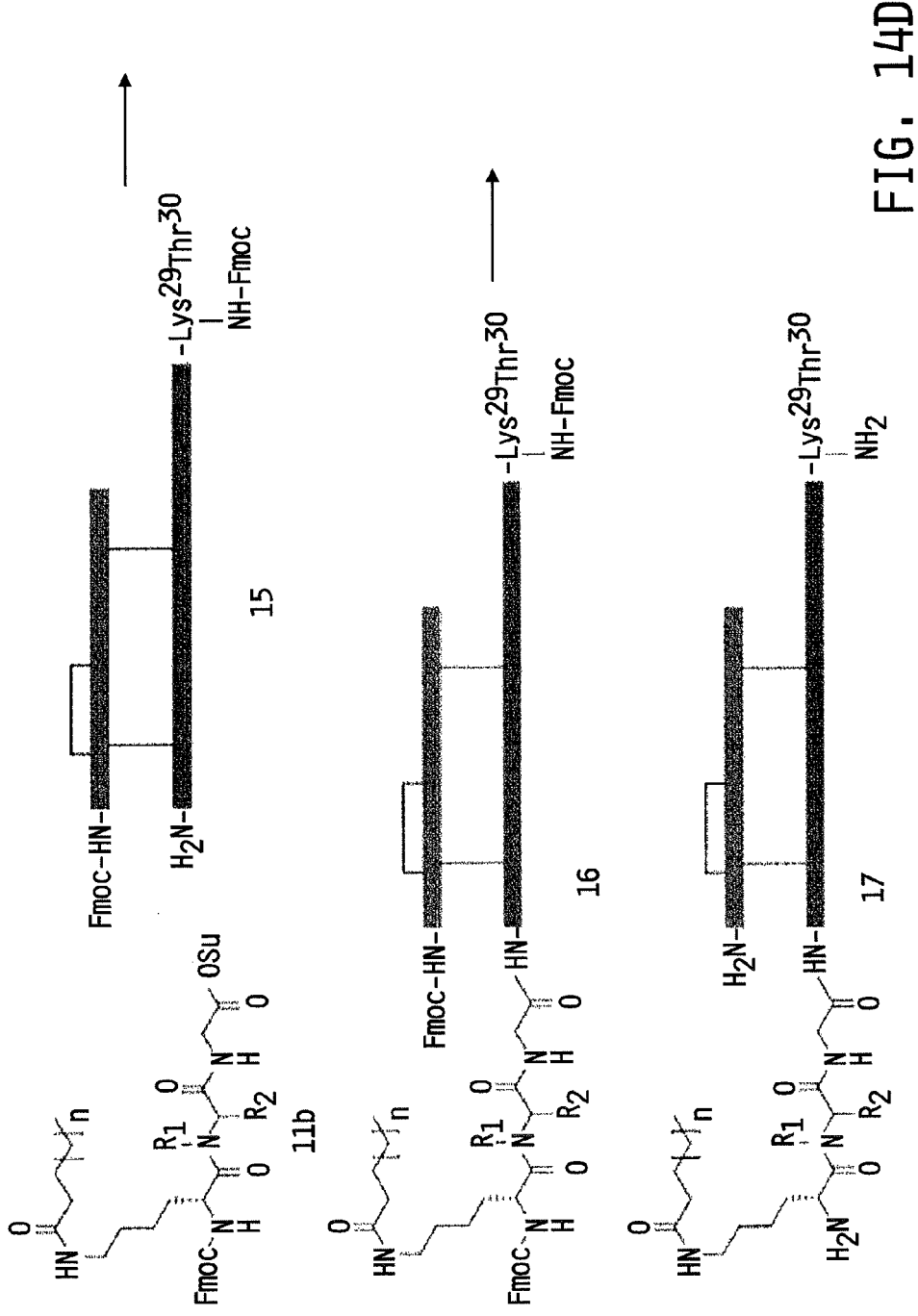
Figure 15A:
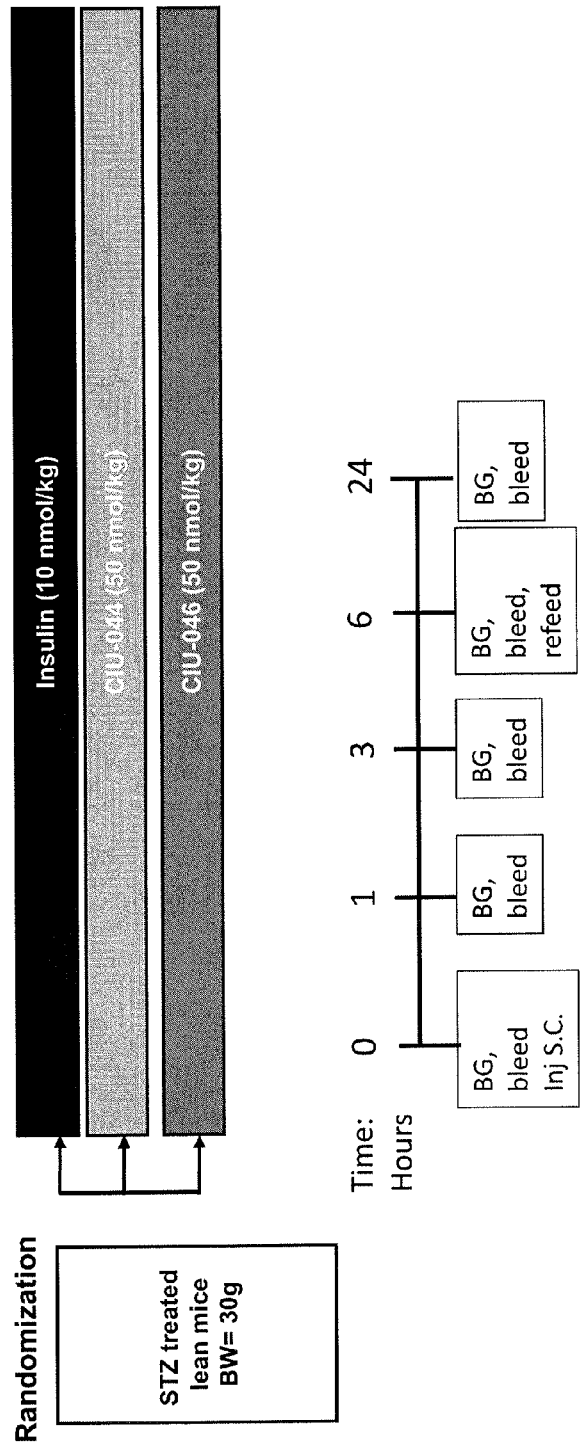
FIGS. 15A-15C provide data for insulin tolerance experiment wherein diabetic model mice are administered either native insulin or native insulin based prodrugs.
Figure 15B:
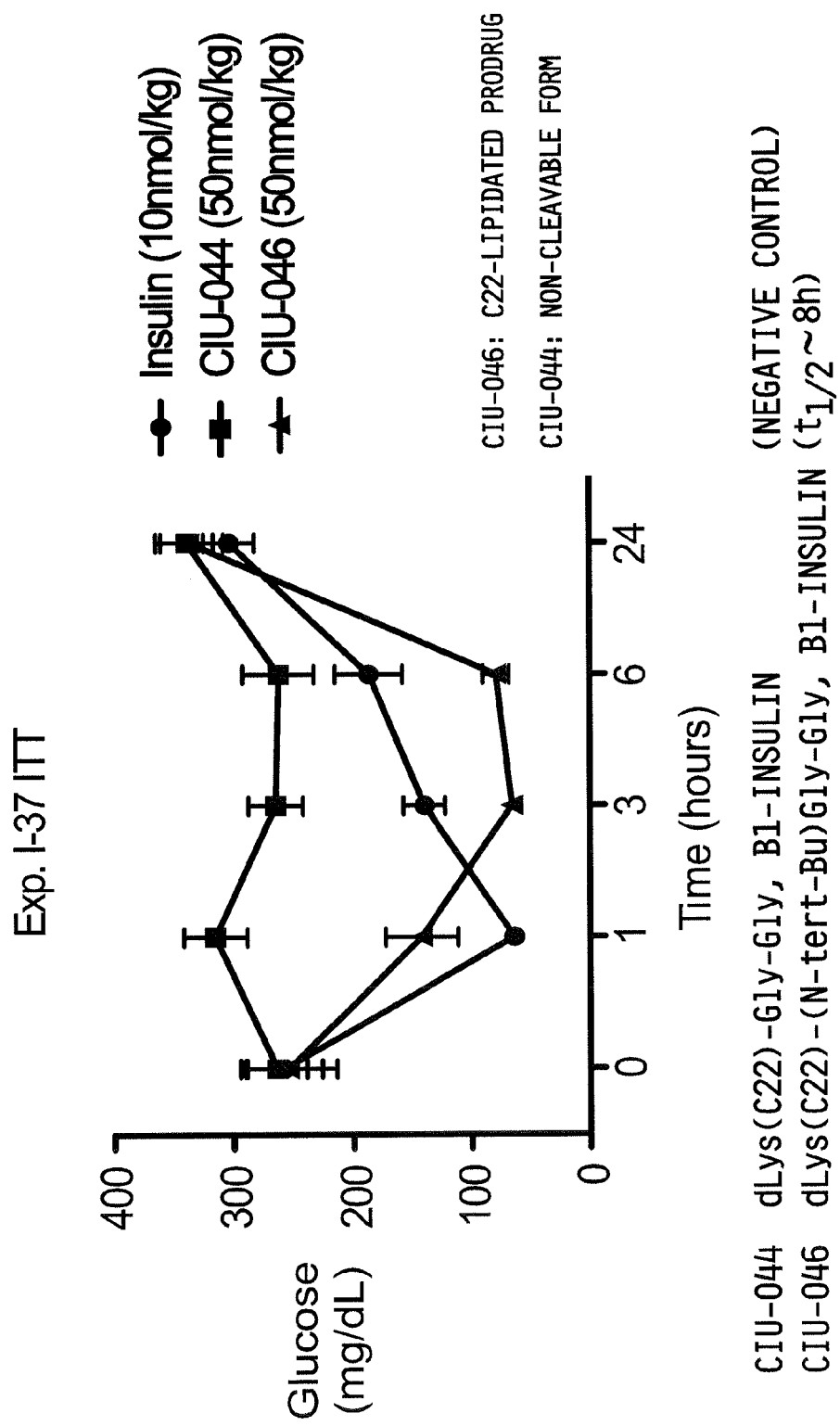
Figure 15C:
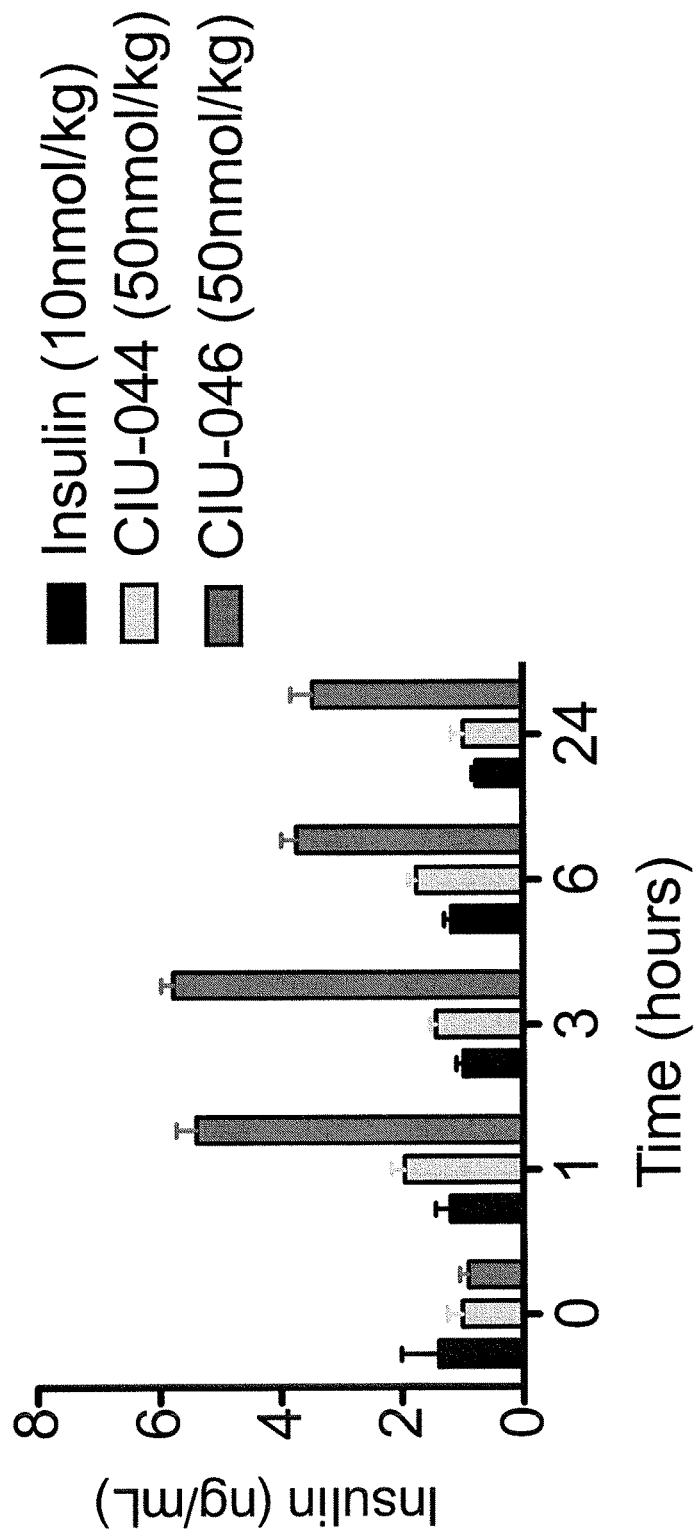
Figure 16A:
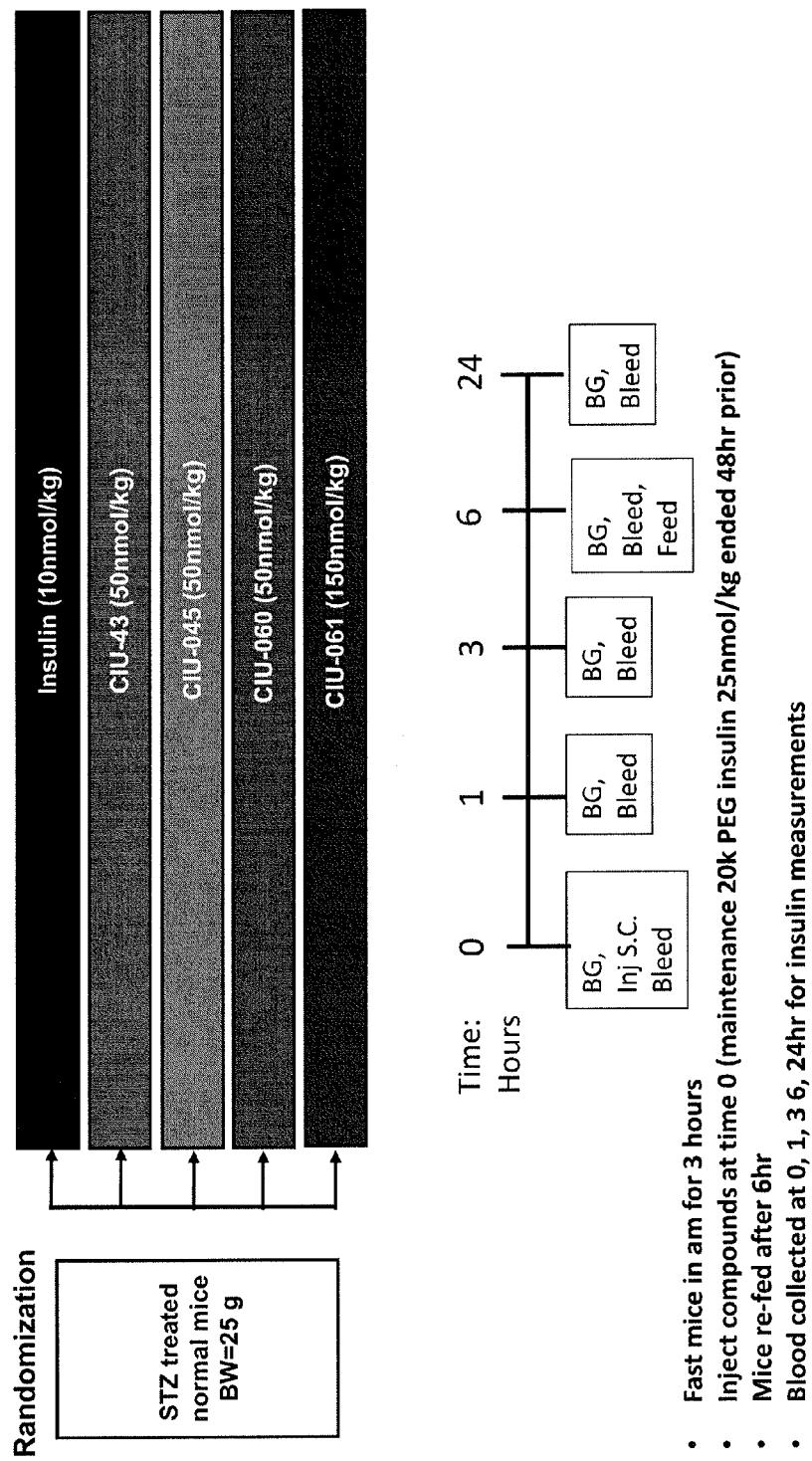
FIGS. 16A-16C provide data for insulin tolerance experiment wherein diabetic model mice are administered either native insulin or native insulin based prodrugs.
Figure 16B:
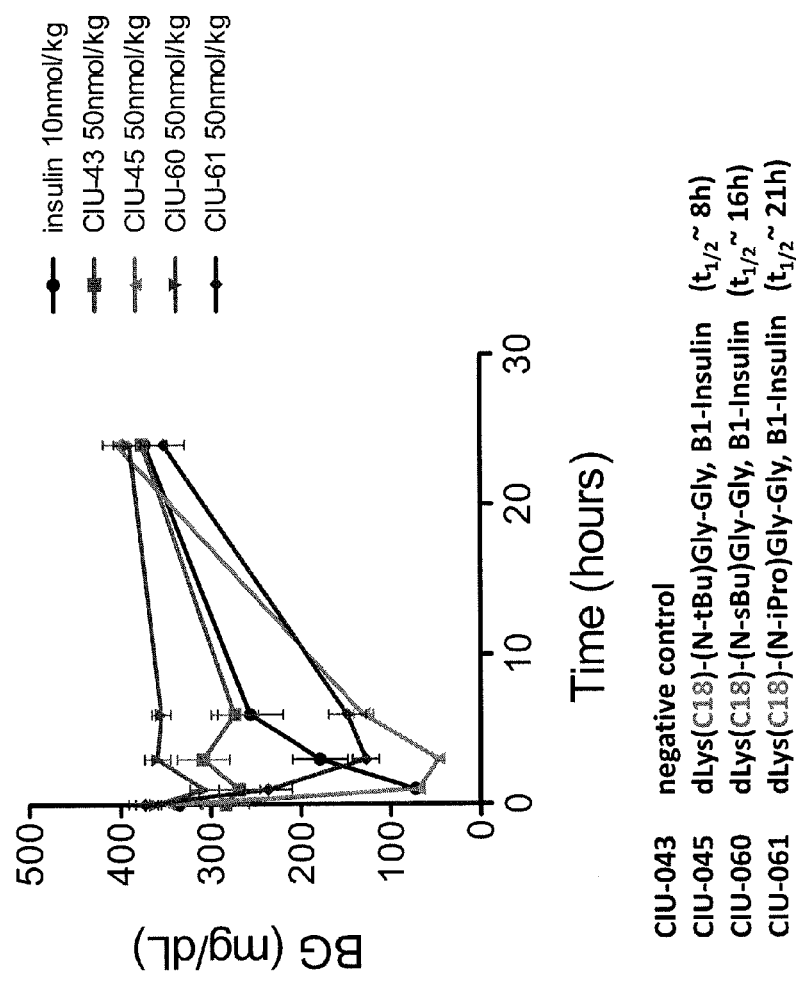
Figure 16C:
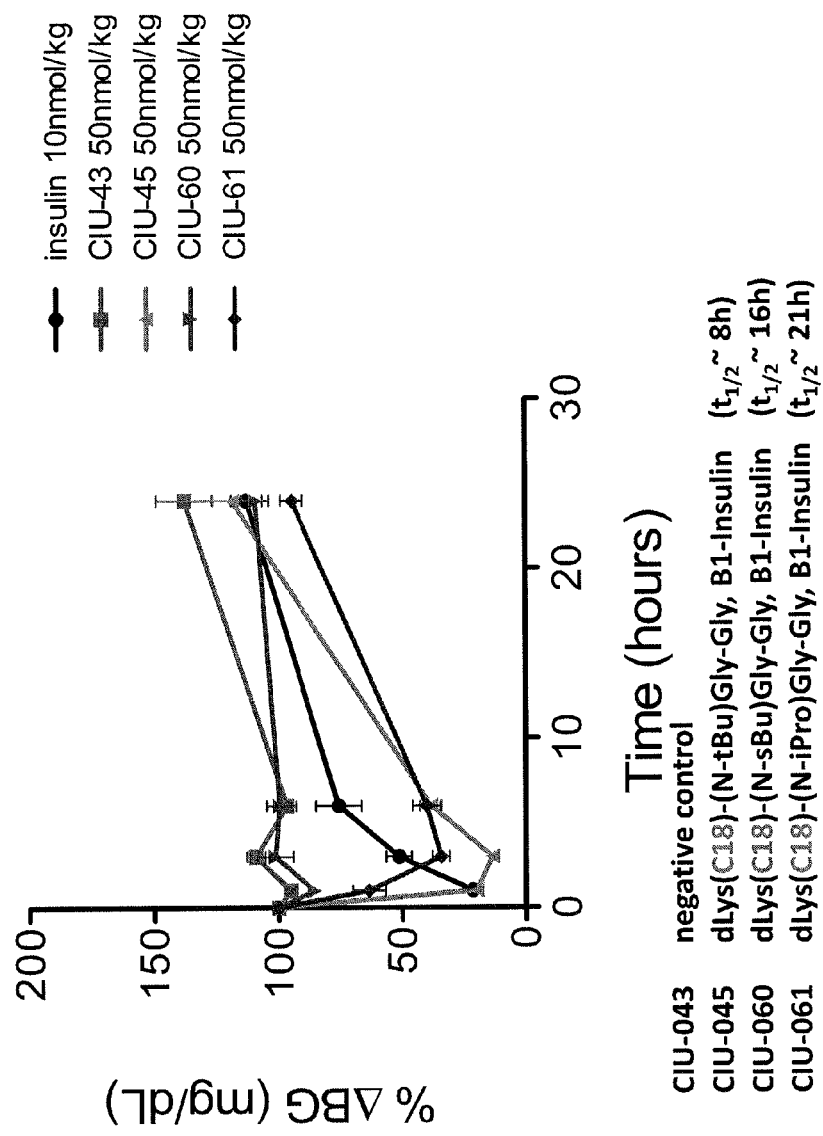
Figure 17B:
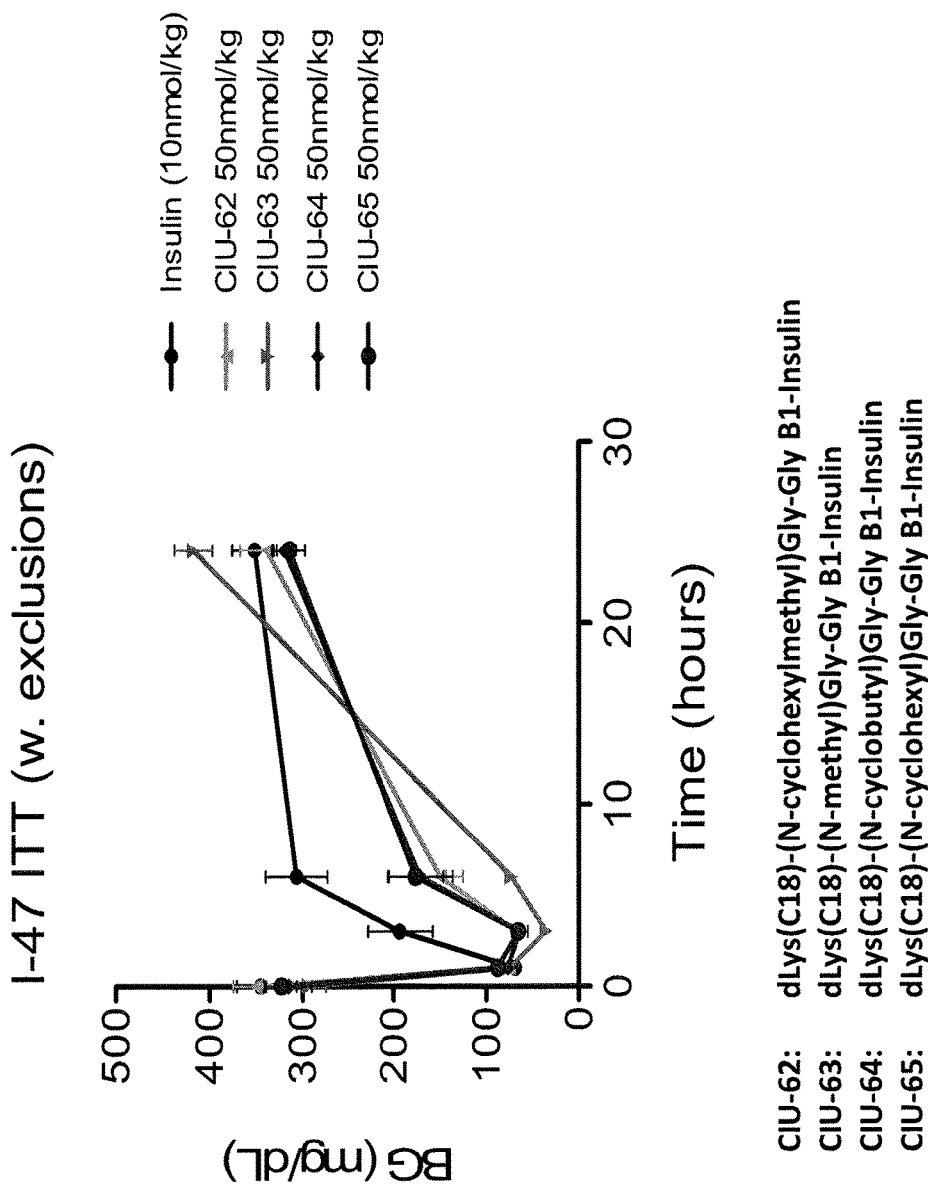

Synthesis of Lipidated Insulin Prodrugs Using A1, B29-di-(Fmoc)-Insulin (FIG. 14D)

A1, B29-di-(Fmoc)-insulin (15)

Insulin (116 mg, 0.02 mmol) was dissolved in a 5 mL mixture of NMP (4 mL) and bicine buffer (pH 8.2) (1 ml). Fmoc-NHS ester (13.5 mg, 0.04 mmol, 2 eq. was slowly added to the resulting solution and the reaction mixture was stirred at room temperature with LC-MS monitoring. After completion, the reaction was quenched with 135 ml 1% AcOH and 20% ACN buffer. Preparative HPLC provided the desired product as white powder (25.2 mg, 20.5% yield).

General Procedure for Coupling Tripeptide Moiety to A1, B29-Di-Fmoc Insulin (17)

The solution of A1, B29-di-Fmoc-insulin in NMP/bicine buffer (pH 8.2) (3:1) was treated with the tripeptide succinate ester (2 eq.) in NMP and the reaction was monitored with LC-MS. After 4 hours at room temperature the reaction mixture was treated with 20% piperidine in DMF, quenched by addition of 0.1 N hydrochloric acid solution and purified with preparative HPLC to give the final prodrug.

What is claimed is:

1. An insulin prodrug comprising the structure:

A-B-C-Q;

wherein Q is an insulin peptide; and
A-B-C comprises the structure:

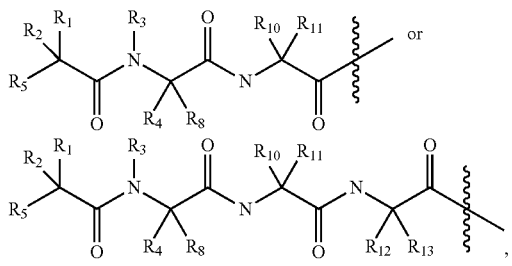

wherein
A-B-C is linked to Q through an amide bond via the N-terminal amino acid of the A chain or the B chain, or an aliphatic amino group on a side chain of an B3, B28 or B29 amino acid of Q,
$R_1$ is $(C_1-C_6$ alkyl)NH—$S_1$—$R_9$, or $(C_1-C_6$ alkyl)NHR$_9$;
$R_3$ is $C_1-C_{18}$ alkyl, $C_3-C_8$ alkenyl, $(C_1-C_4$ alkyl)$(C_4-C_6$ cycloalkyl), $(C_1-C_4$ alkyl)$(C_3-C_5$ heterocyclic), or $(C_1-C_4$ alkyl)$(C_6-C_{10}$ aryl);
$R_2$, $R_4$, $R_{11}$ and $R_{13}$ are each H;
$R_5$ is $NH_2$;
$R_8$ is H or $C_1-C_8$ alkyl;
$R_9$ is selected from the group consisting of $C_{16}-C_{30}$ acyl, and $C_{16}-C_{30}$ alkyl;
$R_{10}$ and $R_{12}$ are independently selected from the group consisting of H, $CH_3$, $(C_1-C_4$ alkyl)COOH, $(C_1-C_4$ alkyl)$NH_2$, $(C_1-C_4$ alkyl)NHC$(NH_2^+)NH_2$, and $CH_2(C_3$—$N_2$ heterocyclic); and
$S_1$ is a spacer consisting of one or two charged amino acids selected from the group consisting of aspartic acid, glutamic acid, cysteic acid, arginine and lysine.

2. The prodrug of claim 1, wherein A-B-C comprises the structure:

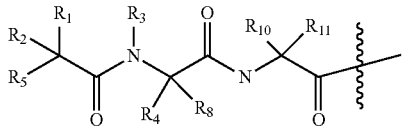

wherein
$R_1$ is $(C_1-C_6$ alkyl)NHR$_9$;
$R_2$, $R_4$, $R_{10}$ and $R_{11}$ are each H;
$R_3$ is $C_1-C_{18}$alkyl;
$R_5$ is $NH_2$;
$R_8$ is H, or $C_1-C_8$ alkyl; and
$R_9$ is $C_{18}-C_{30}$ acyl.

3. The prodrug of claim 2, wherein A-B-C is linked to Q through an amide bond via the N-terminal amino acid of the A chain or the B chain.

4. The prodrug of claim 1, wherein A-B-C comprises the structure:

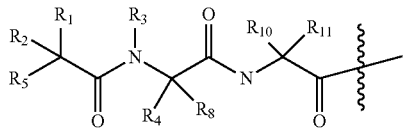

$R_2$, $R_4$, $R_8$, $R_{10}$ and $R_{11}$ are each H;
$R_1$ is $(C_1-C_6$ alkyl)NHR$_9$ or $(C_1-C_6$ alkyl)NH—$S_1$—$R_9$;
$R_3$ is $C_2-C_8$ alkyl;
$R_5$ is $NH_2$; and
$R_9$ is selected from the group consisting of $C_{18}-C_{30}$ acyl and $C_{18}-C_{30}$ alkyl; and
$S_1$ is a spacer consisting of one or two charged amino acids selected from the group consisting of aspartic acid, glutamic acid, cysteic acid, arginine and lysine.

5. The prodrug of claim 4, wherein
$R_1$ is $(CH_2)_4NHR_9$ or $(CH_2)_4NH$—$S_1$—$R_9$;
$R_3$ is $C_3-C_4$ alkyl; and
$R_9$ is $C_{18}-C_{28}$ acyl.

6. The prodrug of claim 5, wherein said insulin peptide comprises an A chain sequence of GIVEQCCX$_8$X$_9$ICSLYQLENYCX$_{21}$-R$_{44}$ (SEQ ID NO: 68) and a B chain sequence of R$_{22}$-X$_{25}$LCGX$_{29}$X$_{30}$LVX$_{33}$X$_{34}$LYLVCGX$_{41}$X$_{42}$GFX$_{45}$ (SEQ ID NO: 20), wherein
said B chain is linked to said A chain through disulfide linkages;
X$_8$ is histidine or threonine;
X$_9$ is serine, lysine, or alanine;
X$_{21}$ is alanine, glycine or asparagine;
X$_{25}$ is histidine or threonine;
X$_{29}$ is selected from the group consisting of alanine, glycine and serine;
X$_{30}$ is selected from the group consisting of histidine, aspartic acid, glutamic acid, homocysteic acid and cysteic acid;
X$_{33}$ is selected from the group consisting of aspartic acid and glutamic acid;
X$_{34}$ is selected from the group consisting of alanine and threonine;
X$_{41}$ is selected from the group consisting of glutamic acid, aspartic acid or asparagine;
X$_{42}$ is selected from the group consisting of alanine, ornithine, lysine and arginine;
X$_{45}$ is tyrosine or phenylalanine;

$R_{22}$ is selected from the group consisting of FVNQ (SEQ ID NO: 12), FVKQ (SEQ ID NO: 8), a tripeptide valine-asparagine-glutamine, a dipeptide asparagine-glutamine, glutamine and an N-terminal amine; and $R_{44}$ is COOH or $CONH_2$.

7. The prodrug of claim 6, wherein said A chain comprises a sequence GIVEQCCTSICSLYQLENYCN-$R_{44}$ (SEQ ID NO: 1) and said B chain comprises a sequence selected from the group consisting of

```
                                    (SEQ ID NO: 2)
FVNQHLCGSHLVEALYLVCGERGFFYTPKT (SEQ ID NO: 9)
FVNQHLCGSHLVEALYLVCGERGFFYTKPT (SEQ ID NO: 5)
FVNQHLCGSHLVEALYLVCGERGFFYTDKT
and (SEQ ID NO: 6)
FVKQHLCGSHLVEALYLVCGERGFFYTEKT.
```

8. The prodrug of claim 1, wherein i) $R_2$ is H and B is selected from the group consisting of glycine(N-methyl), glycine(N-ethyl), glycine(N-propyl), glycine(N-butyl), glycine(N-pentyl), glycine(N-hexyl), glycine(N-heptyl), and glycine(N-octyl)

$R_1$ is selected from the group consisting of ($C_1$-$C_8$ alkyl)$OR_9$, ($C_1$-$C_8$ alkyl)$SR_9$, and ($C_1$-$C_4$ alkyl) $NHR_9$; and $R_3$ is $C_1$-$C_8$ alkyl.

9. The prodrug of claim 1, wherein A has D-stereochemistry.

10. A pharmaceutical composition comprising the prodrug of claim 1, and a pharmaceutically acceptable carrier.

11. A method of treating hyperglycemia or diabetes, said method comprising administering an effective amount of a pharmaceutical composition of claim 10 to a subject in need thereof.

12. The method of claim 11, wherein the prodrug is administered daily at a fraction, 1/n, of the optimal dosage of the corresponding non-prodrug formulation, wherein n represents the half-life, in days, of the cleavage of A-B-C from Q in serum under physiological conditions.

13. The prodrug of claim 1, wherein

Q is an insulin peptide comprising an A chain of SEQ ID NO: 1 and a B chain of SEQ ID NO: 2; and A-B-C comprises the structure:

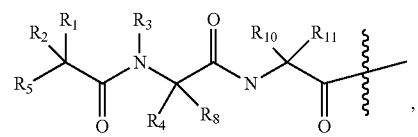

, wherein $R_1$ is $(CH_2)_4NHR_9$ or $(CH_2)_4NH—S_1—R_9$;

$R_2$, $R_4$, $R_8$, $R_{10}$, and $R_{11}$ are each H;

$R_3$ is $C_1$-$C_6$ alkyl;

$R_5$ is $NH_2$; and $R_9$ is $C_{18}$-$C_{28}$ acyl, and

A-B-C is linked to Q through an amide bond via the N-terminal amino acid of the B chain.

* * * * *

SEQUENCE LISTING

```
<160> NUMBER OF SEQ ID NOS: 68

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is threonine or histidine
<220> FEATURE:
```

```
<221> NAME/KEY: MISC_FEATURE
<222> LOCATION: (21)..(21)
<223> OTHER INFORMATION: Xaa at position 21 is asparagine, glycine,
      alanine, glutamine, glutamate, threonine, or serine

<400> SEQUENCE: 3

Gly Ile Val Glu Gln Cys Cys Xaa Ser Ile Cys Ser Leu Tyr Gln Leu
1               5                   10                  15

Glu Asn Tyr Cys Xaa
            20

<210> SEQ ID NO 4
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid

<400> SEQUENCE: 4

Xaa Leu Cys Gly Xaa Xaa Leu Val Glu Ala Leu Tyr Leu Val Cys Gly
1               5                   10                  15

Glu Arg Gly Phe Phe
            20

<210> SEQ ID NO 5
<211> LENGTH: 30
<212> TYPE: PRT
<213> ORGANISM: Homo sapiens

<400> SEQUENCE: 5

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 6
<211> LENGTH: 30
<212> TYPE: PRT
<213> ORGANISM: Homo sapiens

<400> SEQUENCE: 6

Phe Val Lys Gln His Leu Cys Gly Ser His Leu Val Glu Ala Leu Tyr
1               5                   10                  15

Leu Val Cys Gly Glu Arg Gly Phe Phe Tyr Thr Glu Lys Thr
            20                  25                  30

<210> SEQ ID NO 7
<211> LENGTH: 21
<212> TYPE: PRT
<213> ORGANISM: Homo sapiens

<400> SEQUENCE: 7

His Leu Cys Gly Ser His Leu Val Glu Ala Leu Tyr Leu Val Cys Gly
```

```
                1               5                   10                  15
Glu Arg Gly Phe Phe
                20

<210> SEQ ID NO 8
<211> LENGTH: 4
<212> TYPE: PRT
<213> ORGANISM: Homo sapiens

<400> SEQUENCE: 8

Phe Val Lys Gln
1

<210> SEQ ID NO 9
<211> LENGTH: 30
<212> TYPE: PRT
<213> ORGANISM: Homo sapiens

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
                20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is phenylalanine or desamino-
      phenylalanine.
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid

<400> SEQUENCE: 10

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Pro Lys Thr
                20                  25                  30

<210> SEQ ID NO 11
<211> LENGTH: 4
<212> TYPE: PRT
<213> ORGANISM: Homo sapiens

<400> SEQUENCE: 11

Pro Gly Pro Glu
1

<210> SEQ ID NO 12
<211> LENGTH: 4
<212> TYPE: PRT
```

<213> ORGANISM: Homo sapiens

<400> SEQUENCE: 12

Phe Val Asn Gln
1

<210> SEQ ID NO 13
<211> LENGTH: 30
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is phenylalanine or desamino-
      phenylalanine.
<220> FEATURE:
<221> NAME/KEY: MISC_FEATURE
<222> LOCATION: (5)..(5)
<223> OTHER INFORMATION: Xaa at position 5 is histidine and threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid

<400> SEQUENCE: 13

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 14
<211> LENGTH: 6
<212> TYPE: PRT
<213> ORGANISM: Homo sapiens

<400> SEQUENCE: 14

Ala Tyr Arg Pro Ser Glu
1               5

<210> SEQ ID NO 15
<211> LENGTH: 21
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: Xaa at position 21 is histidine, tyrosine or
      phenylalanine

<400> SEQUENCE: 15

His Leu Cys Gly Ser His Leu Val Glu Ala Leu Tyr Leu Val Cys Gly
1               5                   10                  15

Glu Arg Gly Phe Xaa
            20

<210> SEQ ID NO 16
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)

```
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid orcysteic acid
<220> FEATURE:
<221> NAME/KEY: MISC_FEATURE
<222> LOCATION: (21)..(21)
<223> OTHER INFORMATION: Xaa at position 21 is histidine, tyrosine or
      phenylalanine

<400> SEQUENCE: 16

Xaa Leu Cys Gly Xaa Xaa Leu Val Glu Ala Leu Tyr Leu Val Cys Gly
1               5                   10                  15

Glu Arg Gly Phe Xaa
            20

<210> SEQ ID NO 17
<211> LENGTH: 6
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (1)..(1)
<223> OTHER INFORMATION: The Xaa at position 1 is histidine or a
      histidine analog
<220> FEATURE:
<221> NAME/KEY: MOD_RES
<222> LOCATION: (6)..(6)
<223> OTHER INFORMATION: Amidation

<400> SEQUENCE: 17

Xaa Ser Arg Gly Thr Phe
1               5

<210> SEQ ID NO 18
<211> LENGTH: 8
<212> TYPE: PRT
<213> ORGANISM: Artificial Sequence
<220> FEATURE:
<223> OTHER INFORMATION: model synthetic peptide
<220> FEATURE:
<221> NAME/KEY: MISC_FEATURE
<222> LOCATION: (2)..(2)
<223> OTHER INFORMATION: The Xaa at position 2 is sarcosine
<220> FEATURE:
<221> NAME/KEY: MOD_RES
<222> LOCATION: (8)..(8)
<223> OTHER INFORMATION: AMIDATION

<400> SEQUENCE: 18

Lys Xaa His Ser Arg Gly Thr Phe
1               5

<210> SEQ ID NO 19
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (4)..(4)
<223> OTHER INFORMATION: Xaa at position 5 is aspartic acid or glutamic
      acid
```

```
<220> FEATURE:
<221> NAME/KEY: MISC_FEATURE
<222> LOCATION: (5)..(5)
<223> OTHER INFORMATION: Xaa at position 5 is glutamine or glutamic acid
<220> FEATURE:
<221> NAME/KEY: MISC_FEATURE
<222> LOCATION: (8)..(8)
<223> OTHER INFORMATION: Xaa at position 8 is histidine, threonine or
      phenylalanine
<220> FEATURE:
<221> NAME/KEY: MISC_FEATURE
<222> LOCATION: (9)..(9)
<223> OTHER INFORMATION: Xaa at position 9 is serine, arginine,
      ornithine, lysine or alanine
<220> FEATURE:
<221> NAME/KEY: MISC_FEATURE
<222> LOCATION: (10)..(10)
<223> OTHER INFORMATION: Xaa at position 10 is isoleucine or serine
<220> FEATURE:
<221> NAME/KEY: MISC_FEATURE
<222> LOCATION: (12)..(12)
<223> OTHER INFORMATION: Xaa at position 12 is aspartic acid or serine
<220> FEATURE:
<221> NAME/KEY: MISC_FEATURE
<222> LOCATION: (14)..(14)
<223> OTHER INFORMATION: Xaa at position 14 is tyrosine, arginine,
      ornathine, lysine or alanine
<220> FEATURE:
<221> NAME/KEY: MISC_FEATURE
<222> LOCATION: (15)..(15)
<223> OTHER INFORMATION: Xaa at position 15 is glutamine, glutamic acid,
      arginine, ornithine, alanine, lysine or leucine
<220> FEATURE:
<221> NAME/KEY: MISC_FEATURE
<222> LOCATION: (17)..(17)
<223> OTHER INFORMATION: Xaa at position 17 is glutamine or glutamic
      acid
<220> FEATURE:
<221> NAME/KEY: MISC_FEATURE
<222> LOCATION: (18)..(18)
<223> OTHER INFORMATION: Xaa at position 18 is methionine, asparagine,
      glutamine, glutamic acid, aspartic acid or threonine
<220> FEATURE:
<221> NAME/KEY: MISC_FEATURE
<222> LOCATION: (21)..(21)
<223> OTHER INFORMATION: Xaa at position 21 is alanine, glycine, serine,
      valine, threonine, isoleucine, leucine, glutamine, glutamic acid,
      asparagine, aspartic acid, histidine, tryptophan, tyrosine, or
      methionine

<400> SEQUENCE: 19

Gly Ile Val Xaa Xaa Cys Cys Xaa Xaa Xaa Cys Xaa Leu Xaa Xaa Leu
1               5                   10                  15

Xaa Xaa Tyr Cys Xaa
            20

<210> SEQ ID NO 20
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
```

```
<221> NAME/KEY: MISC_FEATURE
<222> LOCATION: (9)..(9)
<223> OTHER INFORMATION: Xaa at position 9 is aspartic acid, glutamine
      or glutamic acid
<220> FEATURE:
<221> NAME/KEY: MISC_FEATURE
<222> LOCATION: (10)..(10)
<223> OTHER INFORMATION: Xaa at position 10 is alanine or threonine
<220> FEATURE:
<221> NAME/KEY: MISC_FEATURE
<222> LOCATION: (17)..(17)
<223> OTHER INFORMATION: Xaa at position 12 is glutamic acid, aspartic
      acid or asparagine
<220> FEATURE:
<221> NAME/KEY: MISC_FEATURE
<222> LOCATION: (18)..(18)
<223> OTHER INFORMATION: Xaa at position 18 is alanine, ornithine,
      lysine or arginine
<220> FEATURE:
<221> NAME/KEY: MISC_FEATURE
<222> LOCATION: (21)..(21)
<223> OTHER INFORMATION: Xaa at position 21 is tyrosine or 4-amino-
      phenylalanine

<400> SEQUENCE: 20

Xaa Leu Cys Gly Xaa Xaa Leu Val Xaa Xaa Leu Tyr Leu Val Cys Gly
1               5                   10                  15

Xaa Xaa Gly Phe Xaa
            20

<210> SEQ ID NO 21
<211> LENGTH: 6
<212> TYPE: PRT
<213> ORGANISM: Artificial Sequence
<220> FEATURE:
<223> OTHER INFORMATION: glucagon analogue
<220> FEATURE:
<221> NAME/KEY: MOD_RES
<222> LOCATION: (1)..(1)
<223> OTHER INFORMATION: Xaa at position 1 is d-histidine
<220> FEATURE:
<221> NAME/KEY: MOD_RES
<222> LOCATION: (2)..(2)
<223> OTHER INFORMATION: Xaa at position 2 is d-threonine
<220> FEATURE:
<221> NAME/KEY: MOD_RES
<222> LOCATION: (3)..(3)
<223> OTHER INFORMATION: Xaa at position 3 is d-arginine
<220> FEATURE:
<221> NAME/KEY: MOD_RES
<222> LOCATION: (5)..(5)
<223> OTHER INFORMATION: Xaa at position 5 is d-threonine
<220> FEATURE:
<221> NAME/KEY: MOD_RES
<222> LOCATION: (6)..(6)
<223> OTHER INFORMATION: Xaa at position 6 is d-phenylalanine

<400> SEQUENCE: 21

Xaa Xaa Xaa Gly Xaa Xaa
1               5

<210> SEQ ID NO 22
<211> LENGTH: 7
<212> TYPE: PRT
<213> ORGANISM: Artificial Sequence
<220> FEATURE:
<223> OTHER INFORMATION: peptide linker

<400> SEQUENCE: 22

Gly Gly Gly Pro Gly Lys Arg
1               5
```

```
<210> SEQ ID NO 23
<211> LENGTH: 12
<212> TYPE: PRT
<213> ORGANISM: Artificial Sequence
<220> FEATURE:
<223> OTHER INFORMATION: peptide linker

<400> SEQUENCE: 23

Gly Tyr Gly Ser Ser Ser Arg Arg Ala Pro Gln Thr
1               5                   10

<210> SEQ ID NO 24
<211> LENGTH: 7
<212> TYPE: PRT
<213> ORGANISM: Artificial Sequence
<220> FEATURE:
<223> OTHER INFORMATION: peptide linker

<400> SEQUENCE: 24

Gly Gly Gly Gly Gly Lys Arg
1               5

<210> SEQ ID NO 25
<211> LENGTH: 7
<212> TYPE: PRT
<213> ORGANISM: Artificial Sequence
<220> FEATURE:
<223> OTHER INFORMATION: peptide linker

<400> SEQUENCE: 25

Arg Arg Gly Gly Gly Gly Gly
1               5

<210> SEQ ID NO 26
<211> LENGTH: 9
<212> TYPE: PRT
<213> ORGANISM: Artificial Sequence
<220> FEATURE:
<223> OTHER INFORMATION: peptide linker

<400> SEQUENCE: 26

Gly Gly Ala Pro Gly Asp Val Lys Arg
1               5

<210> SEQ ID NO 27
<211> LENGTH: 9
<212> TYPE: PRT
<213> ORGANISM: Artificial Sequence
<220> FEATURE:
<223> OTHER INFORMATION: peptide linker

<400> SEQUENCE: 27

Arg Arg Ala Pro Gly Asp Val Gly Gly
1               5

<210> SEQ ID NO 28
<211> LENGTH: 9
<212> TYPE: PRT
<213> ORGANISM: Artificial Sequence
<220> FEATURE:
<223> OTHER INFORMATION: peptide linker

<400> SEQUENCE: 28

Gly Gly Tyr Pro Gly Asp Val Lys Arg
1               5

<210> SEQ ID NO 29
```

```
<211> LENGTH: 9
<212> TYPE: PRT
<213> ORGANISM: Artificial Sequence
<220> FEATURE:
<223> OTHER INFORMATION: peptide linker

<400> SEQUENCE: 29

Arg Arg Tyr Pro Gly Asp Val Gly Gly
1               5

<210> SEQ ID NO 30
<211> LENGTH: 9
<212> TYPE: PRT
<213> ORGANISM: Artificial Sequence
<220> FEATURE:
<223> OTHER INFORMATION: peptide linker

<400> SEQUENCE: 30

Gly Gly His Pro Gly Asp Val Lys Arg
1               5

<210> SEQ ID NO 31
<211> LENGTH: 9
<212> TYPE: PRT
<213> ORGANISM: Artificial Sequence
<220> FEATURE:
<223> OTHER INFORMATION: peptide linker

<400> SEQUENCE: 31

Arg Arg His Pro Gly Asp Val Gly Gly
1               5

<210> SEQ ID NO 32
<211> LENGTH: 7
<212> TYPE: PRT
<213> ORGANISM: Artificial Sequence
<220> FEATURE:
<223> OTHER INFORMATION: peptide linker

<400> SEQUENCE: 32

Arg Arg Gly Pro Gly Gly Gly
1               5

<210> SEQ ID NO 33
<211> LENGTH: 51
<212> TYPE: PRT
<213> ORGANISM: Artificial Sequence
<220> FEATURE:
<223> OTHER INFORMATION: single chain human insulin analog
<220> FEATURE:
<221> NAME/KEY: MISC_FEATURE
<222> LOCATION: (49)..(49)
<223> OTHER INFORMATION: Xaa at position 49 is 4-amino phenylalanine or
      4-methoxy phenylalanine

<400> SEQUENCE: 33

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Ile
            20                  25                  30

Val Glu Gln Cys Cys Thr Ser Ile Cys Ser Leu Tyr Gln Leu Glu Asn
        35                  40                  45

Xaa Cys Asn
    50

<210> SEQ ID NO 34
```

```
<211> LENGTH: 63
<212> TYPE: PRT
<213> ORGANISM: Artificial Sequence
<220> FEATURE:
<223> OTHER INFORMATION: single-chain human insulin analog
<220> FEATURE:
<221> NAME/KEY: MISC_FEATURE
<222> LOCATION: (61)..(61)
<223> OTHER INFORMATION: Xaa at position 61 is 4-amino phenylalanine or
      4-methoxy phenylalanine

<400> SEQUENCE: 34

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gln Pro
            20                  25                  30

Leu Ala Leu Glu Gly Ser Leu Gln Lys Arg Gly Ile Val Glu Gln Cys
        35                  40                  45

Cys Thr Ser Ile Cys Ser Leu Tyr Gln Leu Glu Asn Xaa Cys Asn
    50                  55                  60

<210> SEQ ID NO 35
<211> LENGTH: 7
<212> TYPE: PRT
<213> ORGANISM: Artificial Sequence
<220> FEATURE:
<223> OTHER INFORMATION: peptide linker

<400> SEQUENCE: 35

Ala Gly Arg Gly Ser Gly Lys
1               5

<210> SEQ ID NO 36
<211> LENGTH: 7
<212> TYPE: PRT
<213> ORGANISM: Artificial Sequence
<220> FEATURE:
<223> OTHER INFORMATION: peptide linker

<400> SEQUENCE: 36

Ala Gly Leu Gly Ser Gly Lys
1               5

<210> SEQ ID NO 37
<211> LENGTH: 7
<212> TYPE: PRT
<213> ORGANISM: Artificial Sequence
<220> FEATURE:
<223> OTHER INFORMATION: peptide linker

<400> SEQUENCE: 37

Ala Gly Met Gly Ser Gly Lys
1               5

<210> SEQ ID NO 38
<211> LENGTH: 7
<212> TYPE: PRT
<213> ORGANISM: Artificial Sequence
<220> FEATURE:
<223> OTHER INFORMATION: peptide linker

<400> SEQUENCE: 38

Ala Ser Trp Gly Ser Gly Lys
1               5

<210> SEQ ID NO 39
```

```
<211> LENGTH: 7
<212> TYPE: PRT
<213> ORGANISM: Artificial Sequence
<220> FEATURE:
<223> OTHER INFORMATION: peptide linker

<400> SEQUENCE: 39

Thr Gly Leu Gly Ser Gly Gln
1               5

<210> SEQ ID NO 40
<211> LENGTH: 7
<212> TYPE: PRT
<213> ORGANISM: Artificial Sequence
<220> FEATURE:
<223> OTHER INFORMATION: peptide linker

<400> SEQUENCE: 40

Thr Gly Leu Gly Arg Gly Lys
1               5

<210> SEQ ID NO 41
<211> LENGTH: 7
<212> TYPE: PRT
<213> ORGANISM: Artificial Sequence
<220> FEATURE:
<223> OTHER INFORMATION: peptide linker

<400> SEQUENCE: 41

Thr Gly Leu Gly Ser Gly Lys
1               5

<210> SEQ ID NO 42
<211> LENGTH: 7
<212> TYPE: PRT
<213> ORGANISM: Artificial Sequence
<220> FEATURE:
<223> OTHER INFORMATION: peptide linker

<400> SEQUENCE: 42

His Gly Leu Tyr Ser Gly Lys
1               5

<210> SEQ ID NO 43
<211> LENGTH: 7
<212> TYPE: PRT
<213> ORGANISM: Artificial Sequence
<220> FEATURE:
<223> OTHER INFORMATION: peptide linker

<400> SEQUENCE: 43

Lys Gly Leu Gly Ser Gly Gln
1               5

<210> SEQ ID NO 44
<211> LENGTH: 7
<212> TYPE: PRT
<213> ORGANISM: Artificial Sequence
<220> FEATURE:
<223> OTHER INFORMATION: peptide linker

<400> SEQUENCE: 44

Val Gly Leu Met Ser Gly Lys
1               5

<210> SEQ ID NO 45
<211> LENGTH: 7
```

<212> TYPE: PRT
<213> ORGANISM: Artificial Sequence
<220> FEATURE:
<223> OTHER INFORMATION: peptide linker

<400> SEQUENCE: 45

Val Gly Leu Ser Ser Gly Gln
1               5

<210> SEQ ID NO 46
<211> LENGTH: 7
<212> TYPE: PRT
<213> ORGANISM: Artificial Sequence
<220> FEATURE:
<223> OTHER INFORMATION: peptide linker

<400> SEQUENCE: 46

Val Gly Leu Tyr Ser Gly Lys
1               5

<210> SEQ ID NO 47
<211> LENGTH: 7
<212> TYPE: PRT
<213> ORGANISM: Artificial Sequence
<220> FEATURE:
<223> OTHER INFORMATION: peptide linker

<400> SEQUENCE: 47

Val Gly Leu Ser Ser Gly Lys
1               5

<210> SEQ ID NO 48
<211> LENGTH: 7
<212> TYPE: PRT
<213> ORGANISM: Artificial Sequence
<220> FEATURE:
<223> OTHER INFORMATION: peptide linker

<400> SEQUENCE: 48

Val Gly Met Ser Ser Gly Lys
1               5

<210> SEQ ID NO 49
<211> LENGTH: 7
<212> TYPE: PRT
<213> ORGANISM: Artificial Sequence
<220> FEATURE:
<223> OTHER INFORMATION: peptide linker

<400> SEQUENCE: 49

Val Trp Ser Ser Ser Gly Lys
1               5

<210> SEQ ID NO 50
<211> LENGTH: 7
<212> TYPE: PRT
<213> ORGANISM: Artificial Sequence
<220> FEATURE:
<223> OTHER INFORMATION: peptide linker

<400> SEQUENCE: 50

Val Gly Ser Ser Ser Gly Lys
1               5

<210> SEQ ID NO 51
<211> LENGTH: 7
<212> TYPE: PRT

```
<213> ORGANISM: Artificial Sequence
<220> FEATURE:
<223> OTHER INFORMATION: peptide linker

<400> SEQUENCE: 51

Val Gly Met Ser Ser Gly Lys
1               5

<210> SEQ ID NO 52
<211> LENGTH: 7
<212> TYPE: PRT
<213> ORGANISM: Artificial Sequence
<220> FEATURE:
<223> OTHER INFORMATION: peptide linker

<400> SEQUENCE: 52

Thr Gly Leu Gly Ser Gly Arg
1               5

<210> SEQ ID NO 53
<211> LENGTH: 7
<212> TYPE: PRT
<213> ORGANISM: Artificial Sequence
<220> FEATURE:
<223> OTHER INFORMATION: peptide linker

<400> SEQUENCE: 53

Thr Gly Leu Gly Lys Gly Gln
1               5

<210> SEQ ID NO 54
<211> LENGTH: 7
<212> TYPE: PRT
<213> ORGANISM: Artificial Sequence
<220> FEATURE:
<223> OTHER INFORMATION: peptide linker

<400> SEQUENCE: 54

Lys Gly Leu Ser Ser Gly Gln
1               5

<210> SEQ ID NO 55
<211> LENGTH: 7
<212> TYPE: PRT
<213> ORGANISM: Artificial Sequence
<220> FEATURE:
<223> OTHER INFORMATION: peptide linker

<400> SEQUENCE: 55

Val Lys Leu Ser Ser Gly Gln
1               5

<210> SEQ ID NO 56
<211> LENGTH: 7
<212> TYPE: PRT
<213> ORGANISM: Artificial Sequence
<220> FEATURE:
<223> OTHER INFORMATION: peptide linker

<400> SEQUENCE: 56

Val Lys Leu Ser Ser Gly Gln
1               5

<210> SEQ ID NO 57
<211> LENGTH: 7
<212> TYPE: PRT
<213> ORGANISM: Artificial Sequence
```

```
<220> FEATURE:
<223> OTHER INFORMATION: peptide linker

<400> SEQUENCE: 57

Thr Gly Leu Gly Lys Gly Gln
1               5

<210> SEQ ID NO 58
<211> LENGTH: 7
<212> TYPE: PRT
<213> ORGANISM: Artificial Sequence
<220> FEATURE:
<223> OTHER INFORMATION: peptide linker

<400> SEQUENCE: 58

Val Gly Leu Ser Lys Gly Gln
1               5

<210> SEQ ID NO 59
<211> LENGTH: 8
<212> TYPE: PRT
<213> ORGANISM: Artificial Sequence
<220> FEATURE:
<223> OTHER INFORMATION: glucagon analogue
<220> FEATURE:
<221> NAME/KEY: MOD_RES
<222> LOCATION: (1)..(1)
<223> OTHER INFORMATION: Xaa at position 1 is d-lysine
<220> FEATURE:
<221> NAME/KEY: MOD_RES
<222> LOCATION: (2)..(2)
<223> OTHER INFORMATION: Xaa at position 2 is d-sarcosine
<220> FEATURE:
<221> NAME/KEY: MOD_RES
<222> LOCATION: (3)..(3)
<223> OTHER INFORMATION: Xaa at position 3 is d-histidine
<220> FEATURE:
<221> NAME/KEY: MOD_RES
<222> LOCATION: (4)..(4)
<223> OTHER INFORMATION: Xaa at position 4 is d-threonine
<220> FEATURE:
<221> NAME/KEY: MOD_RES
<222> LOCATION: (5)..(5)
<223> OTHER INFORMATION: Xaa at position 5 is d-arginine
<220> FEATURE:
<221> NAME/KEY: MOD_RES
<222> LOCATION: (7)..(7)
<223> OTHER INFORMATION: Xaa at position 7 is d-threonine
<220> FEATURE:
<221> NAME/KEY: MOD_RES
<222> LOCATION: (8)..(8)
<223> OTHER INFORMATION: d-phenylalanine
<220> FEATURE:
<221> NAME/KEY: MOD_RES
<222> LOCATION: (8)..(8)
<223> OTHER INFORMATION: Xaa at position 8 is d-phenylalanine

<400> SEQUENCE: 59

Xaa Xaa Xaa Xaa Xaa Gly Xaa Xaa
1               5

<210> SEQ ID NO 60
<211> LENGTH: 8
<212> TYPE: PRT
<213> ORGANISM: Homo sapiens

<400> SEQUENCE: 60

Ser Arg Val Ser Arg Arg Ser Arg
1               5

<210> SEQ ID NO 61
```

```
<211> LENGTH: 8
<212> TYPE: PRT
<213> ORGANISM: Homo sapiens

<400> SEQUENCE: 61

Gly Tyr Gly Ser Ser Ser Arg Arg
1               5

<210> SEQ ID NO 62
<211> LENGTH: 8
<212> TYPE: PRT
<213> ORGANISM: Homo sapiens

<400> SEQUENCE: 62

Gly Ser Ser Ser Arg Arg Ala Pro
1               5

<210> SEQ ID NO 63
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa at position 7 is ornithine

<400> SEQUENCE: 63

Gly Tyr Gly Ser Ser Ser Xaa Arg
1               5

<210> SEQ ID NO 64
<211> LENGTH: 12
<212> TYPE: PRT
<213> ORGANISM: Homo sapiens

<400> SEQUENCE: 64

Gly Ala Gly Ser Ser Ser Arg Arg Ala Pro Gln Thr
1               5                   10

<210> SEQ ID NO 65
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (18)..(18)
<223> OTHER INFORMATION: Xaa at position 18 is alanine ornithine or
      arginine

<400> SEQUENCE: 65

Xaa Leu Cys Gly Ala Xaa Leu Val Asp Ala Leu Tyr Leu Val Cys Gly
1               5                   10                  15

Asp Xaa Gly Phe Tyr
            20

<210> SEQ ID NO 66
<211> LENGTH: 8
```

<212> TYPE: PRT
<213> ORGANISM: Homo sapiens

<400> SEQUENCE: 66

Gly Tyr Gly Ser Ser Ser Arg Arg
1               5

<210> SEQ ID NO 67
<211> LENGTH: 23
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
    glutamic acid, homocysteic acid or cysteic acid
<220> FEATURE:
<221> NAME/KEY: MISC_FEATURE
<222> LOCATION: (9)..(9)
<223> OTHER INFORMATION: Xaa at position 9 is histidine, aspartic acid
    or glutamic acid
<220> FEATURE:
<221> NAME/KEY: MISC_FEATURE
<222> LOCATION: (10)..(10)
<223> OTHER INFORMATION: Xaa at position 10 is alanine or threonin
<220> FEATURE:
<221> NAME/KEY: MISC_FEATURE
<222> LOCATION: (17)..(17)
<223> OTHER INFORMATION: Xaa at position 17 is glutamic acid, aspartic
    acid or asparagine
<220> FEATURE:
<221> NAME/KEY: MISC_FEATURE
<222> LOCATION: (18)..(18)
<223> OTHER INFORMATION: Xaa at position 18 is alanine ornithine, lysine
    or arginine
<220> FEATURE:
<221> NAME/KEY: MISC_FEATURE
<222> LOCATION: (21)..(21)
<223> OTHER INFORMATION: Xaa at position 21 is tyrosine or phenylalanine

<400> SEQUENCE: 67

Xaa Leu Cys Gly Xaa Xaa Leu Val Xaa Xaa Leu Tyr Leu Val Cys Gly
1               5                   10                  15

Xaa Xaa Gly Phe Xaa Tyr Thr
            20

<210> SEQ ID NO 68
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is threonine or histidine
<220> FEATURE:
<221> NAME/KEY: MISC_FEATURE
<222> LOCATION: (9)..(9)
<223> OTHER INFORMATION: Xaa at position 9 is serine, lysine or alanine
<220> FEATURE:
<221> NAME/KEY: MISC_FEATURE
<222> LOCATION: (21)..(21)
<223> OTHER INFORMATION: Xaa at position 21 is asparagine, glycine or

```
        alanine

<400> SEQUENCE: 68

Gly Ile Val Glu Gln Cys Cys Xaa Xaa Ile Cys Ser Leu Tyr Gln Leu
1               5                   10                  15

Glu Asn Tyr Cys Xaa
                20
```